US010392395B2

United States Patent
Koshino et al.

(10) Patent No.: US 10,392,395 B2
(45) Date of Patent: Aug. 27, 2019

(54) NITROGEN-CONTAINING AROMATIC COMPOUNDS AND METAL COMPLEXES

(75) Inventors: Nobuyoshi Koshino, Tsukuba (JP); Hideyuki Higashimura, Tsukuba (JP); Klaus Muellen, Cologne (DE); Christian von Malotki, Windesheim (DE); Qi Su, Beijing (CN); Martin Baumgarten, Mainz (DE); Hassan Norouzi-Arasi, Montreal (CA); Lena Arnold, Russelsheim (DE); Ruili Liu, Shanghai (CN)

(73) Assignees: SUMITOMO CHEMICAL COMPANY, LIMITED, Chuo-ku, Tokyo (JP); MAX PLANCK GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 901 days.

(21) Appl. No.: 13/504,820

(22) PCT Filed: Oct. 29, 2010

(86) PCT No.: PCT/JP2010/069769
§ 371 (c)(1),
(2), (4) Date: Jul. 13, 2012

(87) PCT Pub. No.: WO2011/052805
PCT Pub. Date: May 5, 2011

(65) Prior Publication Data
US 2012/0270141 A1 Oct. 25, 2012

(30) Foreign Application Priority Data

Oct. 30, 2009 (JP) .............................. P2009-251005
Jun. 10, 2010 (JP) .............................. P2010-133114

(51) Int. Cl.
C07D 487/22 (2006.01)
B01J 31/18 (2006.01)
C07D 471/22 (2006.01)
H01M 4/90 (2006.01)
H01M 8/1007 (2016.01)

(52) U.S. Cl.
CPC .......... *C07D 487/22* (2013.01); *B01J 31/183* (2013.01); *C07D 471/22* (2013.01); *H01M 4/9008* (2013.01); *B01J 2231/62* (2013.01); *B01J 2531/72* (2013.01); *B01J 2531/842* (2013.01); *B01J 2531/845* (2013.01); *H01M 8/1007* (2016.02)

(58) Field of Classification Search
None
See application file for complete search history.

(56) References Cited

U.S. PATENT DOCUMENTS

| | | |
|---|---|---|
| 4,637,988 A | 1/1987 | Hinshaw et al. |
| 4,670,572 A | 6/1987 | Hinshaw et al. |
| 4,794,191 A | 12/1988 | Hinshaw et al. |
| 4,801,722 A | 1/1989 | Hinshaw et al. |
| 4,837,169 A | 6/1989 | Toner |
| 4,859,777 A | 8/1989 | Toner |
| 6,262,257 B1 | 7/2001 | Gale et al. |
| 2002/0082422 A1 | 6/2002 | Paidi et al. |
| 2003/0017941 A1 | 1/2003 | Busch et al. |
| 2005/0139257 A1 | 6/2005 | Islam et al. |
| 2007/0131929 A1 | 6/2007 | Bae et al. |
| 2008/0161574 A1 | 7/2008 | Ohrui et al. |
| 2008/0219916 A1 | 9/2008 | Ishiyama et al. |
| 2009/0062110 A1 | 3/2009 | Koshino et al. |
| 2010/0004443 A1 | 1/2010 | Dubreuil et al. |
| 2010/0101643 A1 | 4/2010 | Takahashi et al. |
| 2010/0298562 A1 | 11/2010 | Dubreuil et al. |
| 2010/0327265 A1 | 12/2010 | Kimura et al. |
| 2011/0015059 A1 | 1/2011 | Matsunaga et al. |
| 2011/0282063 A1 | 11/2011 | Ohrui et al. |

FOREIGN PATENT DOCUMENTS

| | | |
|---|---|---|
| CN | 101252991 A | 8/2008 |
| CN | 101415693 A | 4/2009 |
| DE | 102007025424 A1 | 12/2008 |
| JP | S64-45365 A | 7/1989 |
| JP | 2000-511880 A | 9/2000 |
| JP | 2001-513817 A | 9/2001 |
| JP | 2001-348387 A | 12/2001 |
| JP | 2002-193935 A | 7/2002 |

(Continued)

OTHER PUBLICATIONS

Warnmark. Chemical Communications, 1996, 2603-2604.*
Sun. Dalton Transactions, 2012, 41, 12434-12438.*
Bu. Chemical Communications, 2000, 1953-1954.*
Fox. Journal of the American Chemical Society, 2002, 124, 13613-13623.*
Du. Journal of Chemical Research (S), 2002, 493-495.*
Catalano. Inorganic Chemistry, 1994, 33(20), 4502-9.*
Esposito. Inorganic Chemistry, 1967, 6 (6), 1116-20.*
Honeybourne. Journal of the Chemical Society, Faraday Transactions I, 1984, 80, 851-63.*
Liu (Journal of the American Chemical Society, 2011, 133, 10372-375 (Year: 2011).*

(Continued)

*Primary Examiner* — Noble E Jarrell
(74) *Attorney, Agent, or Firm* — Sughrue Mion, PLLC

(57) ABSTRACT

To provide nitrogen-containing aromatic compounds with excellent oxygen reduction activity, metal complexes containing them, and catalysts and electrodes employing the same, the present invention provides an aromatic compound satisfying the following conditions (a) and (b):
(a) It has 2 or more structures surrounded by at least 4 coordinatable nitrogen atoms (which structures may be the same or different),
(b) At least one of the nitrogen atoms composing the structure is a nitrogen atom in a 6-membered nitrogen-containing heterocyclic ring.

11 Claims, No Drawings

(56) References Cited

FOREIGN PATENT DOCUMENTS

| | | |
|---|---|---|
| JP | 2005-108552 A | 4/2005 |
| JP | 2005-190875 A | 7/2005 |
| JP | 2006-057014 A | 3/2006 |
| JP | 2006-202688 A | 8/2006 |
| JP | 2006-298776 A | 11/2006 |
| JP | 2007-038213 A | 2/2007 |
| JP | 2007-169267 A | 7/2007 |
| JP | 2007-194506 A | 8/2007 |
| JP | 2007-238601 A | 9/2007 |
| JP | 2007-302564 A | 11/2007 |
| JP | 2008-156515 A | 7/2008 |
| JP | 2008-162911 A | 7/2008 |
| JP | 2008-266634 A | 11/2008 |
| JP | 2009-516652 A | 4/2009 |
| JP | 2009-173627 A | 8/2009 |
| JP | 2009-544671 A | 12/2009 |
| JP | 2009-544672 A | 12/2009 |
| JP | 2011-98948 A | 5/2011 |
| WO | 03/018548 A2 | 3/2003 |
| WO | 2007/137430 A1 | 12/2007 |
| WO | 2008/059960 A1 | 5/2008 |

OTHER PUBLICATIONS

Extended European Search Report dated Jun. 20, 2014 in counterpart European Patent Application No. 10826934.1.

Igor O. Fritsky, et al., "Allosteric Regulation of Artificial Phosphoesterase Activity by Metal Ions," Angewandte Chemie International Edition, vol. 39, No. 18, Sep. 15, 2000, pp. 3255-3258, XP055122733.

Edwin C. Constable and Juliet V. Walker, "Ruthenium complexes of 2,2':6',2":6",2"':6"',2""-quinquepyridine (qpy) and its derivatives," Polyhedron, vol. 17, No. 18, Aug. 1, 1998, pp. 3089-3100, XP055122785.

Igor O. Fritsky, et al., "Toward the redox-based allosteric control of the activity of a trinuclear metal complex catalyst," Inorganica Chimica Acta, vol. 346, Mar. 1, 2003, pp. 111-118, XP055122735.

Qudsia Khamker, et al., "Bis(imino)quaterpyridine-bearing multimetallic late transition metal complexes as ethylene oligomerisation catalysts", Dalton Transactions, No. 41, Jan. 1, 2009, pp. 8935-8944, XP055122753.

Ho-Lun Yeung, et al., "Stereoselective Formation of Helical Binuclear Metal Complexes: Synthesis, Characterization, and Crystal Structures of Chiral Bis-Rhenium( I ) Quaterpyridine Complexes," Inorganic Chemistry, vol. 48, No. 9, May 4, 2009, pp. 4108-4117, XP055122759.

Andrew P. Armitage, et al., "Probing the Effect of Binding Site and Metal Centre Variation in Pentadentate Oligopyridylimine-Bearing Bimetallic ($Fe_2$, $Co_2$, $Ni_2$) Ethylene Oligomerisation Catalysts," European Journal of Inorganic Chemistry, vol. 2008, No. 29, Oct. 1, 2008, pp. 4597-4607, XP055122763.

Chi-Tung Yeung, et al., "Supramolecular double helical Cu(I) complexes for asymmetric cyclopropanation," Chemical Communications, No. 48, Jan. 1, 2007, pp. 5203-5205, XP055122770.

Hoi-Lun Kwong, et al., "Stereoselective formation of a single-stranded helicate: Structure of a bis(palladium-allyl)quaterpyridine complex and its use in catalytic enantioselective allylic substitution," Chemical Communications, No. 46, Jan. 1, 2006, pp. 4841-4843, XP055122771.

Hilde Grove, et al., "Crystalline products isolated from solutions with commercially available 2,3-bis(2-pyridyl)pyrazine (dpp) as reactant: Detection of a dimerized form of dpp," Journal of Molecular Structure, Elsevier, Amsterdam, NL, vol. 800, No. 1-3, Dec. 4, 2006, pp. 1-17, XP028046076.

Daniela Belli Dell'Amico, et al., "A planar silver complex of 2,2':6',2":6"'-quaterpyridine," Inorganic Chemistry Communications, Elsevier, Amsterdam, NL, vol. 8, No. 8, Aug. 1, 2005, pp. 673-675, XP027705693.

Javier E. Aguado, et al., "Synthesis and Theoretical Studies of a Double Helical Complex with the Ligand 4',4'''-Bis(ferrocenyl)-2,2':6',2":6",2"':6"',2""-quinquepyridine," European Journal of Inorganic Chemistry, vol. 2004, No. 15, Aug. 1, 2004, pp. 3038-3047, XP055122774.

Ruifa Zong and Randolph P. Thummel, "2,9-Di-(2'-pyridyl)-1,10-phenanthroline: A Tetradentate Ligand for Ru( II)", Journal of the American Chemical Society, vol. 126, No. 35, Sep. 1, 2004, pp. 10800-10801, XP055122777.

Daniela Belli Dell'Amico, et al., "Bis-qtpy(qtpy=2,2':6',2":6",2'''-quaterpyridine) Metal Complexes, $[M(qtpy) 2]^{2+}$," Inorganic Chemistry, vol. 43, No. 17, Aug. 1, 2004, pp. 5459-5465, XP055122778.

Luc Jacquet, et al., "Formation of a covalently-linked bimetallic compound upon irradiation of tris(1,4,5,8-tetraazaphenanthrene)ruthenium(II) in the presence of 5'-guanosine-monophosphate," Inorganic Chemistry Communications, vol. 2, No. 4, Apr. 1, 1999, pp. 135-138, XP055122780.

Edwin C. Constable, et al., "Heteroleptic ruthenium complexes containing 2,2':6',2":6",2"':6"',2""-quinquepyridine (qpy) and its derivatives," Polyhedron, vol. 18, No. 1-2, Dec. 1, 1998, pp. 159-173, XP055122782.

Gunther R. Pabst, et al., "The new and simple 'LEGO' System: Its Application for the Synthesis of 6-Oligopyridyl-1,5,12-triazatriphenylenes", Tetrahedron Letters, Pergamon, GB, vol. 39, No. 48, Nov. 26, 1998, pp. 8825-8828, XP005591347.

Edwin C. Constable, et al., "Heterodimetallic double helicates from redistribution reactions," Chemical Communications, No. 22, Jan. 1, 1996, pp. 2551-2552, XP055122787.

Kevin T. Potts, et al., "Di-, Tri-, and Tetrametallic Double-Stranded Helical Complexes Derived from Alkylthio-Substituted Septipyridines: Synthesis, Structure, and Redox Properties," Inorganic Chemistry, vol. 32, No. 24, Nov. 1, 1993, pp. 5477-5484, XP055122792.

Christopher J. Cathey, et al., "A Single Stranded Diruthenium(II) Helical Complex," J. Chem. Soc., Chem. Commun., No. 8, Jan. 1, 1990, pp. 621-622, XP055122797.

Gang Zhang, et al., "Ru(II) Complexes of Tetradentate Ligands Related to 2,9-Di(pyrid-2'-yl)-1,10-phenanthroline," Inorganic Chemistry, vol. 47, No. 3, Feb. 1, 2008, pp. 990-998, XP055122766.

Lei Zhang, et al., "Fe loading of a carbon-supported Fe—N electrocatalyst and its effect on the oxygen reduction reaction", Electrochmica Acta, Elsevier Science Publishers, Barking, GB, vol. 54, No. 26, 2009, pp. 6631-6636, XP026546236.

Cicero W.B. Bezerra, et al., "Novel carbon-supported Fe—N electrocatalysts synthesized through heat treatment of iron tripyridyl triazine complexes for the PEM fuel cell oxygen reduction reaction," Electrochimica Acta, Elsevier Science Publishers, Barking, GB, vol. 53, No. 26, Nov. 1, 2008, pp. 7703-7710, XP023907531.

Office Action dated Feb. 13, 2014 in counterpart European Patent Application No. 10826934.1.

First Office Action dated Jan. 10, 2014 in counterpart Chinese Patent Application No. 201080048761.4 with English translation.

Jude T. Rademacher, et al., "Improved Synthesis of 1,4,5,8,9,12-Hexaazatriphenylenehexacarboxylic Acid", Synthesis, vol. 1994, No. 4, Apr. 30, 1994, pp. 378-380.

Second Office Action dated Sep. 23, 2014 in counterpart Chinese Patent Application No. 201080048761.4 with translation.

Edwin C. Constable, et al., "Regioselective metal-directed self-assembly of a prototype double helical hairpin dinuclear complex", Inorganic Chemistry Communications, vol. 7, 2004, pp. 1128-1131.

Kevin T. Potts, et al., "Multimetallic, double-stranded helical complexes derived from hexa(n-propylthio)novipyridine: synthesis, structure and redox properties", Inorganica Chimica Acta, vol. 288, 1999, pp. 189-199.

Raffaella Crescenzi, et al., "The Intra- and Intermolecular Oxidative Coupling of Ni(II)-meso-Octaethyl Mono(pyridine)-Tris(pyrrole) Complex Leading to C—C Bonds: Pathways to Oligomeric Porphyrinogens", Inorganic Chemistry, vol. 37, No. 23, 1998, pp. 6044-6051.

Kevin T. Potts, et al., "Metal-Ion-Induced Self-Assembly of Functionalized 2,6-Oligopyridines. 1. Ligand Design, Synthesis, and Characterization," Journal of American Chemical Society, vol. 115, 1993, pp. 2793-2807.

Jun-ichiro Setsune and Keigo Watanabe, "Cryptand-like Porphyrinoid Assembled with Three Dipyrrylpyridine Chains: Synthesis, Struc-

(56) References Cited

OTHER PUBLICATIONS ture, and Homotropic Positive Allosteric Binding of Carboxylic Acids", Journal of American Chemical Society, vol. 130, No. 8, 2008, pp. 2404-2405.

Gunther R. Pabst and Jurgen Sauer, "The New and Simple 'LEGO' System: Its Application to the Synthesis of 4-Stannyl-, 4-Bromo- and Branched Oligopyridines", Tetrahedron, vol. 55, 1999, pp. 5067-5088.

Gunther R. Pabst, et al., "A New and Simple 'LEGO' System for the Synthesis of Branched Oligopyridines", Tetrahedron Letters, vol. 39, 1998, pp. 6691-6694.

Kurt Berlin and Eberhard Breitmaier, "New Porphyrinoid Macrocycles Containing Pyridine", Angew. Chem. Int. Ed. Engl., vol. 33, No. 2, 1994, pp. 219-220.

Hiroshi Tsukube, "Specific recognition of copper ion by lipid-bound double armed crown ether", Inorganica Chimica Acta, vol. 214, 1993, pp. 1-3.

Heinrich R. Karfunkel, et al., "Heterofullerenes: Structure and property predictions, possible uses and synthesis proposals", Journal of Computer-Aided Molecular Design, vol. 6, 1992, pp. 521-535.

Jun'ichi Uenishi, et al., "Coupling of Consecutive Pyridine Ring Units for Oligopyridine Synthesis", Heterocycles, vol. 50, No. 1, 1999, pp. 341-351.

Edwin C. Constable, et al., "Hairpin helicates: a missing link between double-helicates and trefoil knots", Dalton Transactions, No. 7, 2005, pp. 1168-1175.

Communication dated Oct. 20, 2015 from the Japanese Patent Office in counterpart application No. 2010-244194.

Communication dated Oct. 29, 2015 from the European Patent Office in counterpart application No. 10826934.1.

Jürgens, et al., "Melem (2,5,8-Triamino-tri-s-triazine), an important intermediate during condensation of melamine rings to graphitic carbon nitride: synthesis, structure determination by x-ray powder diffractometry, solid-state NMR, and theoretical studies", Journal American Chemical Society, 2003, vol. 125, No. 34, pp. 10288-10300 (13 pages).

Nakamura, et al., "A directly fused tetrameric porphyrin sheet and its anomalous electronic properties that arise from the planar cyclooctatetraene core", Journal American Chemical Society, 2006, vol. 128, No. 12, pp. 4119-4127 (9 pages).

* cited by examiner

NITROGEN-CONTAINING AROMATIC COMPOUNDS AND METAL COMPLEXES

CROSS REFERENCE TO RELATED APPLICATION

This application is a National Stage of International Application No. PCT/JP2010/069769, filed on Oct. 29, 2010, which claims priority from JP 2009-251005, filed on Oct. 30, 2009 and JP 2010-133114, filed on Jun. 10, 2010, the contents of all of which are incorporated herein by reference in their entirety.

TECHNICAL FIELD

The present invention relates to nitrogen-containing aromatic compounds and metal complexes.

BACKGROUND ART

Certain nitrogen-containing aromatic compounds are known that function as catalyst materials or electrode materials, and specifically, catalytic activity is known to be exhibited by metal complexes comprising, as ligands, nitrogen-containing aromatic compounds synthesized from melamine (see Patent document 1).

CITATION LIST

Patent Literature

[Patent document 1] Japanese Unexamined Patent Publication No. 2006-202688

SUMMARY OF INVENTION

Technical Problem

Such nitrogen-containing aromatic compounds are useful as catalyst materials or electrode materials, but nitrogen-containing aromatic compounds with excellent catalytic activity (oxygen reduction activity) are required for increased catalyst and electrode function.

It is an object of the present invention to provide nitrogen-containing aromatic compounds with excellent oxygen reduction activity, metal complexes containing them, and catalysts, electrodes, polymer electrolyte fuel cell and the like employing the same.

Solution to Problem

Specifically, the invention provides aromatic compounds, metal complexes, modified compounds, compositions, catalysts, electrodes, electrode catalysts for fuel cell, and polymer electrolyte fuel cell according to [1]-[22] below. The invention further provides compounds to serve as starting materials for synthesis of aromatic compounds of the invention according to [23] below.

[1] An aromatic compound satisfying the following conditions (a) and (b):

(a) It has 2 or more structures surrounded by at least 4 coordinatable nitrogen atoms, and said structures may be the same or different, (b) At least one of the nitrogen atoms composing the structure is a nitrogen atom in a 6-membered nitrogen-containing heterocyclic ring.

[2] The aromatic compound according to [1], wherein the number n of nitrogen atoms composing each said structure and the mean distance r (Å) from the center of the structure to each nitrogen atom satisfies the condition represented by the following formula (A):

$$0 < r/n \leq 0.7 \quad (A).$$

[3] The aromatic compound according to [1] or [2], wherein the number n of nitrogen atoms composing each said structure is from 4 to 6.

[4] The aromatic compound according to any one of [1] to [3], wherein the r/n is from 0.2 to 0.6.

[5] The aromatic compound according to any one of [1] to [4], wherein the ratio of the total mass of nitrogen atoms with respect to the total mass of carbon atoms in the aromatic compound is greater than 0 and no greater than 1.1.

[6] The aromatic compound according to any one of [1] to [5], wherein the structure is a structure represented by the following general formula (1):

[Chemical Formula 1]

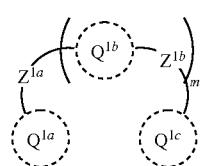

(1)

wherein m is an integer of 1 or greater;

$Q^{1a}$, $Q^{1b}$ and $Q^{1c}$ are optionally substituted nitrogen-containing aromatic heterocyclic rings and each may be the same or different, and when 2 or more $Q^{1b}$ groups exist, each may be the same or different, however, at least one group from $Q^{1a}$, $Q^{1b}$ and $Q^{1c}$ is a 6-membered nitrogen-containing heterocyclic ring;

$Z^{1a}$ and $Z^{1b}$ are direct bonds or linking groups and each may be the same or different, and when 2 or more $Z^{1b}$ groups exist, each may be the same or different;

$Q^{1a}$ and $Q^{1b}$, and $Q^{1b}$ and $Q^{1c}$, each form together a polycyclic aromatic heterocyclic ring, when m is an integer of 2 or greater, the two $Q^{1b}$ groups may form together a polycyclic aromatic heterocyclic ring, and $Q^{1a}$ and $Q^{1c}$ may be bonded together via a direct bond or linking group to form together a polycyclic aromatic heterocyclic ring.

[7] The aromatic compound according to [6], wherein the structure represented by general formula (1) above is a structure represented by the following general formula (2):

[Chemical Formula 2]

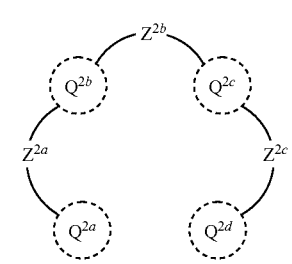

(2)

wherein $Q^{2a}$, $Q^{2b}$, $Q^{2c}$ and $Q^{2d}$ are optionally substituted nitrogen-containing aromatic heterocyclic rings and each may be the same or different, however, at least one group from $Q^{2a}$, $Q^{2b}$, $Q^{2c}$ and $Q^{2d}$ is a 6-membered nitrogen-containing heterocyclic ring;

$Z^{2a}$, $Z^{2b}$ and $Z^{2c}$ are direct bonds or linking groups and each may be the same or different;

$Q^{2a}$ and $Q^{2b}$, $Q^{2b}$ and $Q^{2c}$, and $Q^{2c}$ and $Q^{2d}$ may each form together a polycyclic aromatic heterocyclic ring, and $Q^{2a}$ and $Q^{2d}$ may be bonded together via a direct bond or linking group, or may form together a polycyclic aromatic heterocyclic ring;

and/or a structure represented by the following formula (3):

[Chemical Formula 3]

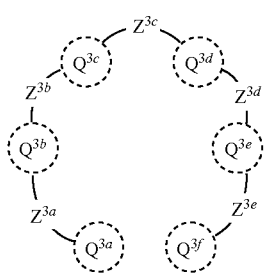

(3)

wherein $Q^{3a}$, $Q^{3b}$, $Q^{3c}$, $Q^{3d}$, $Q^{3e}$ and $Q^{3f}$ are optionally substituted nitrogen-containing aromatic heterocyclic rings and each may be the same or different, however, at least one group from $Q^{3a}$, $Q^{3b}$, $Q^{3c}$, $Q^{3d}$, $Q^{3e}$ and $Q^{3f}$ is a 6-membered nitrogen-containing heterocyclic ring;

$Z^{3a}$, $Z^{3b}$, $Z^{3c}$, $Z^{3d}$ and $Z^{3e}$ are direct bonds or linking groups and each may be the same or different;

$Q^{3a}$ and $Q^{3b}$, $Q^{3b}$ and $Q^{3c}$, $Q^{3c}$ and $Q^{3d}$, $Q^{3d}$ and $Q^{3e}$, and $Q^{3e}$ and $Q^{3f}$ may each form together a polycyclic aromatic heterocyclic ring, and $Q^{3a}$ and $Q^{3f}$ may be bonded together via a direct bond or linking group, or may form together a polycyclic aromatic heterocyclic ring.

[8] The aromatic compound according to [6] or [7], wherein the nitrogen-containing aromatic heterocyclic ring is a ring selected from the group consisting of pyridine ring, pyrazine ring, pyrimidine ring, pyridazine ring, 1,3,5-triazine ring, 1,2,4-triazine ring, 1,2,4,5-tetrazine ring, 1H-pyrrole ring, 2H-pyrrole ring, 3H-pyrrole ring, imidazole ring, pyrazole ring, 1,2,3-triazole ring, 1,2,4-triazole ring, oxazole ring, isooxazole ring, thiazole ring, isothiazole ring, 1,3,4-oxadiazole ring, 1,2,5-oxadiazole ring, 1,3,4-thiadiazole ring, 1,2,5-thiadiazole ring, and polycyclic aromatic heterocyclic ring that contain these rings.

[9] The aromatic compound according to any one of [6] to [8], wherein the two nitrogen-containing aromatic heterocyclic rings bonded together via a direct bond or linking group in $Q^{1a}$ and $Q^{1b}$, $Q^{1b}$ and $Q^{1c}$, $Q^{2a}$ and $Q^{2b}$, $Q^{2b}$ and $Q^{2c}$, $Q^{2c}$ and $Q^{2d}$, $Q^{3a}$ and $Q^{3b}$, $Q^{3b}$ and $Q^{3c}$, $Q^{3c}$ and $Q^{3d}$, $Q^{3d}$ and $Q^{3e}$, or $Q^{3e}$ and $Q^{3f}$ are represented by any one of the following formulas (4-a) to (6-d):

[Chemical Formula 4]

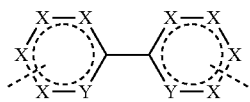

(4-a)

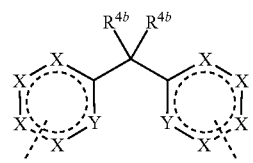

(4-b)

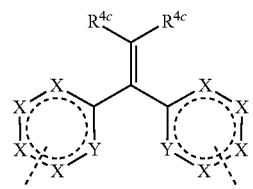

(4-c)

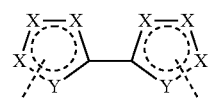

(5-a)

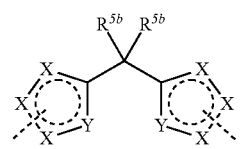

(5-b)

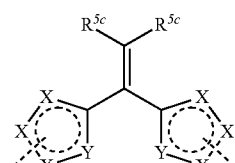

(5-c)

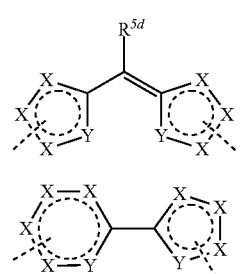

(5-d)

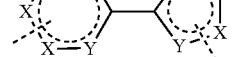

(6-a)

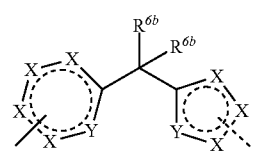

(6-b)

(6-c)

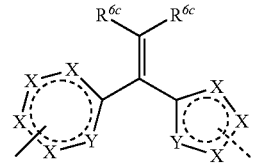

(6-d)

wherein X is $=C(R^{\alpha})-$, $-N(R^{\beta})-$, $=N-$, $-O-$, $-S-$ or $-Se-$, and each may be the same or different;

Y is —NH— or =N— and each may be the same or different; and $R^{4b}$, $R^{4c}$, $R^{5b}$, $R^{5c}$, $R^{5d}$, $R^{6b}$, $R^{6c}$, $R^{6d}$, $R^{\alpha}$ and $R^{\beta}$ are hydrogen or a substituent and each may be the same or different, and adjacent substituents may bond together to form a ring.

[10] The aromatic compound according to any one of [6] to [8], wherein the two nitrogen-containing aromatic heterocyclic rings bonded together via a direct bond or linking group in $Q^{1a}$ and $Q^{1b}$, $Q^{1b}$ and $Q^{1c}$, $Q^{2a}$ and $Q^{2b}$, $Q^{2b}$ and $Q^{2c}$, $Q^{2c}$ and $Q^{2d}$, $Q^{3a}$ and $Q^{3b}$, $Q^{3b}$ and $Q^{3c}$, $Q^{3c}$ and $Q^{3d}$, $Q^{3d}$ and $Q^{3e}$, or $Q^{3e}$ and $Q^{3f}$ are represented by any one of the following general formulas (7-a) to (10-e):

[Chemical Formula 5]

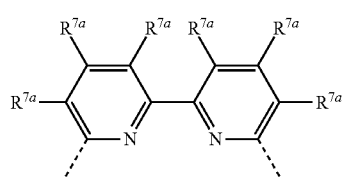
(7-a)

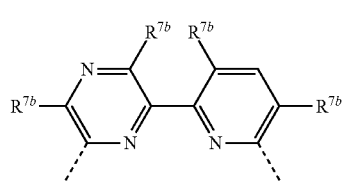
(7-b)

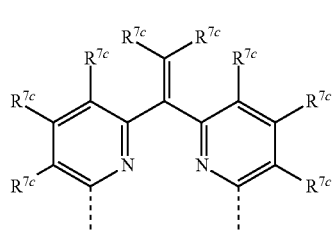
(7-c)

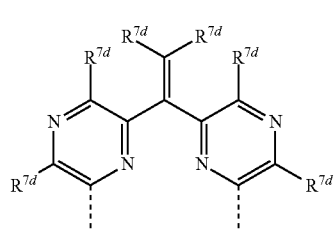
(7-d)

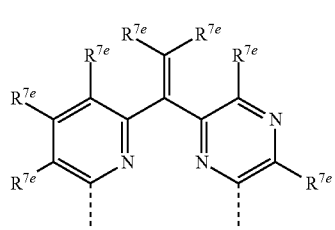
(7-e)

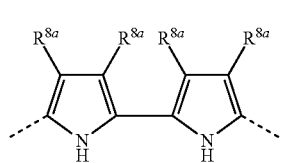
(8-a)

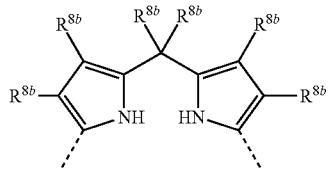
(8-b)

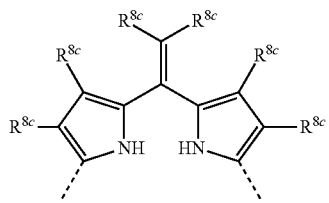
(8-c)

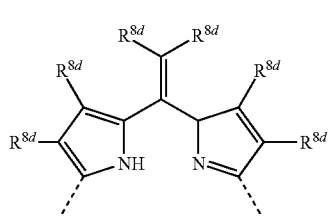
(8-d)

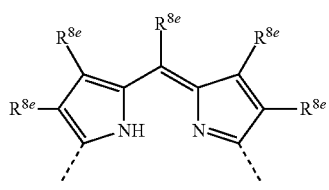
(8-e)

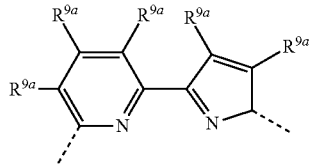
(9-a)

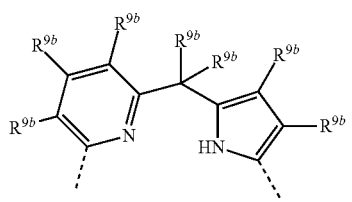
(9-b)

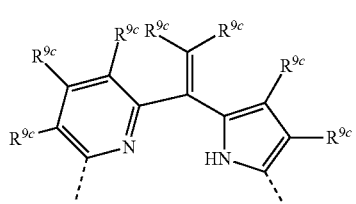
(9-c)

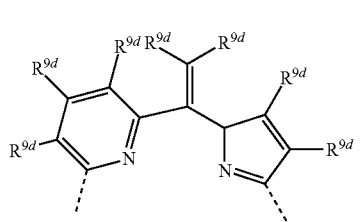
(9-d)

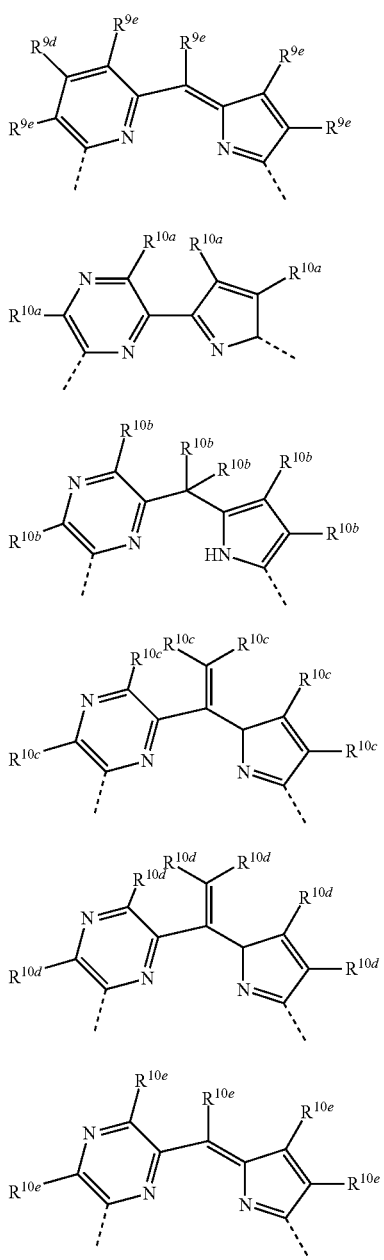

(9-e)

(10-a)

(10-b)

(10-c)

(10-d)

(10-e)

wherein $R^{7a}$—$R^{10e}$ are hydrogen or a substituent and each may be the same or different, and adjacent substituents may bond together to form a ring.

[11] A metal complex having a metal atom or metal ion, and a ligand comprising the aromatic compound according to any one of [1] to [10].

[12] The metal complex according to [11], wherein the metal atom or metal ion is a transition metal atom or its ion, from between period 4 and period 6 of the Periodic Table.

[13] A composition comprising the aromatic compound according to any one of [1] to [10] and/or the metal complex according to [11] or [12], and a carbon material and/or polymer material.

[14] A modified compound obtained by modifying the aromatic compound according to any one of [1] to [10], the metal complex according to [11] or [12] or the composition according to [13], by heat, radiation irradiation or electric discharge.

[15] The modified compound according to [14], wherein the treatment temperature for heat treatment is in the range of 200-1200° C.

[16] A composition comprising the modified compound according to [14] or [15] and a carbon material and/or polymer material.

[17] A catalyst comprising the aromatic compound according to any one of [1] to [10], the metal complex according to [11] or [12], the composition according to [13], the modified compound according to [14] or [15], or the composition according to [16].

[18] An electrode comprising the aromatic compound according to any one of [1] to [10], the metal complex according to [11] or [12], the composition according to [13], the modified compound according to [14] or [15], or the composition according to [16].

[19] An electrode catalysts for fuel cell comprising the aromatic compound according to any one of [1] to [10], the metal complex according to [11] or [12], the composition according to [13], the modified compound according to [14] or [15], or the composition according to [16].

[20] A polymer electrolyte fuel cell using the electrode catalysts for fuel cell according to [19].

[21] The polymer electrolyte fuel cell according to [20], wherein a polymer electrolyte membrane of the polymer electrolyte fuel cell is the one having proton conductivity.

[22] The polymer electrolyte fuel cell according to [20], wherein a polymer electrolyte membrane of the polymer electrolyte fuel cell is the one having anion conductivity.

[23] A compound represented by any of the following general formulas (11)-(20), (22) or (23):

[Chemical Formula 6]

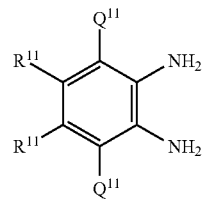

(11)

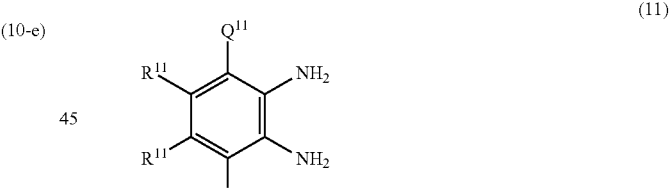

(12)

(13)
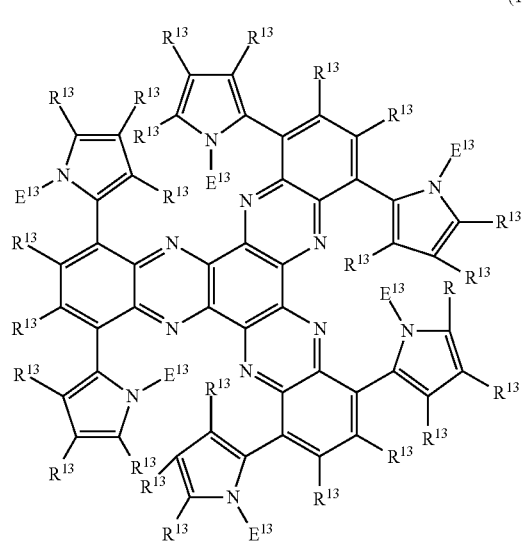
[Chemical Formula 7]
(14)
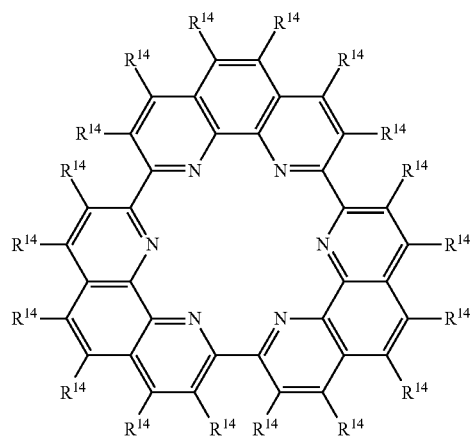
(15)
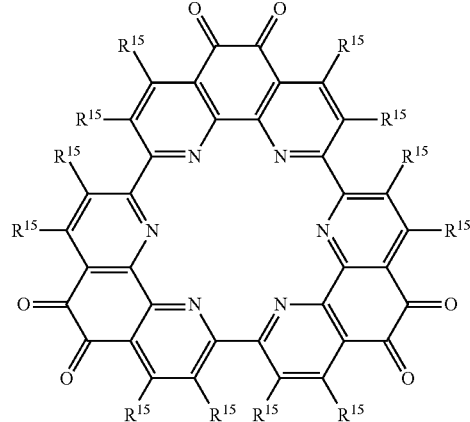
(16)
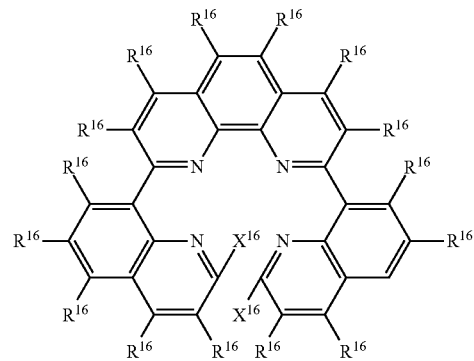
[Chemical Formula 8]
(17)
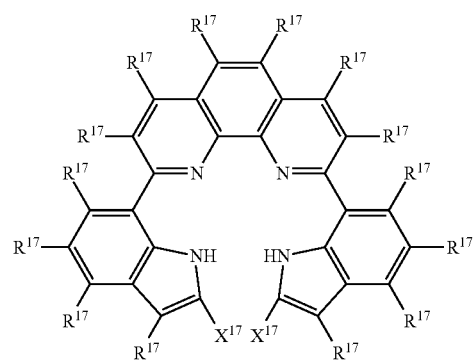
(18)
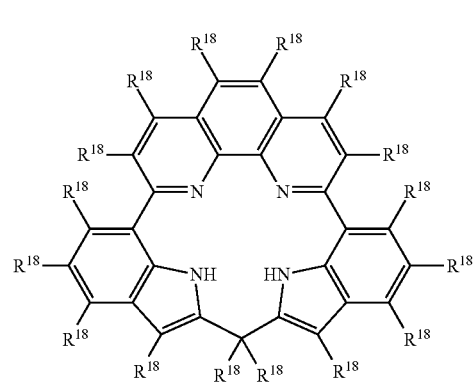
(19)
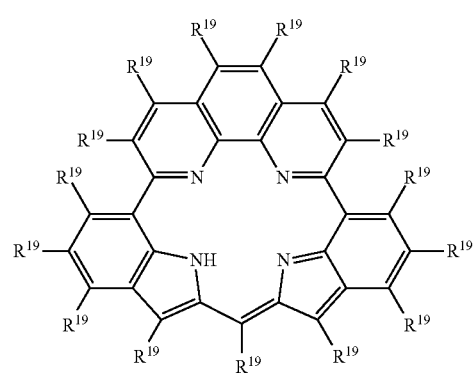

-continued

[Chemical Formula 9]

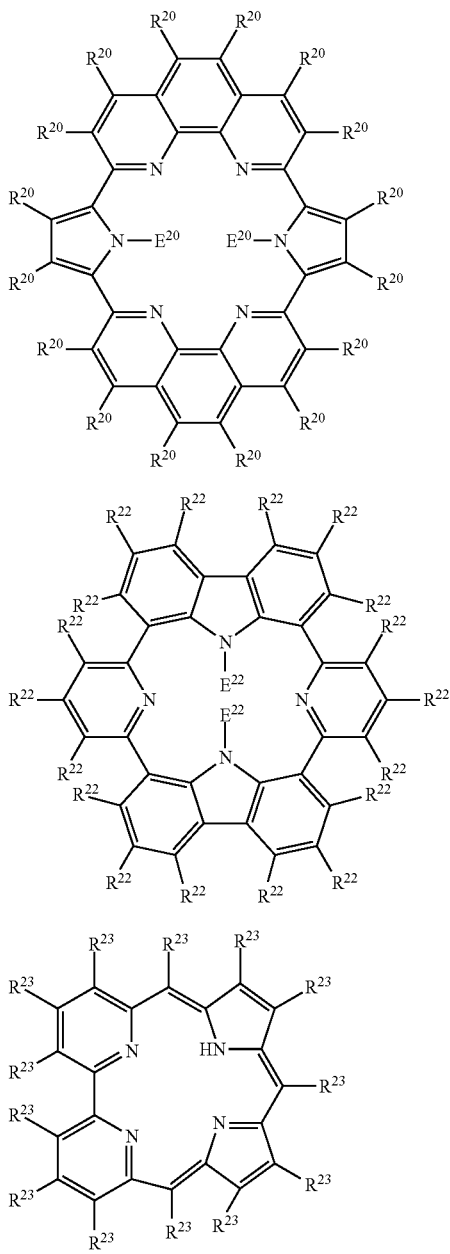

wherein $R^{11}$—$R^{20}$, $R^{22}$ and $R^{23}$ are hydrogen or a substituent and each may be the same or different, with adjacent substituents optionally bonding together to form a ring;

$Q^{11}$ is a nitrogen-containing aromatic heterocyclic ring and each may be the same or different;

$T^{12}$ is bromine atom, chlorine atom or iodine atom and each may be the same or different;

$E^{13}$, $E^{20}$ and $E^{22}$ each independently represent hydrogen or a protecting group; and $X^{16}$ and $X^{17}$ each independently represent hydrogen or a halogeno group, or the $X^{16}$ or $X^{17}$ groups are bonded together as direct bonds.

In the specification, symbols which show substituents described below represents the same meaning as mentioned above.

Advantageous Effects of Invention

The aromatic compounds of the invention, and metal complexes comprising them, have excellent oxygen reduction activity and can be suitably used as catalysts or electrodes.

DESCRIPTION OF EMBODIMENTS

The invention will now be explained in greater detail.

An aromatic compound according to the invention satisfies the following condition (a):

(a) It has 2 or more structures surrounded by at least 4 coordinatable nitrogen atoms (which structures may be the same or different).

Here, "coordinatable nitrogen atom" means a nitrogen atom that has one lone electron pair and can coordinate with a metal atom or metal ion. The nitrogen atom before coordination with the metal atom or metal ion may have its lone electron pair donated to a proton to form an N—H bond.

A structure wherein four or more nitrogen atoms can coordinate with a metal atom or metal ion is a "structure surrounded by at least 4 coordinatable nitrogen atoms" according to condition (a), and the number of coordinatable metal atoms or metal ions is preferably 1-3, more preferably 1-2 and most preferably 1.

The metal atom or metal ion is preferably a manganese ion, iron ion or cobalt ion. The valency of the metal ion is preferably 1-4, more preferably 2-4 and most preferably 2 or 3.

The structure can be confirmed by coordinating the compound containing the structure with a metal atom or metal ion and then obtaining the crystal and performing structural analysis by X-ray crystal structure analysis or the like.

An aromatic compound according to the invention also satisfies the following condition (b).

(b) At least one of the nitrogen atoms composing the structure is a nitrogen atom in a 6-membered nitrogen-containing heterocyclic ring.

Examples of 6-membered nitrogen-containing heterocyclic rings include pyridine ring, pyrazine ring, pyrimidine ring, pyridazine ring, 1,3,5-triazine ring, 1,2,4-triazine ring, 1,2,4,5-tetrazine ring, piperidine ring, piperazine ring and morpholine ring, with pyridine ring, pyrazine ring, pyrimidine ring, pyridazine ring, 1,3,5-triazine ring, 1,2,4-triazine ring and 1,2,4,5-tetrazine ring being preferred and pyridine ring, pyrazine ring, pyrimidine ring and pyridazine ring being more preferred.

From the viewpoint of further improving the catalytic activity, all of the 6-membered nitrogen-containing aromatic rings in the aromatic compound preferably contain only 1 or 2 nitrogen atoms as heteroatoms.

This structure according to the invention is preferably a symmetrical structure with line symmetry, point symmetry or rotational symmetry. The symmetry referred to here is symmetry of the structure itself, and does not depend on the substituents of the aromatic ring. Also, two or more aromatic rings may be fused.

In the case the structure has rotational symmetry, the rotational symmetry is preferably 2 or more-fold rotational symmetry, more preferably from 2 to 12-fold rotational symmetry, and particularly preferably from 2 to 6-fold rotational symmetry.

Specific examples of symmetrical structures are provided below. T in the formulas represents —C(H)= or —N=.

[Chemical Formula 10]
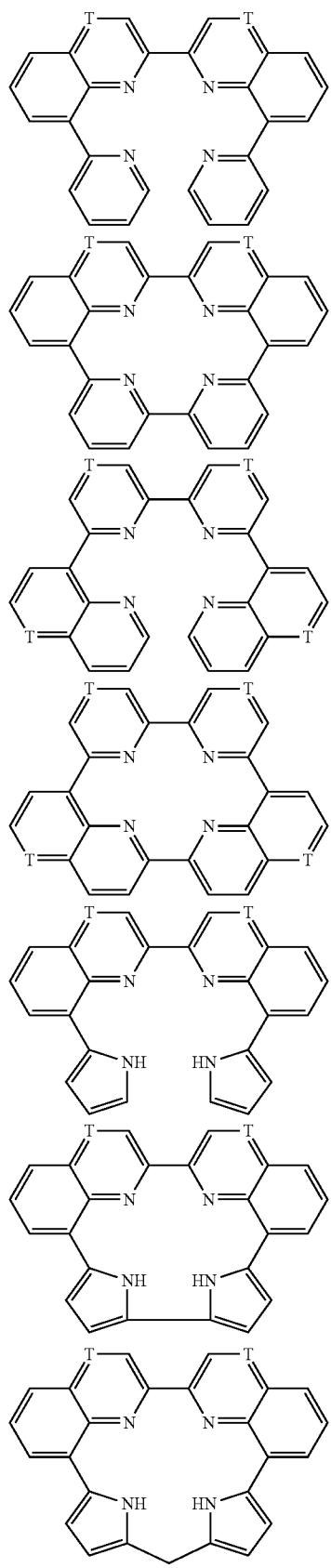
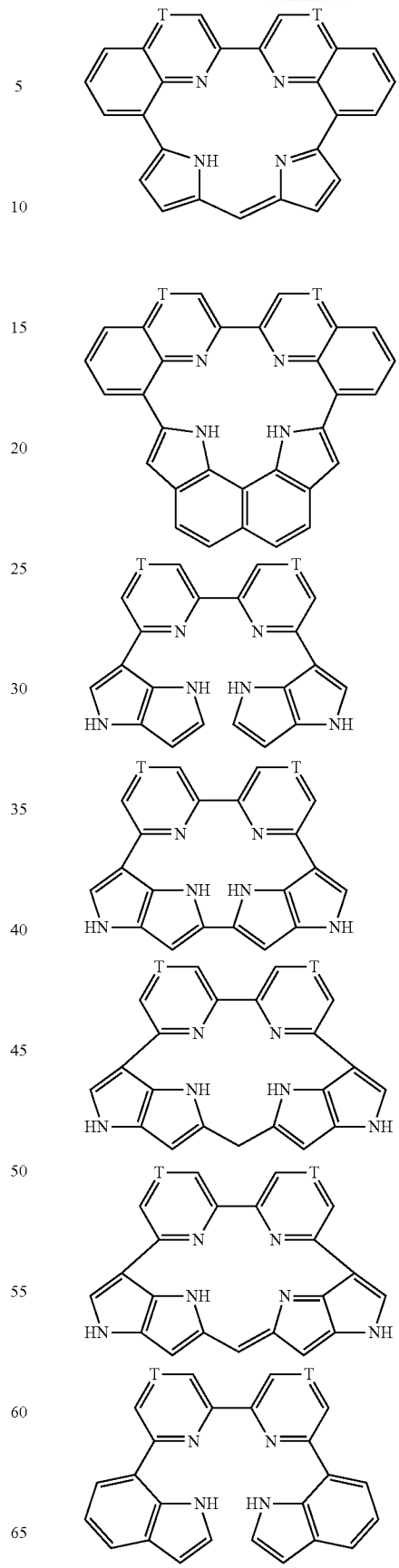

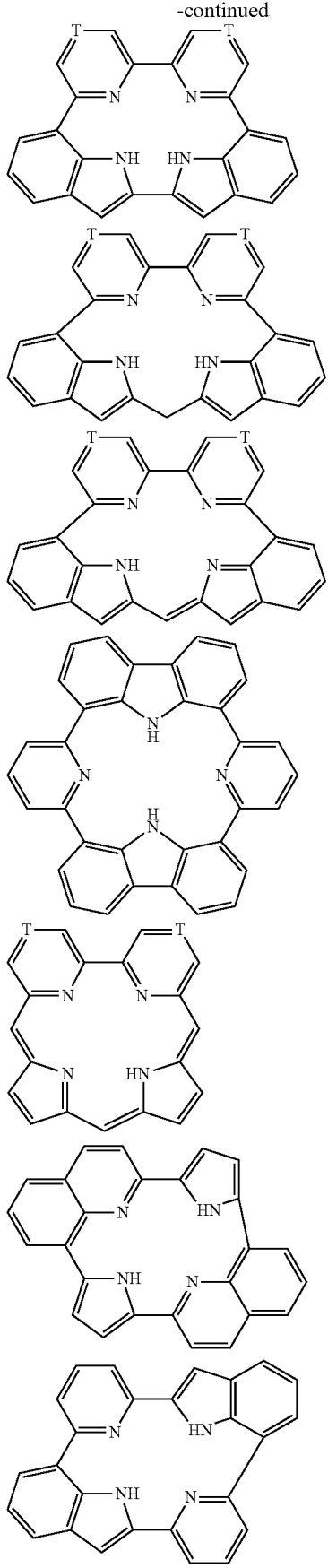
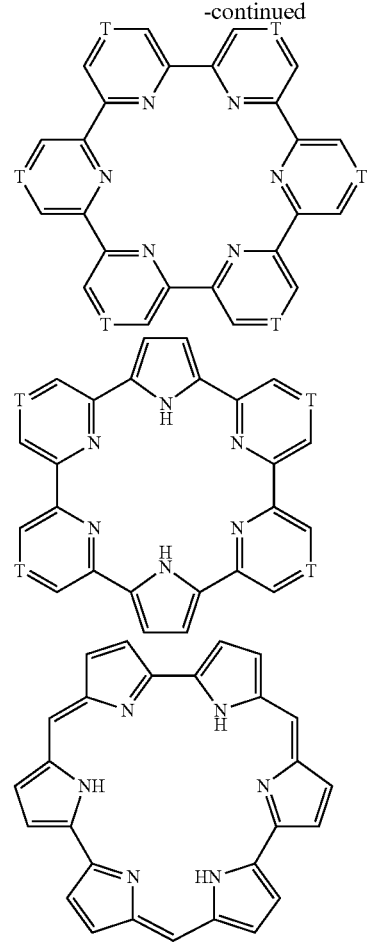

In an aromatic compound according to the invention, preferably the ratio of the total mass of nitrogen atoms with respect to the total mass of carbon atoms in the aromatic compound (N/C) is greater than 0 and no greater than 1.1. The N/C ratio has a lower limit of preferably 0.05 and more preferably 0.1, and an upper limit of preferably 1.0 and more preferably 0.9.

Also, in an aromatic compound according to the invention, the relationship between the number n of nitrogen atoms composing each structure and the mean distance r (Å) from the center of each structure to each nitrogen atom, or the value of r/n, is preferably greater than 0 and no greater than 0.7. The lower limit is more preferably 0.1 and even more preferably 0.2, and the upper limit is more preferably 0.65 and even more preferably 0.6.

The center for the structure surrounded by at least 4 coordinatable nitrogen atoms is defined as follows.

Specifically, for a structure with line symmetry, the center is on the axis of symmetry and is the point with the shortest mean distance from each nitrogen atom.

For a structure with point symmetry, the center is the point of symmetry.

For a structure with rotational symmetry, the center is on the axis of rotational symmetry and is the point with the shortest mean distance from each nitrogen atom.

The value of n is preferably 4-10, more preferably 4-8 and most preferably 4-6.

The lower limit for r is preferably 1.5 Å, more preferably 1.7 Å and even more preferably 1.9 Å, and the upper limit is preferably 3.5 Å, more preferably 3.3 Å and even more preferably 3.1 Å.

The aromatic compound of the invention preferably has a polycyclic aromatic heterocyclic ring from the viewpoint of further improving the catalytic activity.

The structure in the aromatic compound of the invention is preferably a structure represented by the following general formula (1):

[Chemical Formula 11]

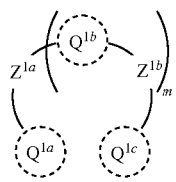

(1)

wherein m is an integer of 1 or greater;

$Q^{1a}$, $Q^{1b}$ and $Q^{1c}$ are optionally substituted nitrogen-containing aromatic heterocyclic rings and each may be the same or different, and when 2 or more $Q^{1b}$ groups exist, each may be the same or different, however, at least one group from $Q^{1a}$ $Q^{1b}$ and $Q^{1c}$ is a 6-membered nitrogen-containing heterocyclic ring;

$Z^{1a}$ and $Z^{1b}$ are direct bonds or linking groups and each may be the same or different, and when 2 or more $Z^{1b}$ groups exist, each may be the same or different;

$Q^{1a}$ and $Q^{1b}$, and $Q^{1b}$ and $Q^{1c}$, each form together a polycyclic aromatic heterocyclic ring, when m is an integer of 2 or greater, the two $Q^{1b}$ groups may form together a polycyclic aromatic heterocyclic ring, and $Q^{1a}$ and $Q^{1c}$ may be bonded together via a direct bond or linking group to form together a polycyclic aromatic heterocyclic ring.

The value of m in general formula (1) is more preferably an integer of 1-5, even more preferably an integer of 2-4, and most preferably 2 or 4.

$Q^{1a}$, $Q^{1b}$ and $Q^{1c}$ in general formula (1) each independently represent an optionally substituted nitrogen-containing aromatic heterocyclic ring, preferably selected from the group consisting of pyridine ring, pyrazine ring, pyrimidine ring, pyridazine ring, 1,3,5-triazine ring, 1,2,4-triazine ring, 1,2,4,5-tetrazine ring, 1H-pyrrole ring, 2H-pyrrole ring, 3H-pyrrole ring, imidazole ring, pyrazole ring, 1,2,3-triazole ring, 1,2,4-triazole ring, oxazole ring, isooxazole ring, thiazole ring, isothiazole ring, 1,3,4-oxadiazole ring, 1,2,5-oxadiazole ring, 1,3,4-thiadiazole ring and 1,2,5-thiadiazole ring (the rings represented by the following formulas), and polycyclic aromatic heterocyclic rings containing these rings, more preferably pyridine ring, pyrazine ring, pyrimidine ring, pyridazine ring, 1,3,5-triazine ring, 1,2,4-triazine ring, 1,2,4,5-tetrazine ring, 1H-pyrrole ring, 2H-pyrrole ring, 3H-pyrrole ring, imidazole ring, pyrazole ring, 1,2,3-triazole ring, 1,2,4-triazole ring and polycyclic aromatic heterocyclic rings containing these rings, and most preferably pyridine ring, pyrazine ring, pyrimidine ring, 1H-pyrrole ring, 2H-pyrrole ring and polycyclic aromatic heterocyclic rings containing these rings.

[Chemical Formula 12]

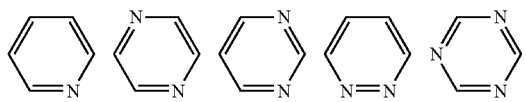

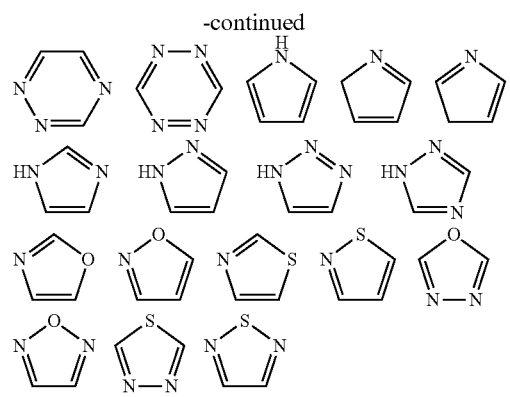

$Z^{1a}$ and $Z^{1b}$ are a direct bond or linking group, and each may be the same or different. As direct bonds there may be mentioned single bonds and double bonds. As linking groups there may be mentioned divalent or trivalent linking groups. $Z^{1a}$ and $Z^{1b}$ are preferably a single bond, double bond, or a linking group represented by $—C(R^{\gamma})_{2}—$, $=C(R^{\delta})—$, $=N(R^{\epsilon})—$ or $=N—$ (linking groups represented by the following formulas), and are most preferably a single bond, double bond or a linking group represented by $—C(R^{\gamma})_{2}—$ or $=C(R^{\delta})—$.

[Chemical Formula 13]

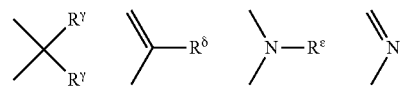

[In these formulas, $R^{\gamma}$, $R^{\delta}$ and $R^{\epsilon}$ are hydrogen or a substituent and each may be the same or different, and adjacent substituents may bond together to form a ring.]

As substituents there may be mentioned halogeno, hydroxy, carboxyl, mercapto, sulfonic acid, nitro, amino, cyano, phosphonic acid, silyl substituted with C1-4 alkyl, C1-50 straight-chain or branched alkyl, C3-50 cyclic alkyl, alkenyl, alkynyl, alkoxy, C6-60 aryl, C7-50 aralkyl, monovalent heterocyclic groups and the like, and preferably halogeno, mercapto, hydroxy, carboxyl, C1-20 straight-chain or branched alkyl, C3-20 cyclic alkyl, alkoxy, C6-30 aryl and monovalent heterocyclic groups. A substituent, according to the present specification, is one of the aforementioned substituents unless otherwise specified.

As halogeno groups there may be mentioned fluoro, chloro, bromo and iodo groups.

As silyl groups substituted with C1-4 alkyl groups there may be mentioned trimethylsilyl, triethylsilyl, tert-butyldimethylsilyl and triisopropylsilyl groups.

As straight-chain or branched alkyl groups there may be mentioned methyl, ethyl, propyl, isopropyl, butyl, isobutyl, tert-butyl, sec-butyl, pentyl, hexyl, heptyl, octyl, nonyl, decyl, dodecyl, pentadecyl, octadecyl and docosyl groups.

As cyclic alkyl groups there may be mentioned cyclopropyl, cyclobutyl, cyclopentyl, cyclohexyl, cyclononyl, cyclododecyl, norbornyl and adamantyl groups.

Examples of the aforementioned alkenyl groups include the straight-chain or branched alkyl groups mentioned above wherein one of the single bonds between carbon atoms (C—C) is replaced with a double bond, with no particular restriction on the location of the double bond. Among the alkenyl groups ethenyl, propenyl, 3-butenyl, 2-butenyl, 2-pentenyl, 2-hexenyl, 2-nonenyl and 2-dodecenyl groups are preferred.

Examples of the aforementioned alkynyl groups include the straight-chain or branched alkyl groups mentioned above wherein one of the single bonds between carbon atoms (C—C) is replaced with a triple bond, with no particular restriction on the location of the triple bond. Preferred alkynyl groups include ethynyl, 1-propynyl, 2-propynyl, 1-butynyl, 2-butynyl, 1-pentynyl, 2-pentynyl, 1-hexynyl, 2-hexynyl and 1-octynyl groups, with ethynyl being most preferred.

Examples of the aforementioned alkoxy groups include monovalent groups comprising straight-chain or branched alkyl groups or cyclic alkyl groups bonded to an oxygen atom. Preferred alkoxy groups include monovalent groups comprising a methyl, ethyl, propyl, isopropyl, butyl, isobutyl, tert-butyl, sec-butyl, pentyl, hexyl, heptyl, octyl, nonyl, decyl, dodecyl, pentadecyl, octadecyl, cyclopropyl, cyclobutyl, cyclopentyl or cyclohexyl group bonded to an oxygen atom.

Aryl groups include phenyl, 1-naphthyl, 2-naphthyl, 1-anthracenyl, 2-anthracenyl, 9-anthracenyl, 1-tetracenyl, 2-tetracenyl, 5-tetracenyl, 1-pyrenyl, 2-pyrenyl, 4-pyrenyl, 2-perylenyl, 3-perylenyl, 2-fluorenyl, 3-fluorenyl, 4-fluorenyl, 1-biphenylenyl, 2-biphenylenyl, 2-phenanthrenyl, 9-phenanthrenyl, 6-chrysenyl and 1-coronenyl. The hydrogen of the aryl group may be optionally substituted with a halogeno, hydroxy, carboxyl, mercapto, sulfonic acid, nitro, amino, cyano or phosphonic acid group, or any of the aforementioned alkyl, alkenyl, alkynyl, alkoxy, aryl or aralkyl groups.

As monovalent heterocyclic groups there may be mentioned pyridyl, pyrazyl, pyrimidyl, pyridazyl, pyrrolyl, furyl, thienyl, imidazolyl, pyrazolyl, thiazolyl and oxazolyl groups. A monovalent heterocyclic group is an atomic group remaining after removing one hydrogen from a heterocyclic compound. Monovalent aromatic heterocyclic groups are preferred as monovalent heterocyclic groups.

As aralkyl groups there may be mentioned benzyl, 1-phenylethyl, 2-phenylethyl, 1-phenyl-1-propyl, 1-phenyl-2-propyl, 2-phenylpropyl and 3-phenyl-1-propyl groups.

The substituents represented by $R^\gamma$, $R^\delta$ and $R^\varepsilon$ above may bond together, or through other bonds with carbon atoms or nitrogen atoms bonding to the substituents, to form rings. As such rings there may be mentioned cyclohexene ring, benzene ring, pyridine ring, pyrazine ring, pyrimidine ring, pyridazine ring, 1H-pyrrole ring, 2H-pyrrole ring, 3H-pyrrole ring, imidazole ring, pyrazole ring, 1,2,3-triazole ring, 1,2,4-triazole ring, oxazole ring, isooxazole ring, thiazole ring, isothiazole ring, 1,3,4-oxadiazole ring, 1,2,5-oxadiazole ring, 1,3,4-thiadiazole ring, 1,2,5-thiadiazole ring, furan ring and thiophene ring. Some or all of the hydrogens on these rings may have substituents, and their substituents may bond together to form additional rings.

In the aromatic compounds of the invention, the structure represented by general formula (1) is more preferably a structure represented by the following general formula (2) and/or general formula (3):

[Chemical Formula 14]

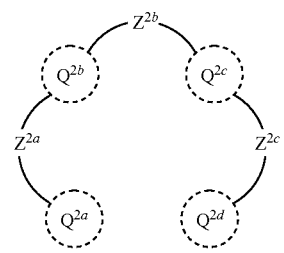

(2)

wherein $Q^{2a}$, $Q^{2b}$, $Q^{2c}$ and $Q^{2d}$ are optionally substituted nitrogen-containing aromatic heterocyclic rings and each may be the same or different, however, at least one group from $Q^{2a}$, $Q^{2b}$, $Q^{2c}$ and $Q^{2d}$ is a 6-membered nitrogen-containing heterocyclic ring;

$Z^{2a}$, $Z^{2b}$ and $Z^{2c}$ are direct bonds or linking groups and each may be the same or different;

$Q^{2a}$ and $Q^{2b}$, $Q^{2b}$ and $Q^{2c}$, and $Q^{2c}$ and $Q^{2d}$ may each form together a polycyclic aromatic heterocyclic ring, and $Q^{2a}$ and $Q^{2d}$ may be bonded together via a direct bond or linking group, or may form together a polycyclic aromatic heterocyclic ring,

[Chemical Formula 15]

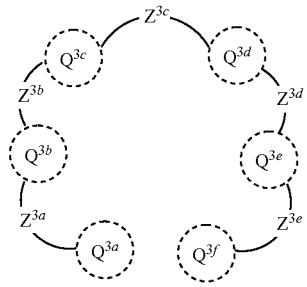

(3)

wherein $Q^{3a}$, $Q^{3b}$, $Q^{3c}$, $Q^{3d}$, $Q^{3e}$ and $Q^{3f}$ are optionally substituted nitrogen-containing aromatic heterocyclic rings and each may be the same or different, however, at least one group from $Q^{3a}$, $Q^{3b}$, $Q^{3c}$, $Q^{3d}$, $Q^{3e}$ and $Q^{3f}$ is a 6-membered nitrogen-containing heterocyclic ring;

$Z^{3a}$, $Z^{3b}$, $Z^{3c}$, $Z^{3d}$ and $Z^{3e}$ are direct bonds or linking groups and each may be the same or different;

$Q^{3a}$ and $Q^{3b}$, $Q^{3b}$ and $Q^{3c}$, $Q^{3c}$ and $Q^{3d}$, $Q^{3d}$ and $Q^{3e}$, and $Q^{3e}$ and $Q^{3f}$ may each form together a polycyclic aromatic heterocyclic ring, and $Q^{3a}$ and $Q^{3f}$ may be bonded together via a direct bond or linking group, or may form together a polycyclic aromatic heterocyclic ring.

$Q^{2a}$, $Q^{2b}$, $Q^{2c}$ and $Q^{2d}$ in general formula (2) and $Q^{3a}$, $Q^{3b}$, $Q^{3c}$, $Q^{3d}$, $Q^{3e}$ and $Q^{3f}$ in general formula (3) each independently represent an optionally substituted nitrogen-containing aromatic ring, and preferred examples are the same as for $Q^{1a}$, $Q^{1b}$ and $Q^{1c}$ in general formula (1) above.

The two nitrogen-containing aromatic heterocyclic rings bonded together via a direct bond or linking group in $Q^{1a}$ and $Q^{1b}$, $Q^{1b}$ and $Q^{1c}$, $Q^{2a}$ and $Q^{2b}$, $Q^{2b}$ and $Q^{2c}$, $Q^{2c}$ and $Q^{2d}$, $Q^{3a}$ and $Q^{3b}$, $Q^{3b}$ and $Q^{3c}$, $Q^{3c}$ and $Q^{3d}$, $Q^{3d}$ and $Q^{3e}$, or $Q^{3e}$ and $Q^{3f}$ are preferably represented by any one of the following formulas (4-a) to (6-d):

[Chemical Formula 16]

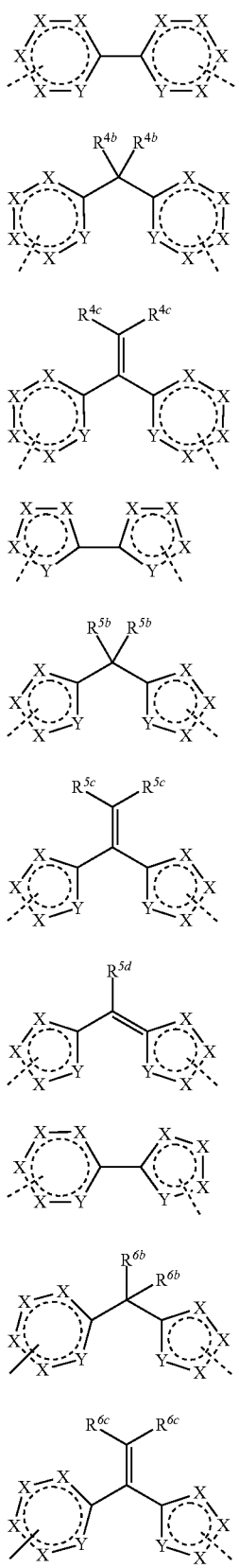

(4-a)
(4-b)
(4-c)
(5-a)
(5-b)
(5-c)
(5-d)
(6-a)
(6-b)
(6-c)

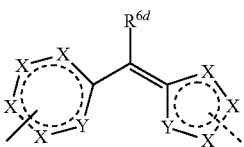

(6-d)

[In the formulas, X is $=C(R^\alpha)-$, $-N(R^\beta)-$, $=N-$, $-O-$, $-S-$ or $-Se-$, and each may be the same or different and is preferably $=C(R^\alpha)-$, $-N(R^\beta)-$, $=N-$, $-O-$ or $-S-$ and more preferably $=C(R^\alpha)-$, $-N(R^\beta)-$ or $=N-$;

Y is $-N(H)-$ or $=N-$ and each may be the same or different; and the dotted lines in the formulas indicate that the structure is bonded to $Z^{1a}$ or the like at the dotted sections.]

In these formulas, $R^{4b}$, $R^{4c}$, $R^{5b}$, $R^{5c}$, $R^{5d}$, $R^{6b}$, $R^{6c}$, $R^{6d}$, $R^\alpha$ and $R^\beta$ are hydrogen or a substituent and each may be the same or different. The substituents have the same substituent definition as above. The adjacent substituents may also bond together to form rings.

Also, the two nitrogen-containing aromatic heterocyclic rings bonded together via a direct bond or linking group in $Q^{1a}$ and $Q^{1b}$, $Q^{1b}$ and $Q^{1c}$, $Q^{2a}$ and $Q^{2b}$, $Q^{2b}$ and $Q^{2c}$, $Q^{2c}$ and $Q^{2d}$, $Q^{3a}$ and $Q^{3b}$, $Q^{3b}$ and $Q^{3c}$, $Q^{3c}$ and $Q^{3d}$, $Q^{3d}$ and $Q^{3e}$, or $Q^{3e}$ and $Q^{3f}$ are more preferably represented by any one of the following general formulas (7-a) to (10-e):

[Chemical Formula 17]

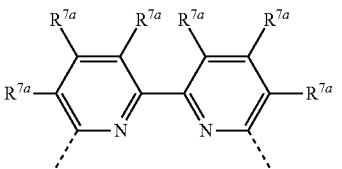

(7-a)
(7-b)
(7-c)
(7-d)

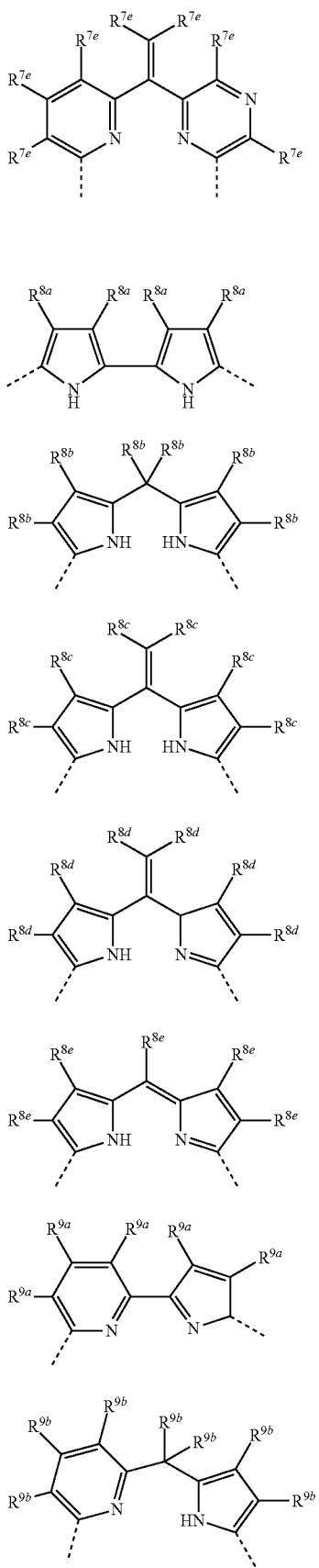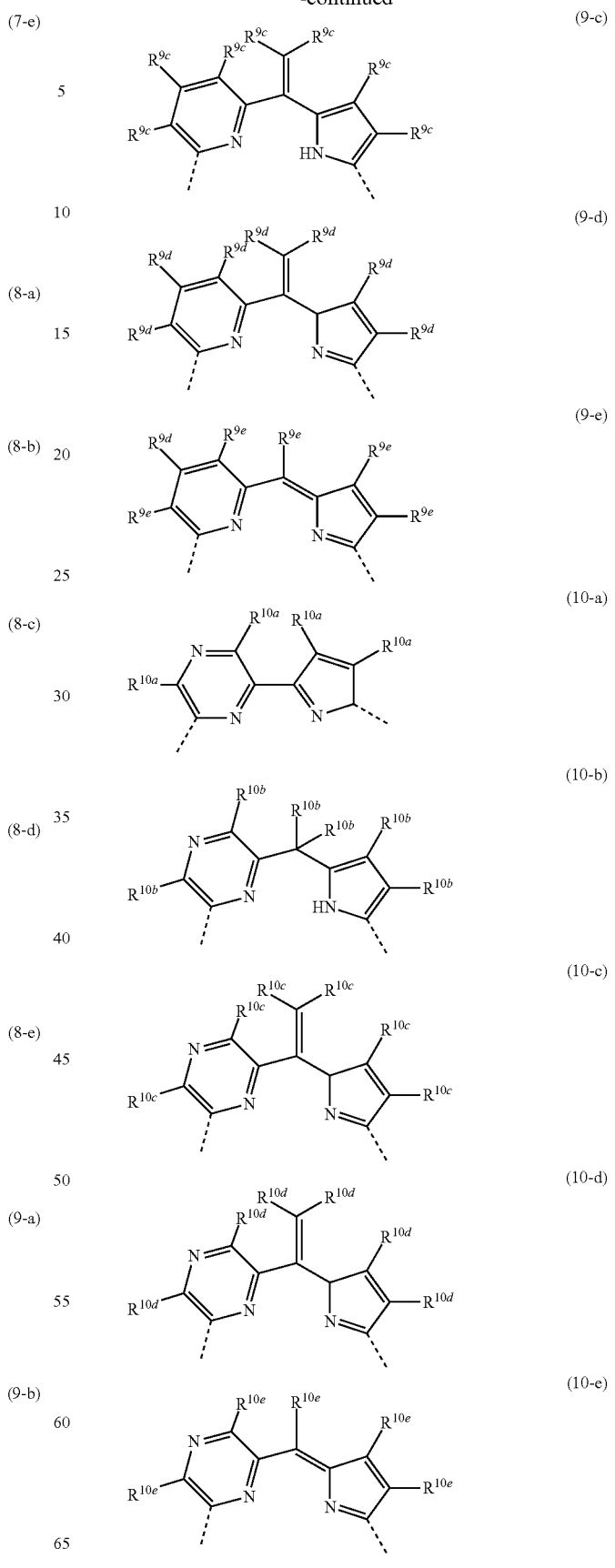

[wherein $R^{7a}$-$R^{10e}$ are hydrogen or a substituent and each may be the same or different, with adjacent substituents optionally bonding together to form a ring, and the substituents having the same substituent definition as above; and the dotted lines in the formulas indicate that the structure is bonded to $Z^{1a}$ or the like at the dotted sections.]

Examples of aromatic compounds according to the invention include compounds represented by the following structural formulas. The hydrogens in the formulas may be substituted with the aforementioned substituents.

[Chemical Formula 18]

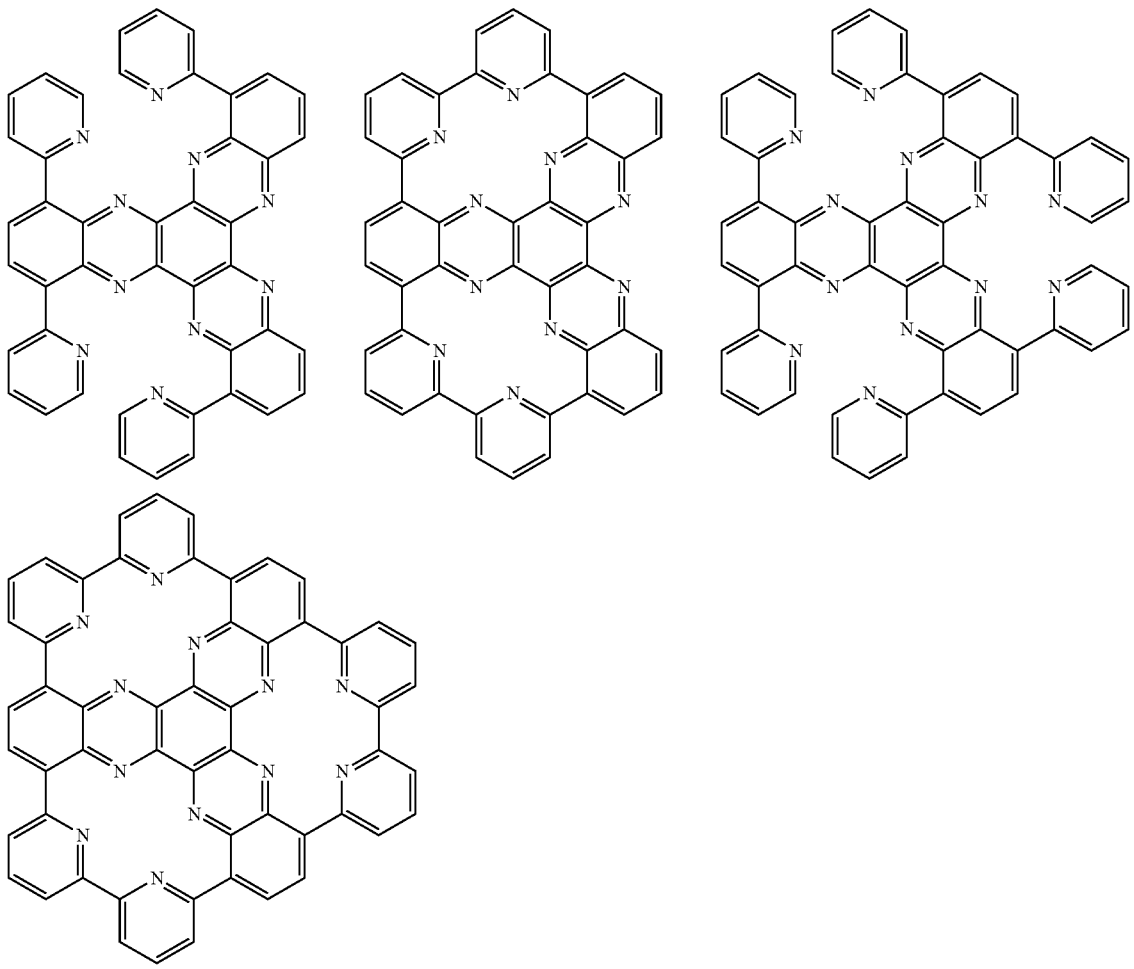

[Chemical Formula 19]

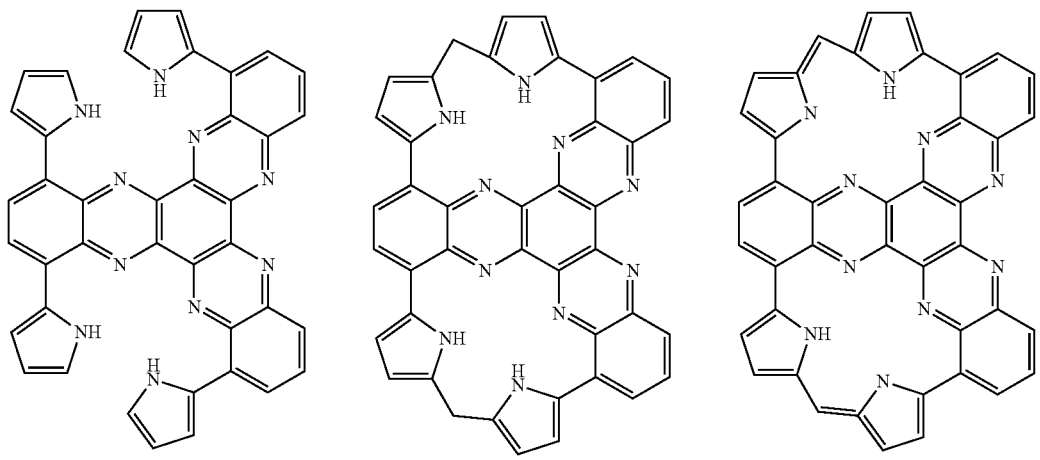

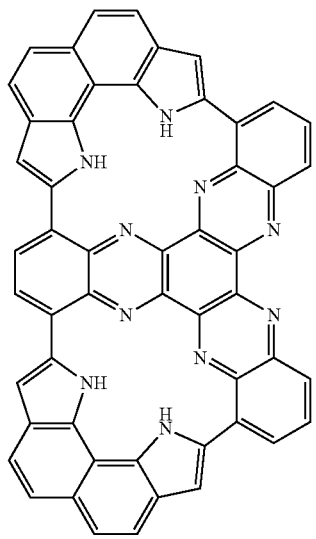
[Chemical Formula 20]
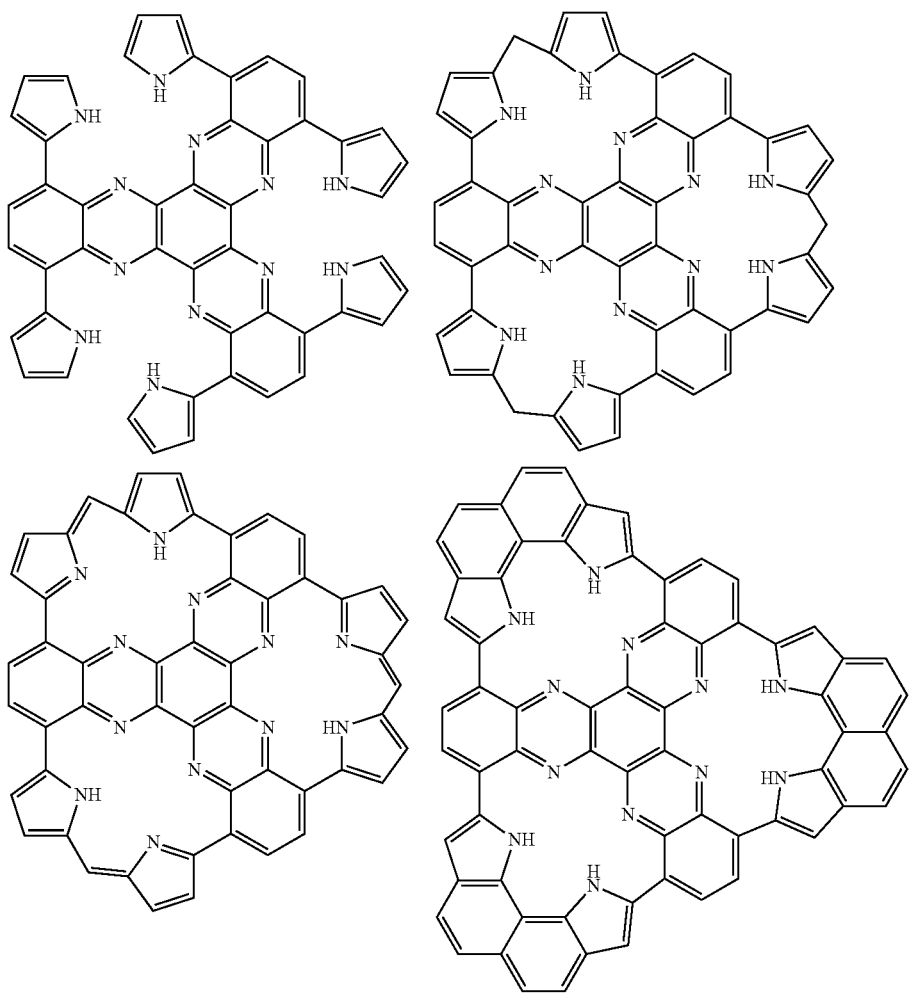

[Chemical Formula 21]
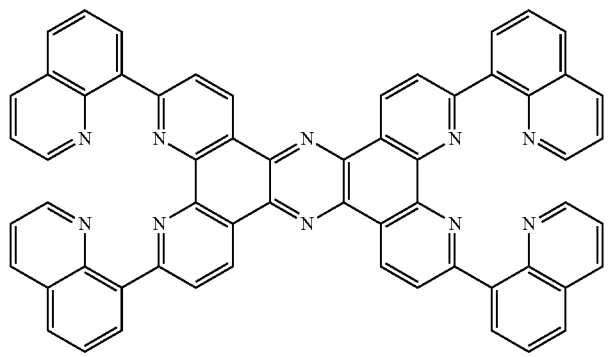
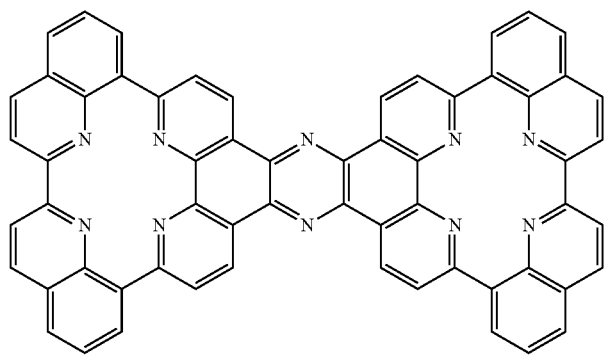
[Chemical Formula 22]
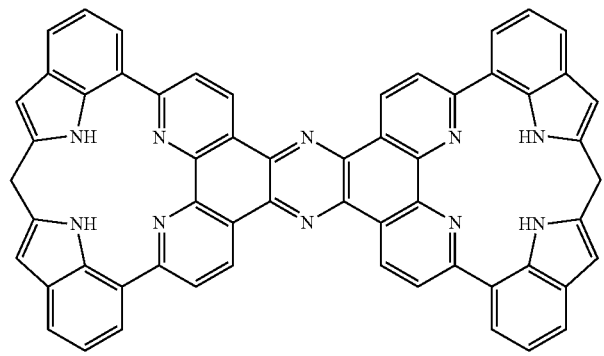
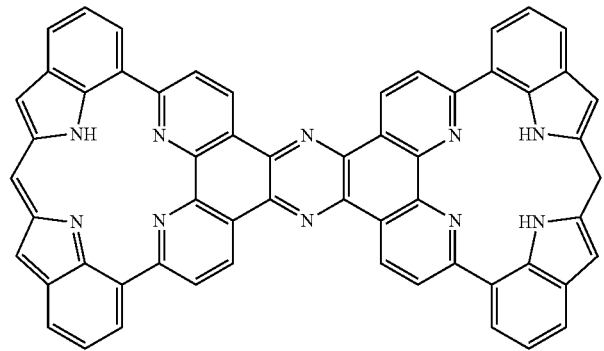

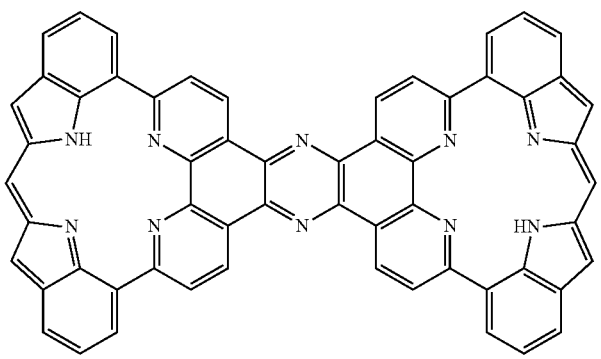
[Chemcial Formula 23]
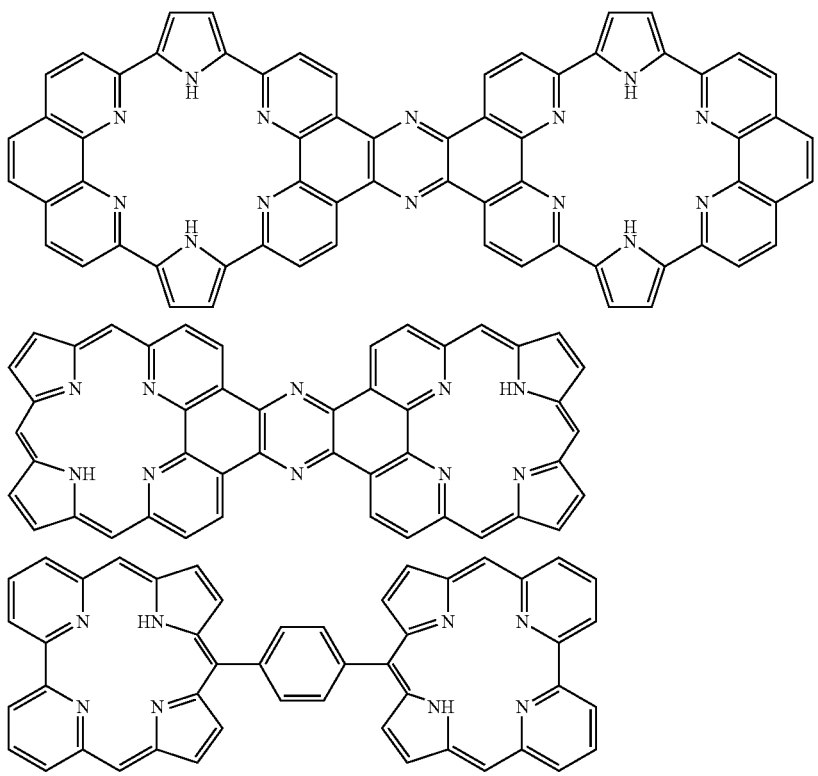
[Chemcial Formula 24]
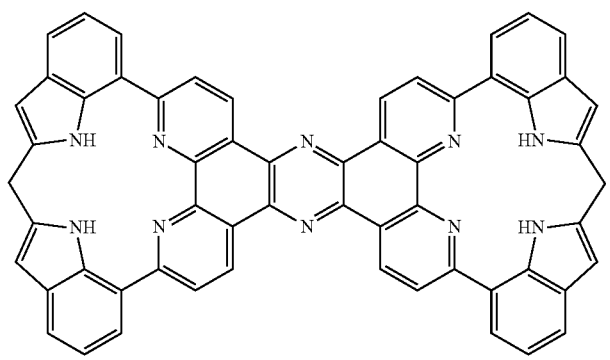

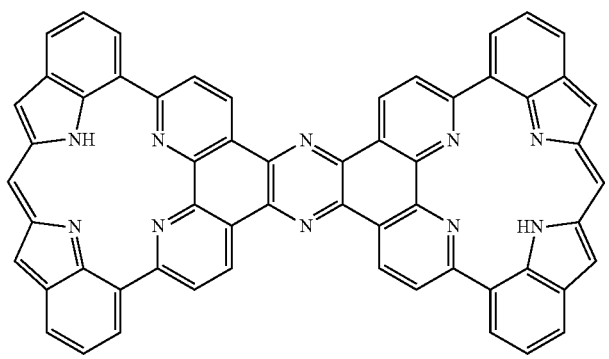
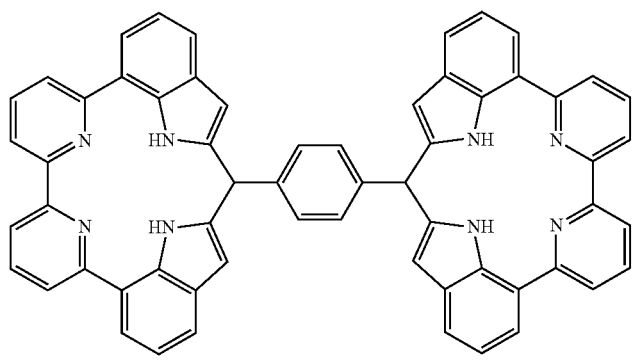
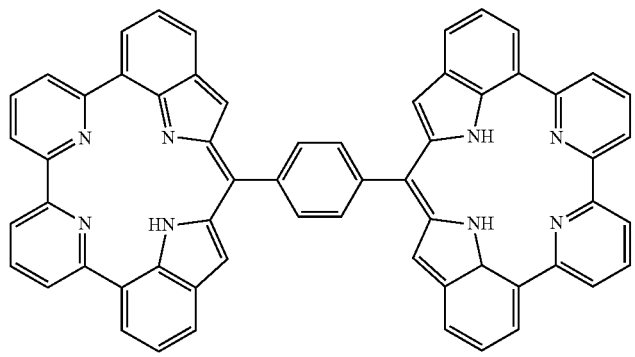
[Chemical Formula 25]
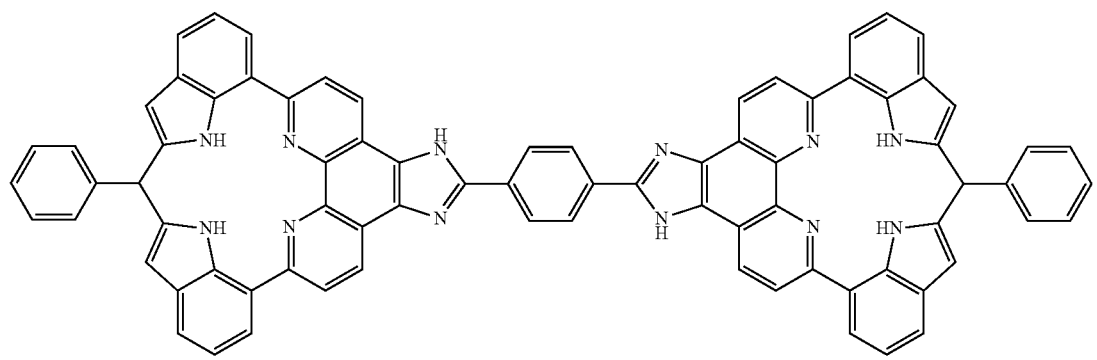

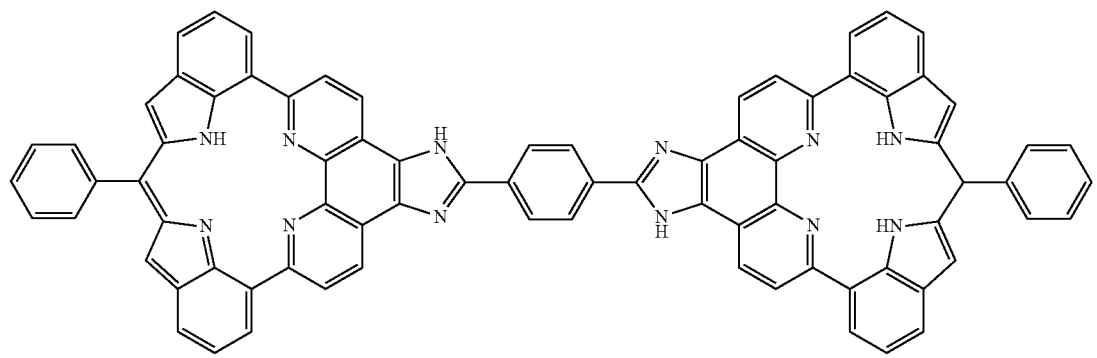
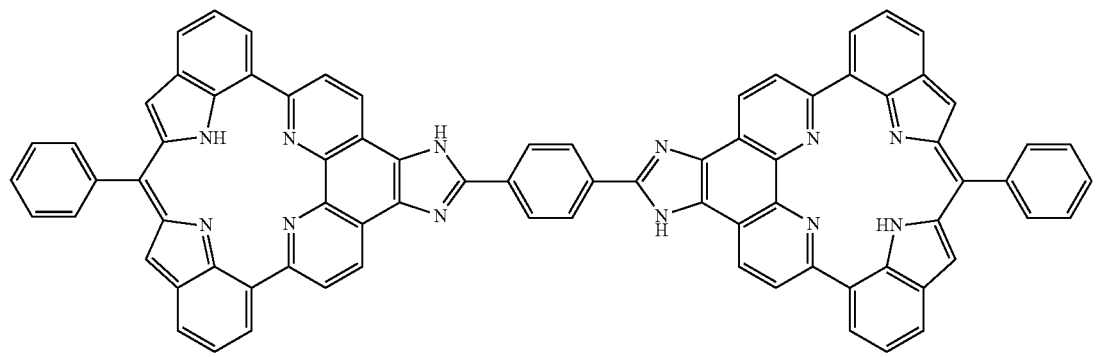
[Chemical Formula 26]
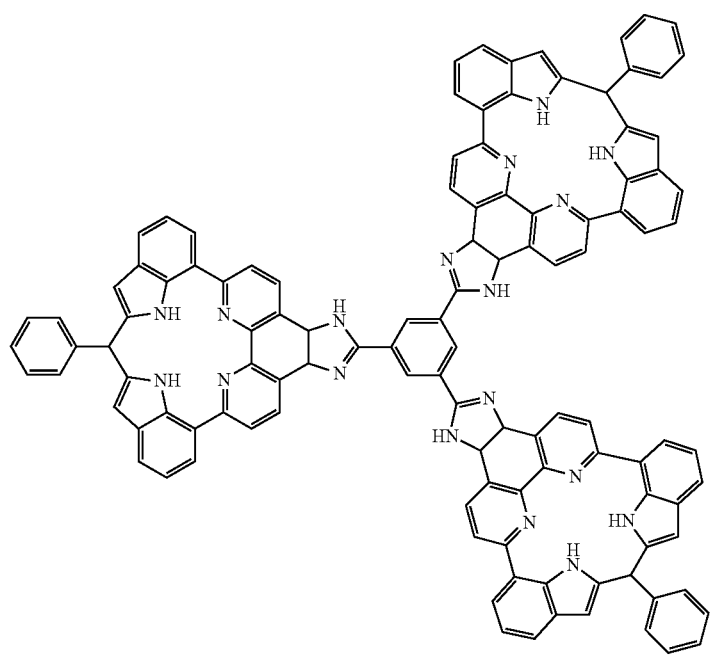

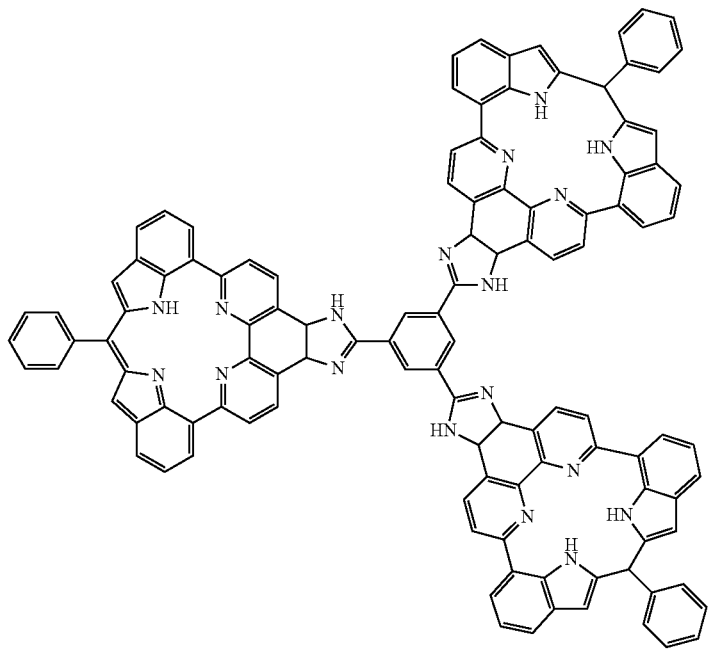
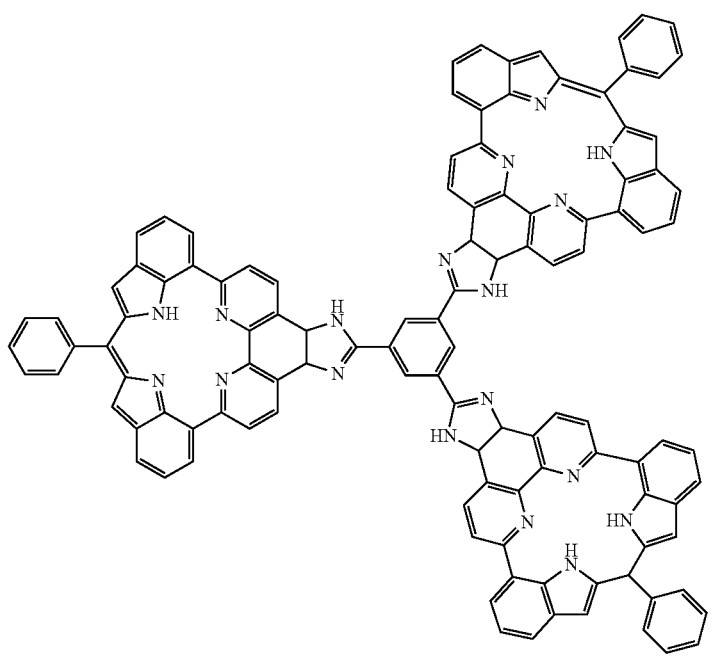

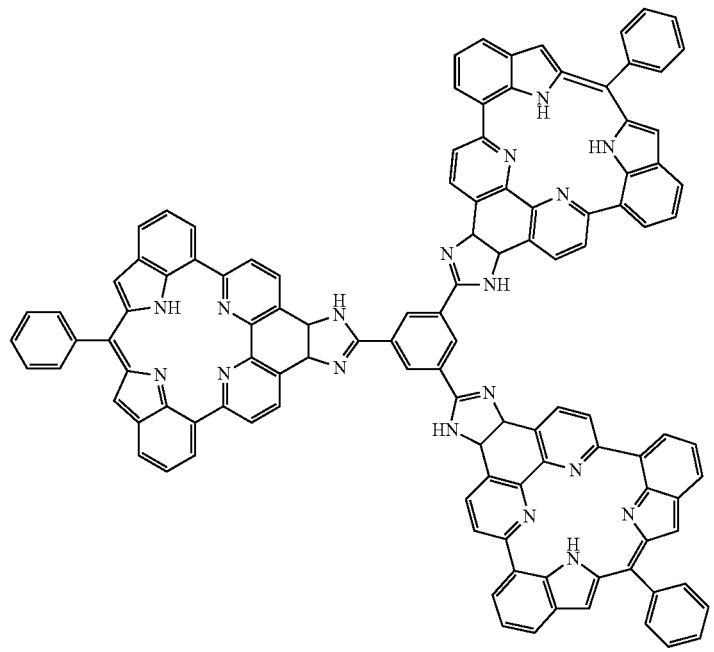
[Chemical Formula 27]
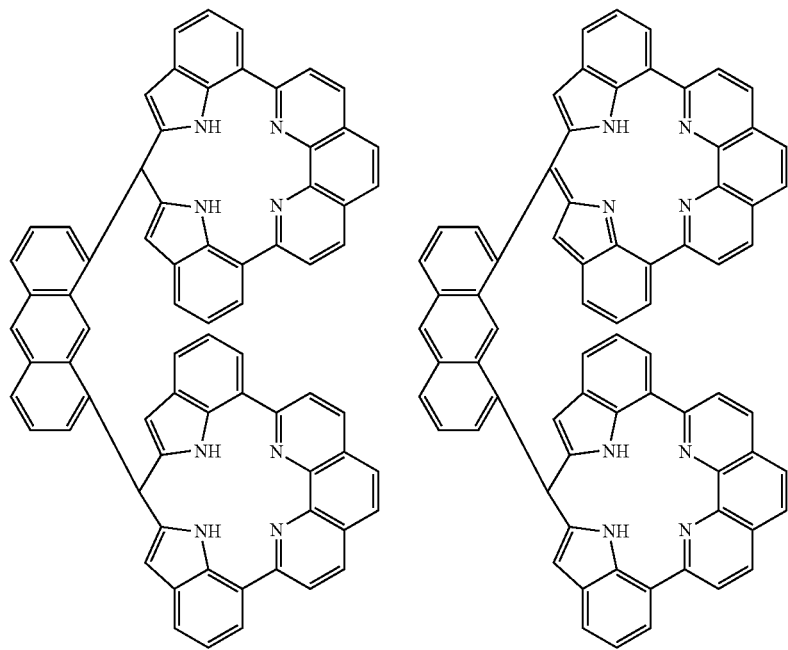

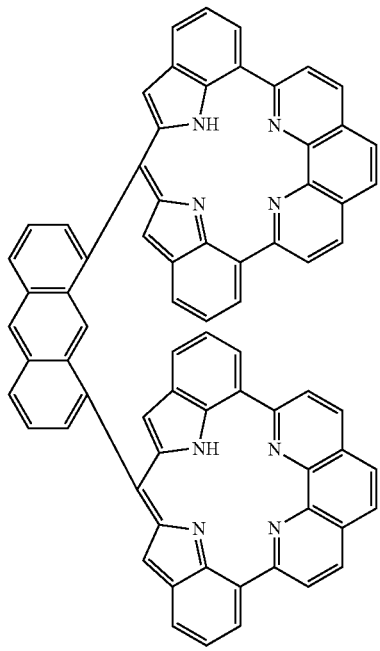
[Chemical Formula 28]
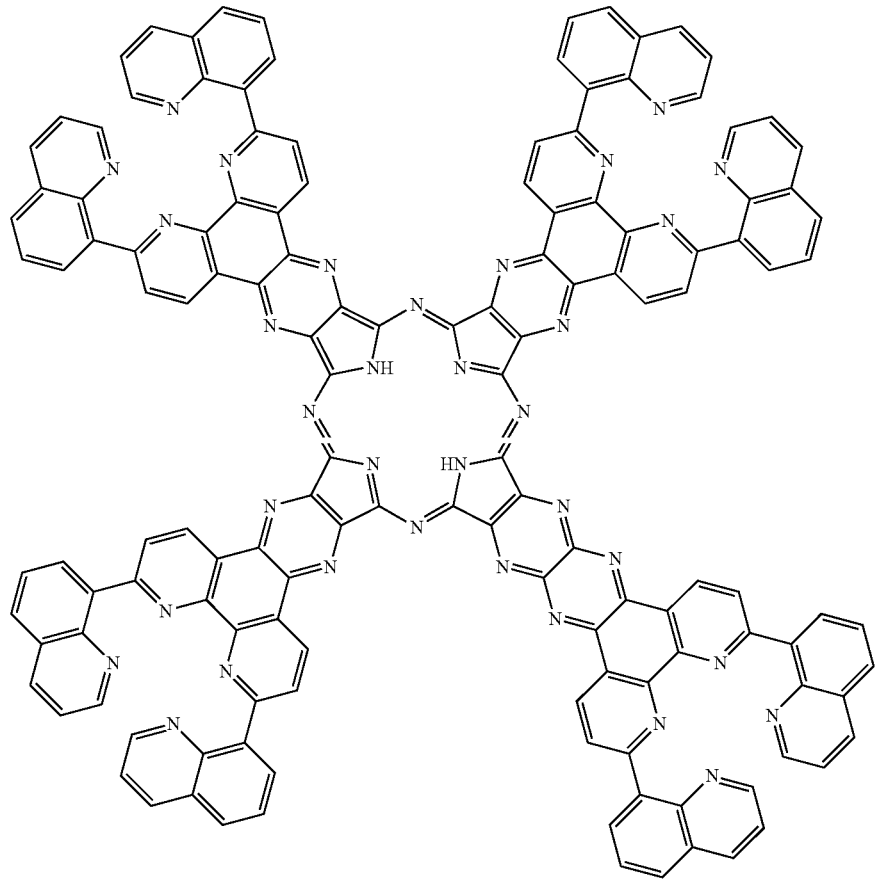

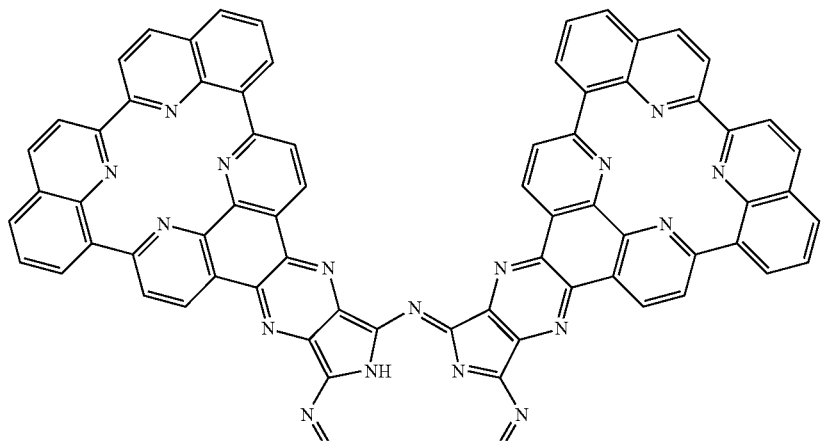
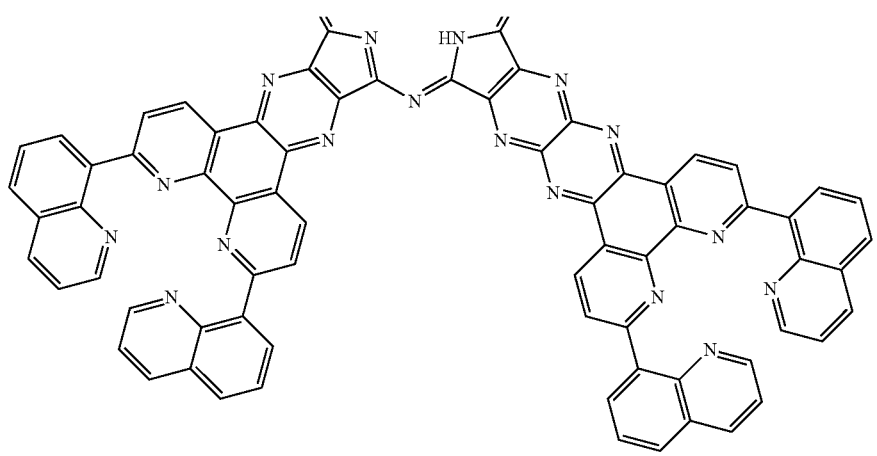
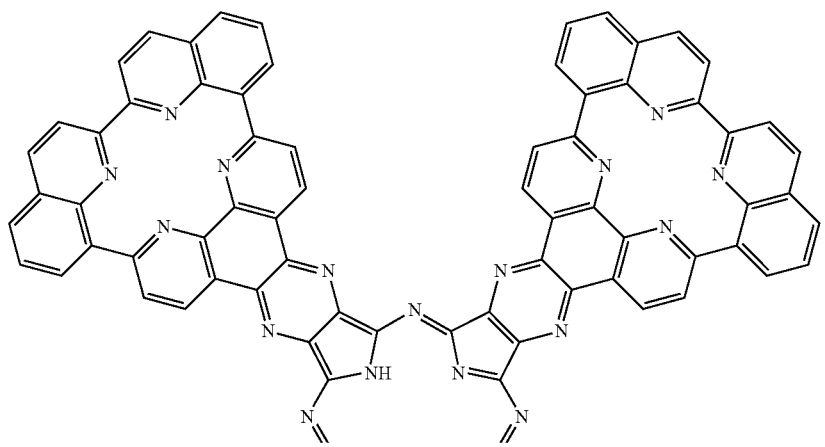

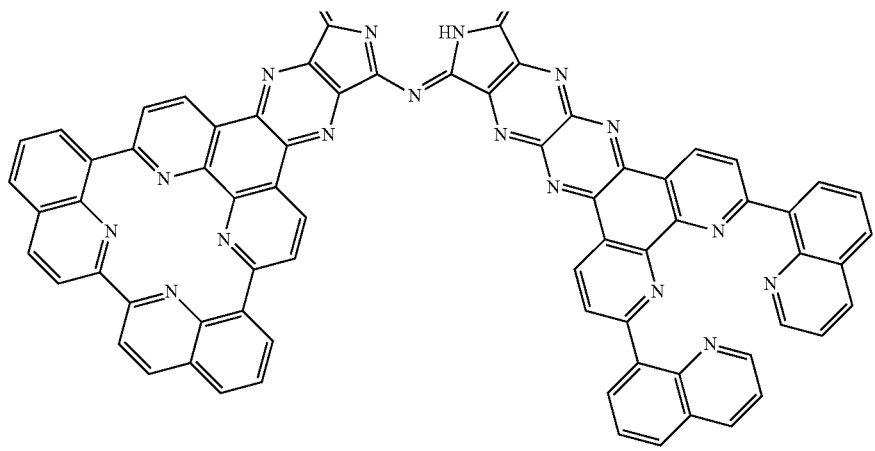
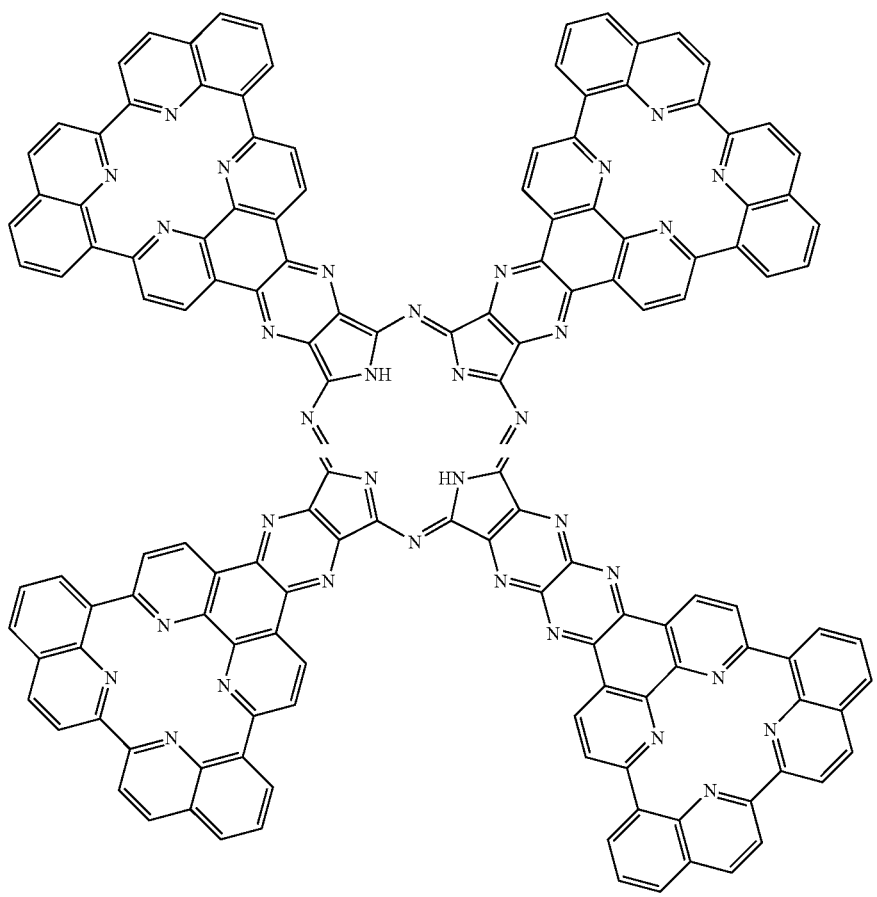

[Chemical Formula 29]
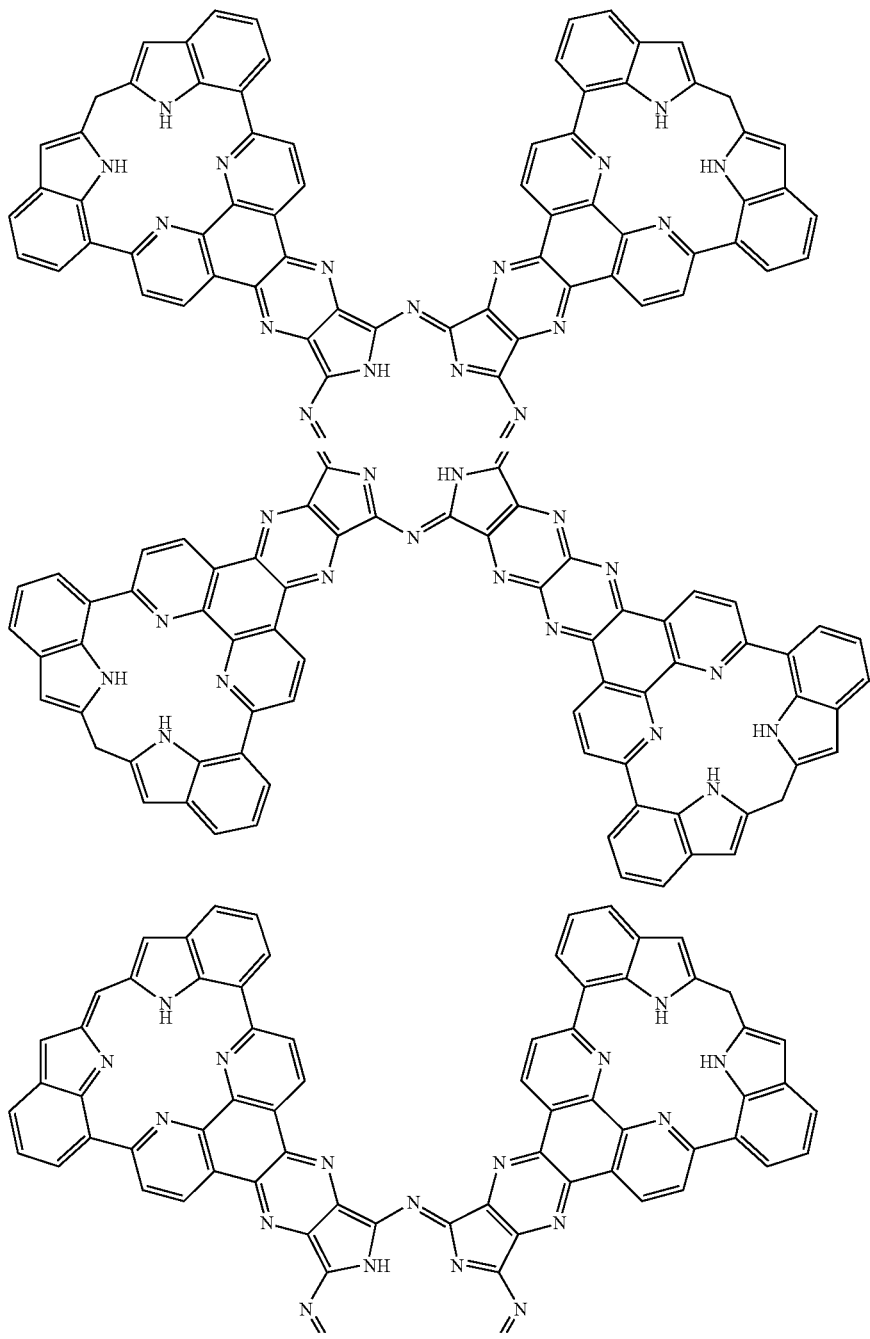

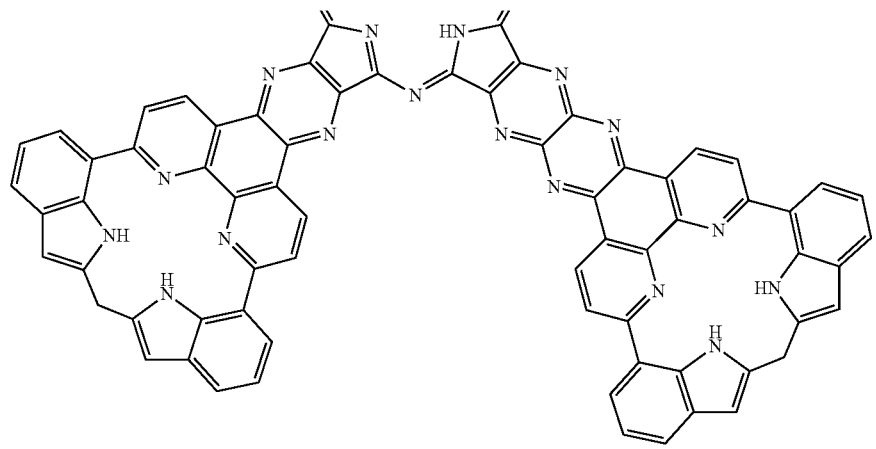
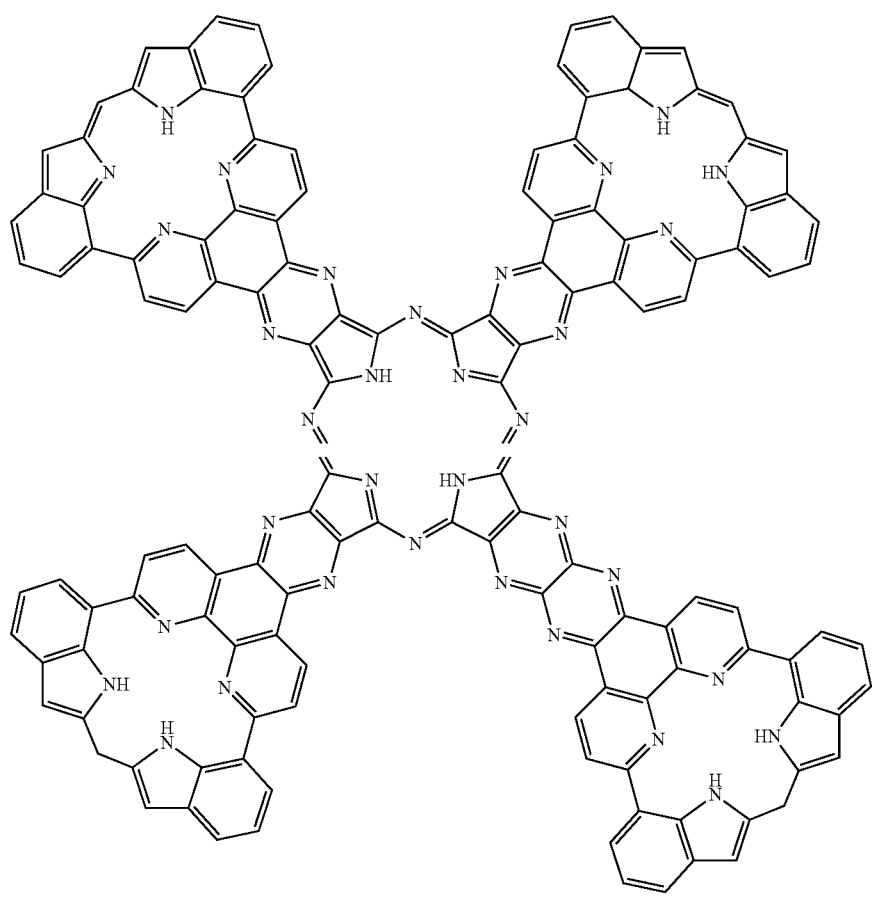

-continued
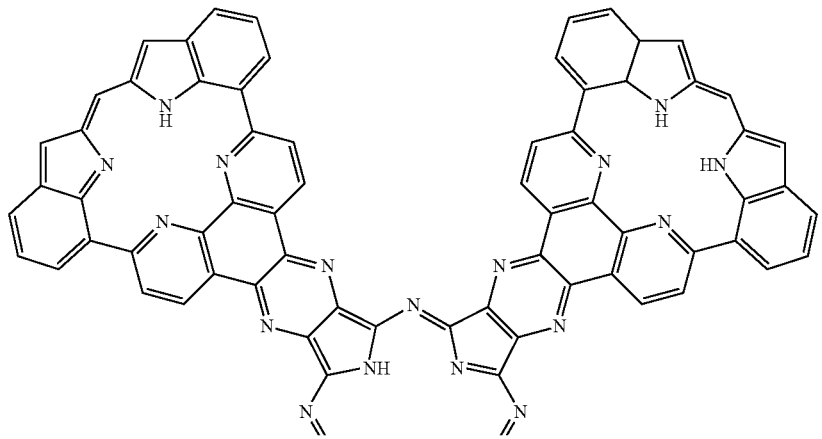
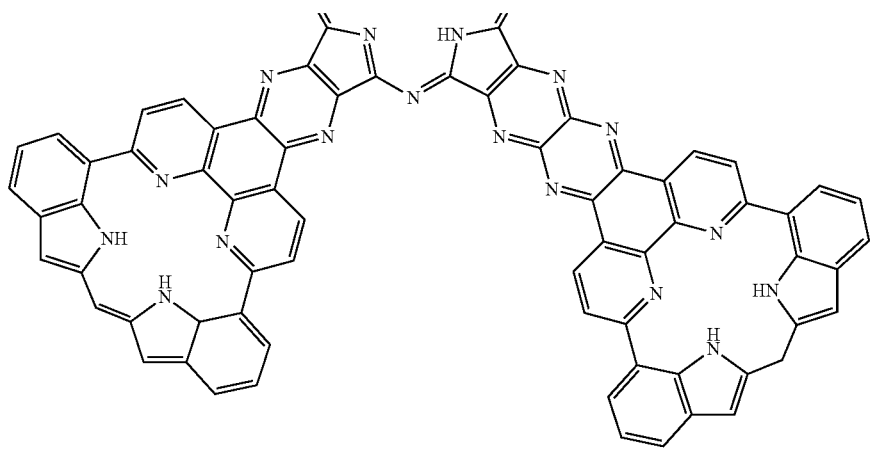
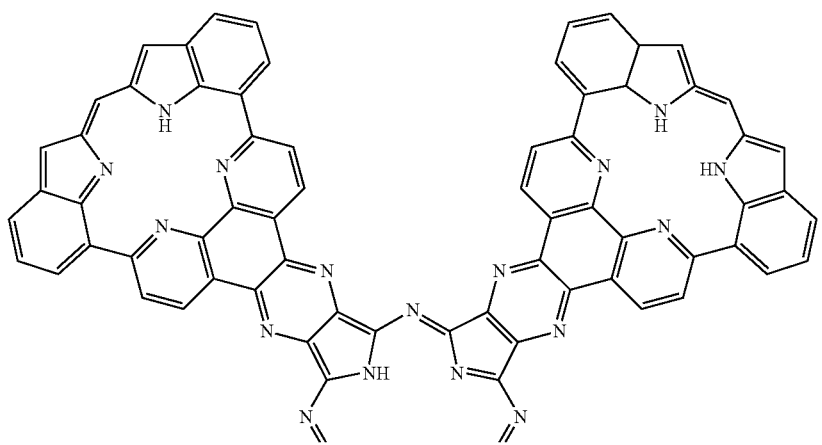

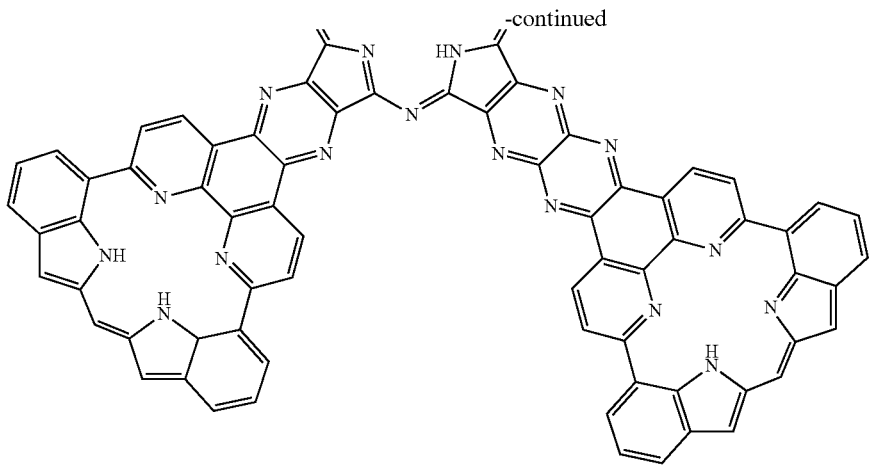
Examples of aromatic compounds according to the invention also include aromatic compounds having following structural unit. The hydrogens in these formulas may also be substituted with the aforementioned substituents.
[Chemical Formula 30]
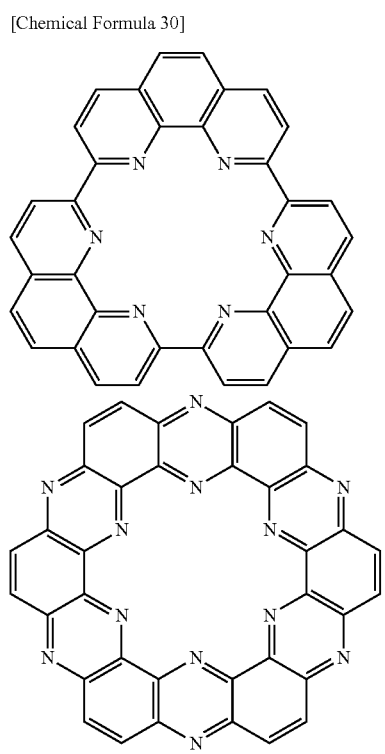
[Chemical Formula 31]
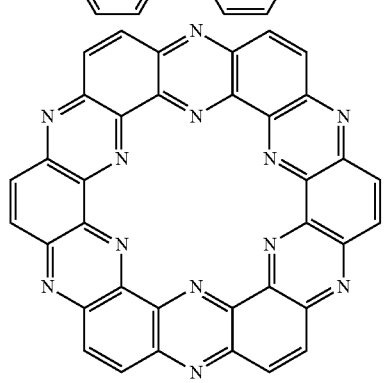
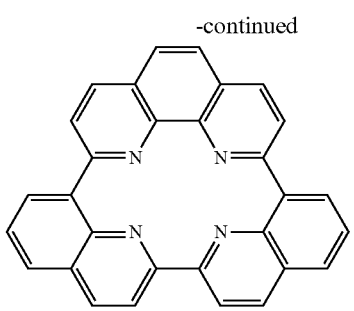
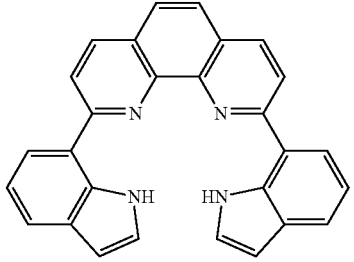
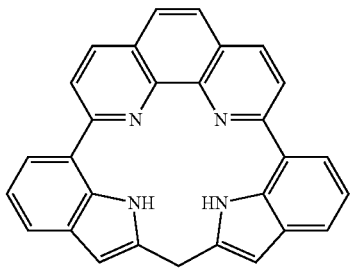
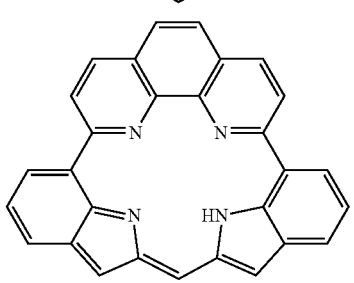
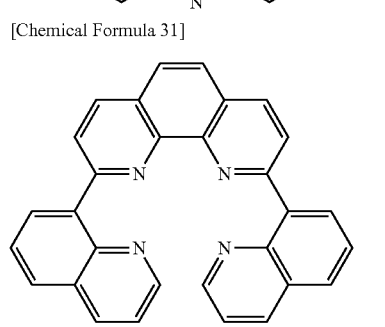

[Chemical Formula 32]
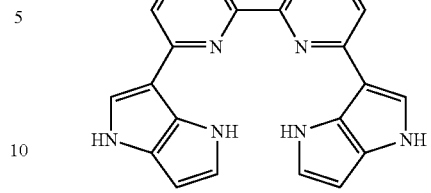
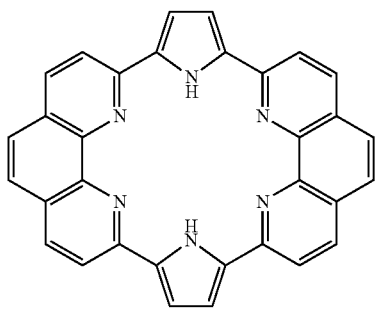
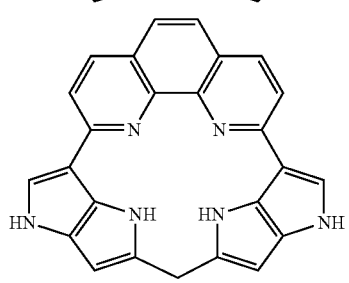
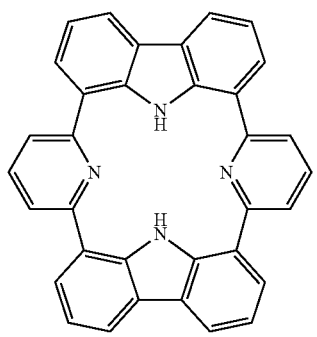
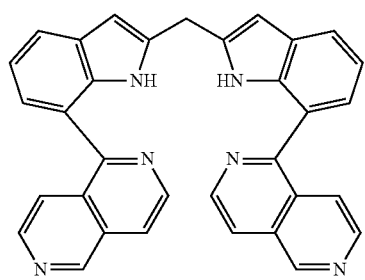
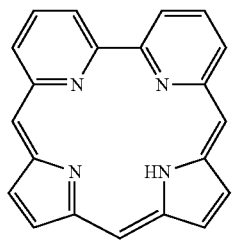
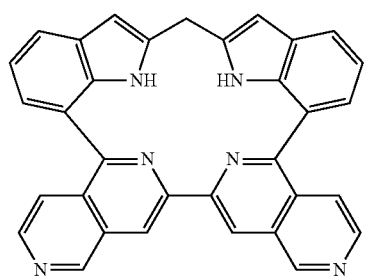
[Chemical Formula 33]
[Chemical Formula 34]
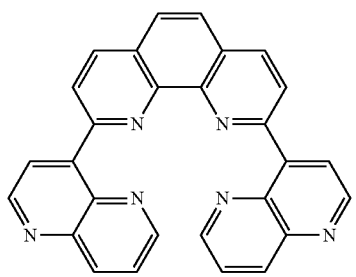
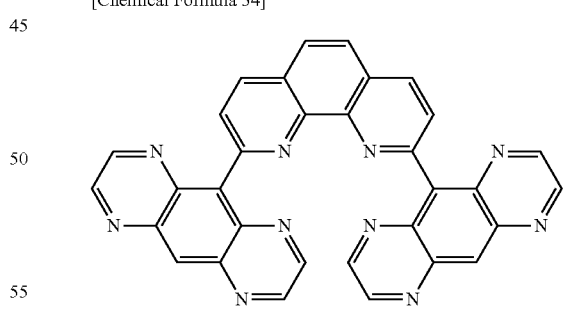
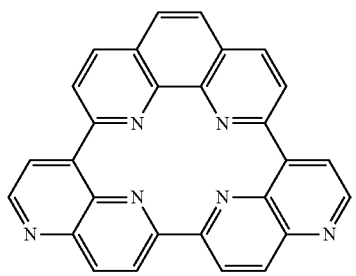
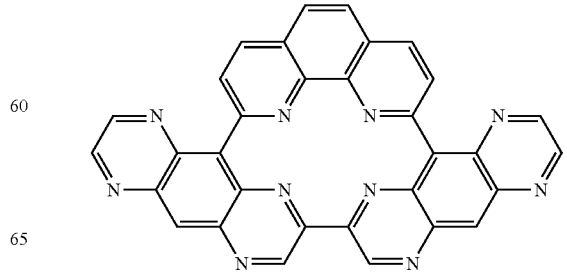

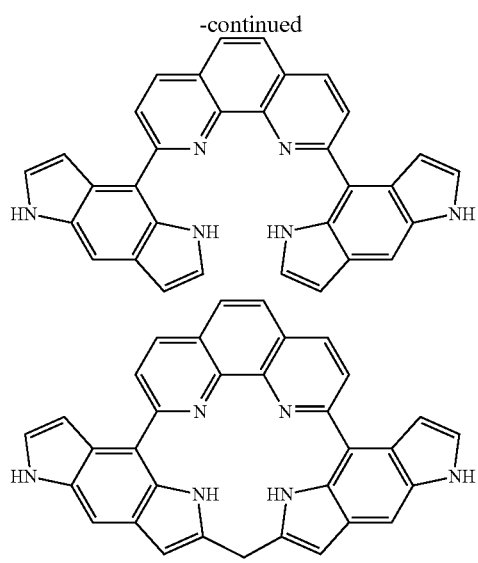
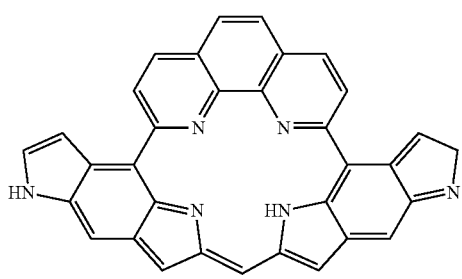
Examples of aromatic compounds having above mentioned structural unit include the following compounds.
[Chemical Formula 35]
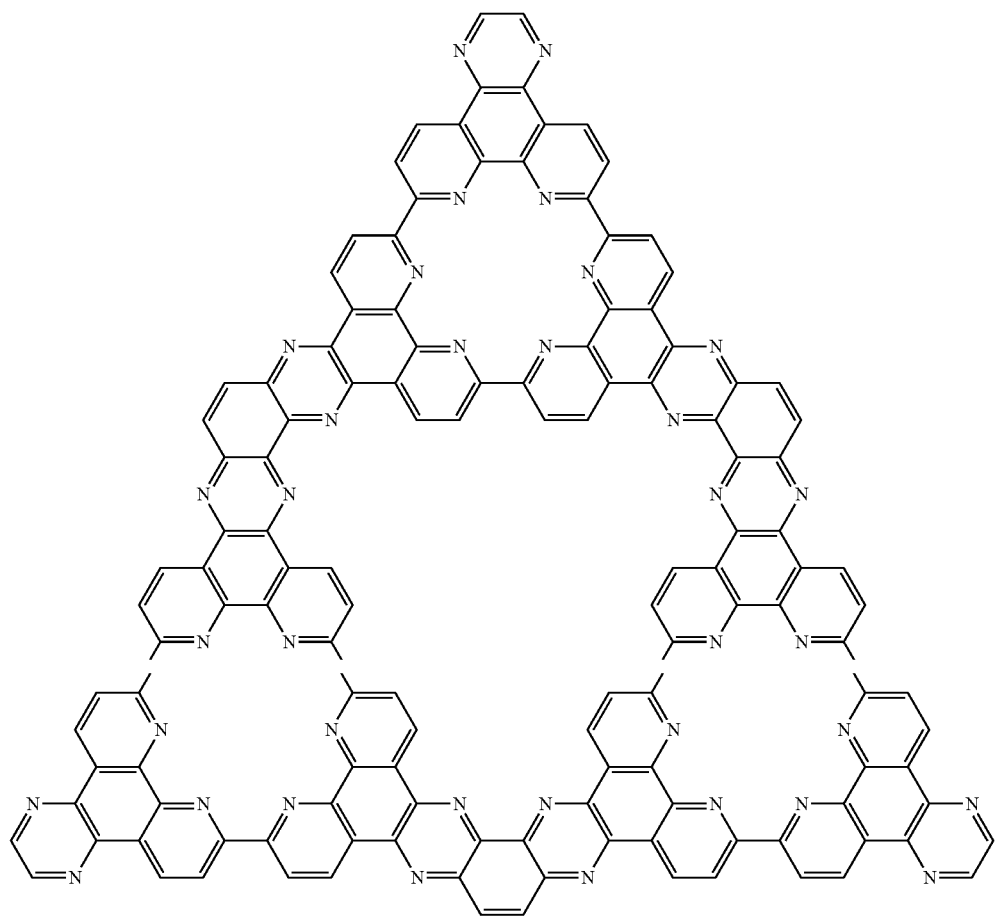

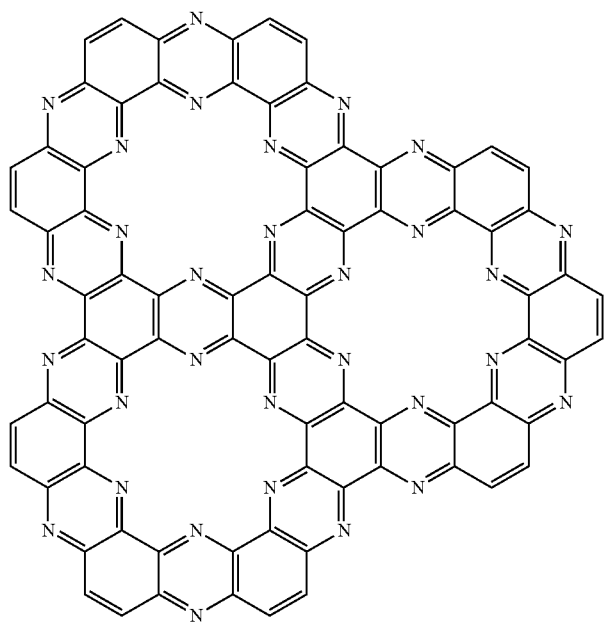
[Chemical Formula 36]
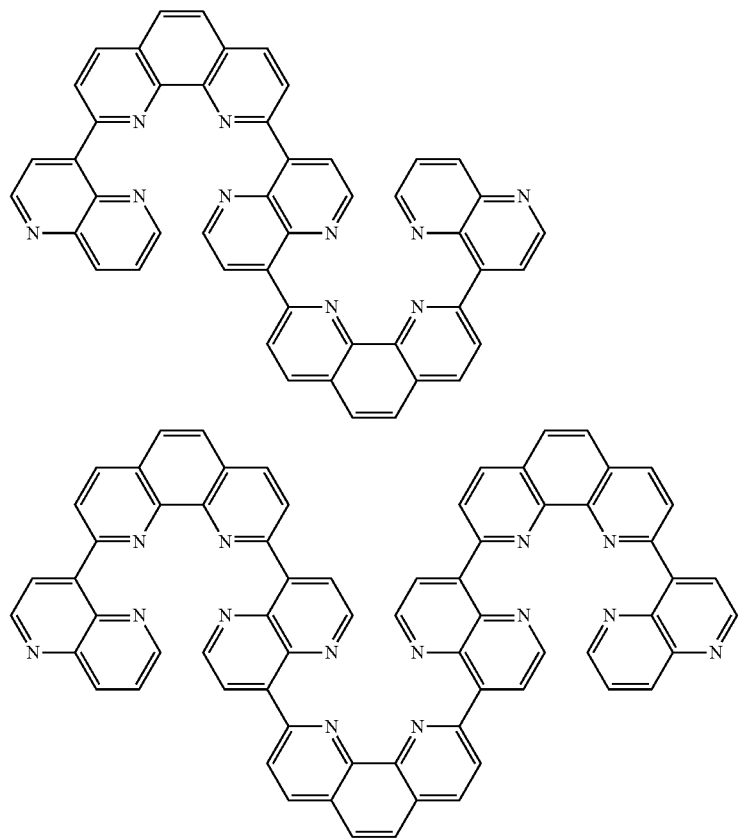

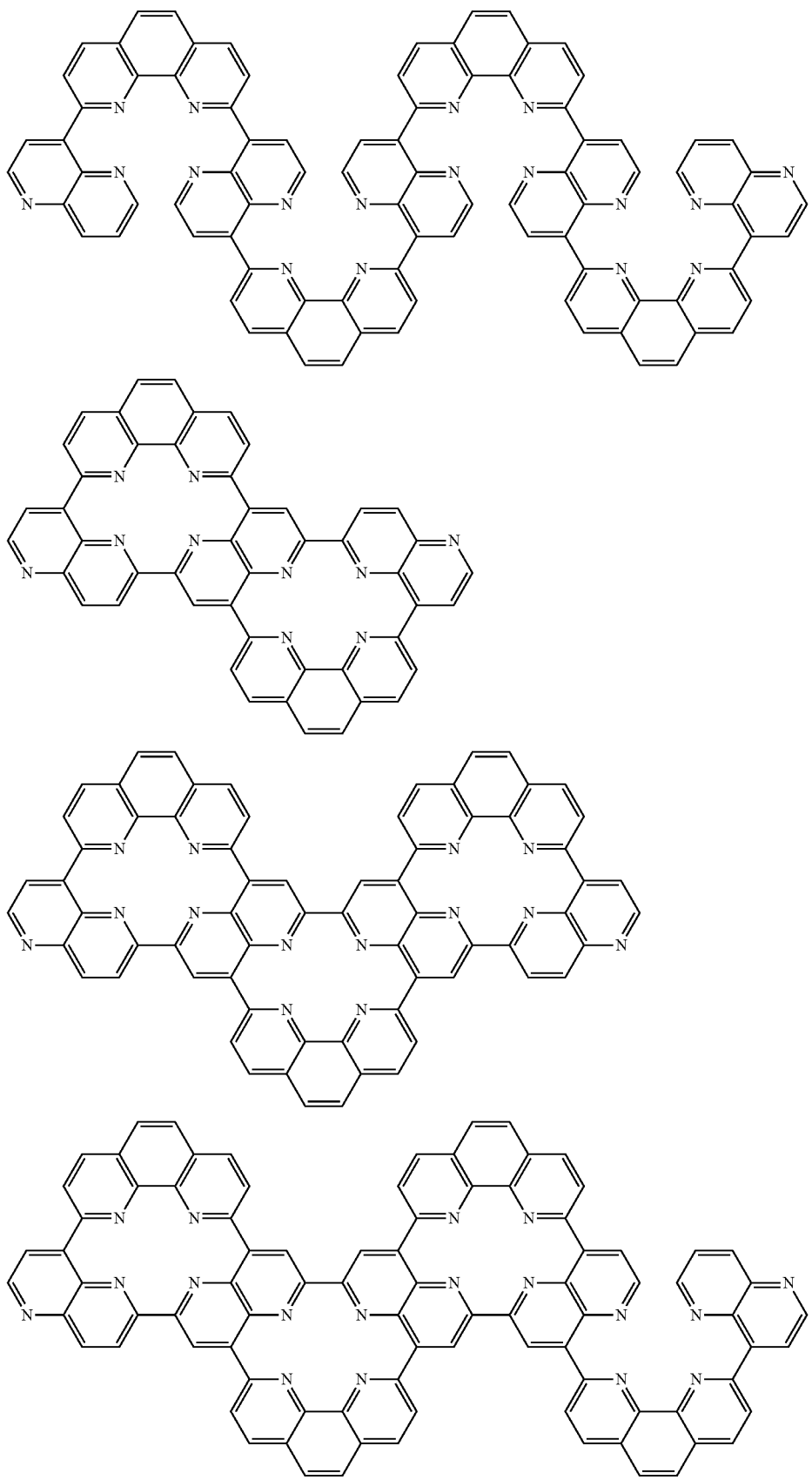

[Chemical Formula 37]
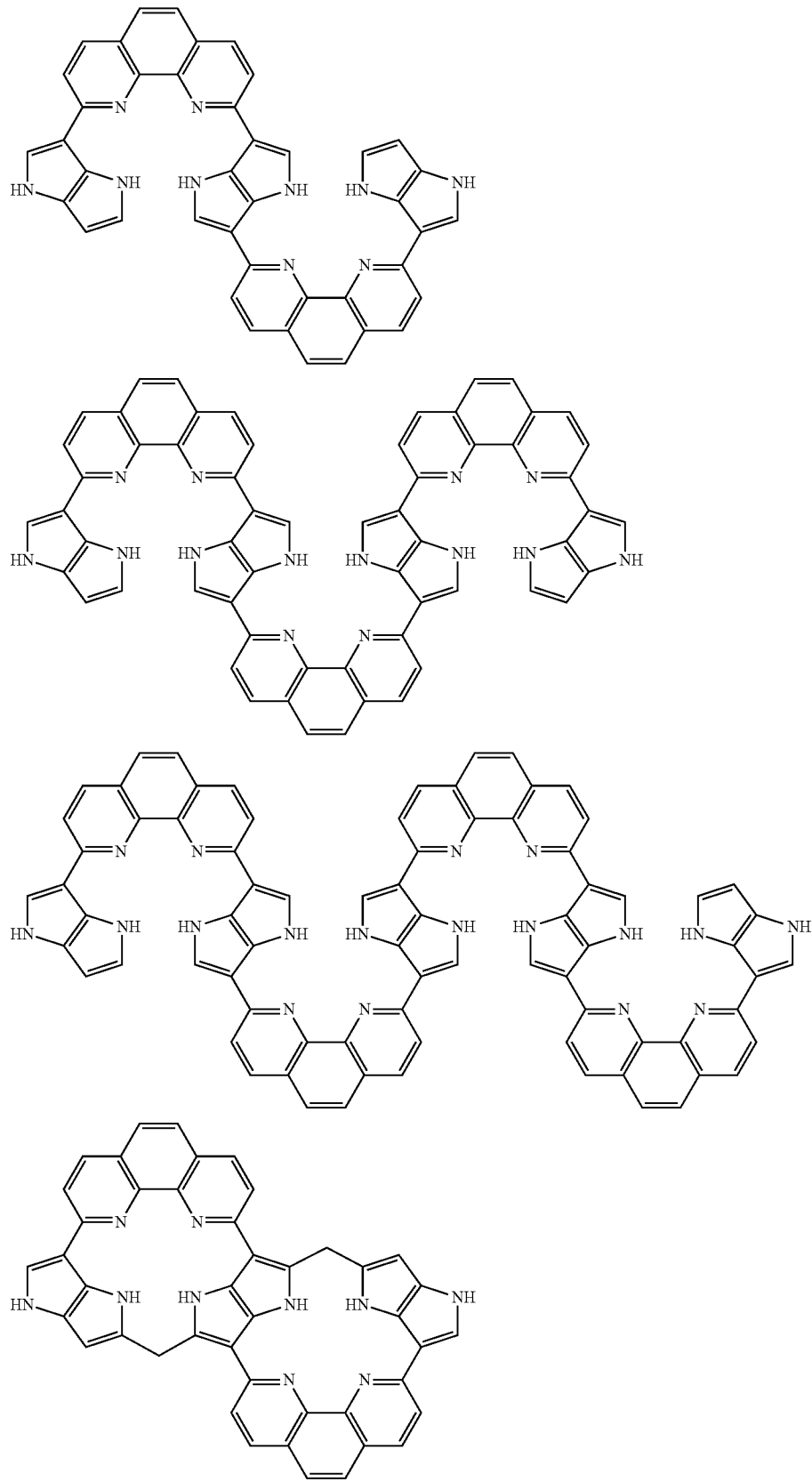

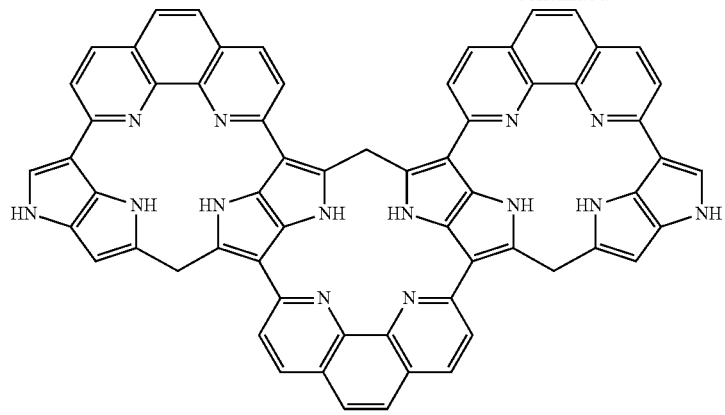
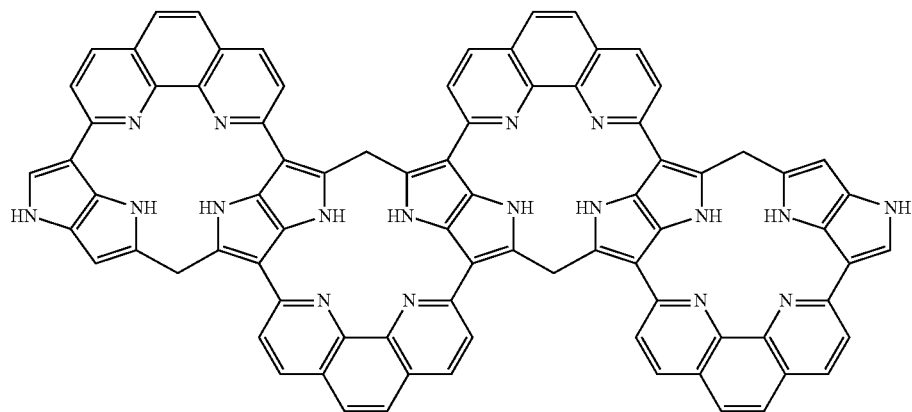
[Chemical Formula 38]
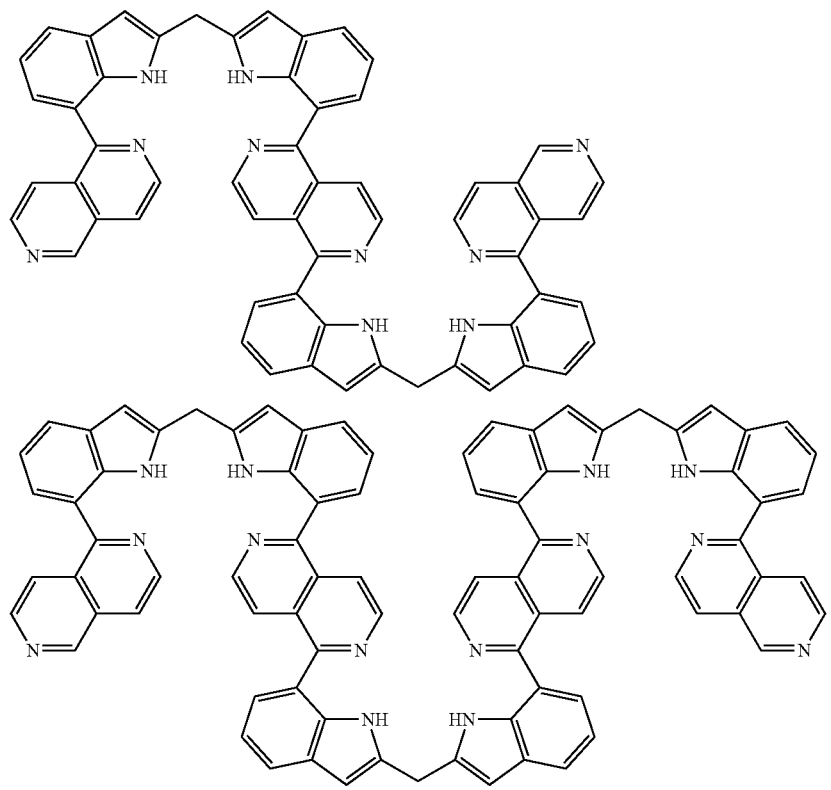

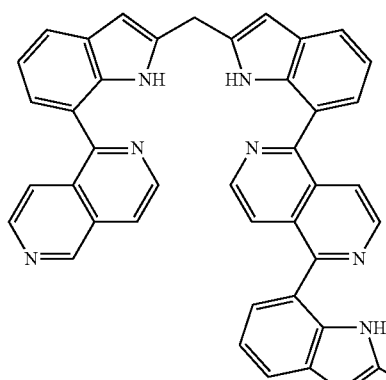
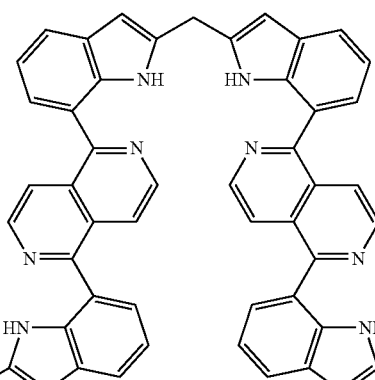
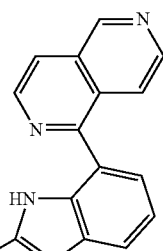
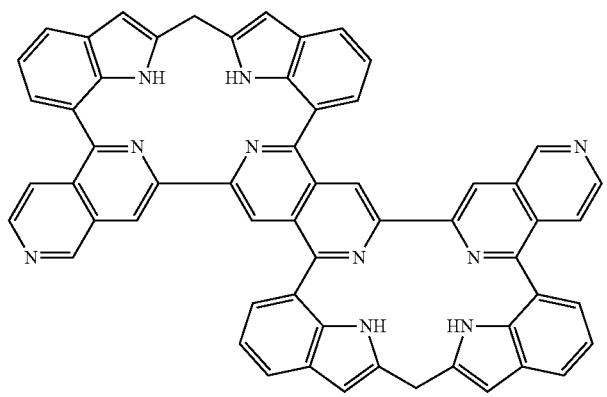
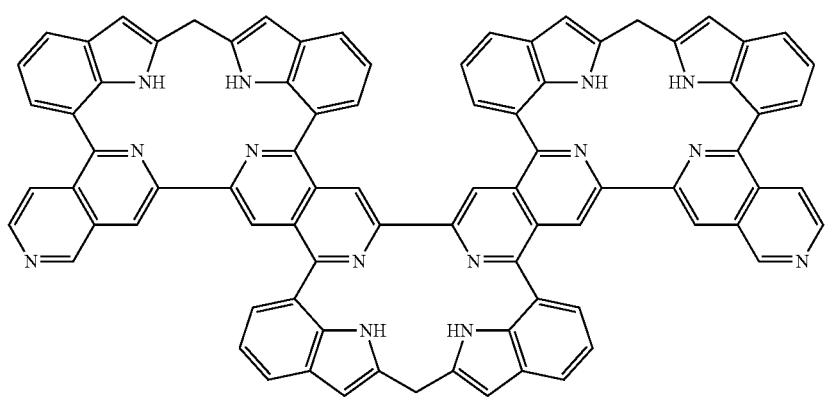

-continued
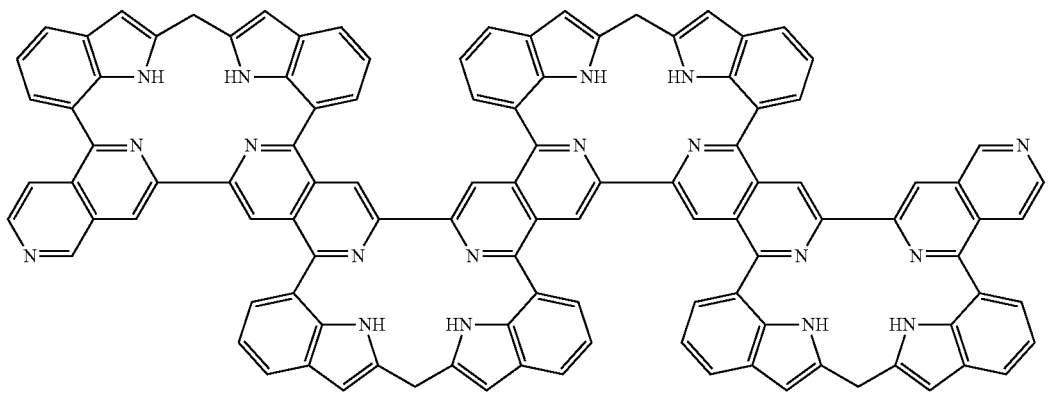

[Chemical Formula 39]
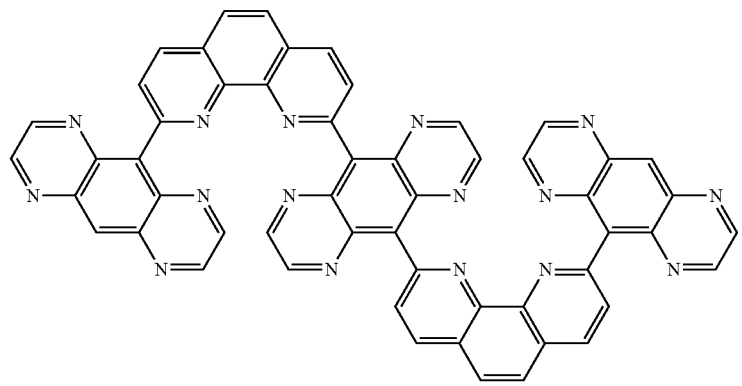
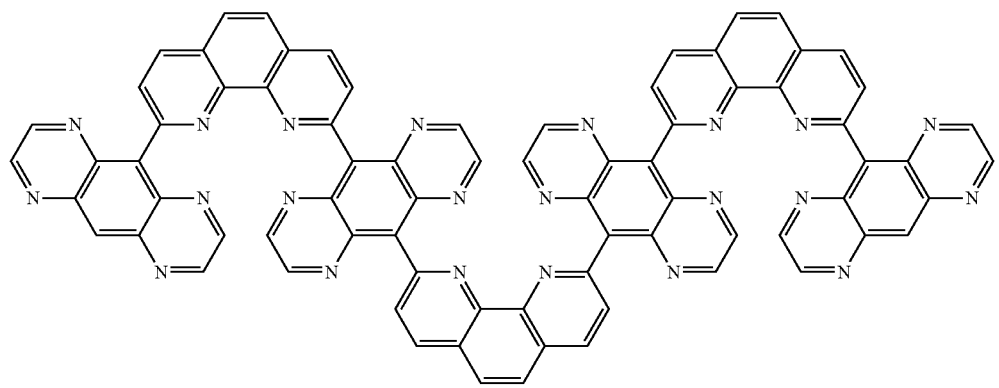
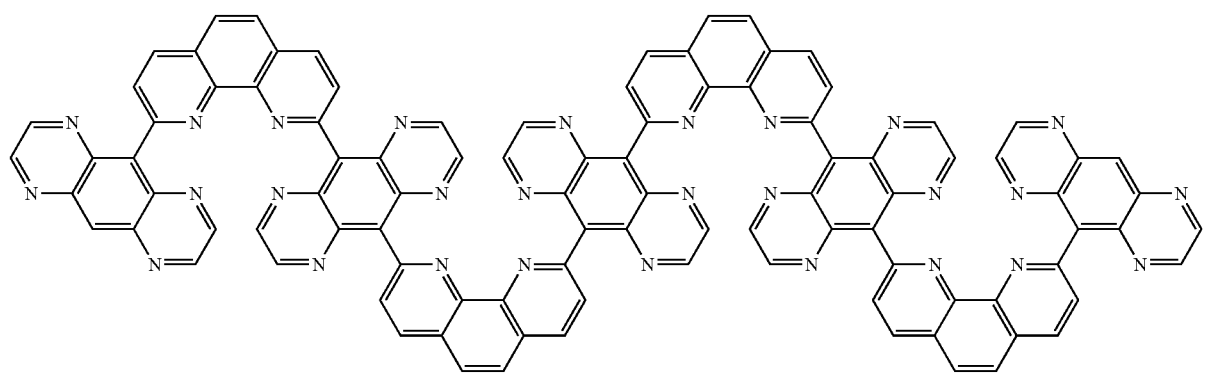

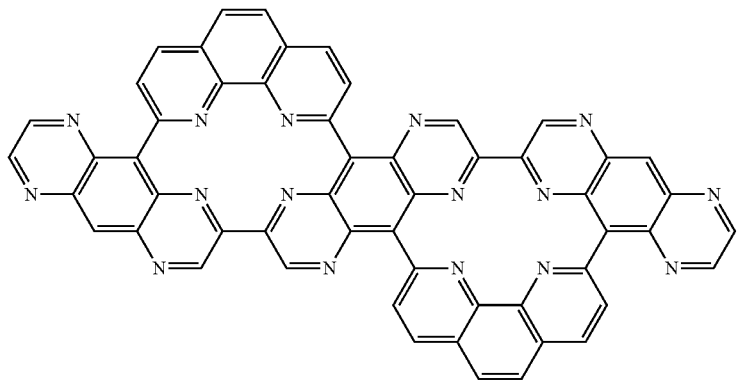
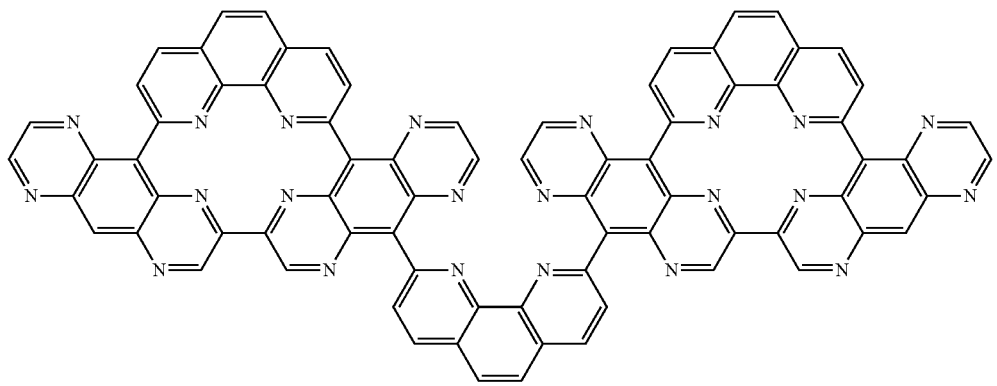
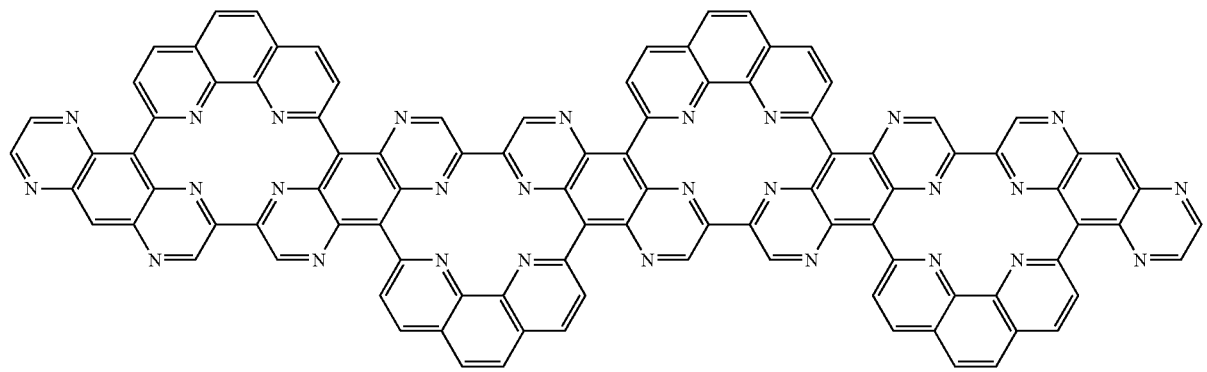
[Chemical Formula 40]

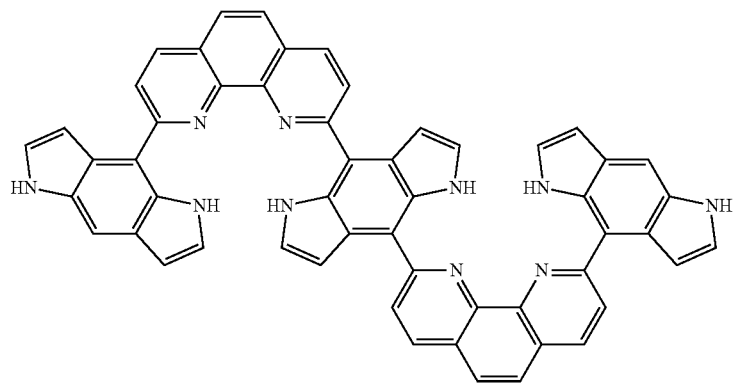
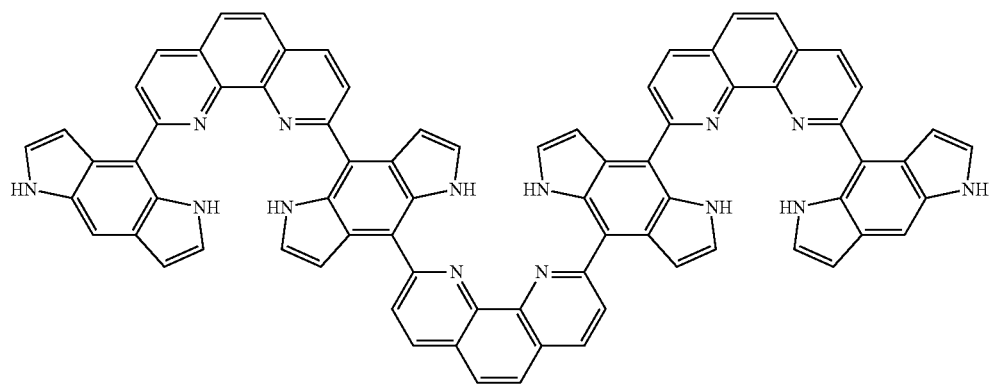
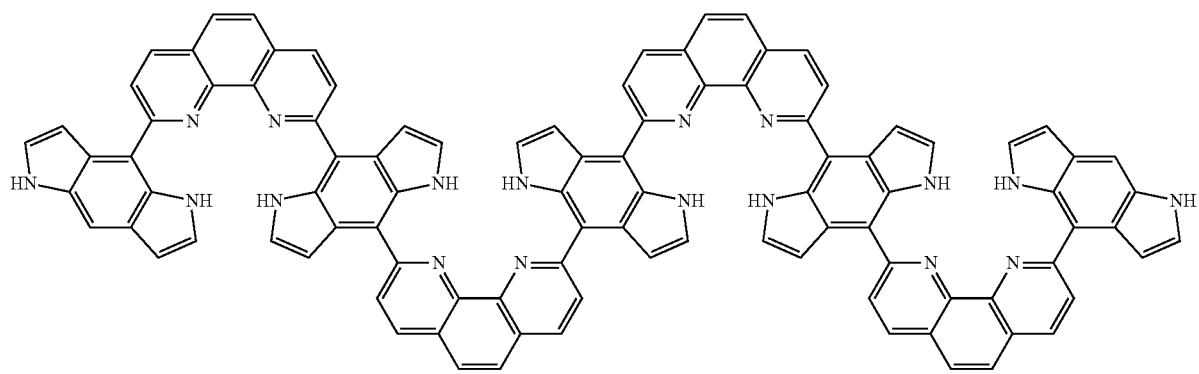
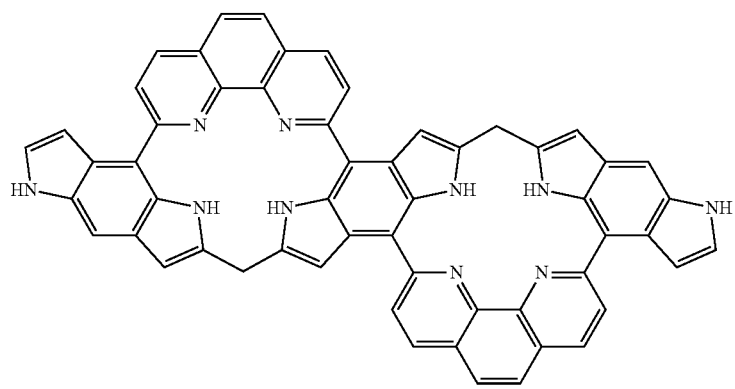

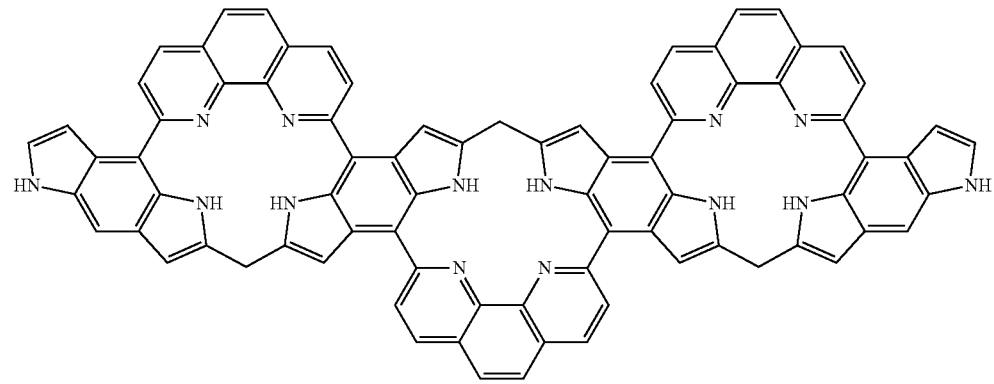
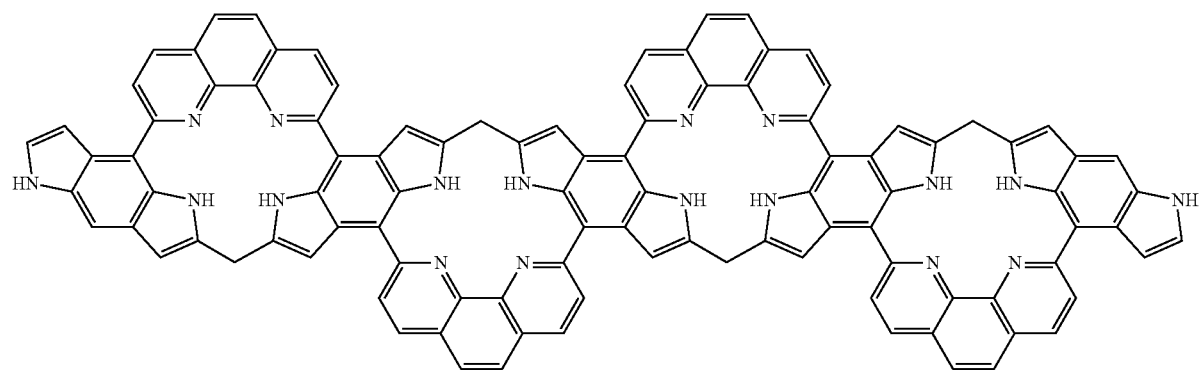
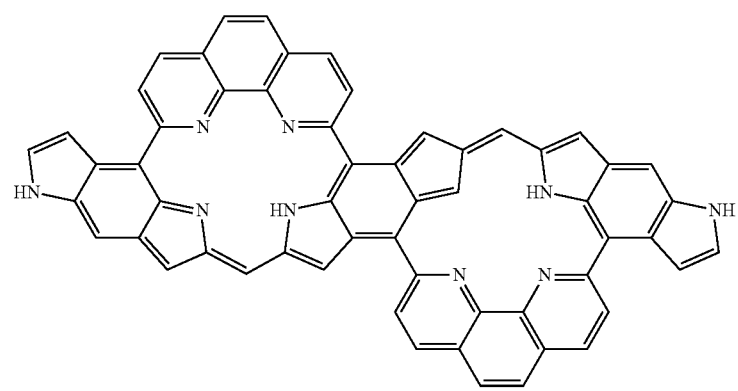
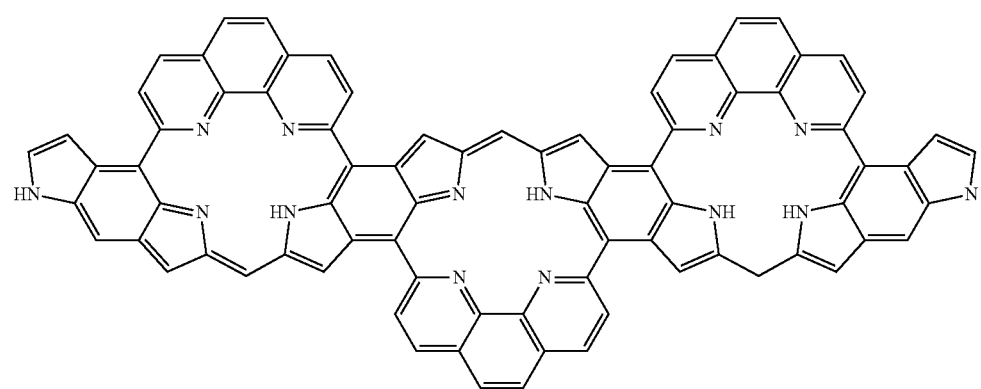

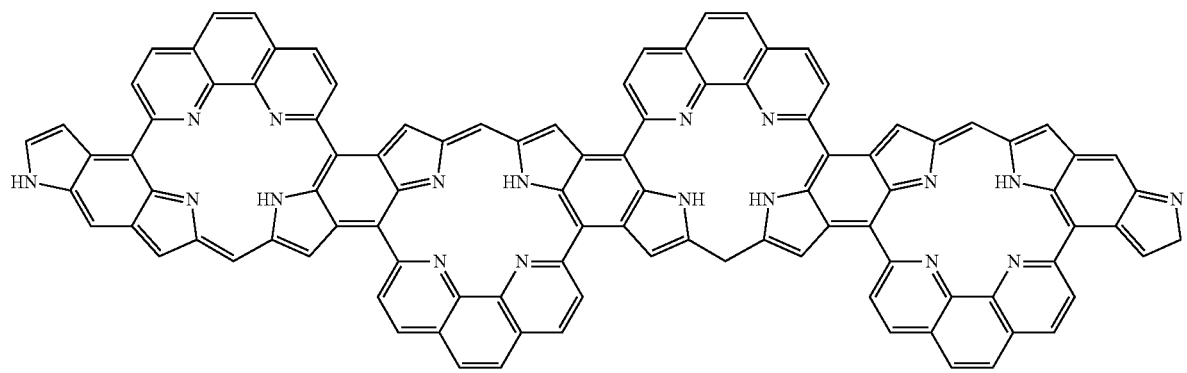 [SMILES: C1=c2c(cc3cc4cc5cc6c7c8[nH]c(cc8c(c8ccc9ccc%10ccc(nc%10c9n8)c2c3[nH]4)c6n5)Cc2cc3c([nH]2)c(c2cc4cc5cc6c(n5)c(c5ccc8ccc9ccc(nc9c8n5)c3c2[nH]4)c2cc3cc4cc5cc8[nH]ccc8c(c8ccc9ccc%10ccc(nc%10c9n8)c6c2[nH]3)c5n4)-c2ccc3ccc4ccc-7nc4c3n2)=NC1]
High molecular compounds having the following repeating units are also examples of aromatic compounds according to the invention.
[Chemical Formula 41]
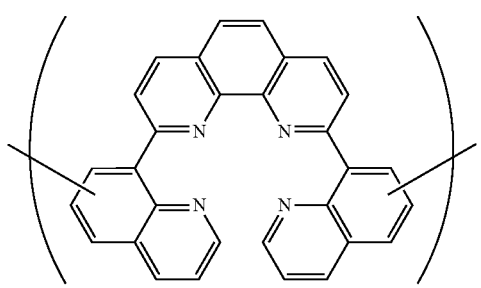
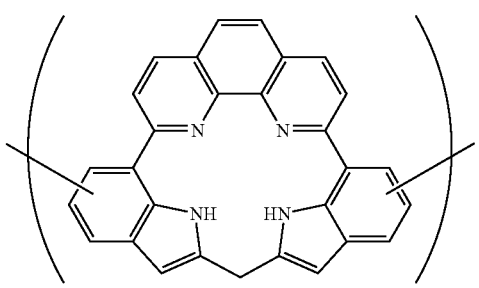
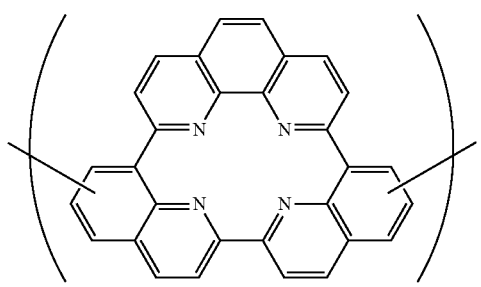
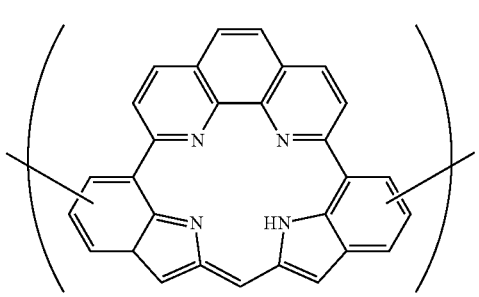
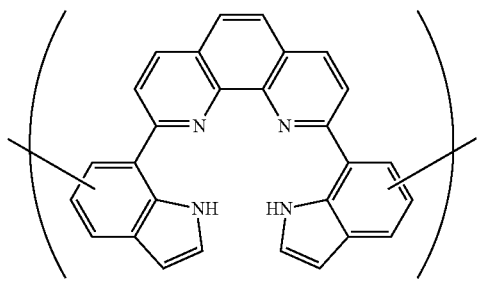

[Chemical Formula 42]
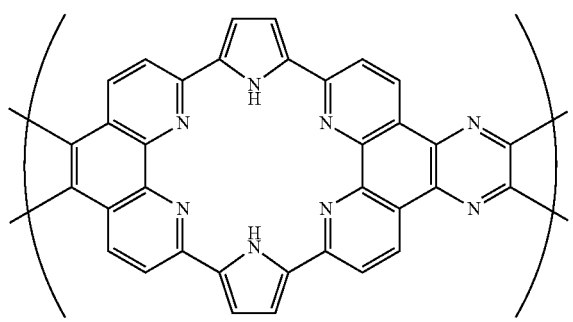
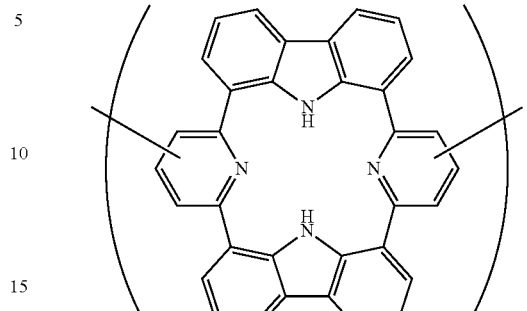
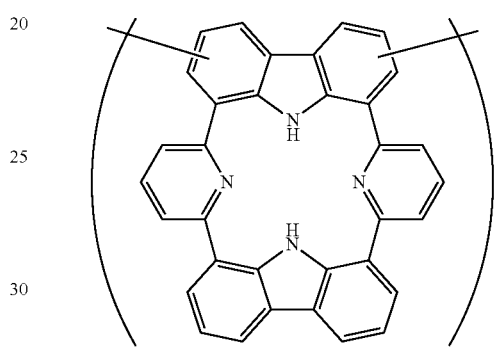
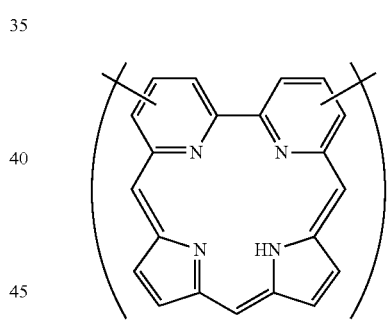
[Chemical Formula 43]
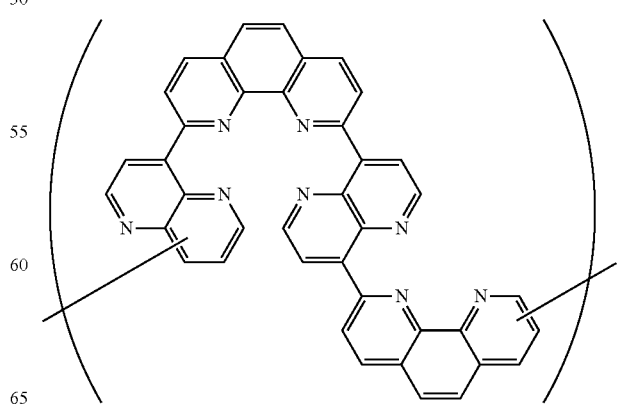

-continued

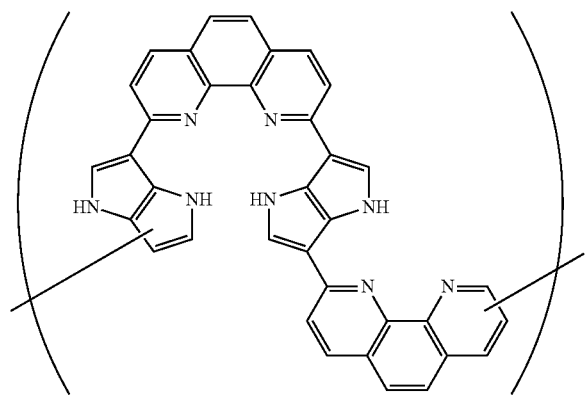

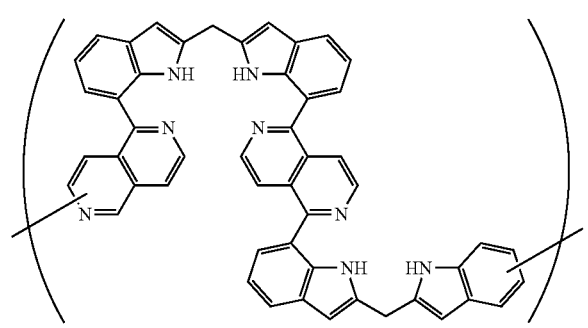

[Chemical Formula 44]

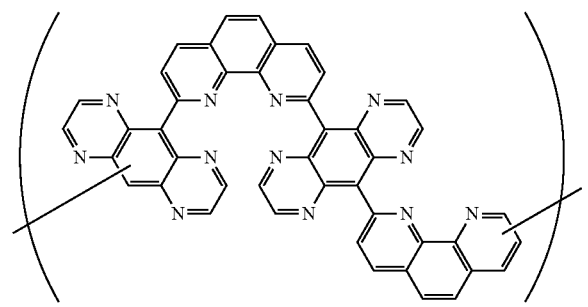

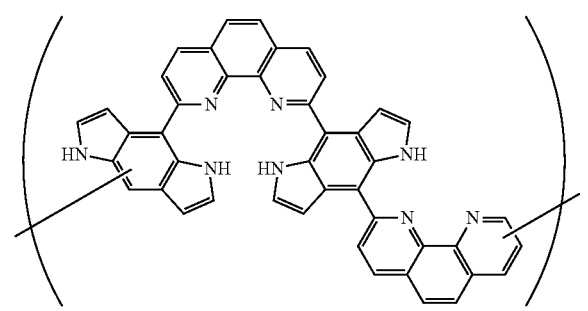

[The hydrogens in these formulas may also be substituted with the aforementioned substituents, and adjacent two hydrogen bonding may be eliminated to form direct-bonding or linking group.]

When the aromatic compound of the invention is a high molecular compound, the number-average molecular weight of the high molecular compound based on polystyrene will normally be from $1 \times 10^3$ to $1 \times 10^8$ and preferably from $2 \times 10^3$ to $1 \times 10^6$, and the weight-average molecular weight based on polystyrene will normally be from $2 \times 10^3$ to $1 \times 10^8$ and preferably from $3 \times 10^3$ to $2 \times 10^6$.

<Metal Complex>

The aromatic compound of the invention may coordinate with a metal atom or metal ion to form a metal complex. As metal atoms and metal ions there may be used metal atoms of alkali metals, alkaline earth metals and transition metals, as well as ions derived therefrom, but most preferred are transition metals from period 4 to period 6 of the Periodic Table and their ions. Specifically, there may be mentioned scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold and mercury atoms and ions, preferably titanium, vanadium, chromium, manganese, iron, cobalt, nickel, copper, zinc, zirconium, niobium, molybdenum, ruthenium, rhodium, palladium, silver, tantalum, tungsten, rhenium, osmium, iridium, platinum and gold atoms and ions, more preferably titanium, vanadium, chromium, manganese, iron, cobalt, nickel, copper, zinc, zirconium, niobium, molybdenum, ruthenium, rhodium, palladium and silver atoms and ions, and most preferably vanadium, chromium, manganese, iron, cobalt, nickel, copper and zinc atoms and ions. The metal atoms or metal ions may be of a single type, or a combination of different types of metal atoms or metal ions may be used.

The metal ions will generally have a positive electrical charge, and therefore the metal complex of the invention may contain an anion to electrically neutralize the metal complex as a whole. As counter ions there may be mentioned inorganic ions such as fluoride ion, chloride ion, bromide ion, iodide ion, sulfide ion, oxide ion, hydroxide ion, hydride ion, sulfite ion, phosphate ion, cyanide ion, acetate ion, carbonate ion, sulfate ion, nitrate ion and hydrogencarbonate ion, and organic acid ions such as trifluoroacetate ion, thiocyanide ion, trifluoromethanesulfonate ion, acetylacetonate ion, tetrafluoroborate ion, hexafluorophosphorate ion, tetraphenylborate ion, phenolate, picolinate ion and their derivative ions, and preferred are chloride ion, bromide ion, iodide ion, oxide ion, hydroxide ion, hydride ion, phosphate ion, cyanide ion, acetate ion, carbonate ion, sulfate ion, nitrate ion, acetylacetonate ion and tetraphenylborate ion. When several counter ions are present, they may be the same or different.

Examples of metal complexes of the invention include the following metal complexes and high molecular compounds having repeating units represented by the following formulas. The hydrogens in the formulas may be substituted with the aforementioned substituents. The molecular weight of the metal complex of the invention will be proportional to the molecular weight of the aromatic compound.

[Chemical Formula 45]
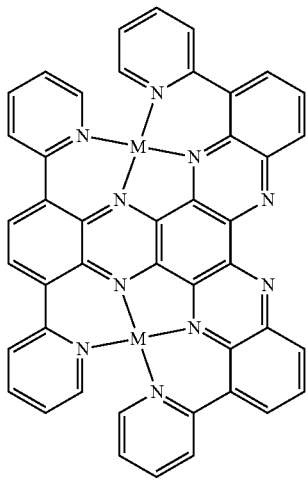
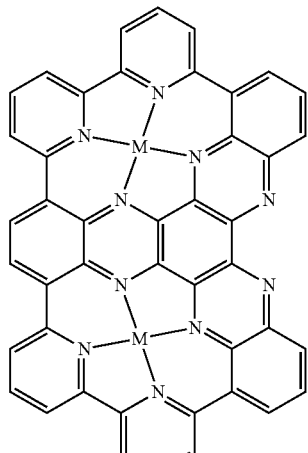
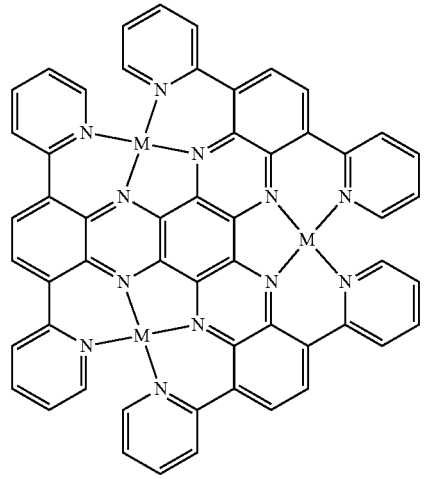
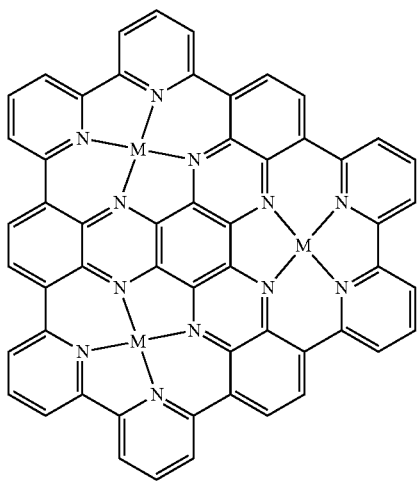
[Chemical Formula 46]
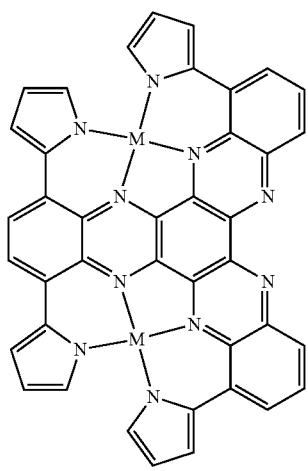
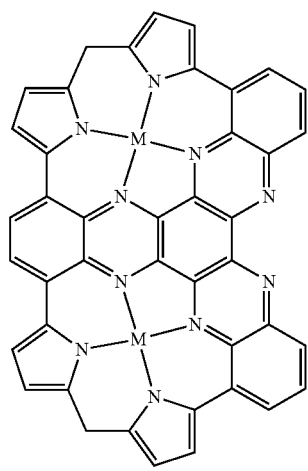
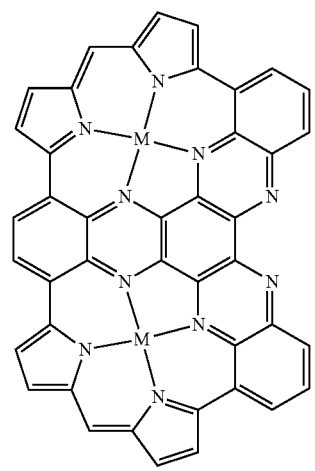

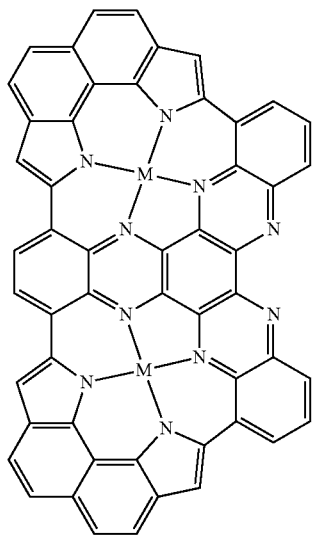
[Chemical Formula 47]
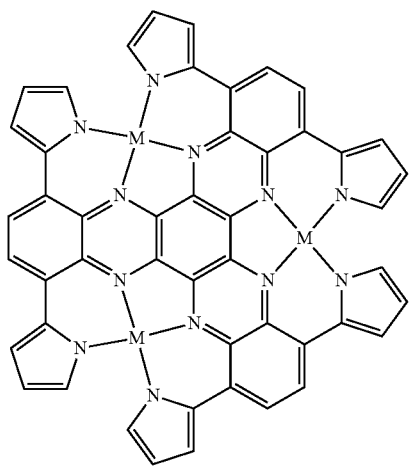 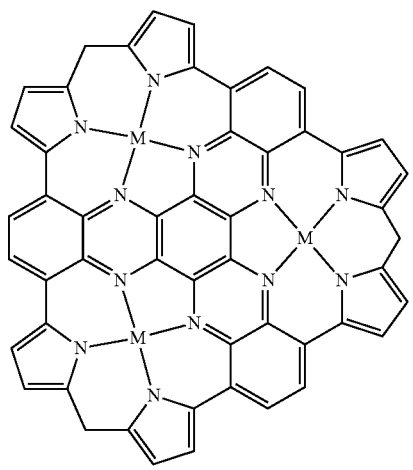
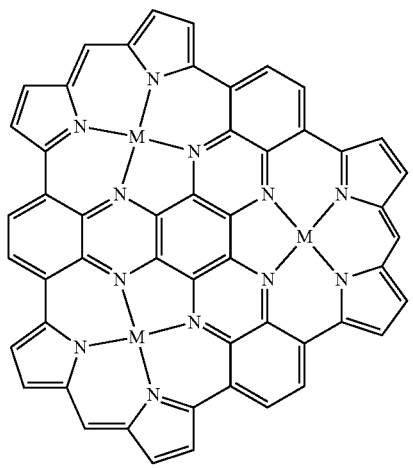 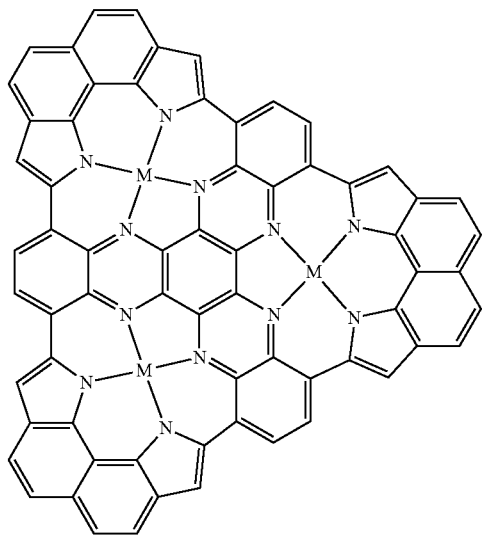

[Chemical Formula 48]
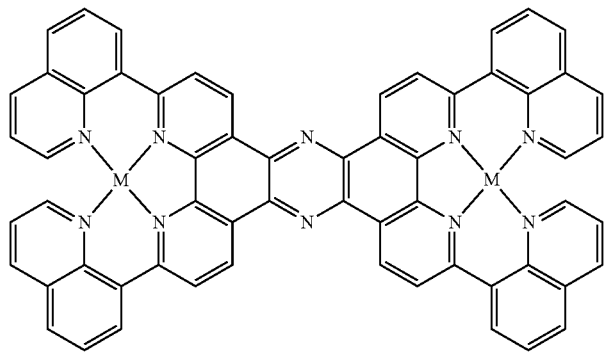
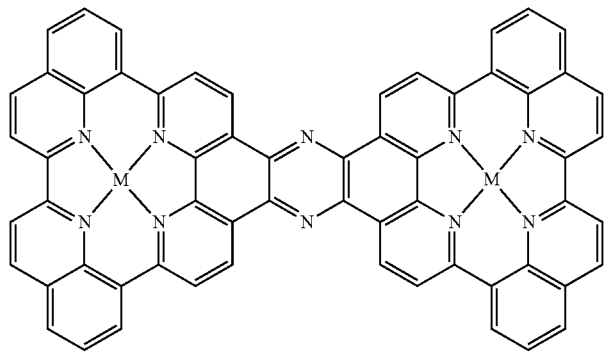
[Chemical Formula 49]
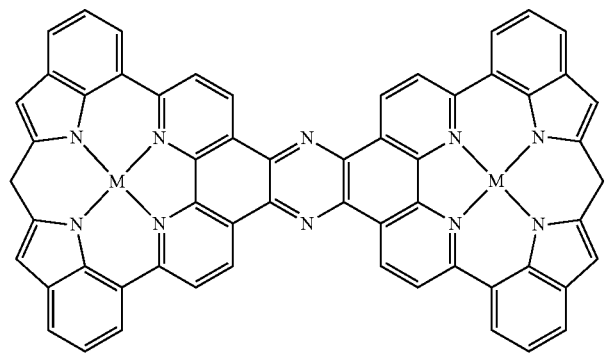
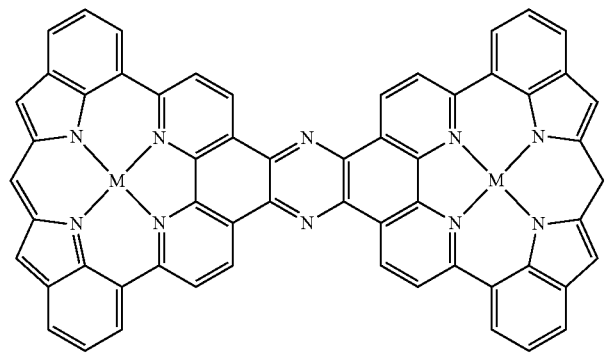

-continued
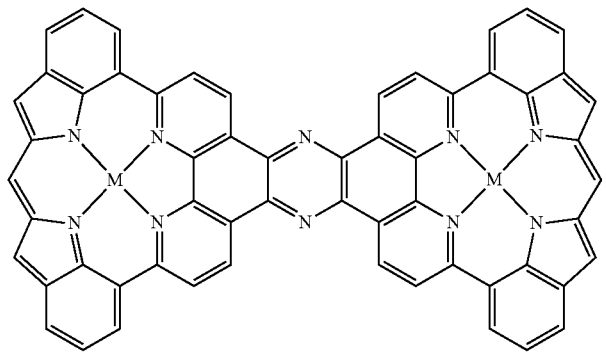
[Chemical Formula 50]
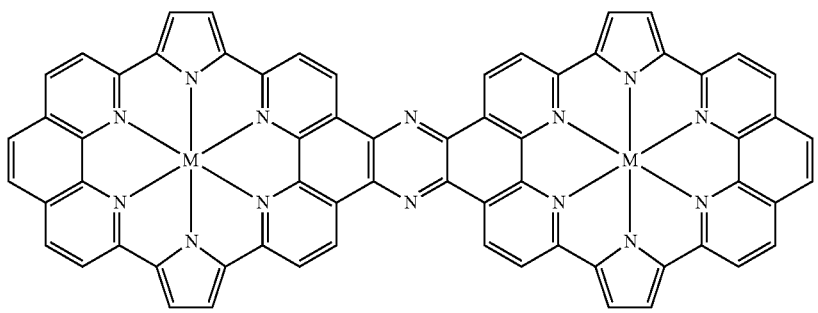
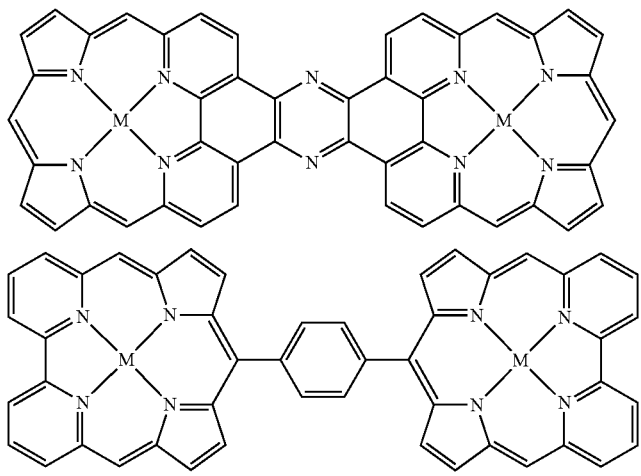
[Chemical Formula 51]
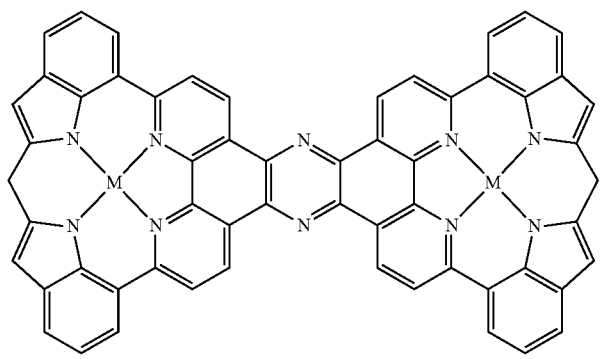

-continued
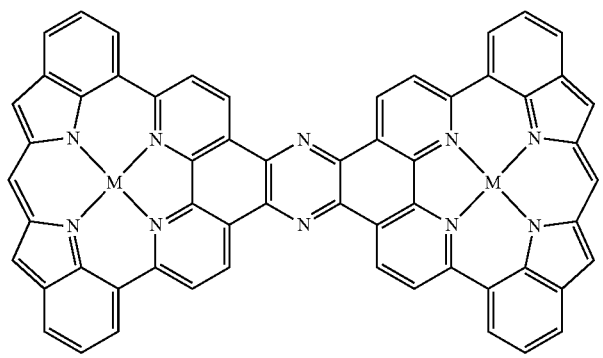
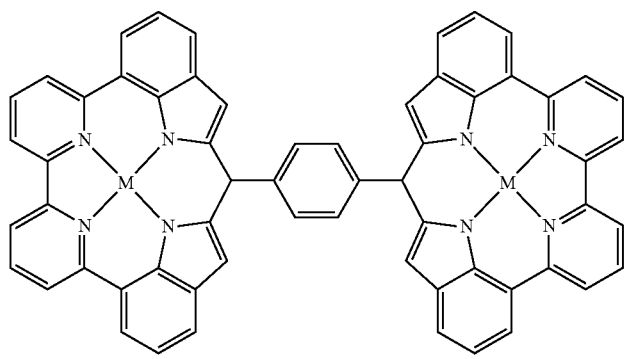
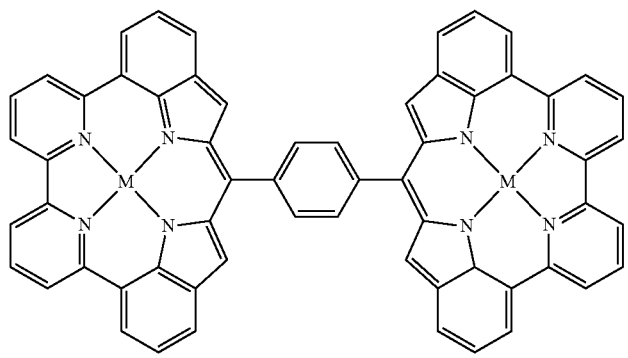
[Chemical Formula 52]
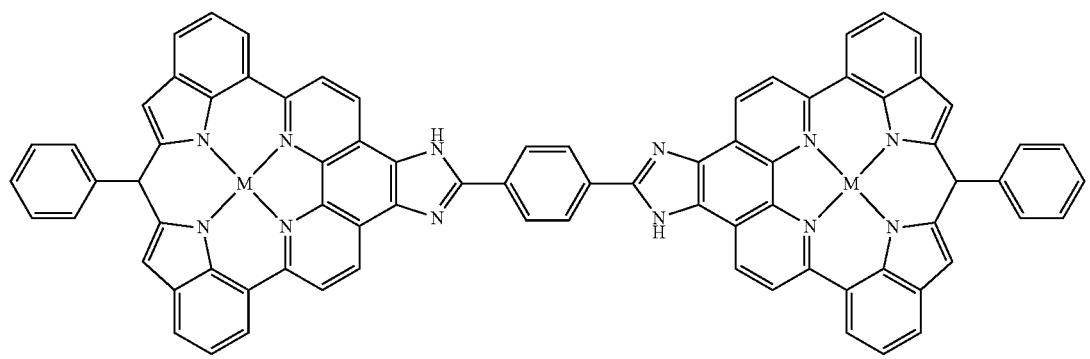

95 96
-continued
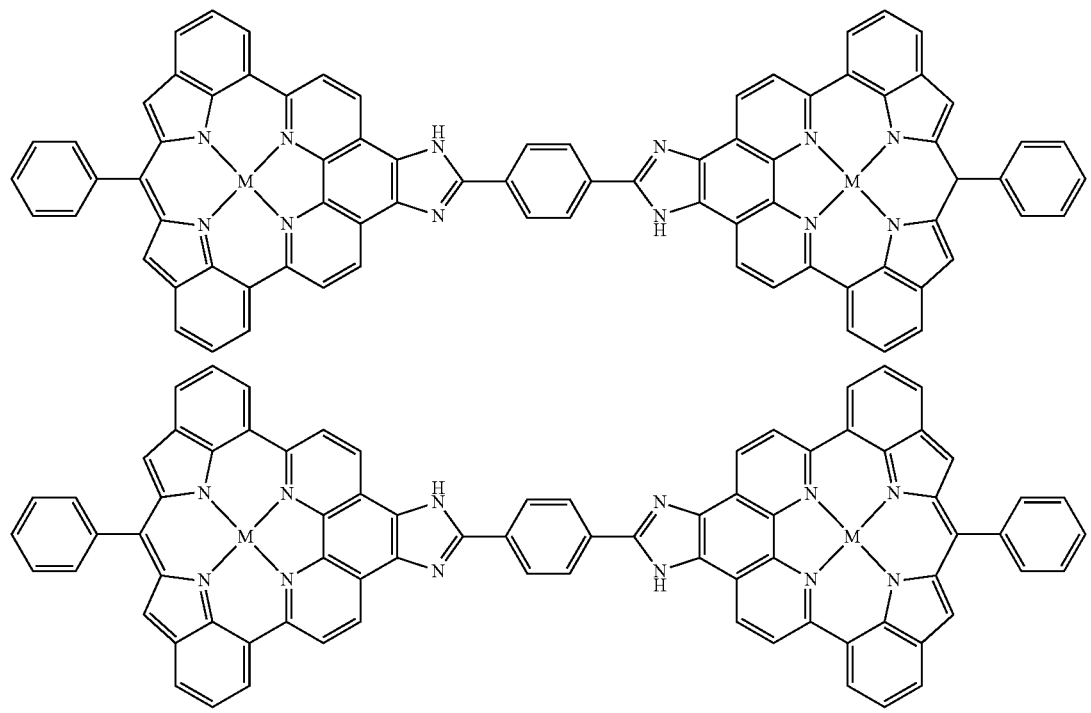
[Chemical Formula 53]
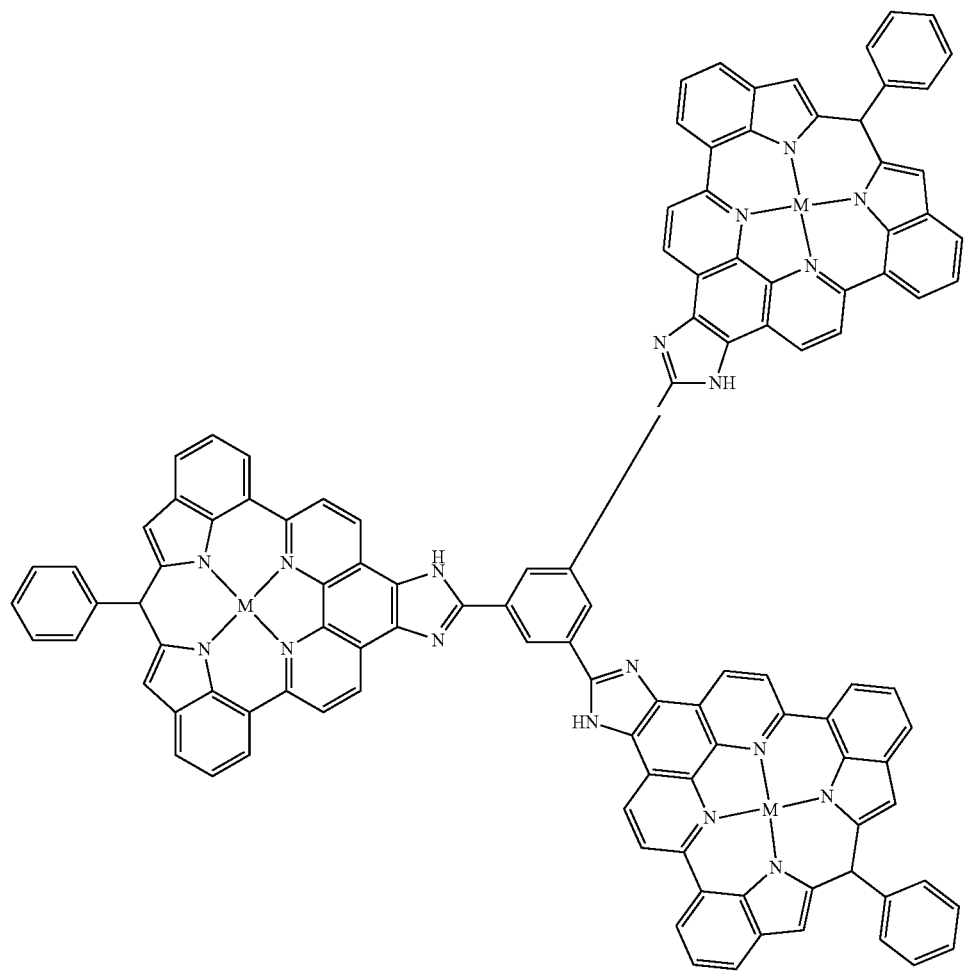

-continued
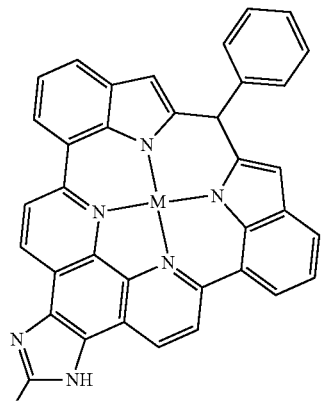
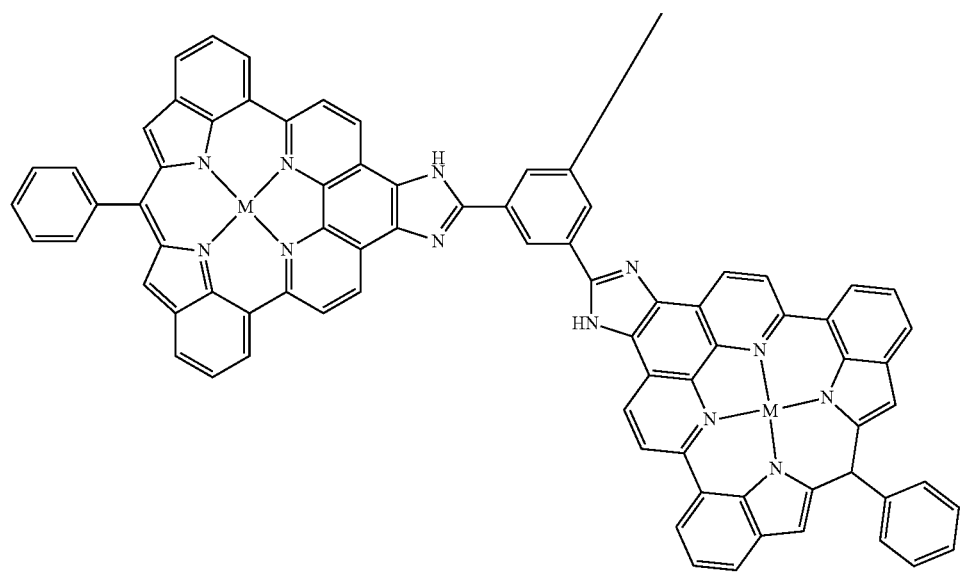
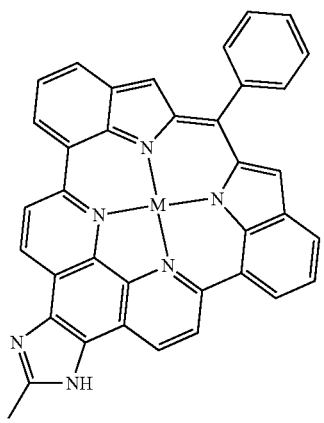

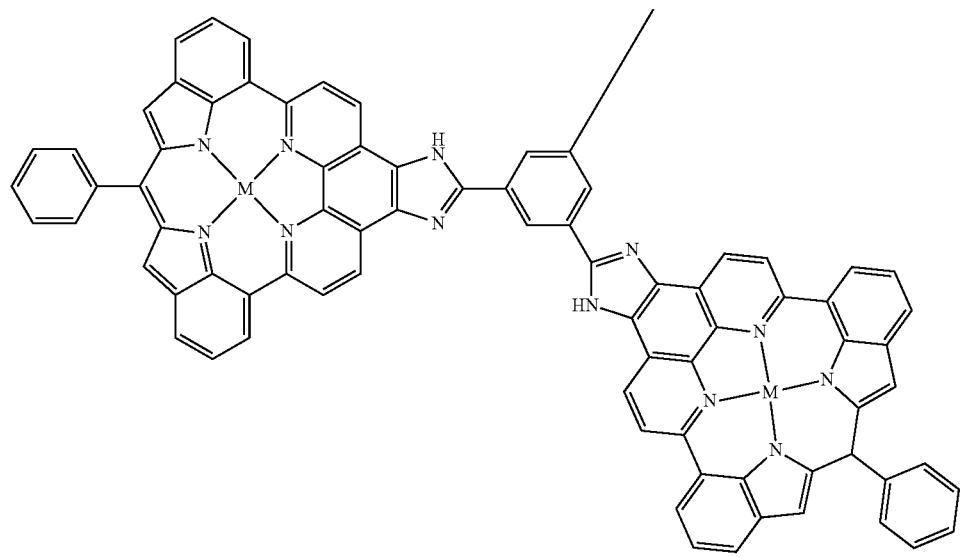
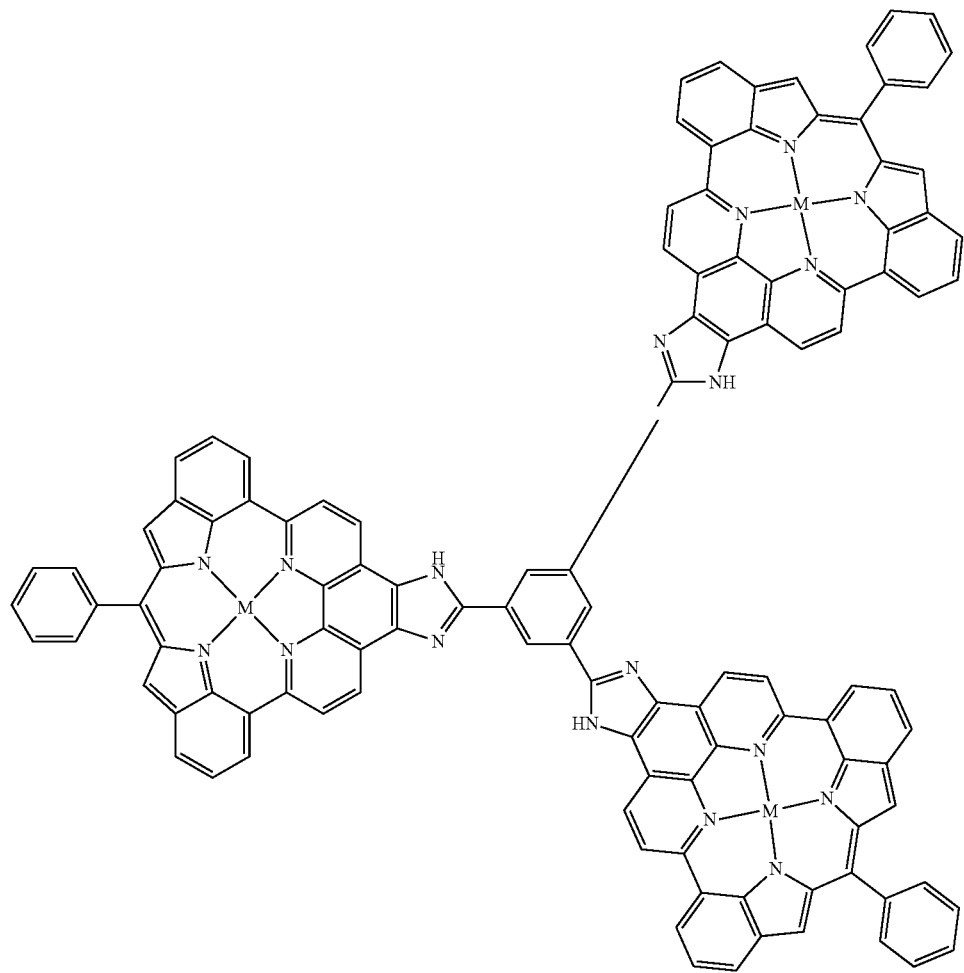

[Chemical Formula 54]
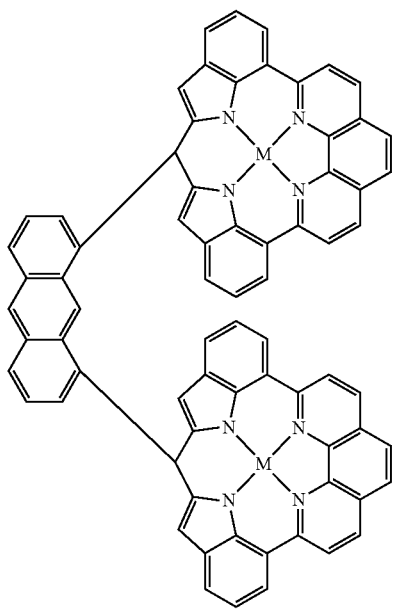
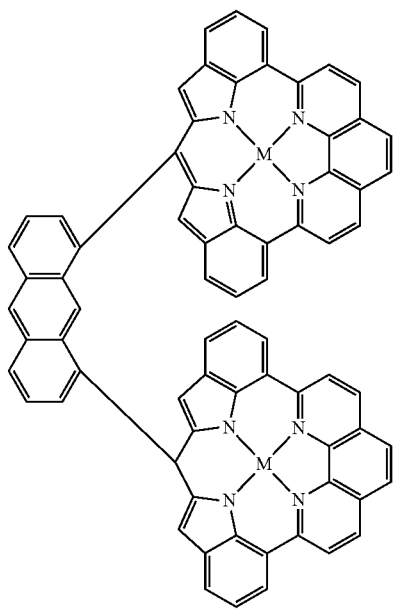
-continued
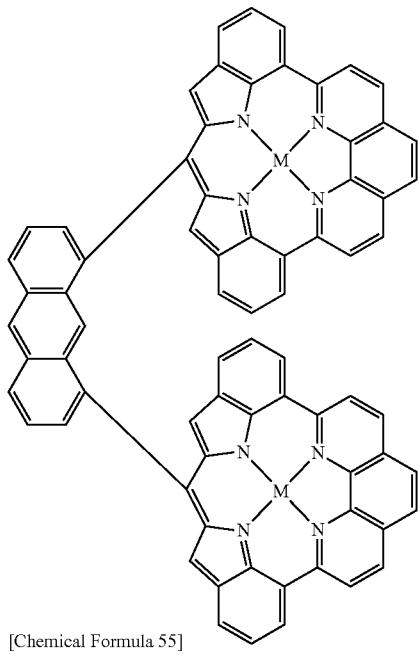
[Chemical Formula 55]
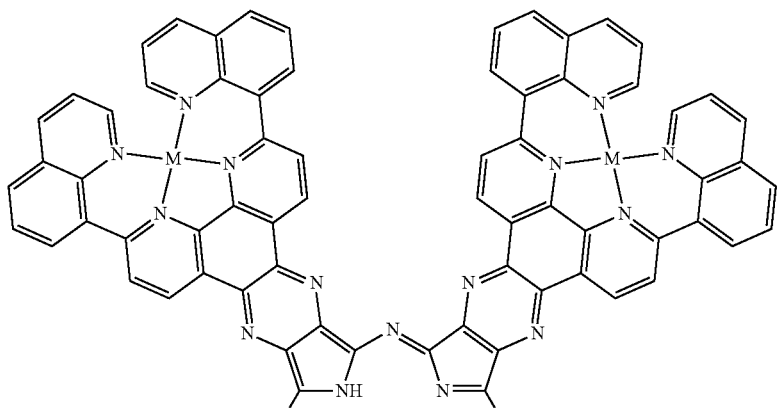

-continued
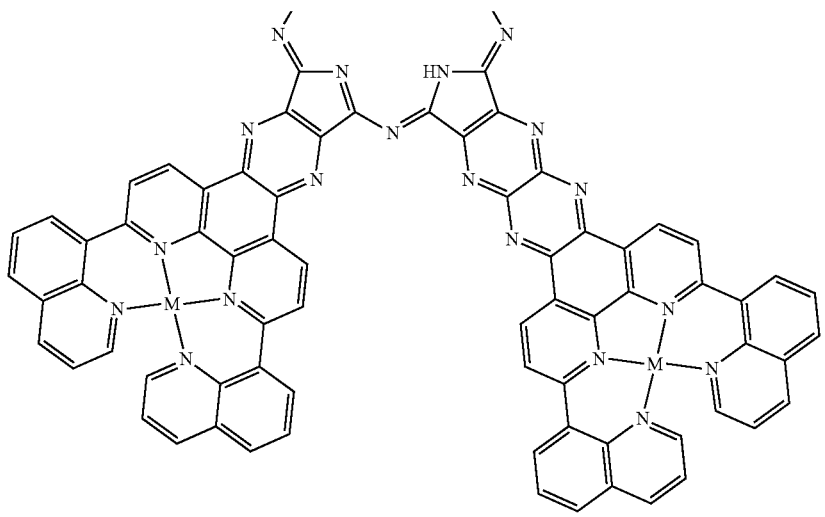
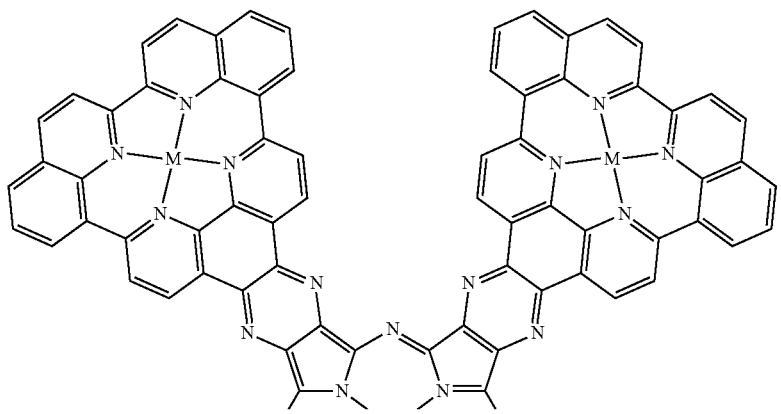
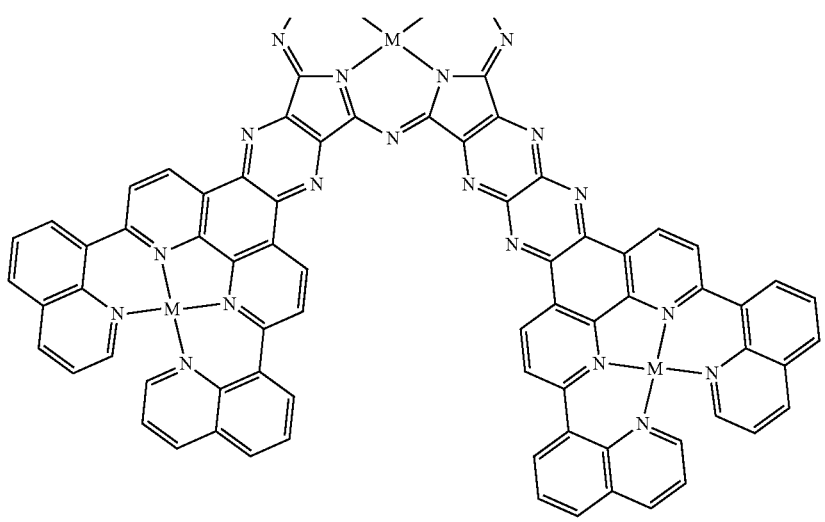

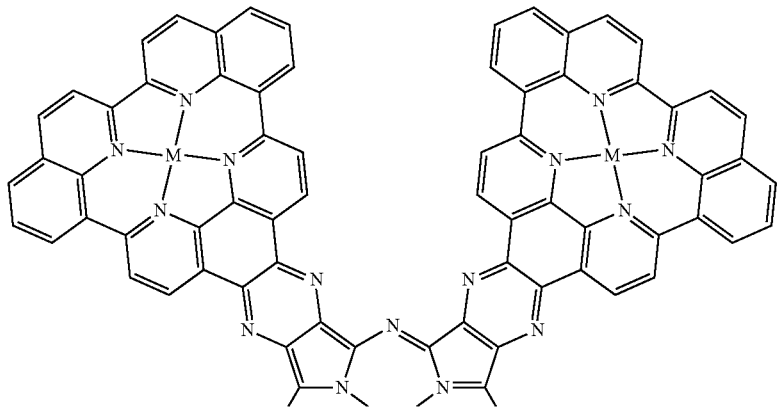
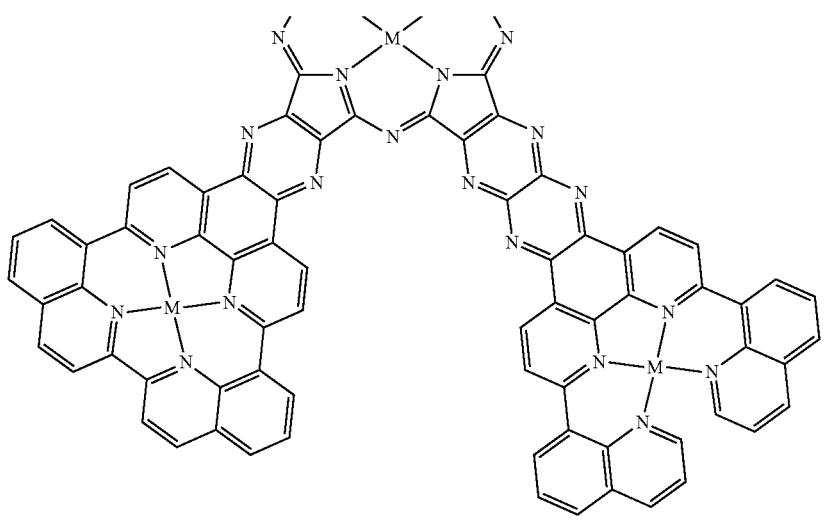
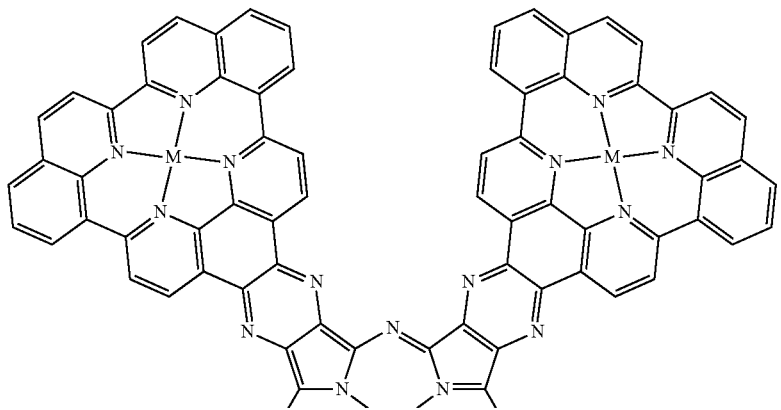

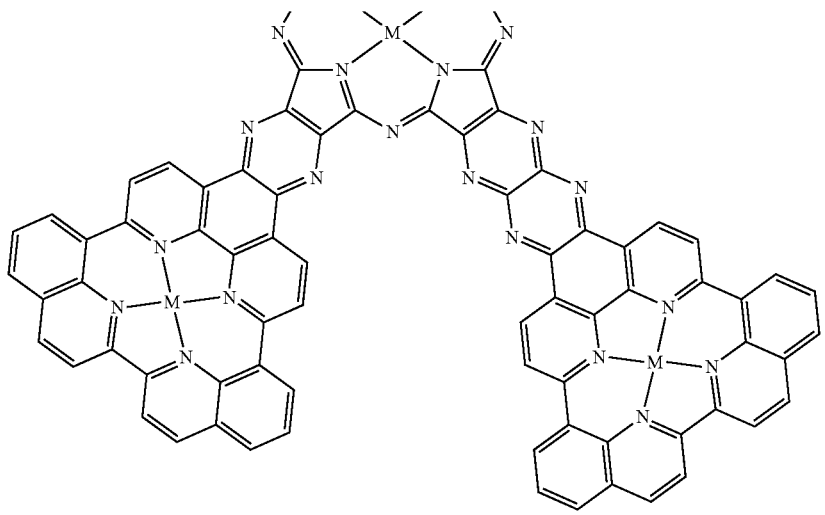
[Chemical Formula 56]
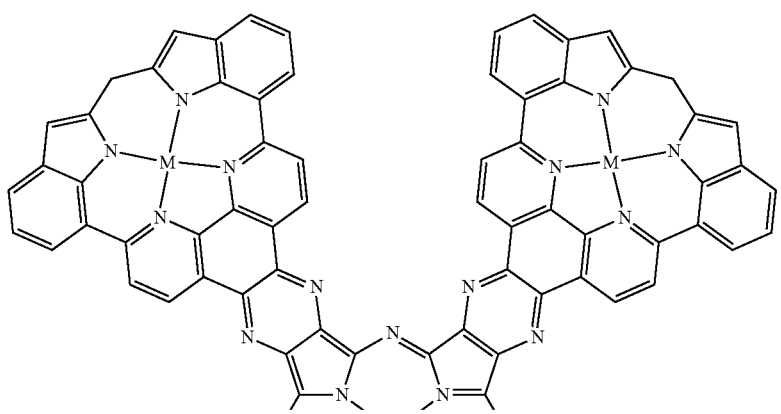
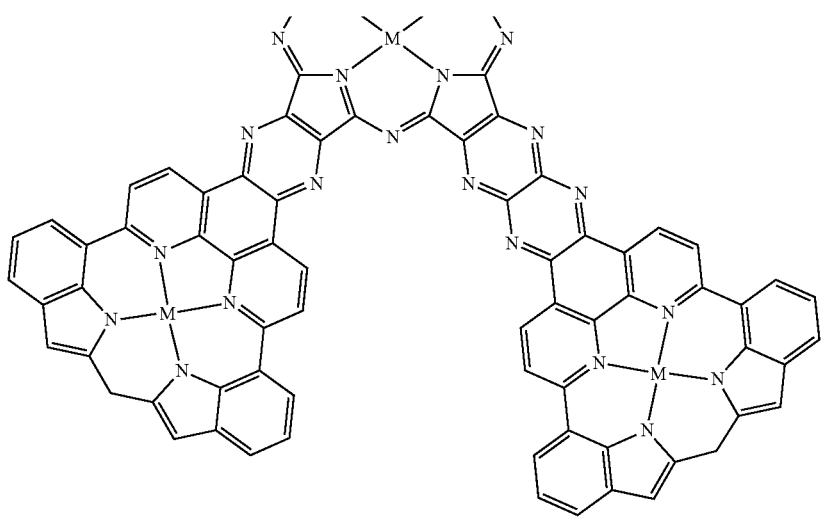

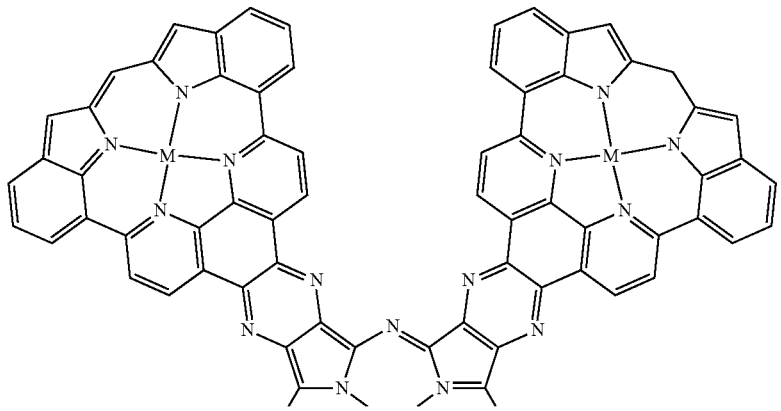
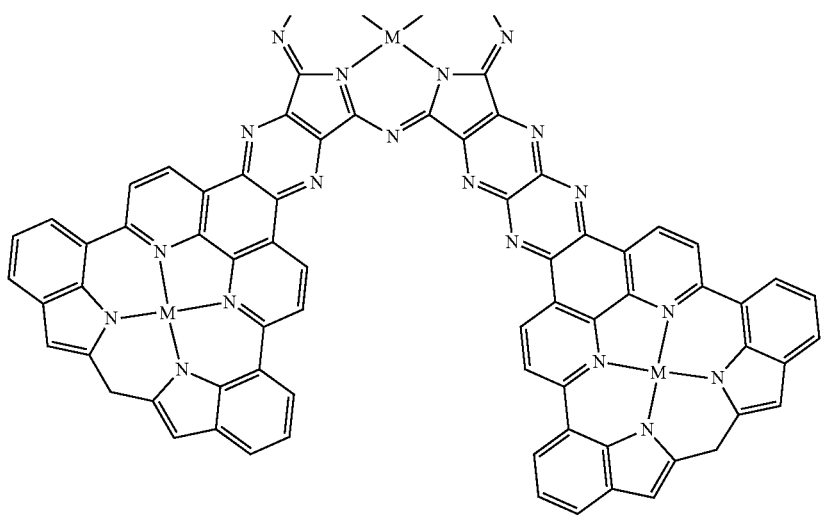
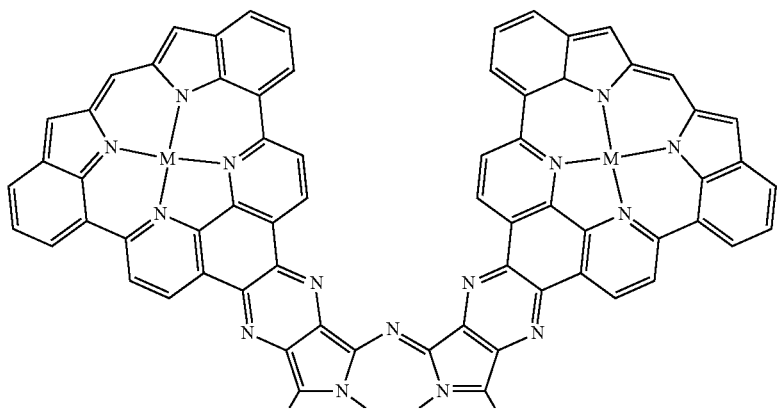

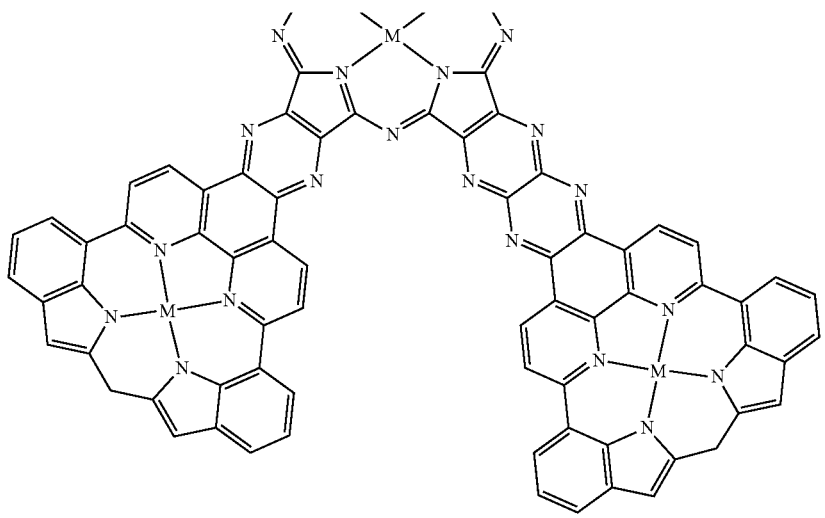
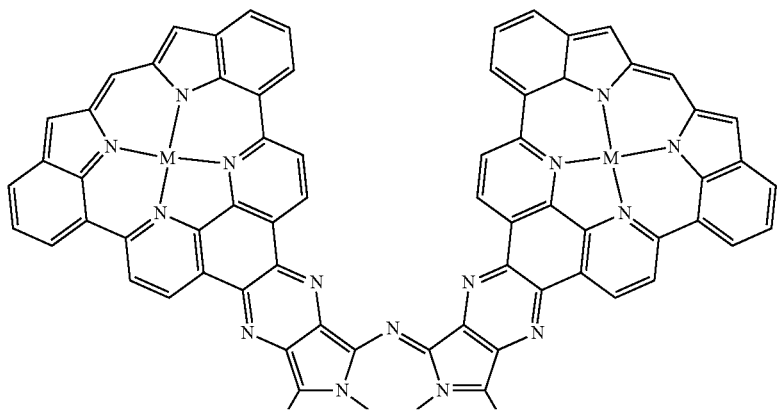
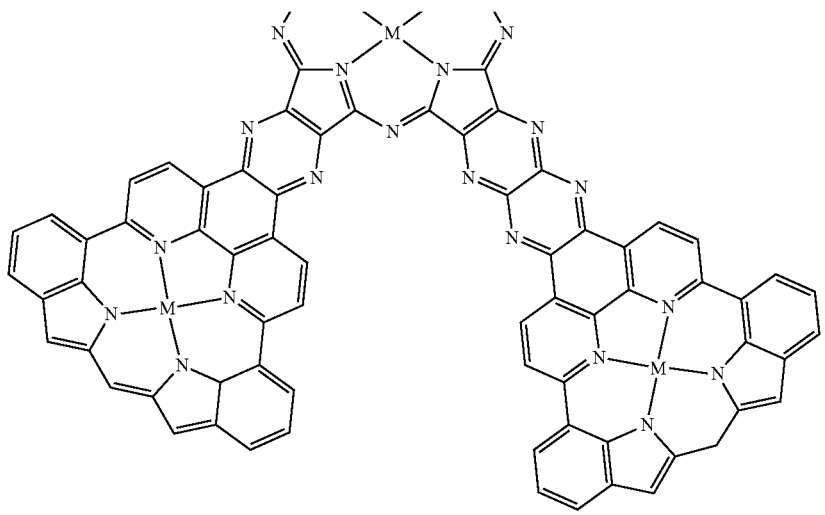

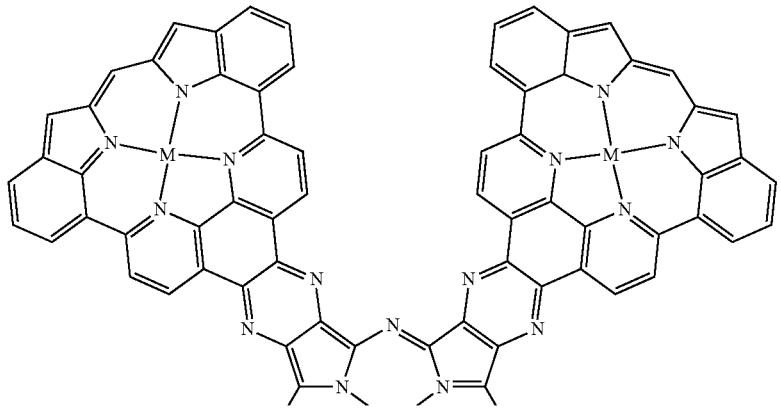
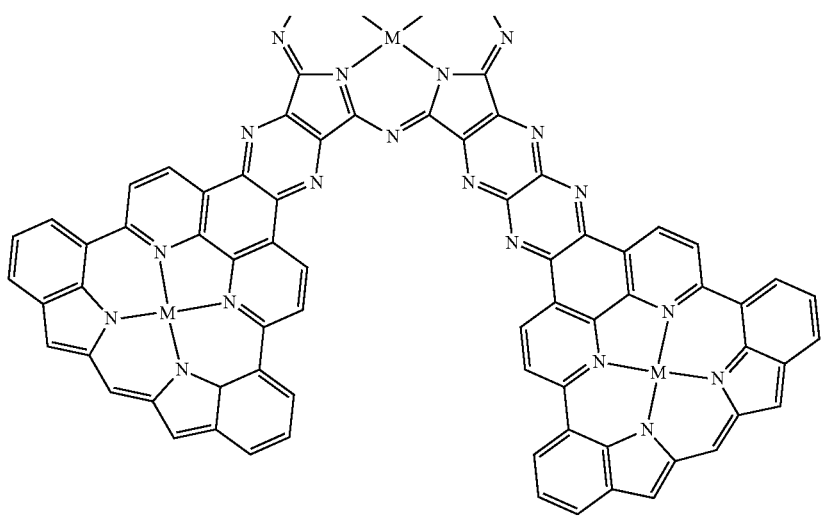
[Chemical Formula 57]
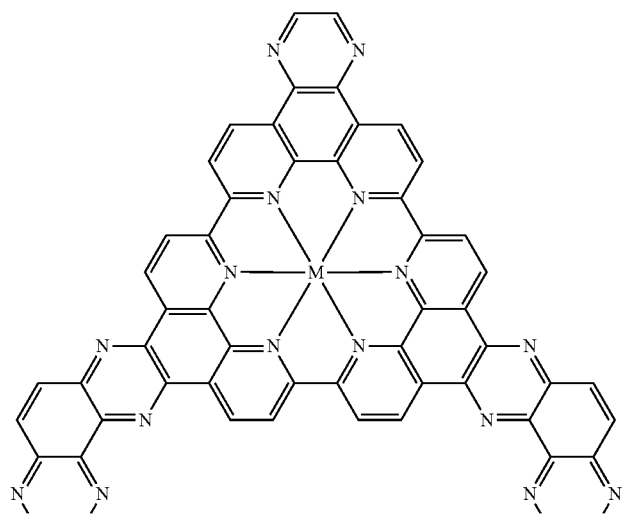

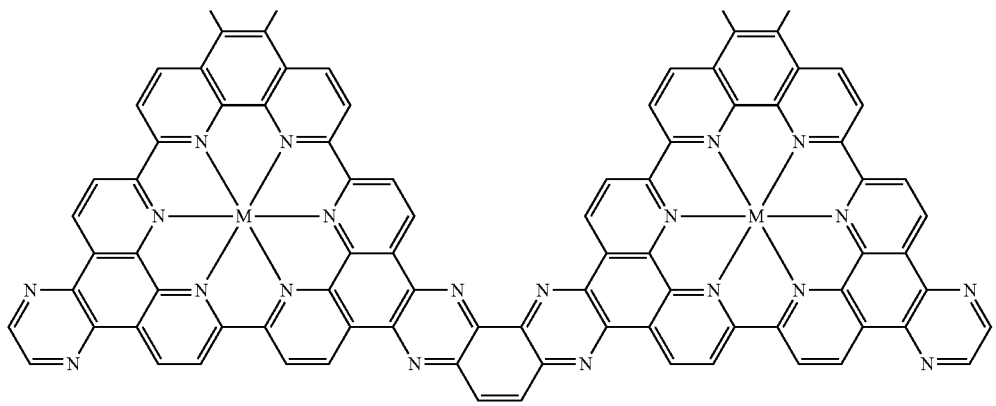
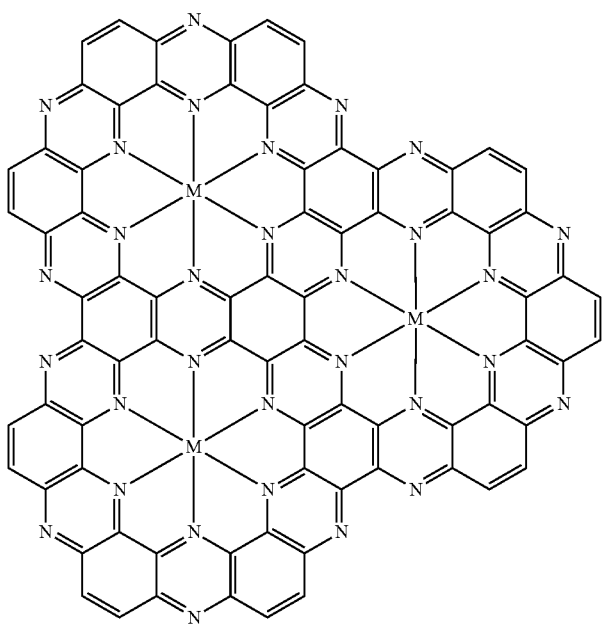
[Chemical Formula 58]
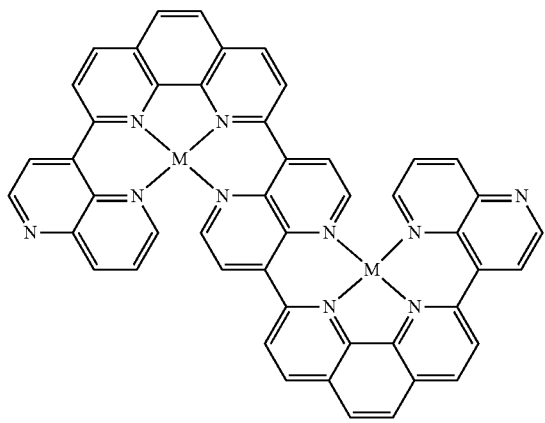

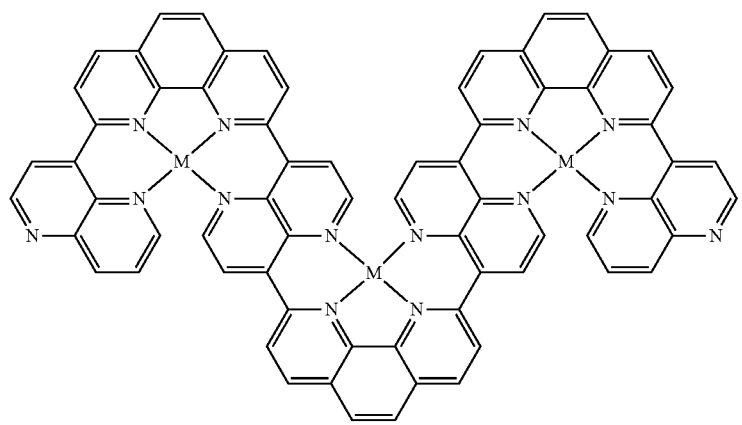
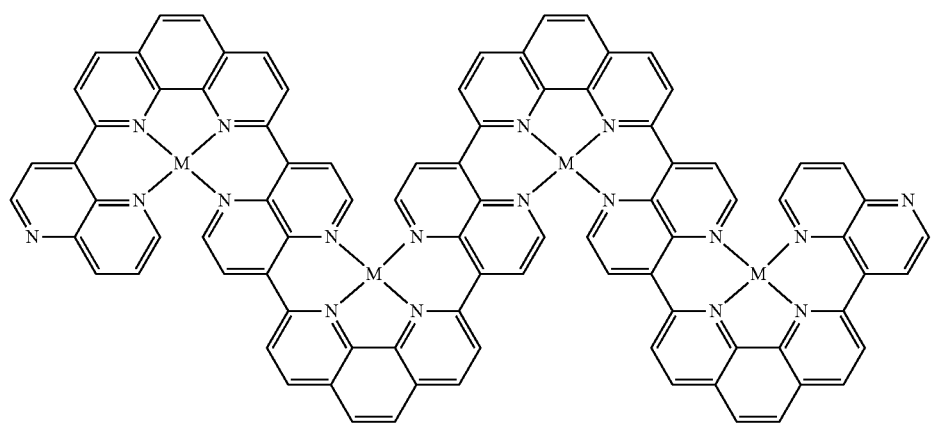
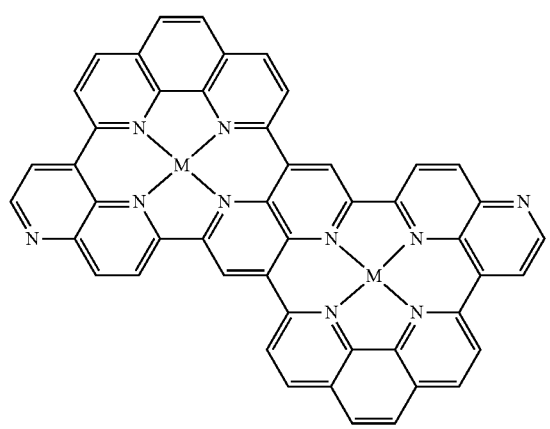
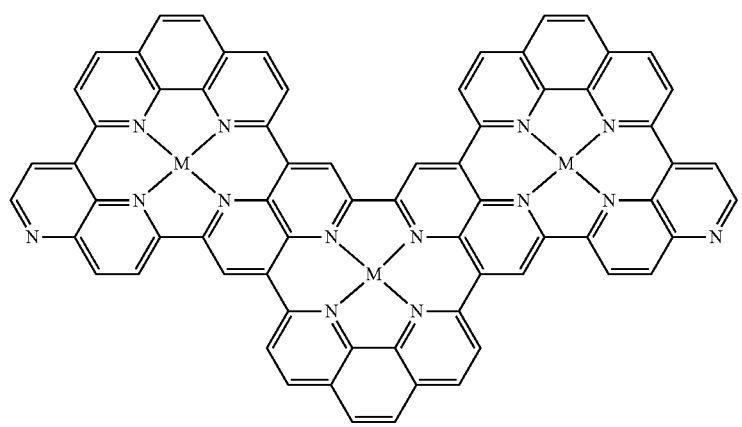

-continued
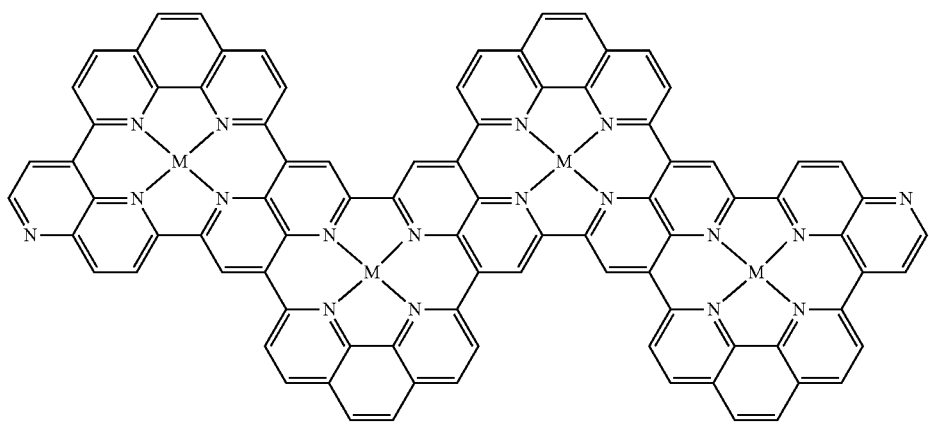
[Chemical Formula 59]
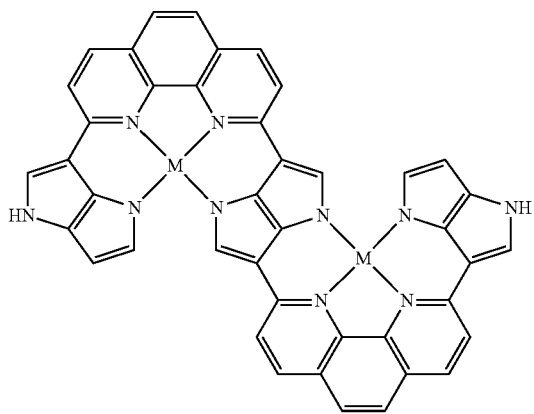
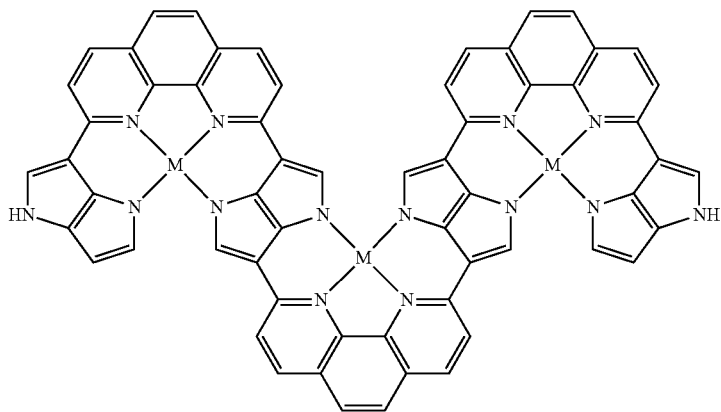
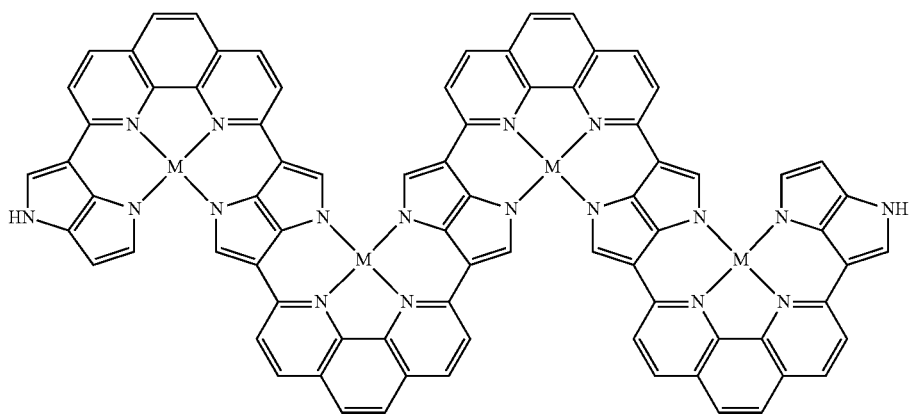

-continued
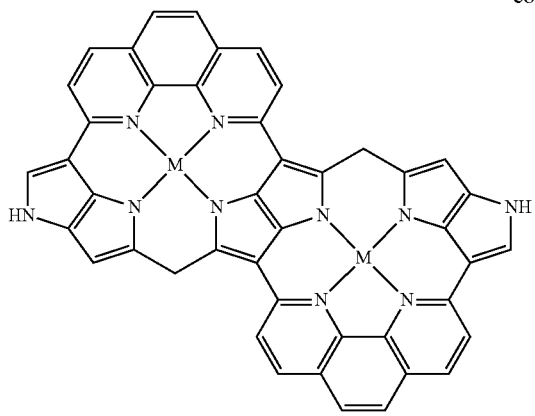
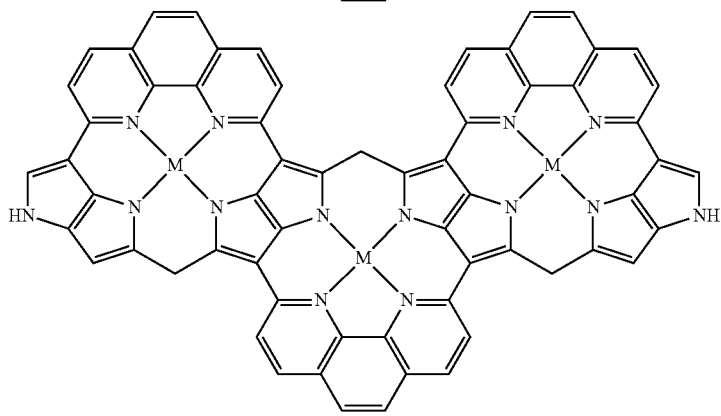
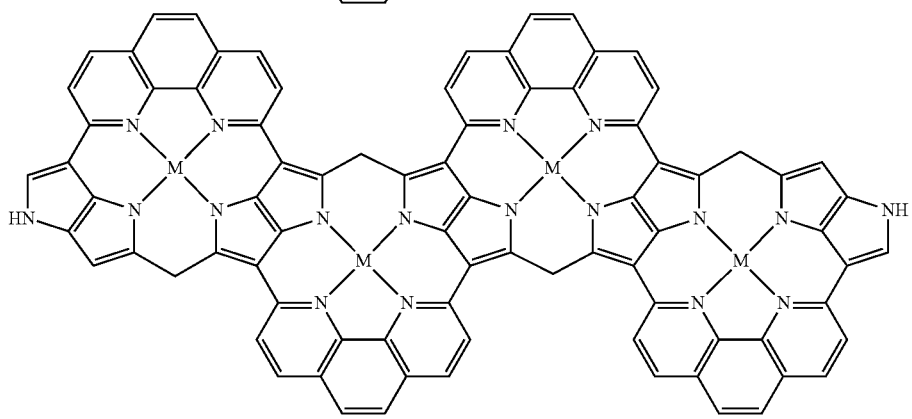
[Chemical Formula 60]
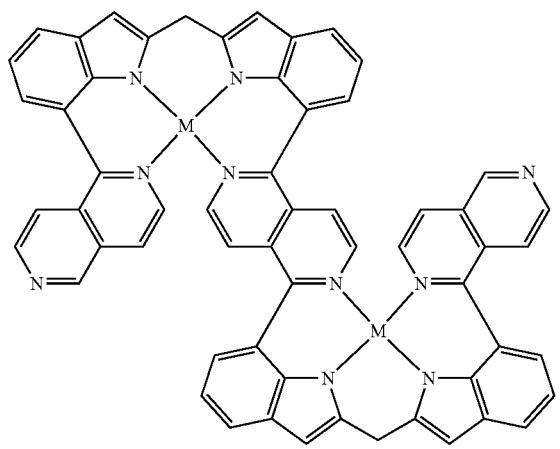

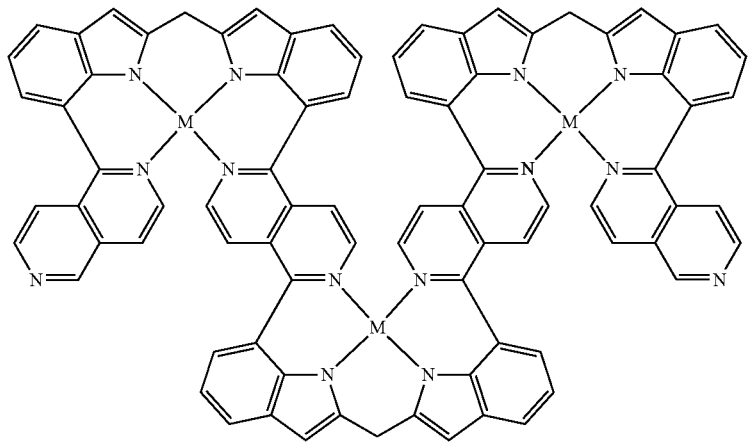
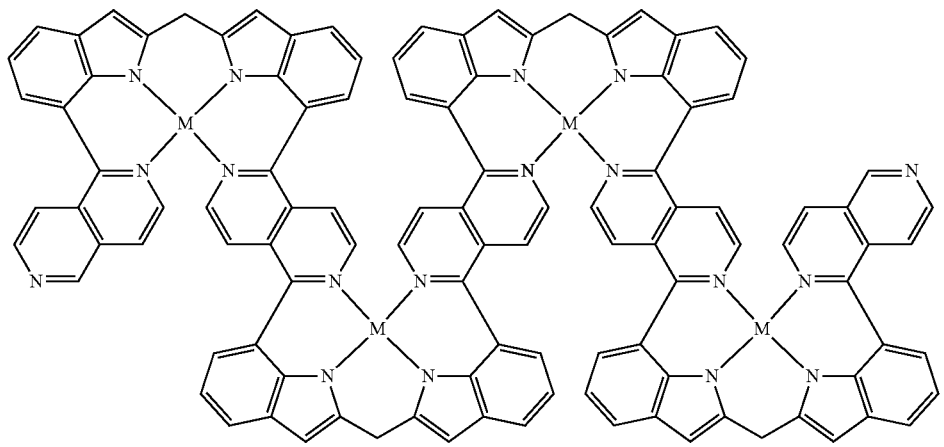
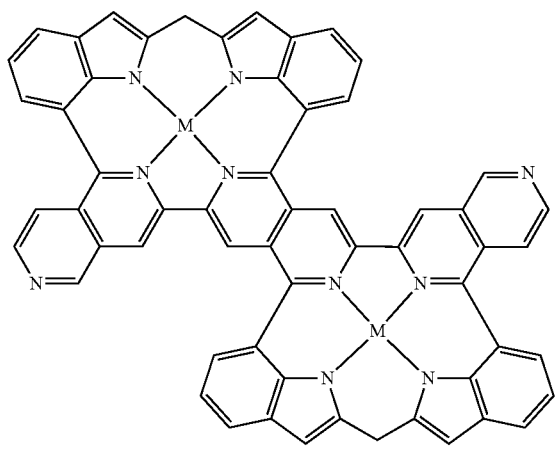

-continued
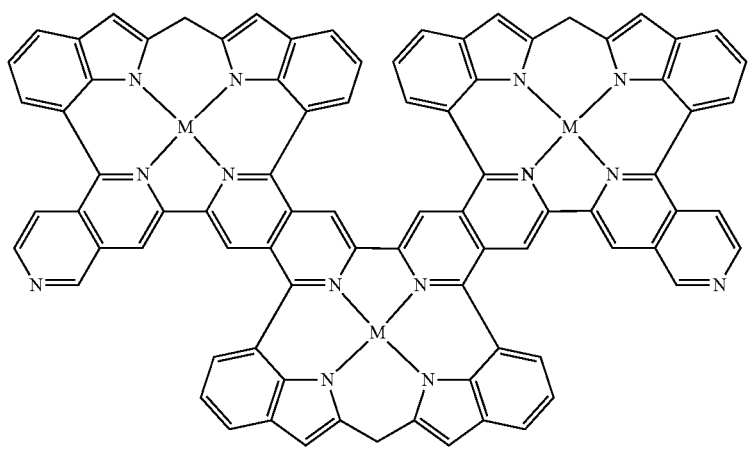
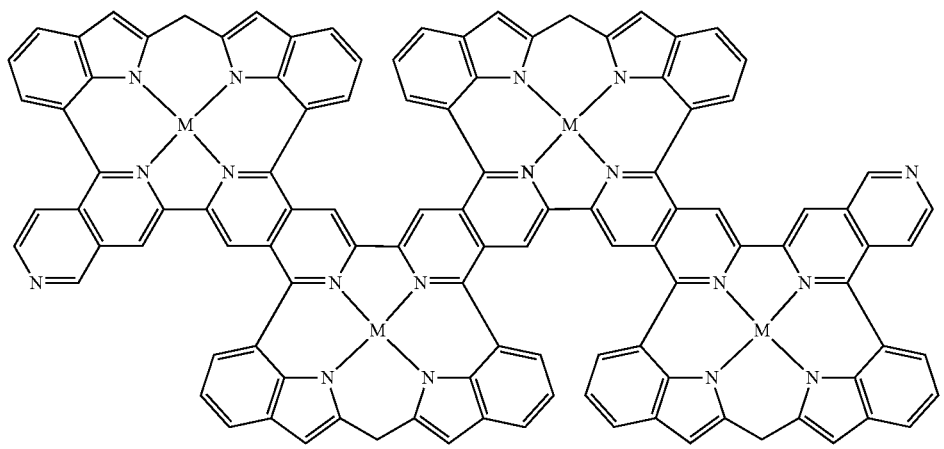
[Chemical Formula 61]
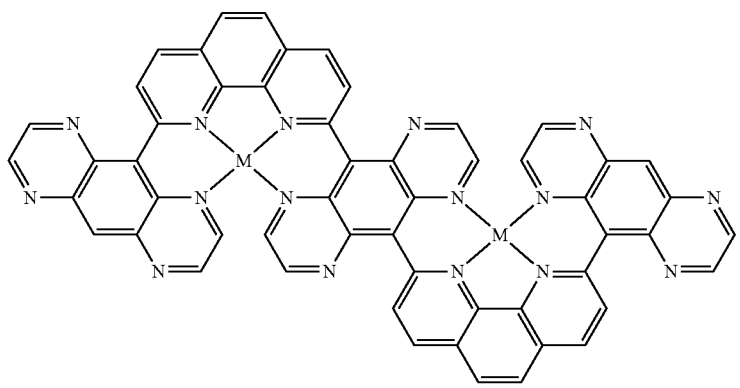
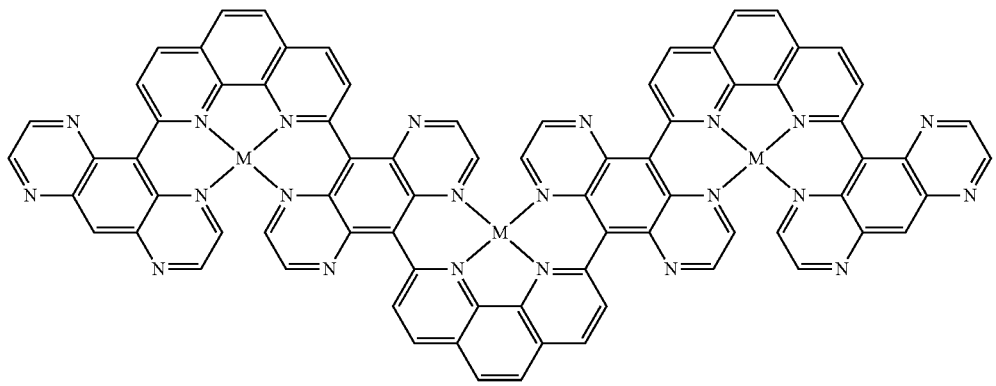

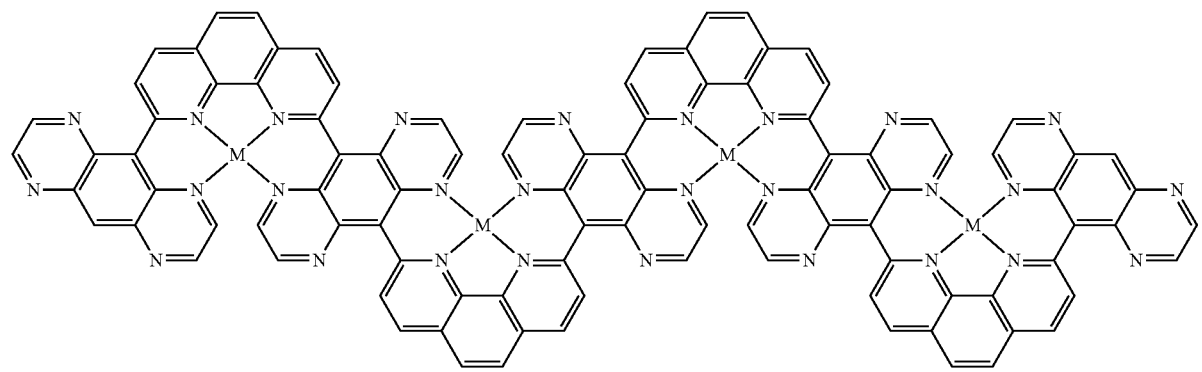
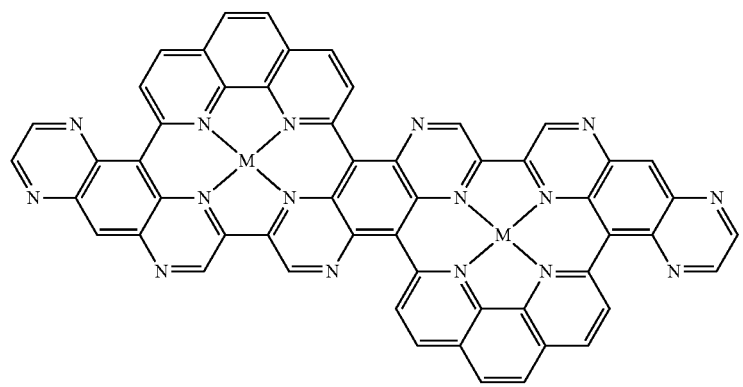
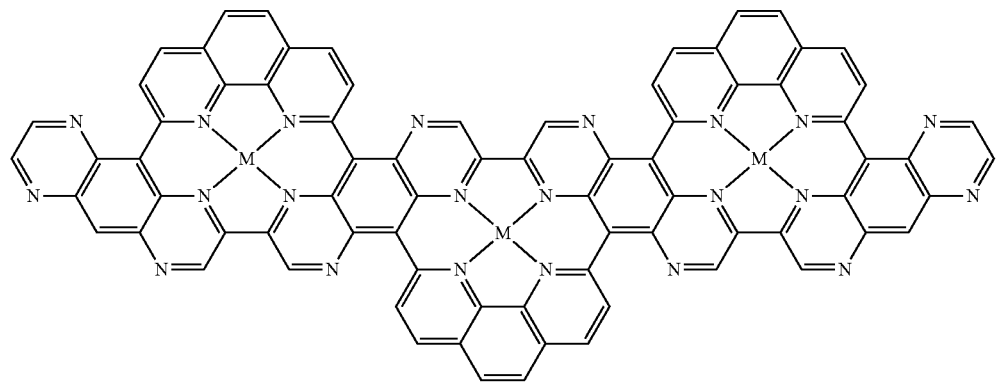
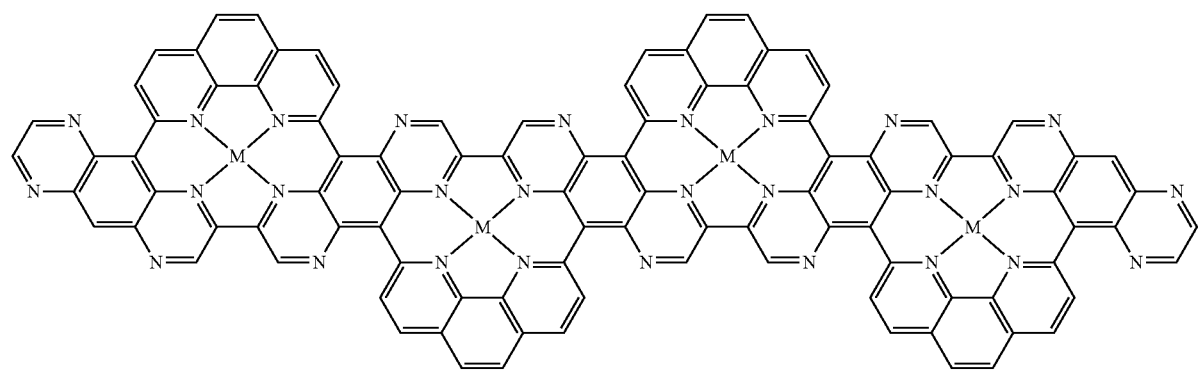

[Chemical Formula 62]
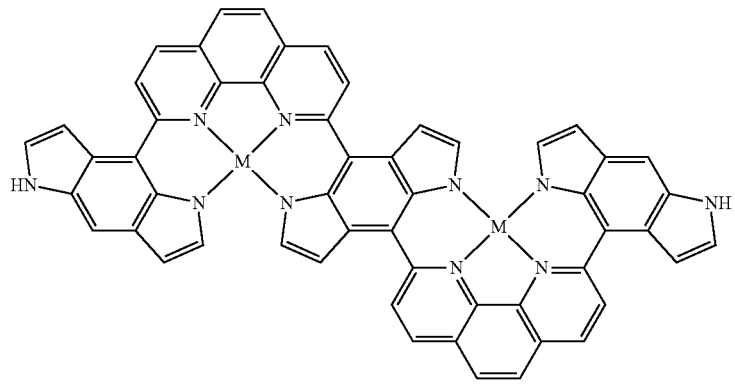
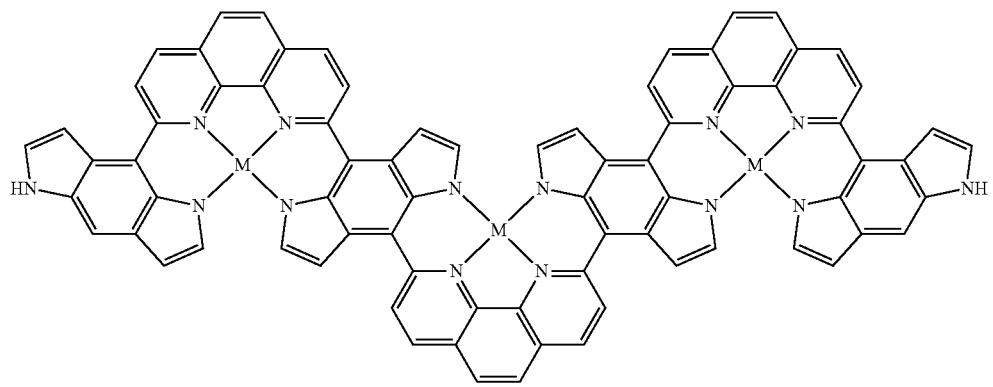
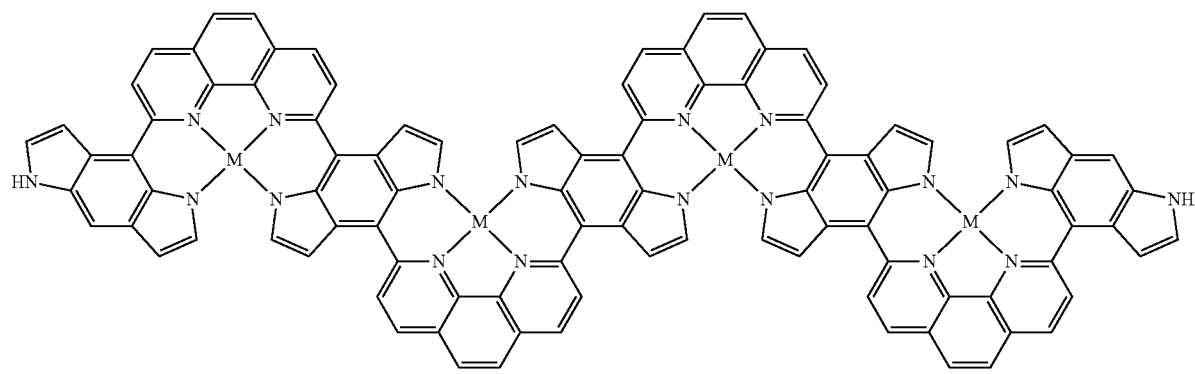
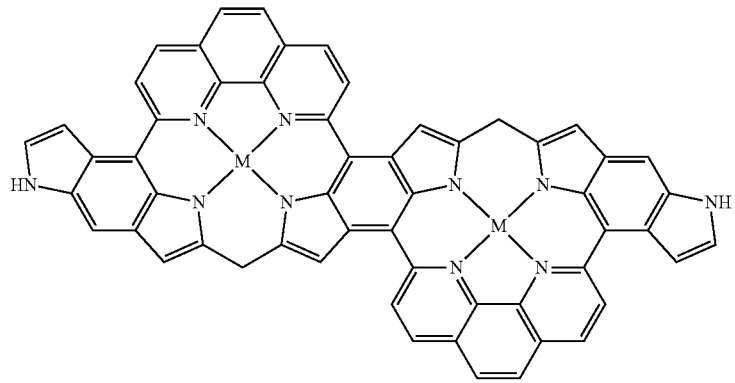

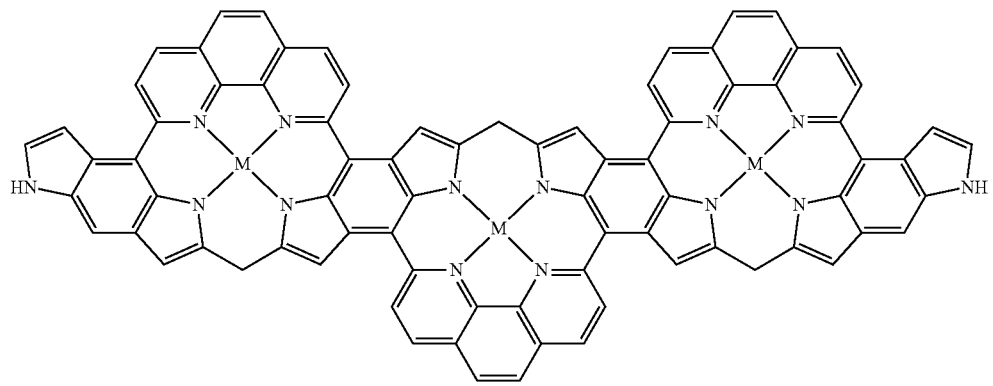
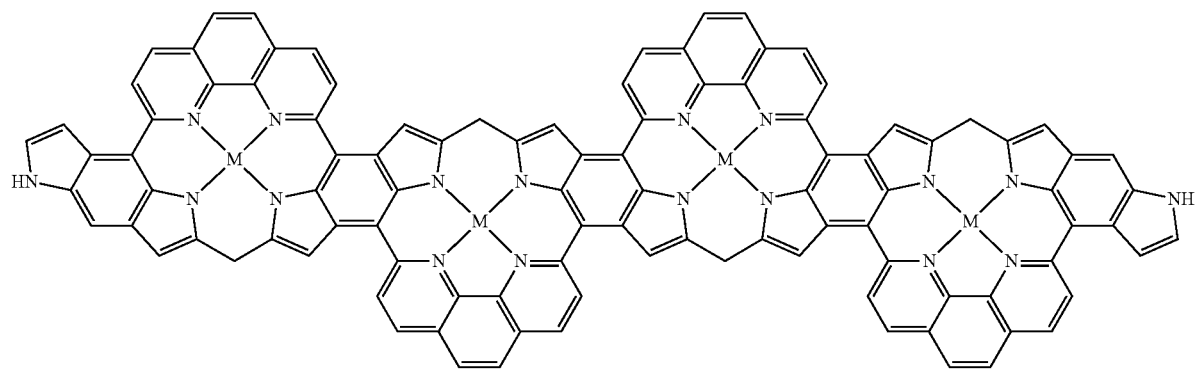
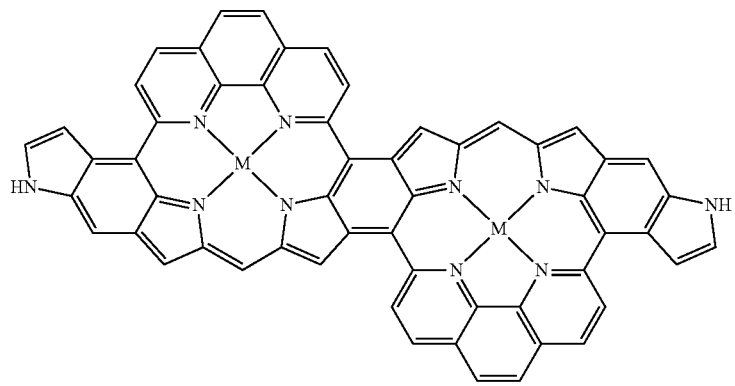
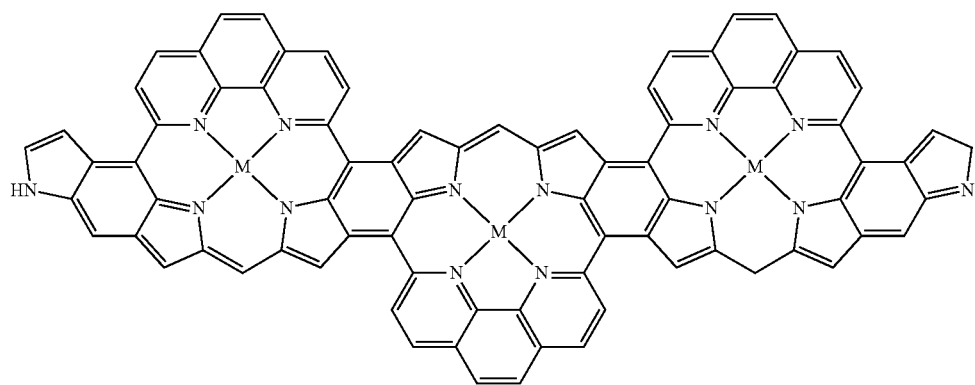

133
-continued
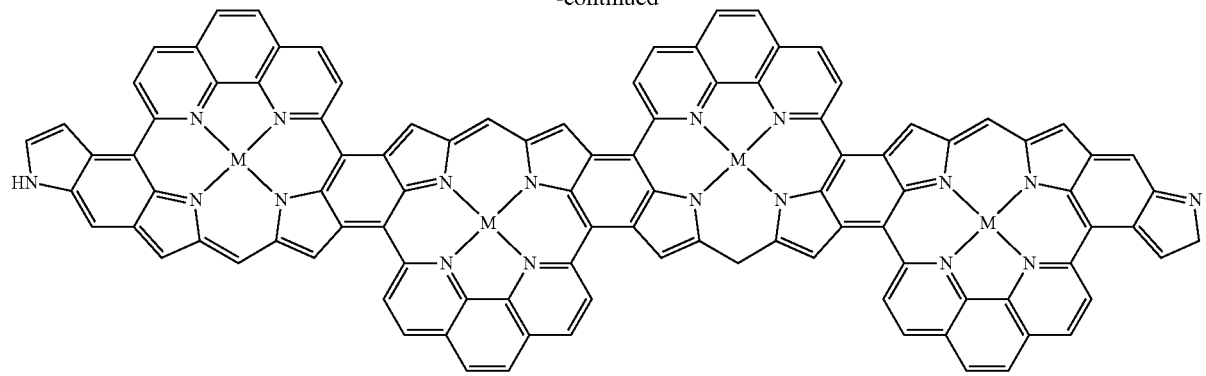
[Chemical Formula 63]
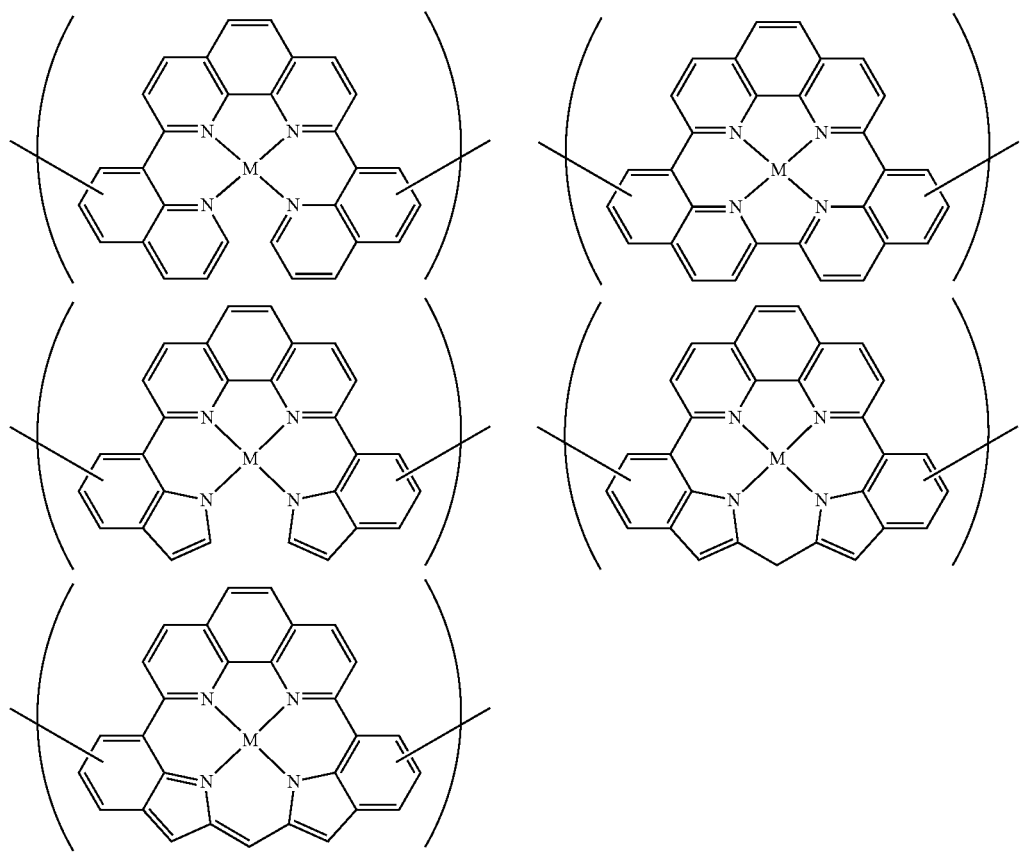
[Chemical Formula 64]
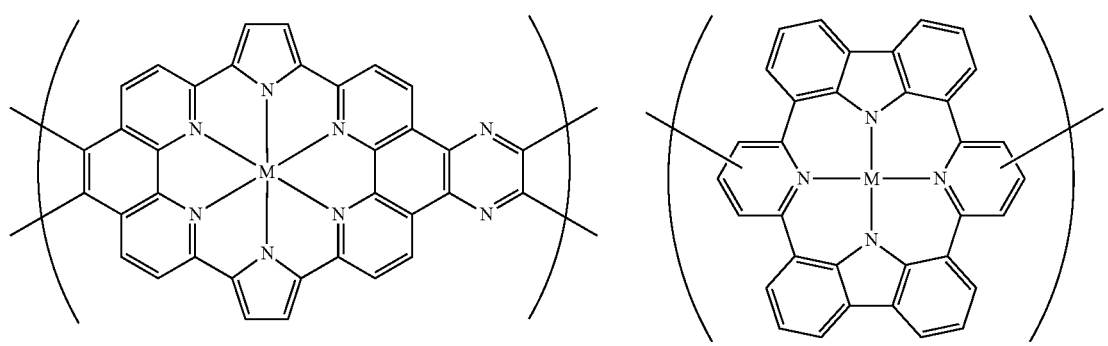

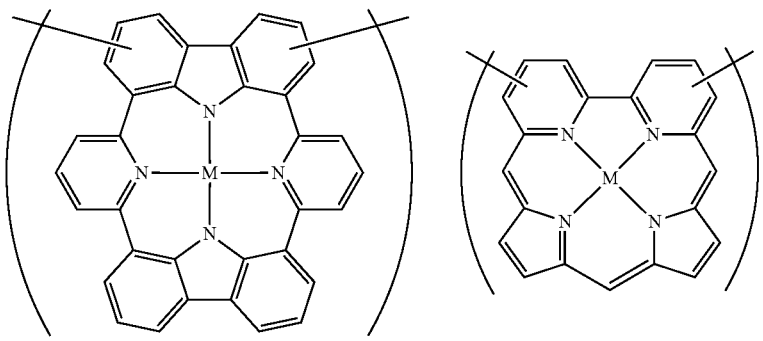
[Chemical Formula 65]
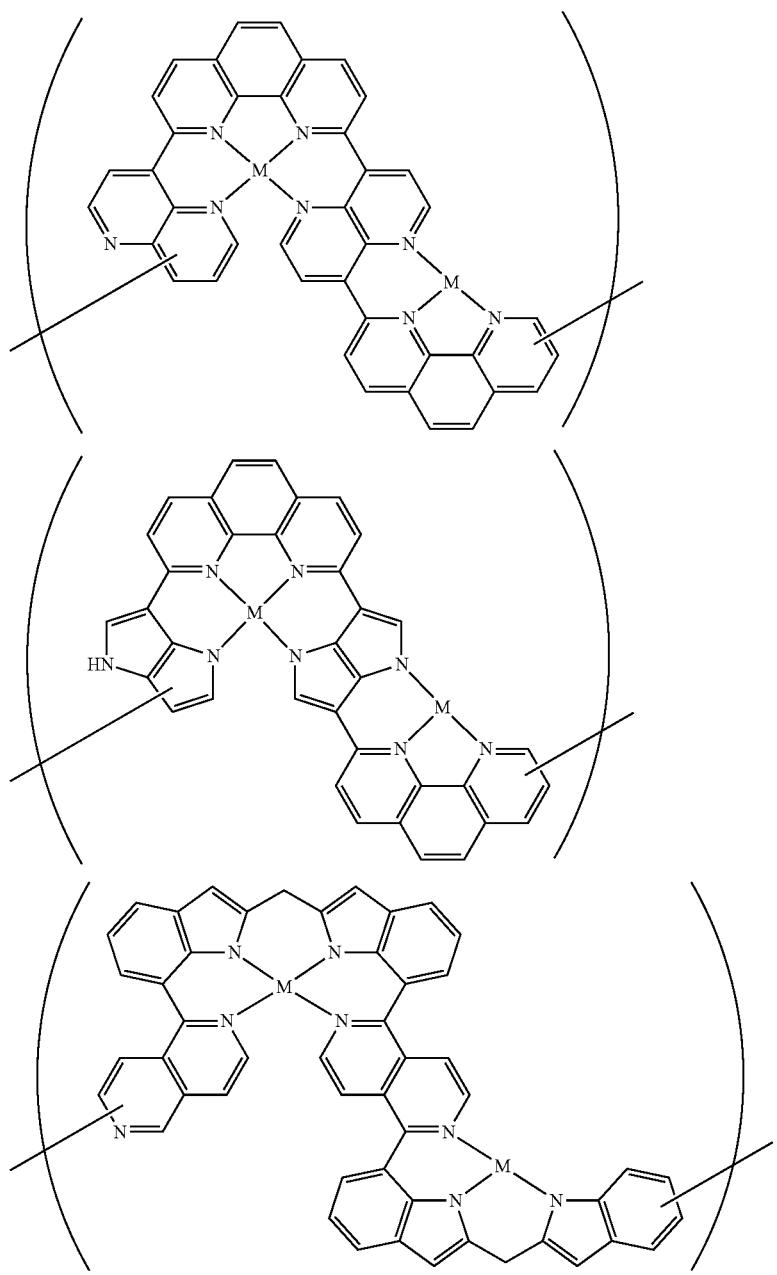

[Chemical Formula 66]

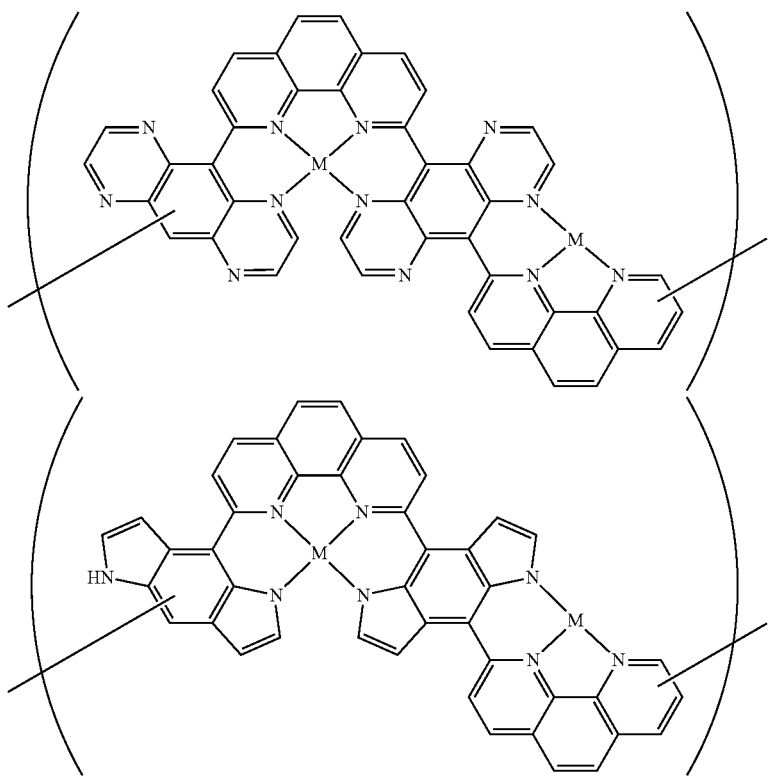

[In the formulas, M represents a metal atom, the metal atom represented by M being the same as the aforementioned metal atoms, and when 2 or more of M are present they may be the same or different; the electrical charges of the metal complexes are omitted.]

When an aromatic compound of the invention is used for synthesis of metal complex, the function of the obtained metal complex can be controlled by adjusting the amount of metal atom or metal ion to be reacted.

An aromatic compound or metal complex of the invention may be used alone, or a mixture of an aromatic compound and metal complex may be used together. The aromatic compound and/or metal complex may also be used as a composition comprising other components in combination. The other components may be carbon materials, polymer materials and the like, and such components may be used alone or in combinations of two or more.

As carbon materials there may be mentioned carbon particles such as NORIT (by Norit), KETCHEN BLACK (Lion Corp.), VULCAN (Cabot), BLACK PEARL (Cabot) and ACETYLENE BLACK (Chevron Corp.) (all the above are trade names), as well as C60 or C70 fullerenes, carbon nanotubes, carbon nanohorns, carbon fibers and the like.

Examples of polymer materials include conductive polymers, dendrimers, natural polymers, solid polymer electrolytes, polyethylene, polyethylene glycol and polypropylene, among which conductive polymers and solid polymer electrolytes are preferred. "Conductive polymer" is a general term for polymer substances that exhibit metallic or metalloid conductivity (Iwanami Dictionary of Physics and Chemistry, 5th Edition, 1988). As conductive polymers there may be mentioned polyacetylene and its derivatives, polyparaphenylene and its derivatives, polyparaphenylenevinylene and its derivatives, polyaniline and its derivatives, polythiophene and its derivatives, polypyrrole and its derivatives, polyfluorene and its derivatives, polyfluorene and its derivatives, polycarbazole and its derivatives and polyindole and its derivatives as well as copolymers of these conductive polymers, mentioned in "Conductive Polymers" (Yoshimura, S., Kyoritsu Publishing) and "New Applied Technology For Conductive Polymers" (Kobayashi, M. ed., CMC Publishing).

For preparation of a composition containing the aromatic compound and/or metal complex, the total amount of the aromatic compound and metal complex is preferably at least 1 part by weight, more preferably at least 5 parts by weight and most preferably at least 10 parts by weight, where 100 parts by weight is the total amount of the composition. The upper limit for this total is preferably 70 parts by weight, more preferably 60 parts by weight and most preferably 50 parts by weight.

A modified compound obtained by modifying the aromatic compound, the metal complex or the composition by heat, radiation irradiation or electric discharge may also be used.

The modified compound may also be used either alone or as a composition in combination with other components. The other components may be carbon materials, polymer materials and the like. The modified compound of the invention and the other components may be of single types or combinations of two or more types.

For preparation of a composition containing the modified compound, the total amount of the modified compound is preferably at least 1 part by weight, more preferably at least 5 parts by weight and most preferably at least 10 parts by weight, where 100 parts by weight is the total amount of the composition. The upper limit for the modified compound is preferably 90 parts by weight, more preferably 80 parts by weight and most preferably 70 parts by weight.

The modification may be the minimum necessary modification, and therefore the weight reduction percentage before and after modification (that is, the percentage reduction in mass of the modified compound obtained after modification, with respect to the mass of the mixture before modification), is preferably 1% or greater, more preferably 2% or greater and most preferably 5% or greater. The upper limit of the weight reduction percentage is preferably 80%, more preferably 70% and most preferably 60%.

A high carbon content in the modified compound will result in more satisfactory stability, and therefore the modification is carried out with a carbon content of preferably 5 wt % or greater, more preferably 10 wt % or greater, even more preferably 20 wt % or greater, most preferably 30 wt % or greater, and especially most preferably 40 wt % or greater.

The heating temperature is preferably 200° C. or higher and more preferably 300° C. or higher. The upper limit for the heating temperature may be a temperature at which the carbon content of the modified compound can be 1 wt % or greater, and it is preferably 1200° C., more preferably 1000° C. and even more preferably 800° C.

For heating, the heating time may be adjusted depending on the heating atmosphere and heating temperature. With sealing or aeration of the gas used as the atmosphere for modification, the temperature may be immediately lowered after it has been slowly raised from room temperature to the target temperature, but slow heating of the metal complex, for example, by holding the temperature after reaching the target temperature, is preferred to allow greater improvement in durability. The holding time after reaching the target temperature is preferably 1-100 hours, more preferably 1-40 hours, even more preferably 2-10 hours and most preferably 2-3 hours.

The heating may be carried out using an apparatus such as an oven, furnace or IH hot plate.

The heating is preferably carried out in an atmosphere of hydrogen gas, helium gas, nitrogen gas, ammonia gas, oxygen gas, neon gas, argon gas, krypton gas, xenon gas or acetonitrile gas, or a mixed gas comprising two or more of the foregoing, more preferably in an atmosphere of hydrogen gas, helium gas, nitrogen gas, ammonia gas, oxygen gas, neon gas, argon gas or a mixed gas comprising two or more of the foregoing, and most preferably hydrogen gas, nitrogen gas, ammonia gas, argon gas, or a mixed gas comprising two or more of the foregoing.

The radiation irradiation may be electromagnetic waves such as α-rays, β-rays, neutron rays, an electron beam, γ-rays, X-rays, vacuum ultraviolet rays, ultraviolet rays, visible light rays, infrared rays, microwaves, electromagnetic waves, laser or the like or radiation such as a particle beam, preferably X-rays, electron beams, ultraviolet rays, visible light rays, infrared rays, microwaves or laser, and more preferably ultraviolet rays, visible light rays, infrared rays, microwaves or laser.

The electric discharge may be corona discharge, glow discharge or plasma (including low-temperature plasma), with low-temperature plasma being preferred.

The radiation irradiation or electric discharge may be carried out with an appliance and treatment method commonly employed for surface modification treatment of polymer films, and for example, methods described in the literature ("Hyoumen Kaiseki/Kaishitsu no Kagaku", edited by Adhesion Society of Japan, Nikkan Kogyo Shimbun, Ltd., Dec. 19, 2003) may be employed.

The radiation irradiation or electric discharge will usually be carried out for no longer than 10 hours, preferably no longer than 3 hours, more preferably no longer than 1 hour and most preferably no longer than 30 minutes.

A process for production of an aromatic compound of the invention will now be described.

The aromatic compound of the invention may be produced by any process, and for example, it may be produced by condensation reaction of a diamine compound and hexaketocyclohexane, represented by the following formulas, in acetic acid.

[Chemical Formula 67]

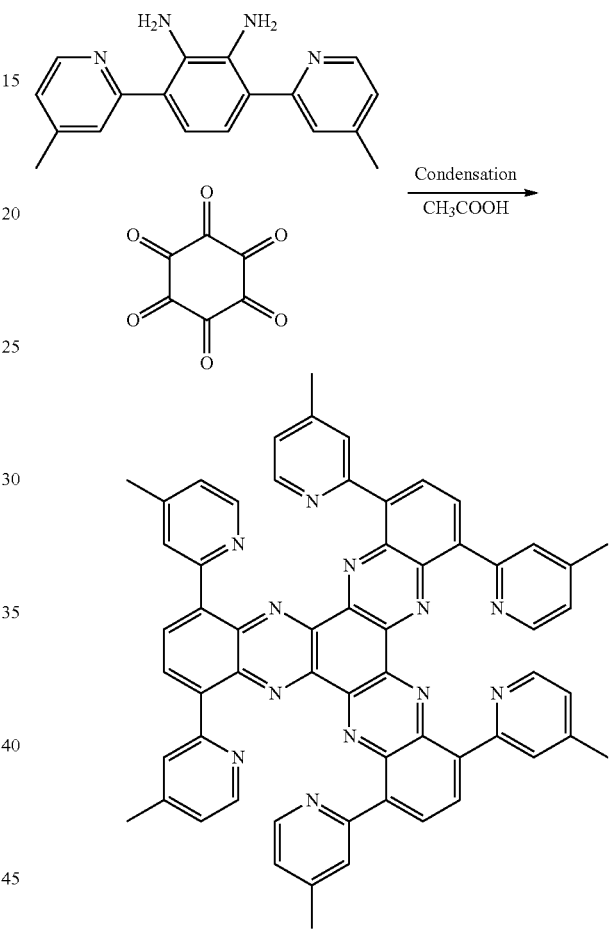

The method for producing an aromatic compound of the invention may involve introducing a halogeno group such as a bromo group and then cyclizing the compound, as in the following reaction formula. The cyclization reaction may be Yamamoto coupling or Ullmann coupling.

[Chemical Formula 68]

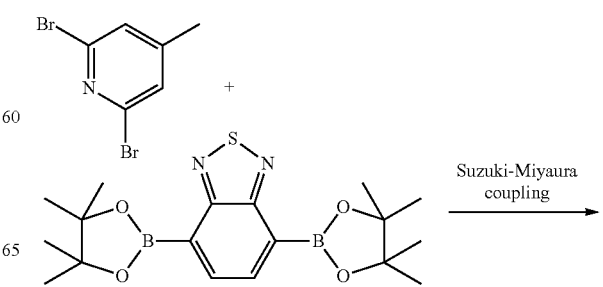

141
-continued
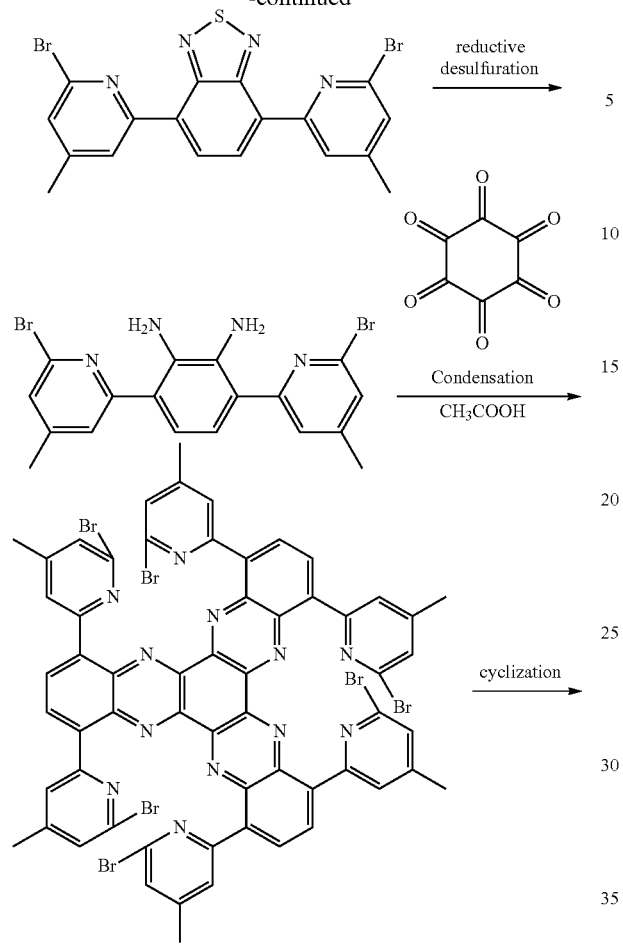
142
-continued
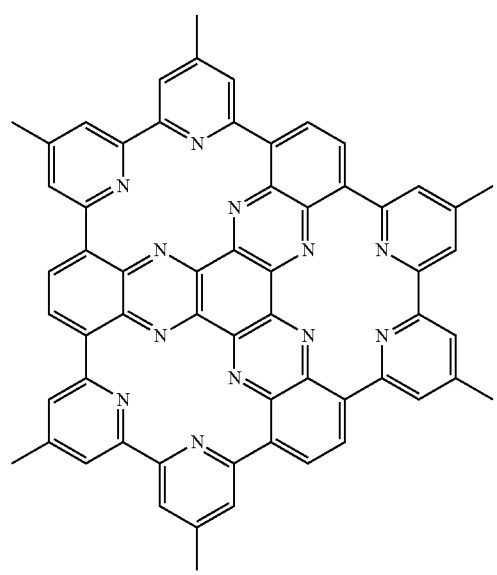
The aromatic compound of the invention may be produced by Suzuki-Miyaura coupling reaction, as in the following reaction formula.
[Chemical Formula 69]
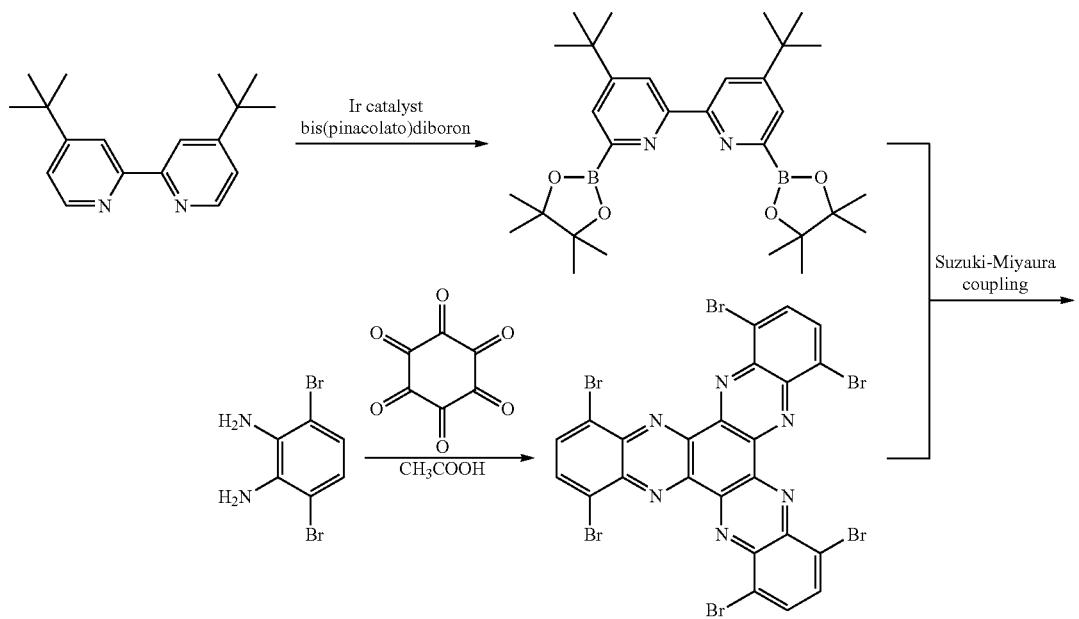

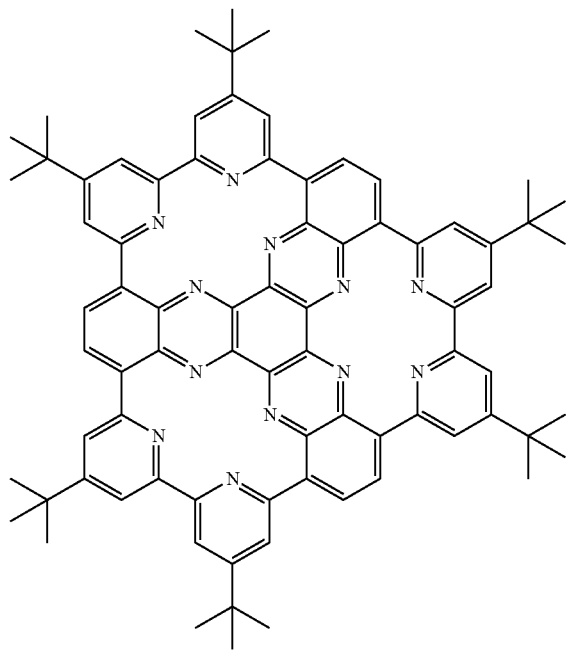
[Chemical Formula 70]
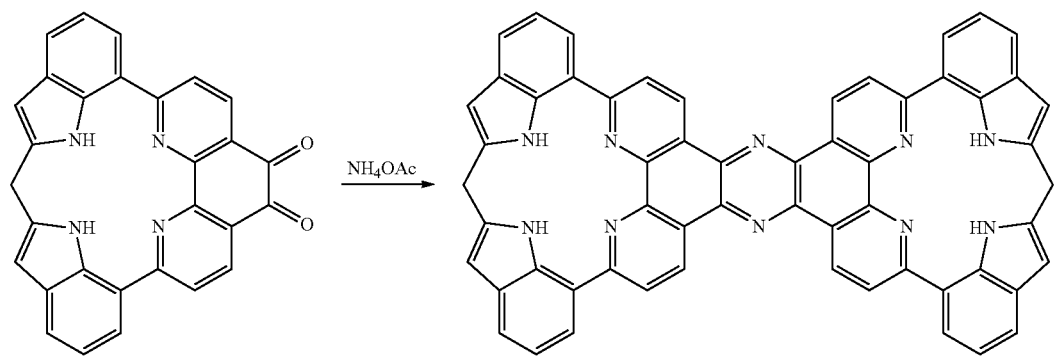
[Chemical Formula 71]
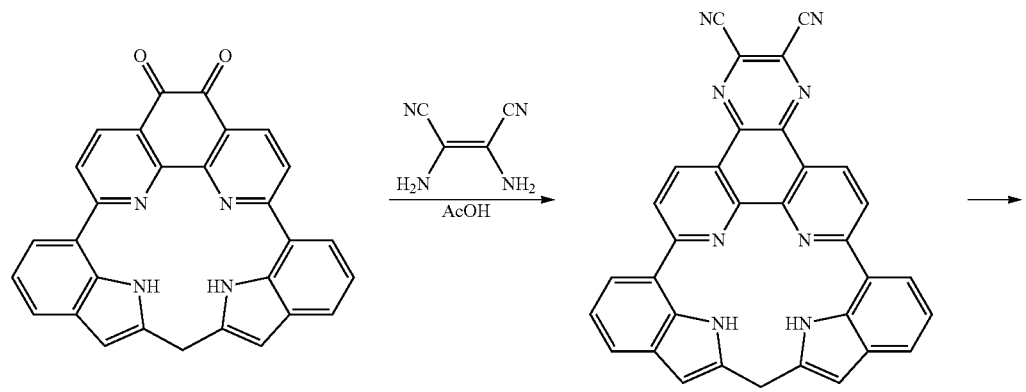

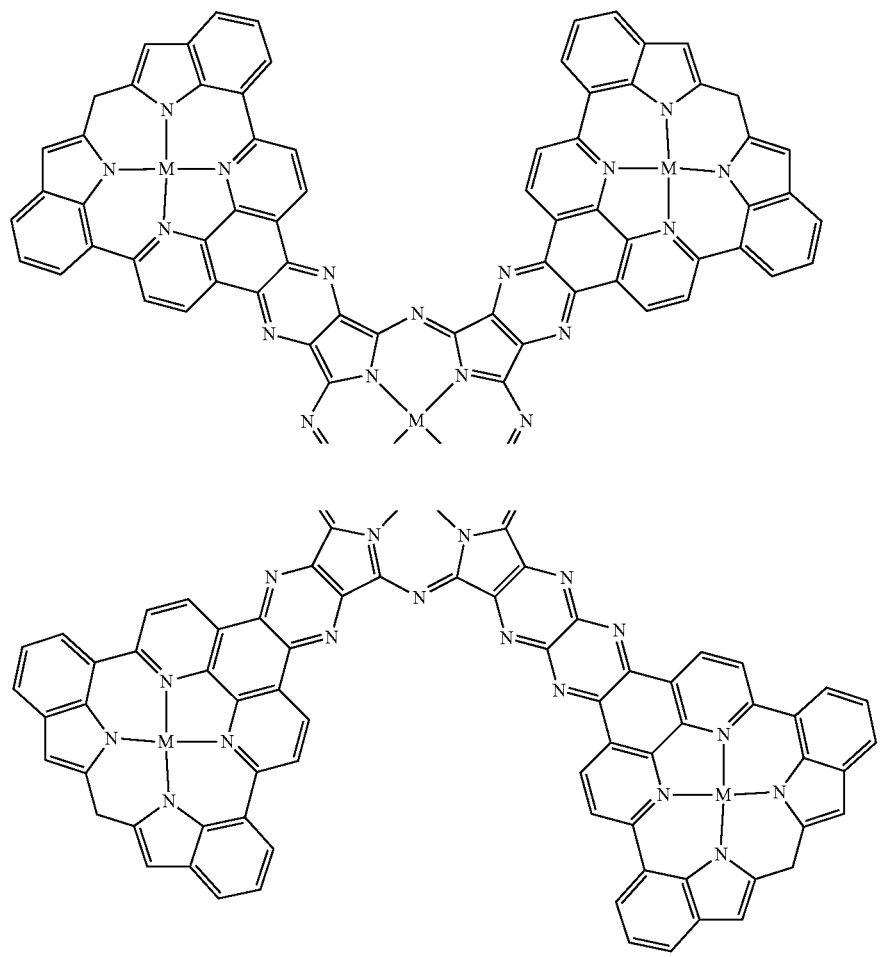

The aromatic compound of the invention may also be produced by introducing the borate form of a nitrogen-containing aromatic compound such as pyrrole into the condensation reaction product of a diamine compound with a halogeno group such as bromine and a hexaketocyclo-hexane, represented by the following reaction formula, by coupling reaction or the like.

[Chemical Formula 72]

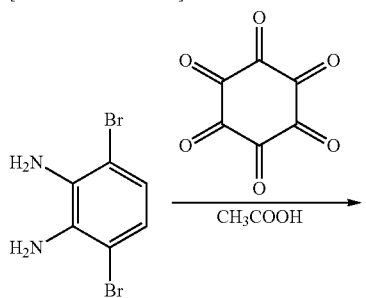

-continued

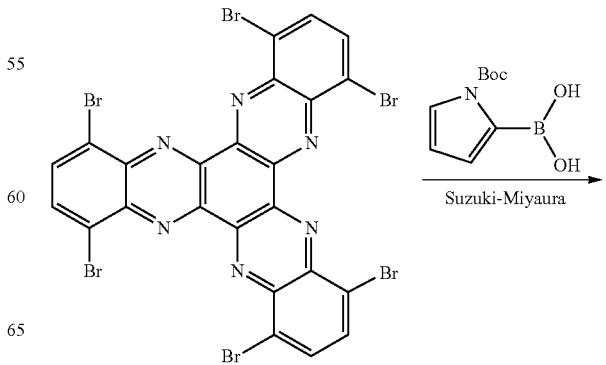

147
-continued
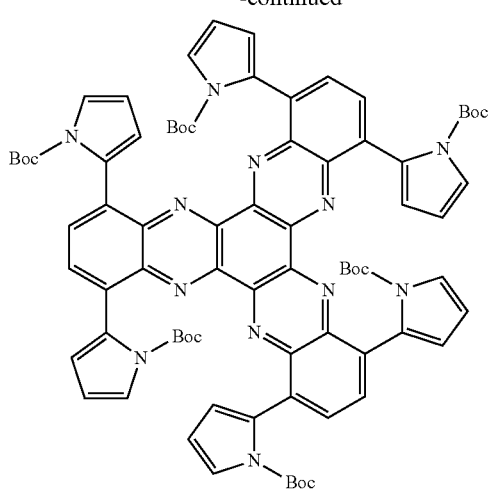
148
-continued
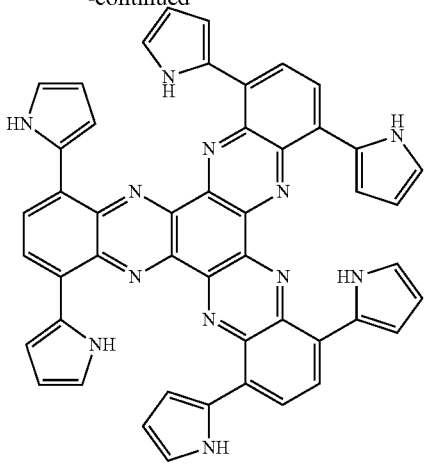
The compound may also be reacted with an aldehyde for cyclization, as illustrated by the following reaction formula.
[Chemical Formula 73]
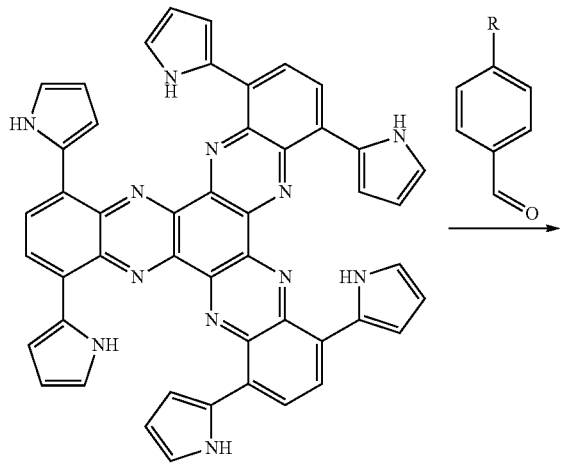

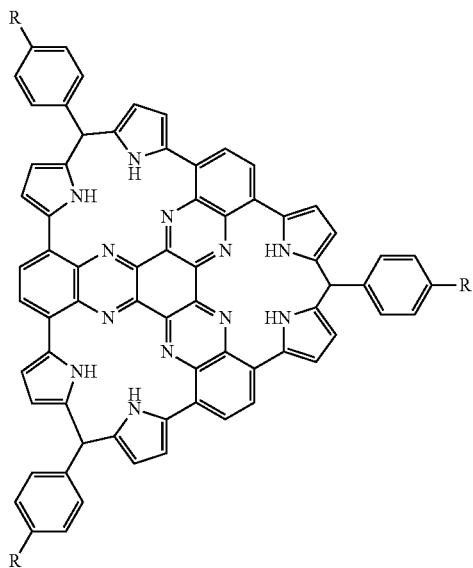
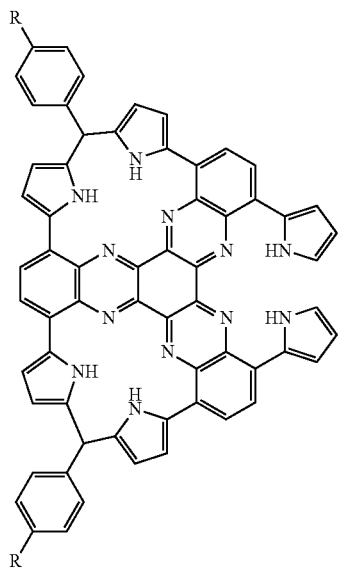
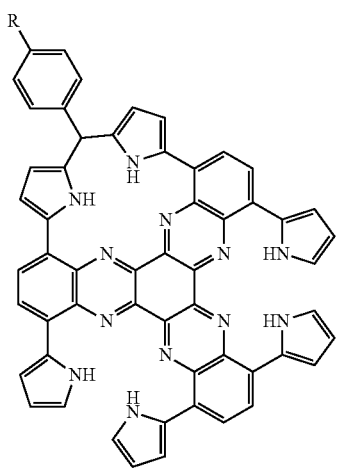
[In the formulas, R is hydrogen.]
The aromatic compounds having such structures may be oxidized with appropriate oxidants. As oxidants there may be mentioned 2,3-dichloro-5,6-dicyano-p-benzoquinone (DDQ) or oxygen. The amount of oxidant added and the reaction time may be adjusted to vary the reaction stage.
[Chemical Formula 74]
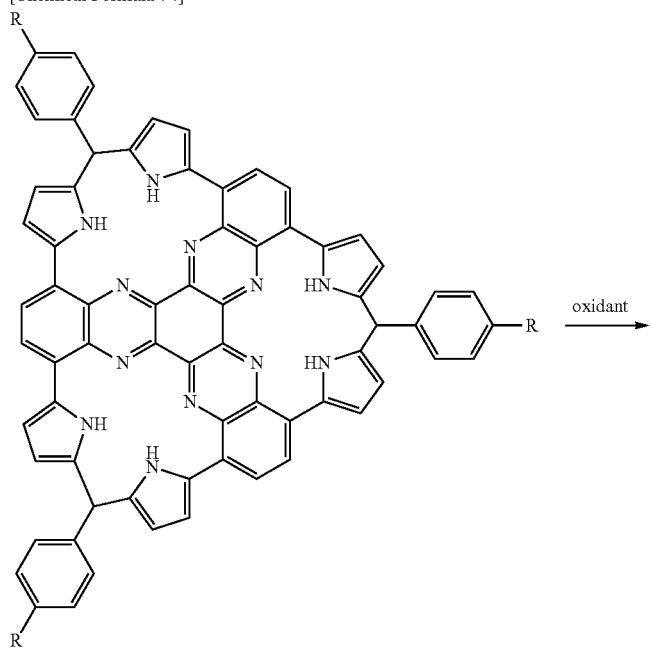
oxidant →

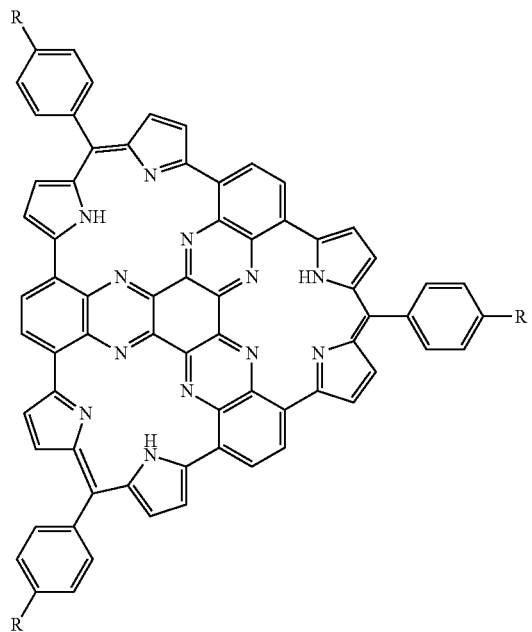
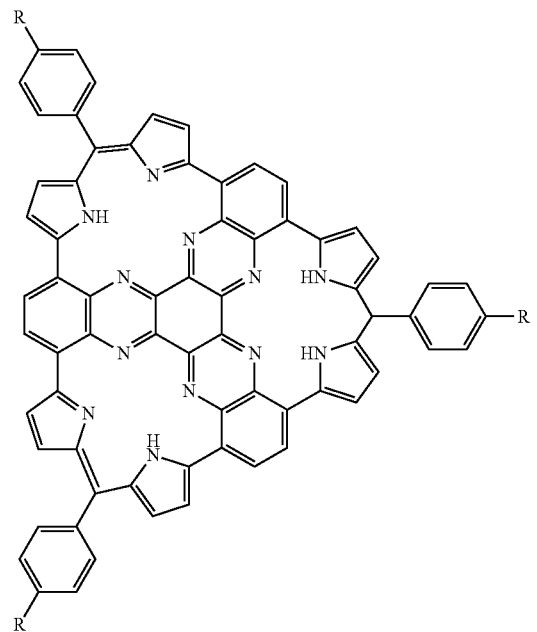
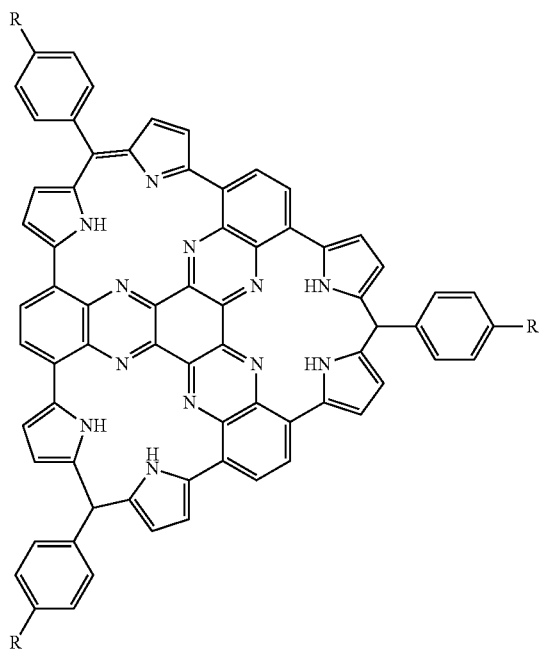
[In the formulas, R is hydrogen.]
The aromatic compound of the invention may also contain a reactive group such as an ethynyl group. A reactive group is preferably introduced from the viewpoint of increasing the catalytic activity. It may be reacted with an aldehyde having an ethynyl group, for introduction of the reactive group.

[Chemical Formula 75]
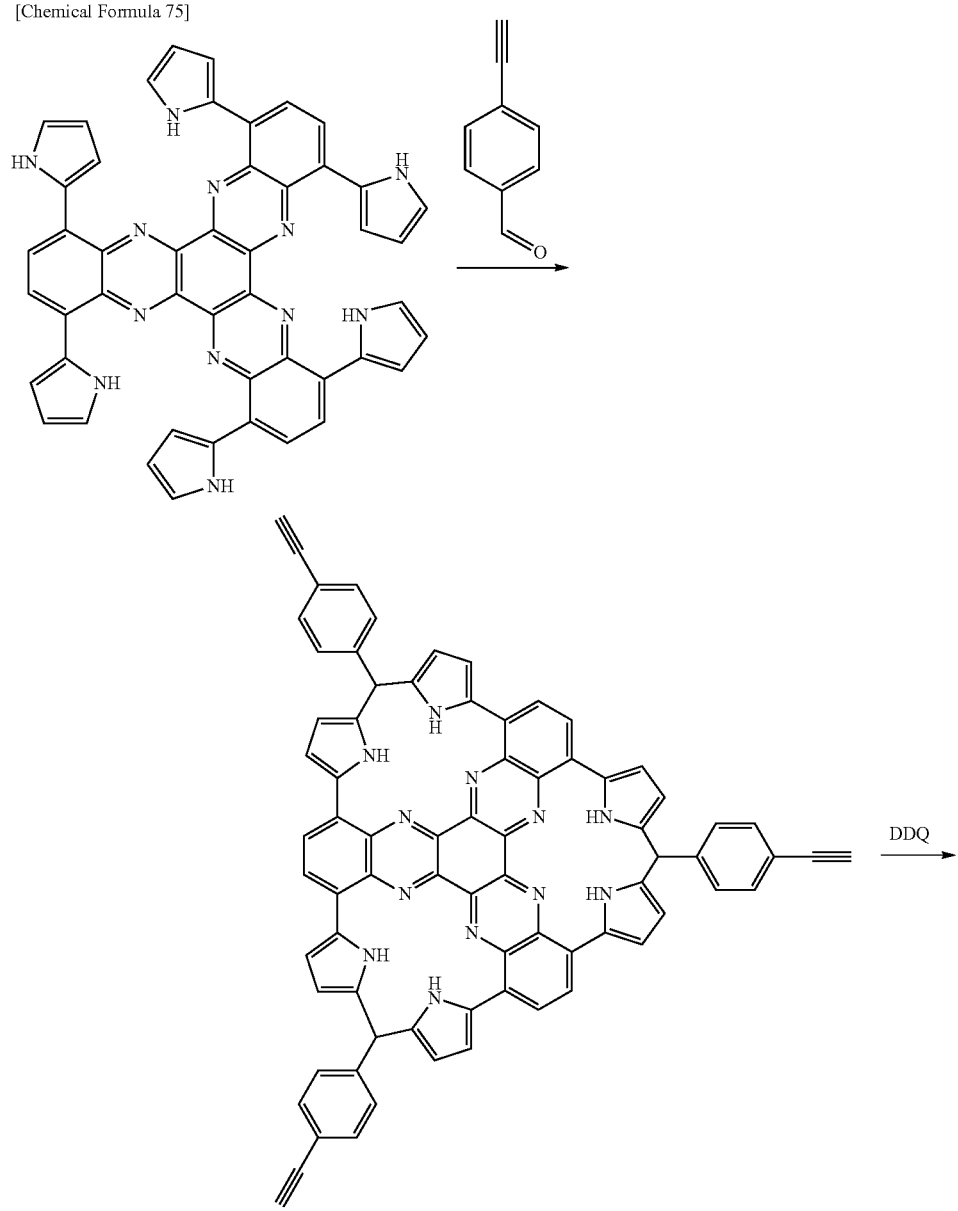

-continued

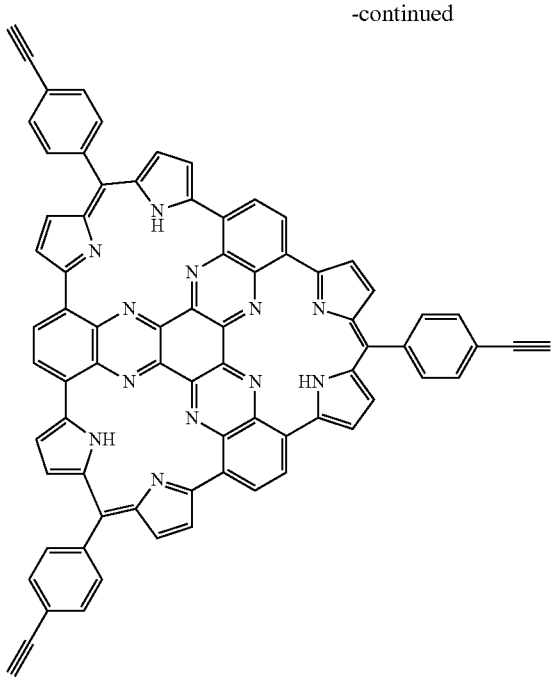

When an ethynyl group is to be introduced by the reaction shown above, the ethynyl group may be protected with a protecting groups such as trimethylsilyl (TMS), triethylsilyl (TES), tert-butyldimethylsilyl (TBS or TBDMS), triisopropylsilyl (TIPS), tert-butyldiphenylsilyl (TBDPS) or the like, and after introducing it into a nitrogen-containing aromatic compound, it may be deprotected under acidic conditions or by the action of a fluoride ion.

The aromatic compound of the invention may also be produced by the following reaction.

[Chemical Formula 76]

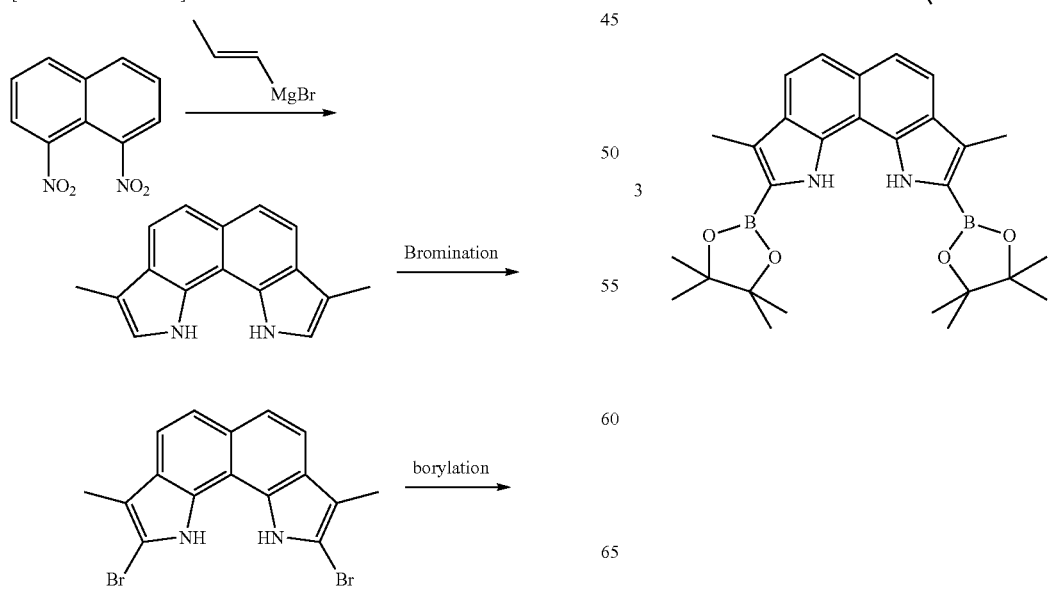

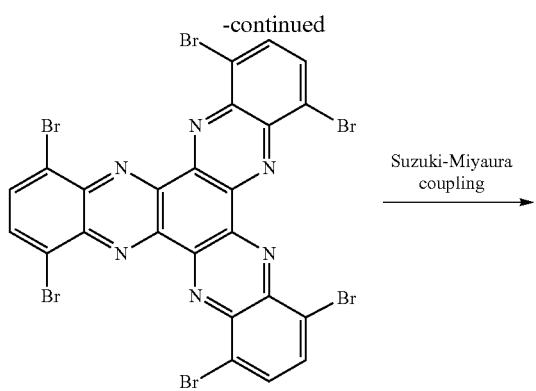

Suzuki-Miyaura coupling →

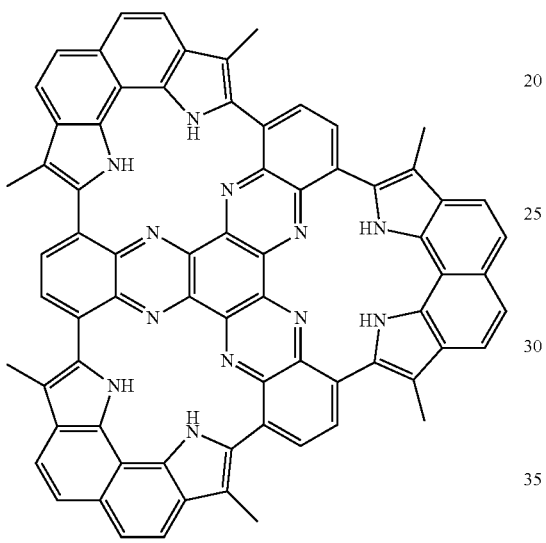

An aromatic compound having one structure surrounded by at least 4 coordinatable nitrogen atoms, and at least one of the nitrogen atoms composing the structure is a nitrogen atom in a 6-membered nitrogen-containing heterocyclic ring may be used as starting material to produce an aromatic compound according to the invention.

[Chemical Formula 77]

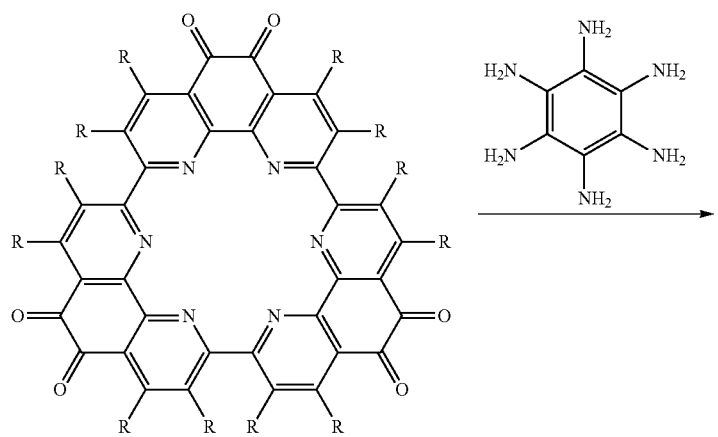

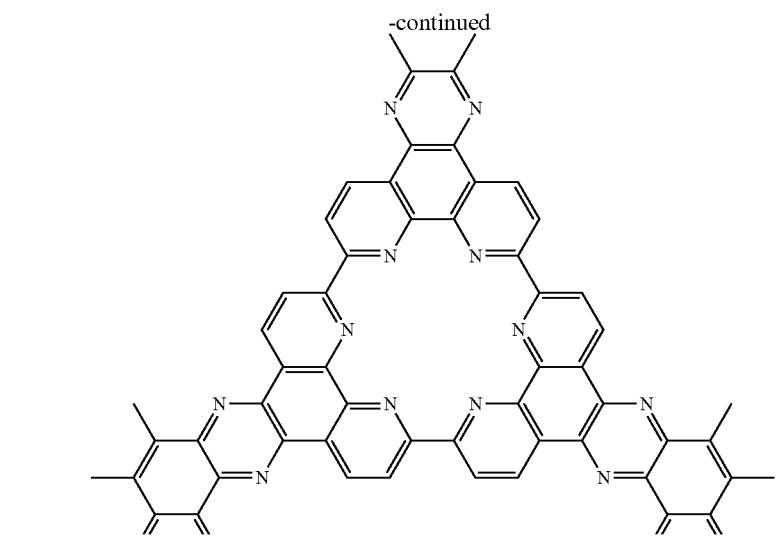

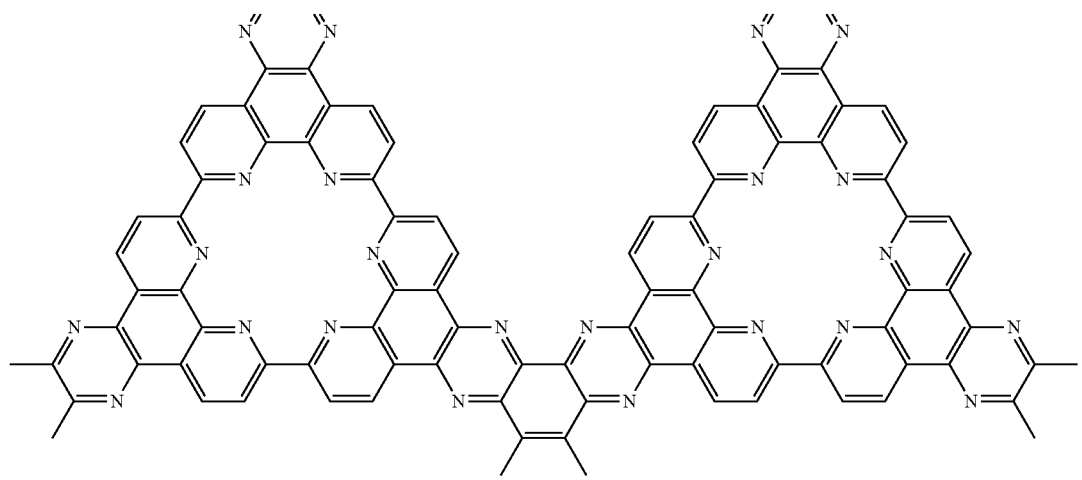

[In the formulas, R is hydrogen.]

In the process for production of an aromatic compound of the invention, a compound represented by any of general formulas (11) to (20), (22) or (23) may be used as the starting material for the aromatic compound of the invention. The aromatic compound of the invention may also be produced by removing one or more hydrogens or substituents in the structural formulas represented by formulas (11) to (20), (22) or (23) and linking them. The commonly employed method of coupling reaction may be used as the linking method, and examples include Suzuki-Miyaura coupling and Mizorogi-Heck reaction using palladium as the catalyst, Yamamoto coupling and Kumada-Tamao coupling using nickel as the catalyst, and Ullmann reaction using copper as the catalyst.

[Chemical Formula 78]

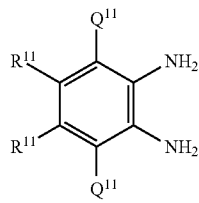

(11)

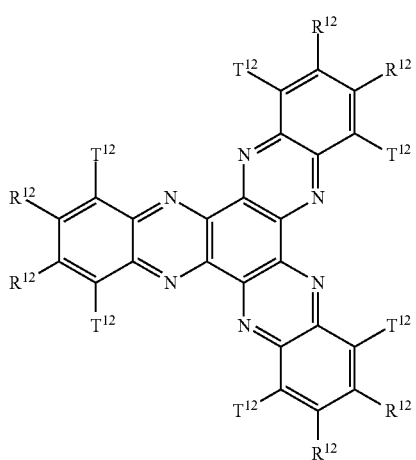

(12)

(13)
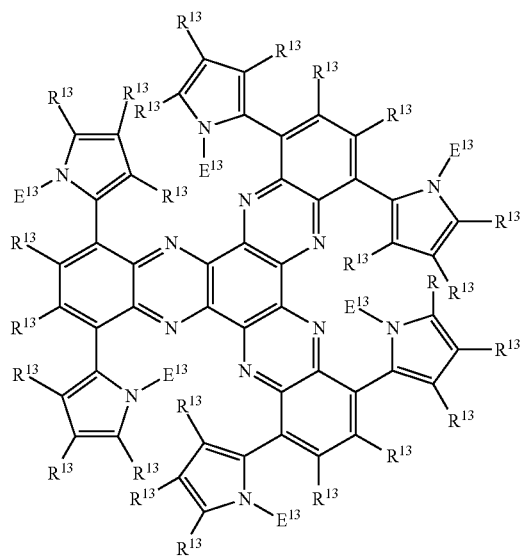
[Chemical Formula 79]
(14)
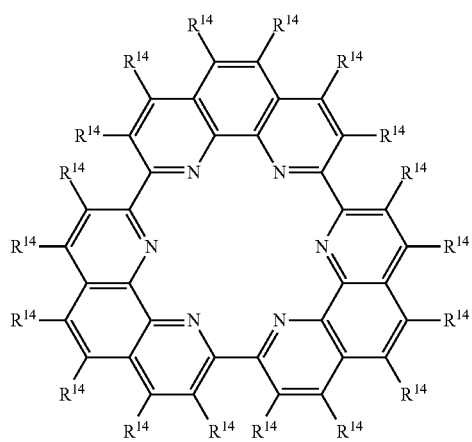
(15)
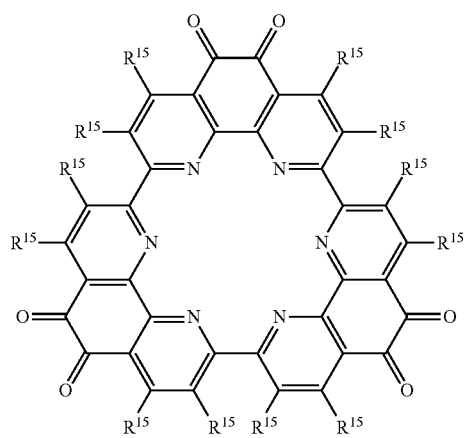
(16)
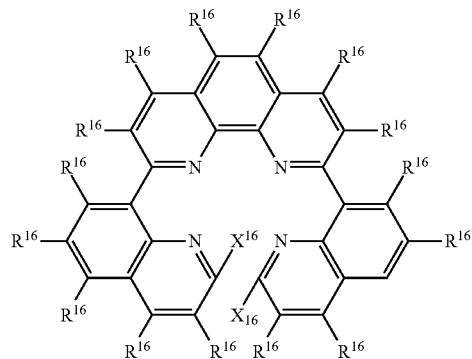
[Chemical Formula 80]
(17)
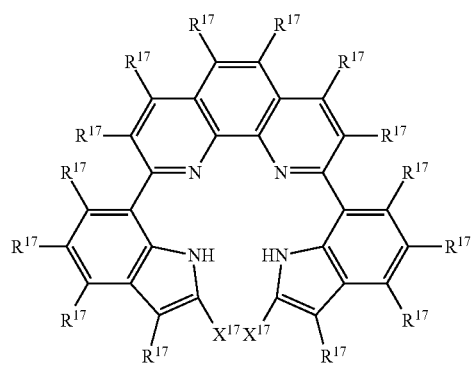
(18)
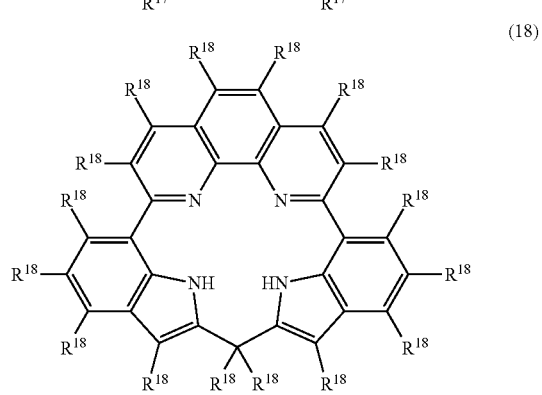
(19)
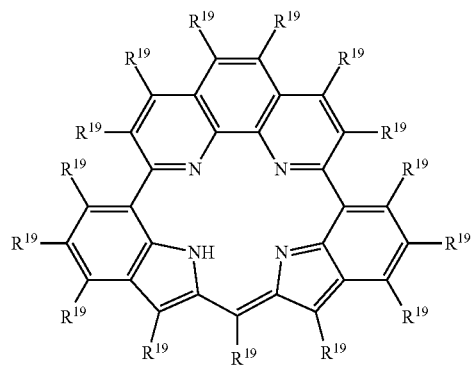

-continued

[Chemical Formula 81]

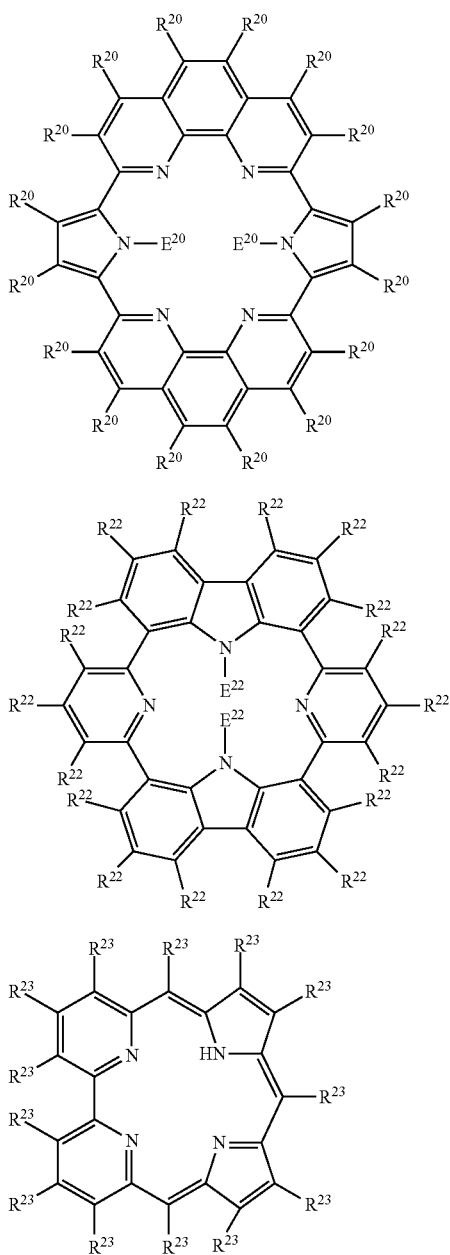

[In the formulas, $R^{11}$—$R^\circ$, $R^{22}$ and $R^{23}$ are hydrogen or a substituent and each may be the same or different, with adjacent substituents optionally bonding together to form a ring;
$Q^{11}$ is a nitrogen-containing aromatic heterocyclic ring and each may be the same or different;
$T^{12}$ is bromine atom, chlorine atom or iodine atom and each may be the same or different;
$E^{13}$, $E^{20}$ and $E^{22}$ each independently represent hydrogen or a protecting group; and
$X^{16}$ and $X^{17}$ each independently represent hydrogen or a halogeno group, or the $X^{16}$ or $X^{17}$ groups are bonded together as direct bonds.]

The substituents represented by $R^{11}$—$R^{20}$, $R^{22}$ and $R^{23}$ are the same as the substituents explained and illustrated above.

$Q^{11}$ is a nitrogen-containing aromatic heterocyclic ring, and is preferably a pyridine ring, pyrazine ring, pyrimidine ring, pyridazine ring, 1,3,5-triazine ring, 1,2,4-triazine ring, 1,2,4,5-tetrazine ring, 1H-pyrrole ring, 2H-pyrrole ring, 3H-pyrrole ring, imidazole ring, pyrazole ring, 1,2,3-triazole ring, 1,2,4-triazole ring, oxazole ring, isooxazole ring, thiazole ring, isothiazole ring, 1,3,4-oxadiazole ring, 1,2,5-oxadiazole ring, 1,3,4-thiadiazole ring, 1,2,5-thiadiazole ring or a polycyclic aromatic heterocyclic ring containing such a ring, more preferably a pyridine ring, pyrazine ring, pyrimidine ring, pyridazine ring, 1H-pyrrole ring, 2H-pyrrole ring, 3H-pyrrole ring, imidazole ring, pyrazole ring, 1,2,3-triazole ring or 1,2,4-triazole ring, and most preferably a pyridine ring, pyrazine ring, pyrimidine ring, pyridazine ring or 1H-pyrrole ring.

$T^{12}$ is preferably bromine atom or chlorine atom, and more preferably bromine atom.

$E^{13}$, $E^{20}$ and $E^{22}$ each independently represent hydrogen or a protecting group. As protecting groups there may be mentioned alkoxycarbonyl groups such as methoxycarbonyl, ethoxycarbonyl, 2,2,2-tri chloroethoxycarbonyl and tert-butoxycarbonyl (Boc), alkenyloxycarbonyl groups such as vinyloxycarbonyl, aralkyloxycarbonyl groups such as benzyloxycarbonyl and 9-fluorenylmethoxycarbonyl, optionally substituted aralkyl groups such as benzyl and 4-methoxybenzyl, acyl groups such as formyl, acetyl, trifluoroacetyl and benzoyl, arylsulfonyl groups such as p-toluenesulfonyl and benzenesulfonyl, and alkylsulfonyl groups such as methanesulfonyl, with tert-butoxycarbonyl being preferred.

Compound (11) can be produced by reacting an o-diaminobenzene derivative and hexaketocyclohexane in acetic acid as shown by the following reaction formula.

[Chemical Formula 82]

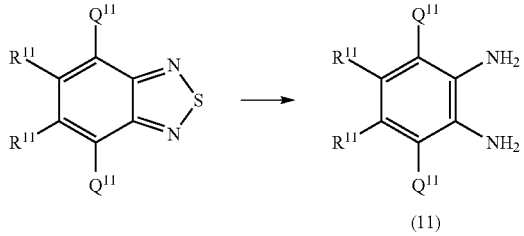

Compound (12) can be produced by reacting an ortho-diaminobenzene derivative and hexaketocyclohexane in acetic acid as shown by the following reaction formula.

[Chemical Formula 83]

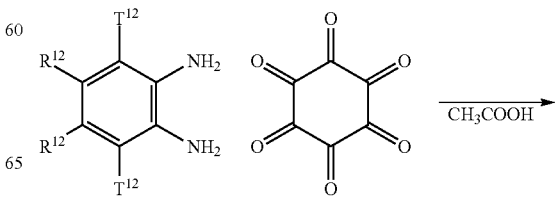

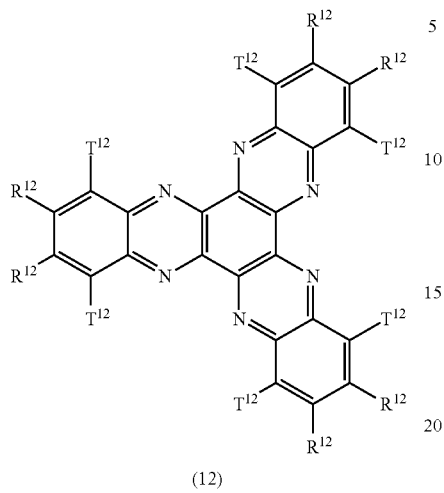

(12)

T$^{12}$ = Br, Cl, I

Compound (13) can be produced by linking compound (12) with each of 6 pyrrole-boric acid molecules, as shown by the following reaction formula. The linking method used may be a common cross-coupling reaction, with Suzuki coupling being particularly preferred.

[Chemical Formula 84]

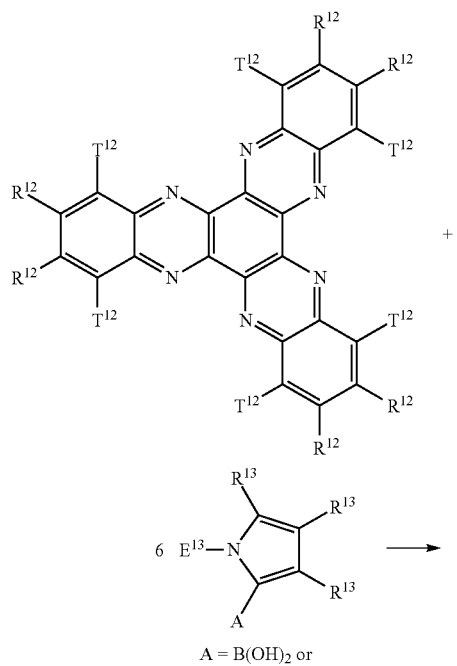

+

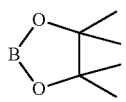

A = B(OH)$_2$ or

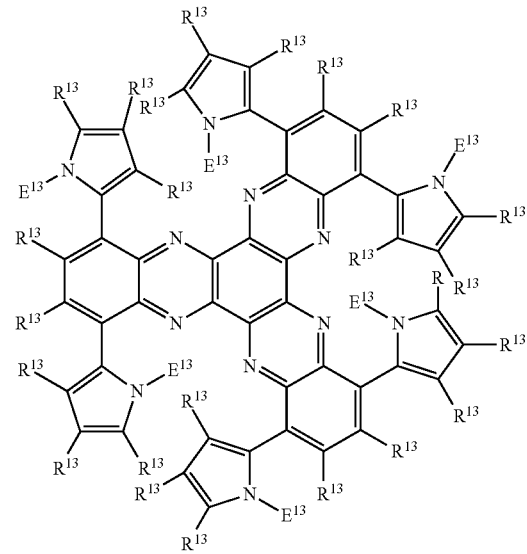

(13)

Compound (14) can be produced by linking three 2,9-dihalogeno-1,10-phenanthroline molecules in a cyclic manner, as shown by the following reaction formula.

[Chemical Formula 85]

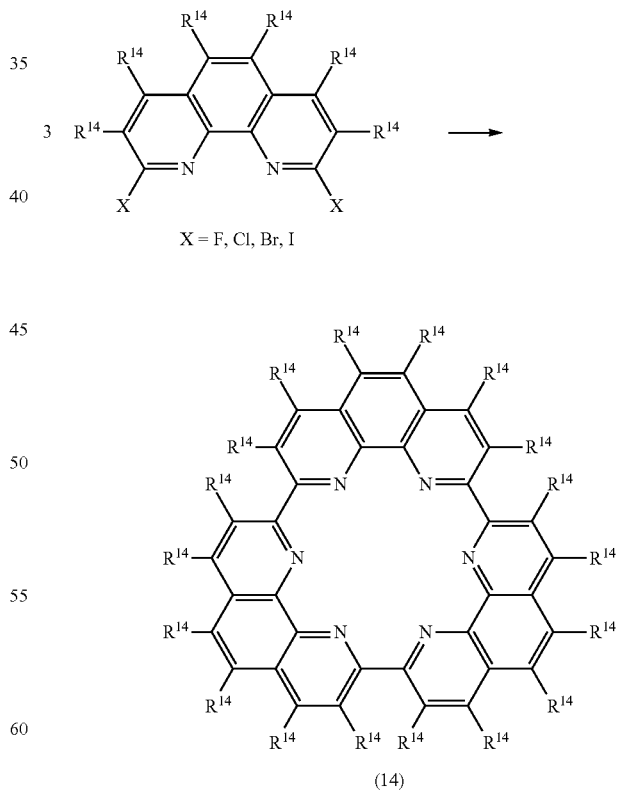

X = F, Cl, Br, I (14)

Compound (15) can be produced by linking three 2,9-dihalogeno-1,10-phenanthroline-5,6-dione molecules in a cyclic manner, as shown by the following reaction formula.

[Chemical Formula 86]

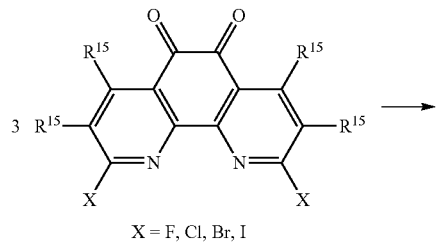

X = F, Cl, Br, I

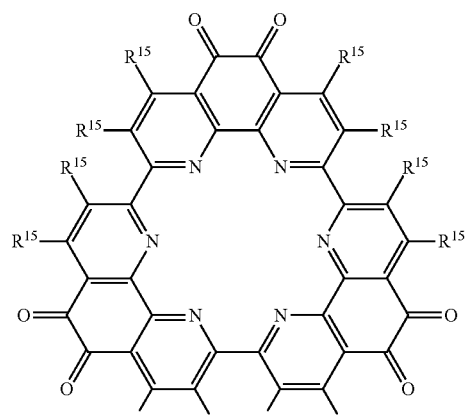

(15)

Compound (16) can be produced by linking 2,9-dihalogeno-1,10-phenanthroline with two quinoline-boric acid molecules, as shown by the following reaction formula.

[Chemical Formula 87]

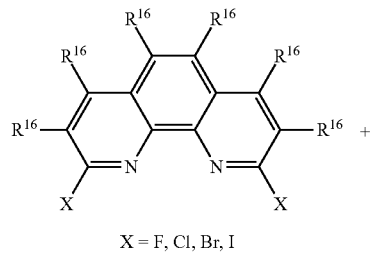

X = F, Cl, Br, I

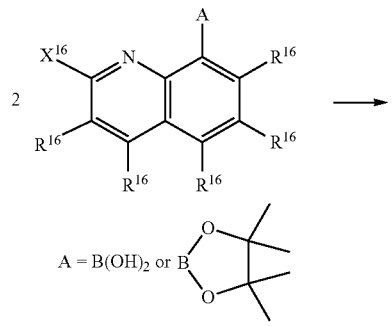

A = B(OH)$_2$ or B with pinacol ester

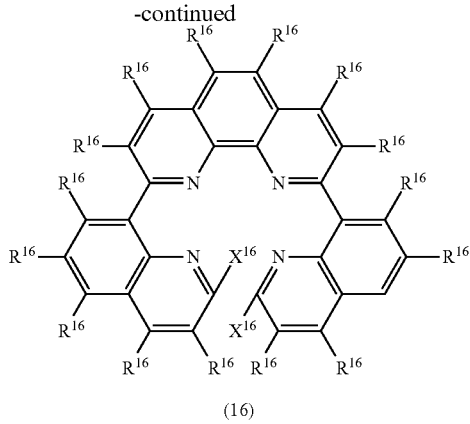

(16)

Compound (17) can be produced by linking 2,9-dihalogeno-1,10-phenanthroline with two indole-boric acid molecules, as shown by the following reaction formula.

[Chemical Formula 88]

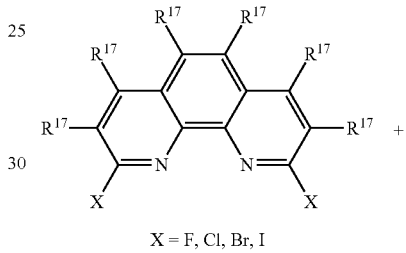

X = F, Cl, Br, I

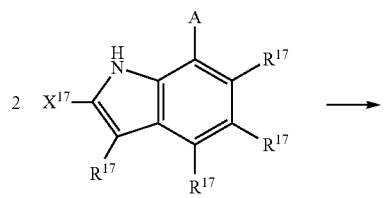

A = B(OH)$_2$ or B with pinacol ester

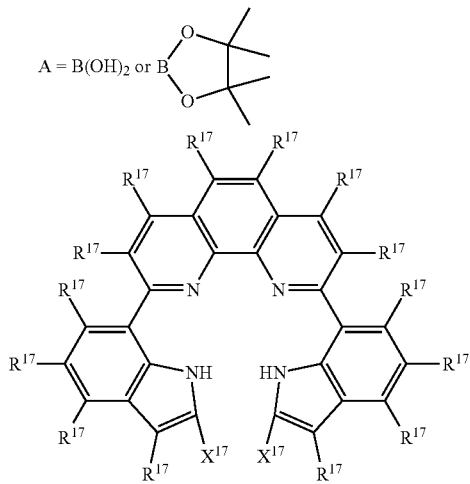

(17)

Compound (18) can be produced by reacting a derivative of compound (17) with an aldehyde or ketone, as shown by the following reaction formula.

[Chemical Formula 89]
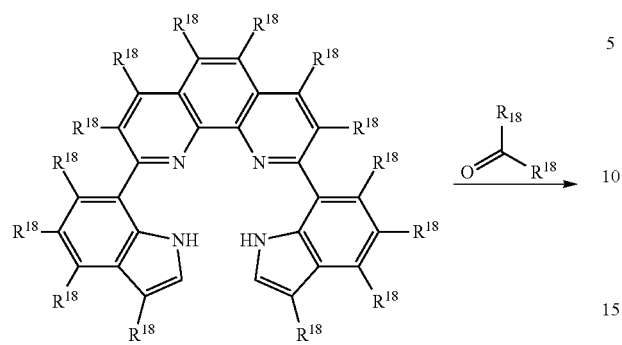 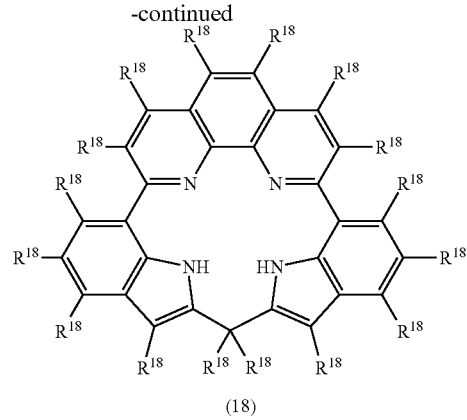
Compound (19) can be produced by reacting a derivative of compound (17) with an aldehyde in the presence of an oxidant, as shown by the following reaction formula. As a separate process for production of compound (19), a derivative of compound (18) may be oxidized with an oxidant.
[Chemical Formula 90]
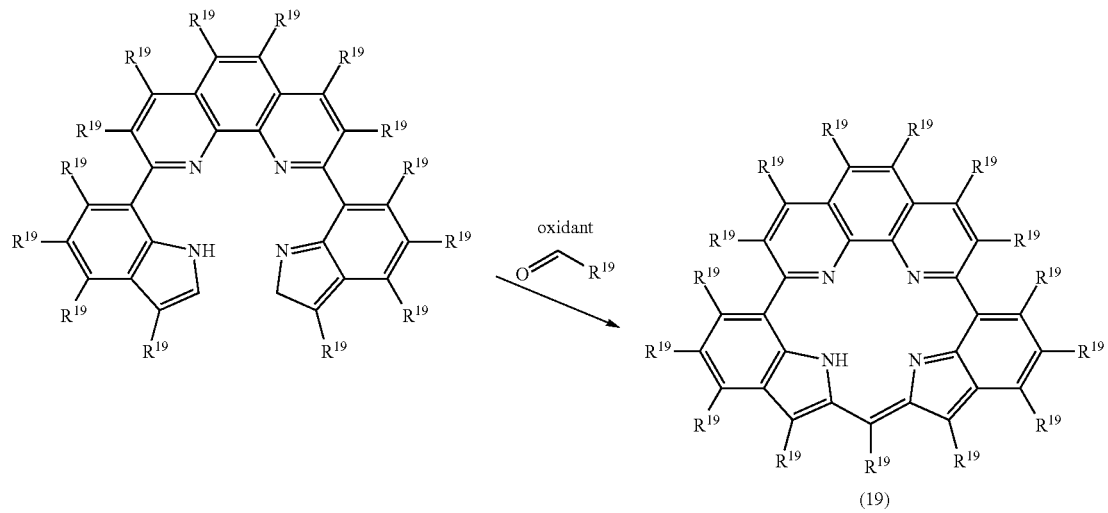
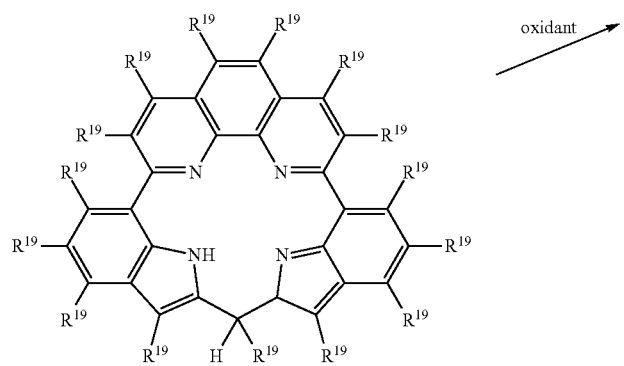

Compound (20) can be produced by linking two molecules each of 2,9-dihalogeno-1,10-phenanthroline and pyrrole-boric acid in a cyclic manner, as shown by the following reaction formula. The linking method used may be cross-coupling reaction, with Suzuki coupling being particularly preferred.

Compound (22) can be produced by linking two molecules each of a carbazole derivative and a pyrrole derivative in a cyclic manner. The linking method used may be cross-coupling reaction, according to the following reaction formula, with Suzuki coupling being particularly preferred.

[Chemical Formula 91]

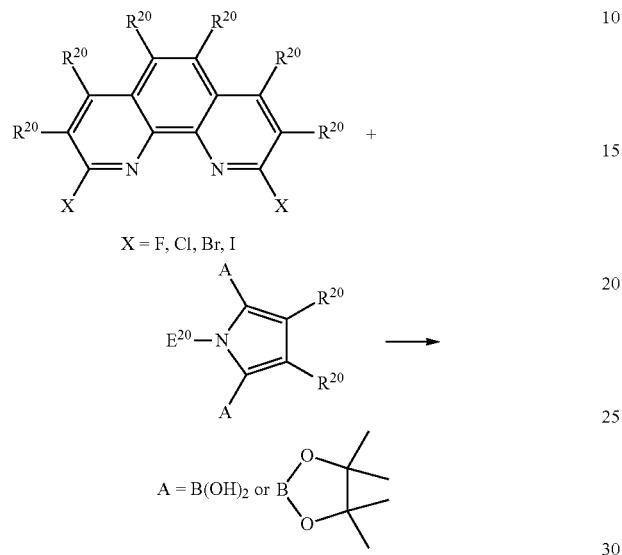

X = F, Cl, Br, I

A = B(OH)$_2$ or 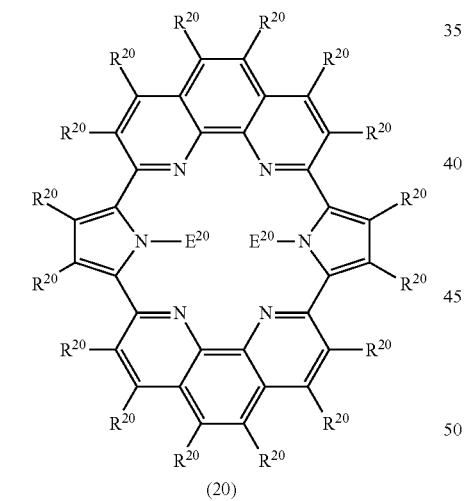

(20)

[Chemical Formula 92]
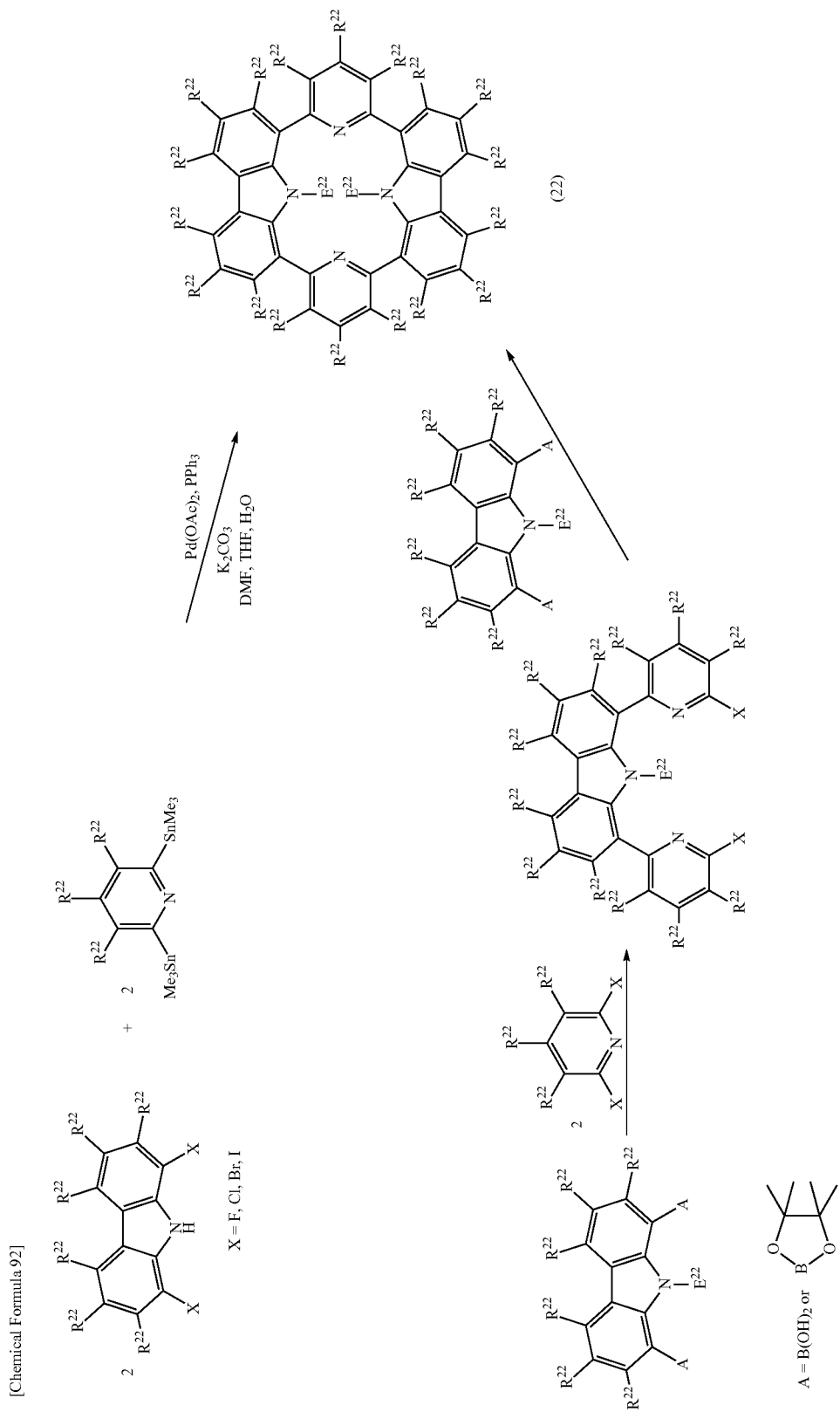

When compound (11) is used as the starting material, an aromatic compound of the invention can be produced by, for example, reacting compound (11) with hexaketocyclohexane in acetic acid, as shown by the following reaction formula.

[Chemical Formula 93]

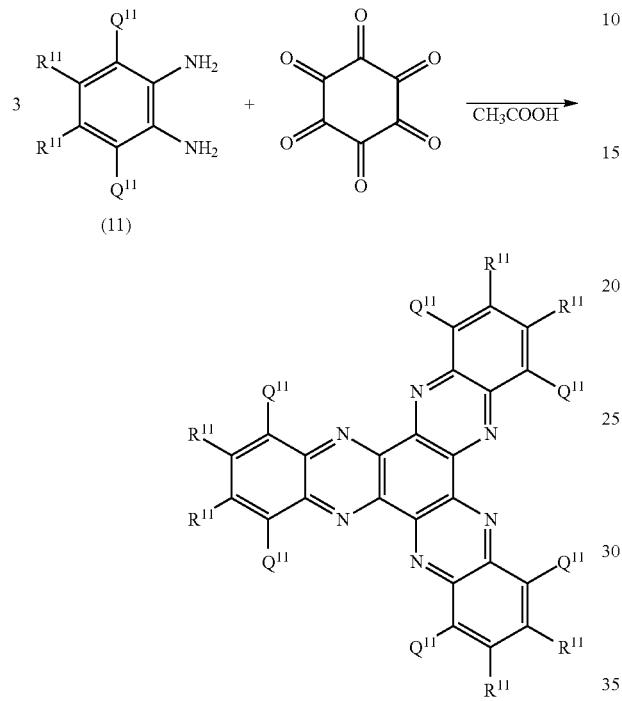

(11)

When compound (12) is used as the starting material, an aromatic compound of the invention can be produced by, for example, linking six nitrogen-containing aromatic heterocyclic rings with compound (12), as shown by the following reaction formula. The linking method may be cross-coupling reaction.

[Chemical Formula 94]

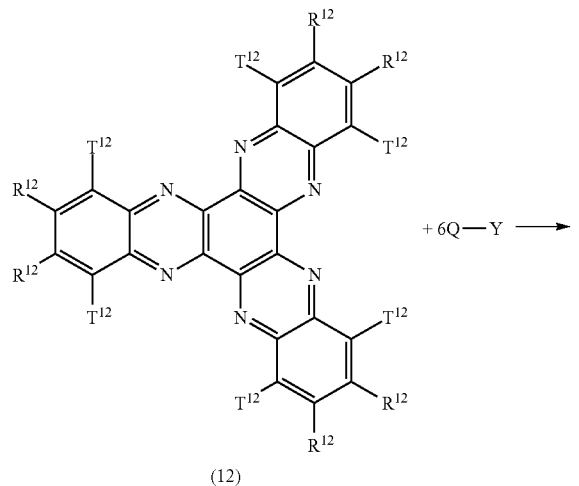

(12)

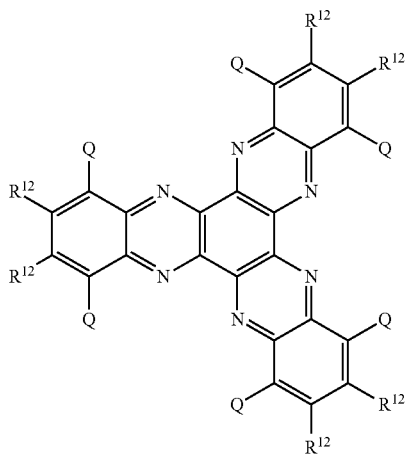

[In the formula, Q is a nitrogen-containing aromatic heterocyclic ring, and Y is a group suitable for cross-coupling, such as boryl or stannyl.]

When compound (13) is used as the starting material, an aromatic compound of the invention can be produced by, for example, deprotecting the protecting group bonded to the nitrogen atom of compound (13), as shown by the following reaction formula. The deprotecting method used may be a commonly employed deprotecting procedure, with heating, microwave irradiation or the like.

[Chemical Formula 95]

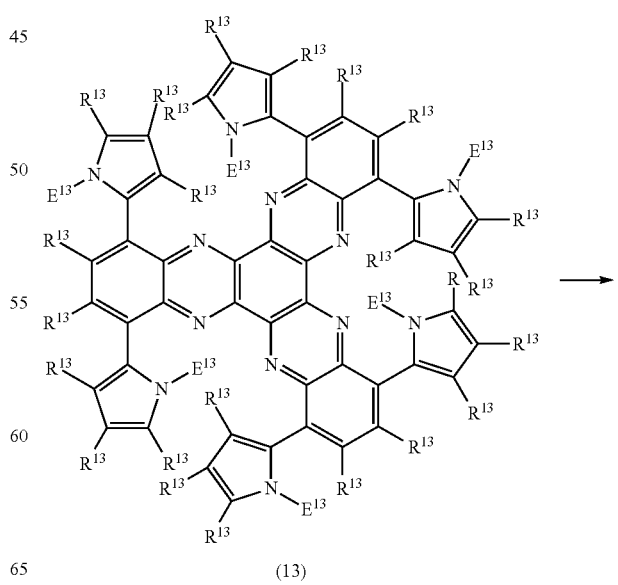

(13)

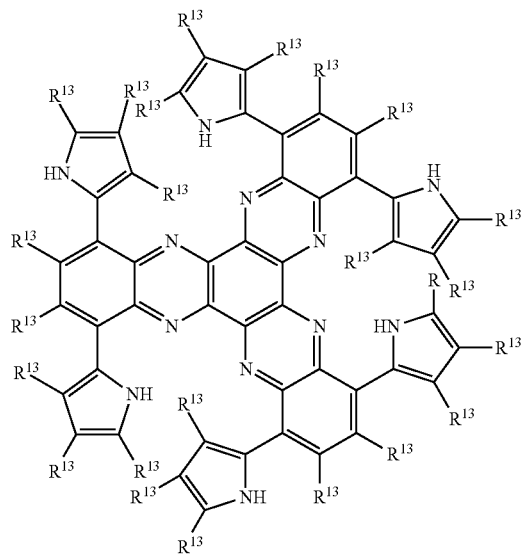

When compound (17) is the starting material, for example, compound (17-a) may be synthesized as represented by the following reaction formula and then converted to an oxo compound with trifluoroacetic acid, after which it may be reacted with a dyad molecule together with ammonium acetate to produce an aromatic compound of the invention.

[Chemical Formula 96]

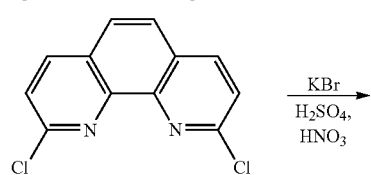

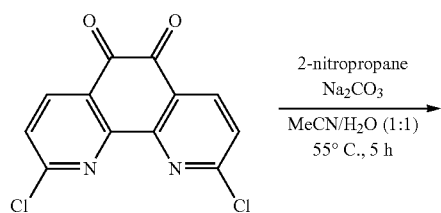

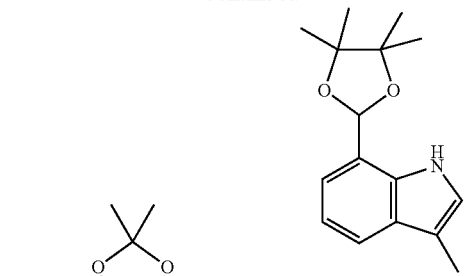

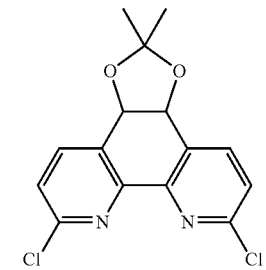

Compound (17-a)

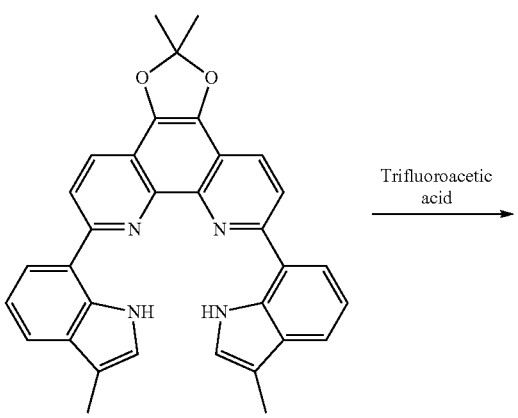

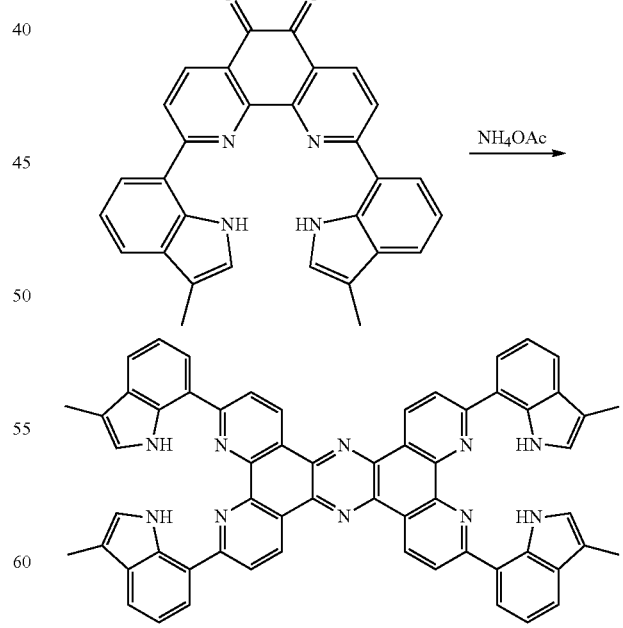

The aromatic compound may further reacted, as in the following reaction formula, to obtain a cyclized structure.

[Chemical Formula 97]
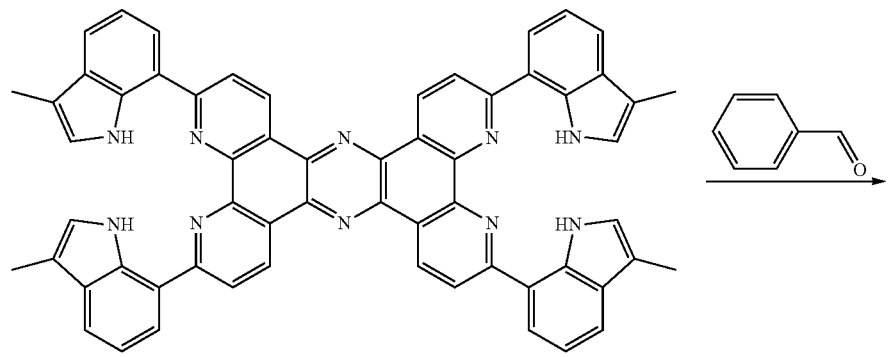
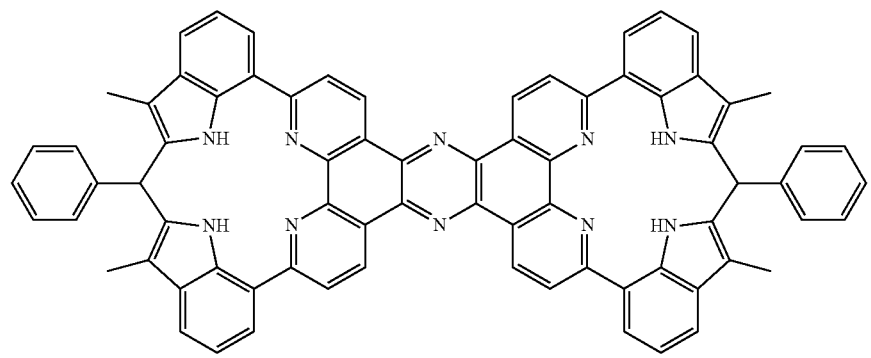
The aromatic compound may also be produced via compound (18-a), as in the following reaction formula.
[Chemical Formula 98]
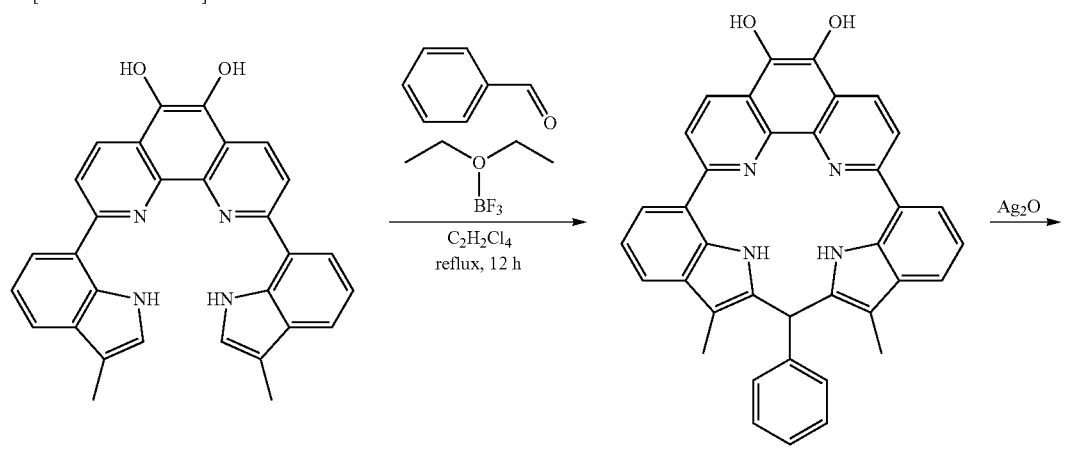
Compound (18-a)

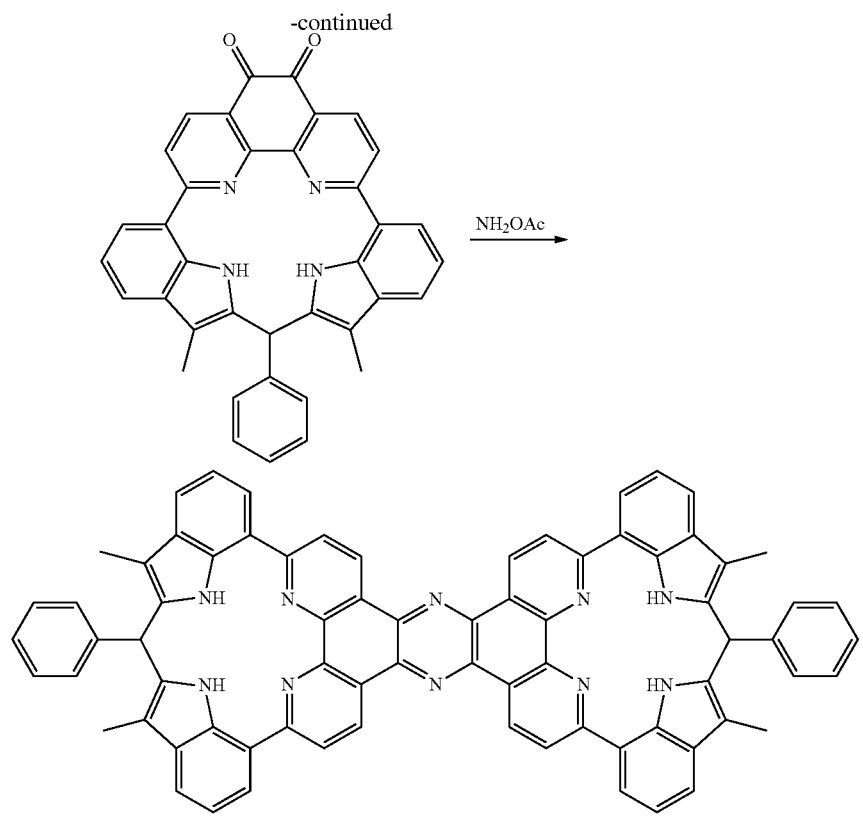
The aromatic compound may also be converted to the oxidized form using an oxidizing agent such as 2,3-dichloro-5,6-dicyano-p-benzoquinone (DDQ).
[Chemical Formula 99]
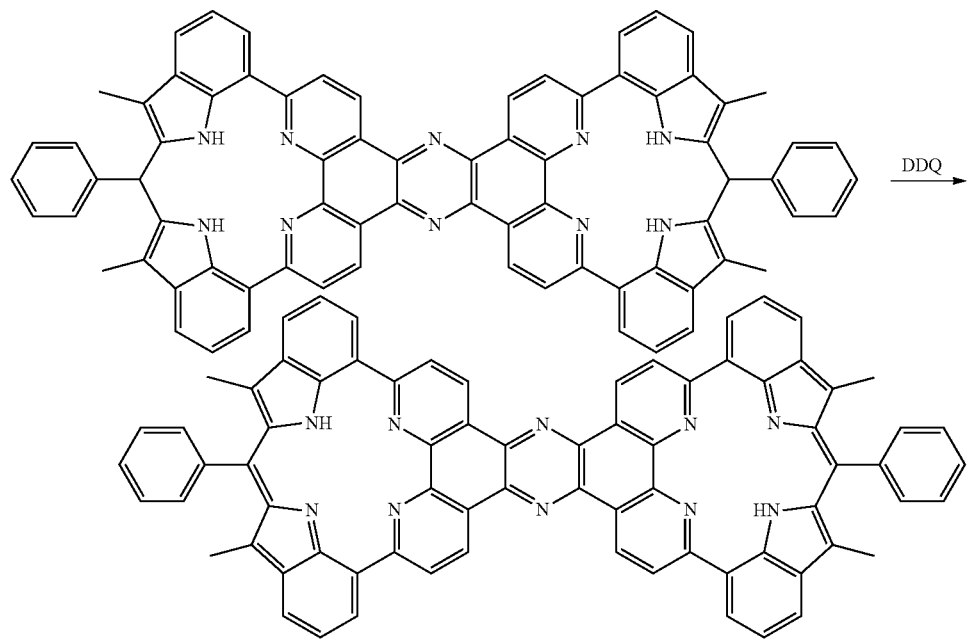
In addition, the aromatic compound of the invention may be produced by synthesis of compound (18-b) followed by heat condensation, as in the following reaction formula.

[Chemical Formula 100]
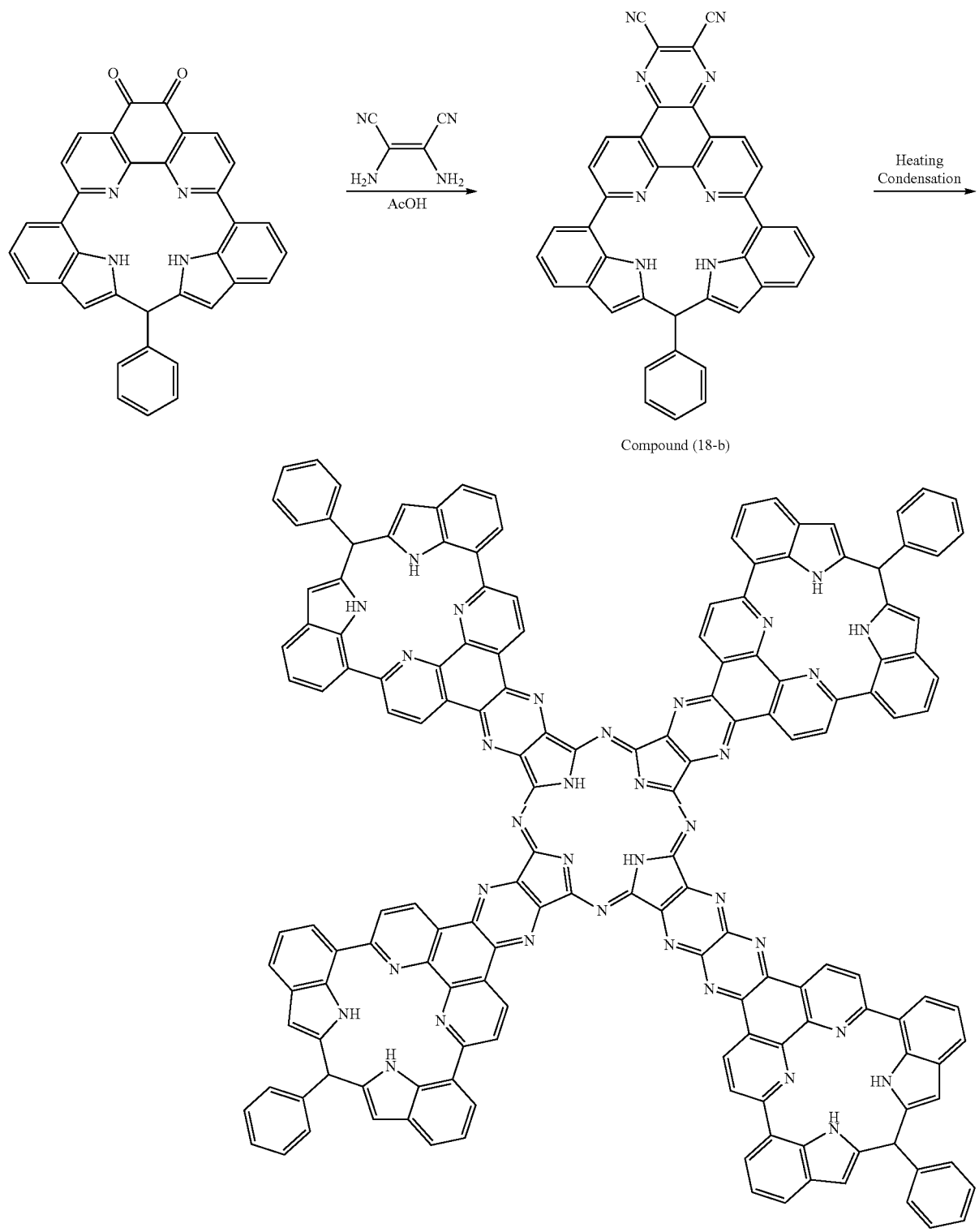
Compound (18-b)
The aromatic compound of the invention can be produced as a high molecular compound having multiple nitrogen-containing aromatic heterocyclic rings linked together. An example is shown in the following reaction formula.

[Chemical Formula 101]

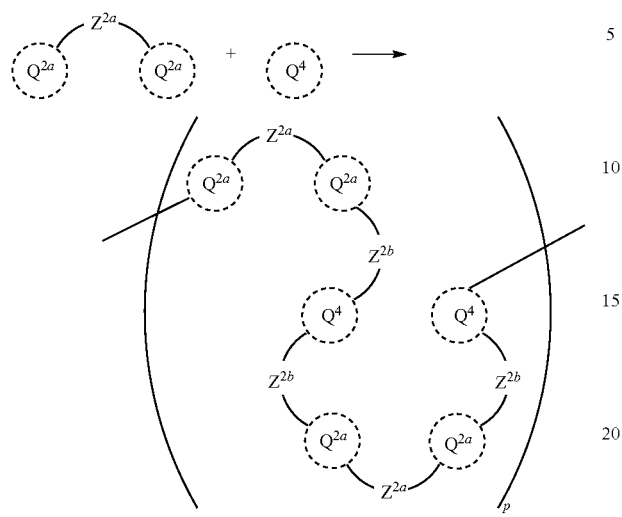

[In this formula, p represents the number of repeating units.]

$Q^4$ in this reaction formula is a nitrogen-containing aromatic heterocyclic ring with two coordinatable nitrogen atoms. Specific structural formulas are shown below. The hydrogens in these structural formulas may be substituted with the aforementioned substituents.

[Chemical Formula 102]

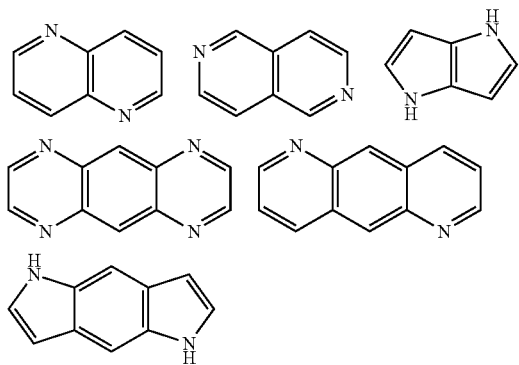

The reaction formula shown above as an example of a method for producing an aromatic compound of the invention, is shown below as a more specific reaction formula.

[Chemical Formula 103]

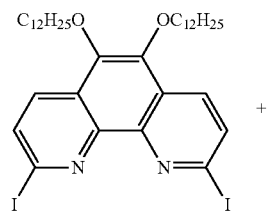

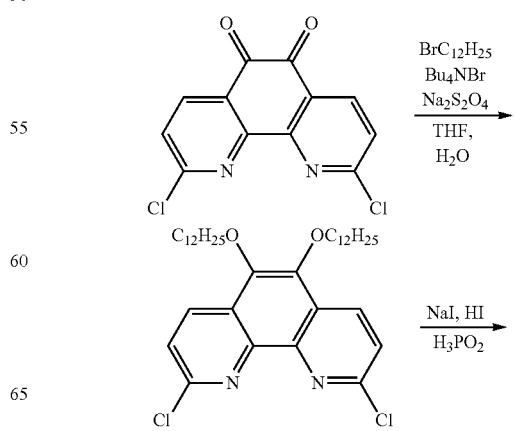

The compounds serving as the starting materials in these reactions can be synthesized by the following reaction formulas, respectively.

[Chemical Formula 104]

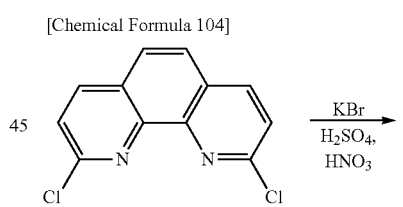

187
-continued
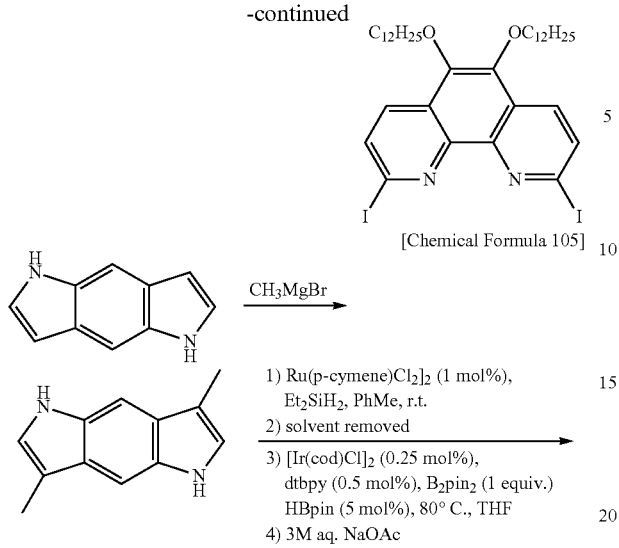
188
-continued
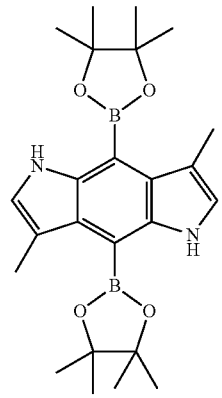
The aromatic compound obtained above may be reacted with an aldehyde to give high molecular compound, as a cyclized form of a structure in which it is surrounded by at least four coordinatable nitrogen atoms.
[Chemical Formula 106]
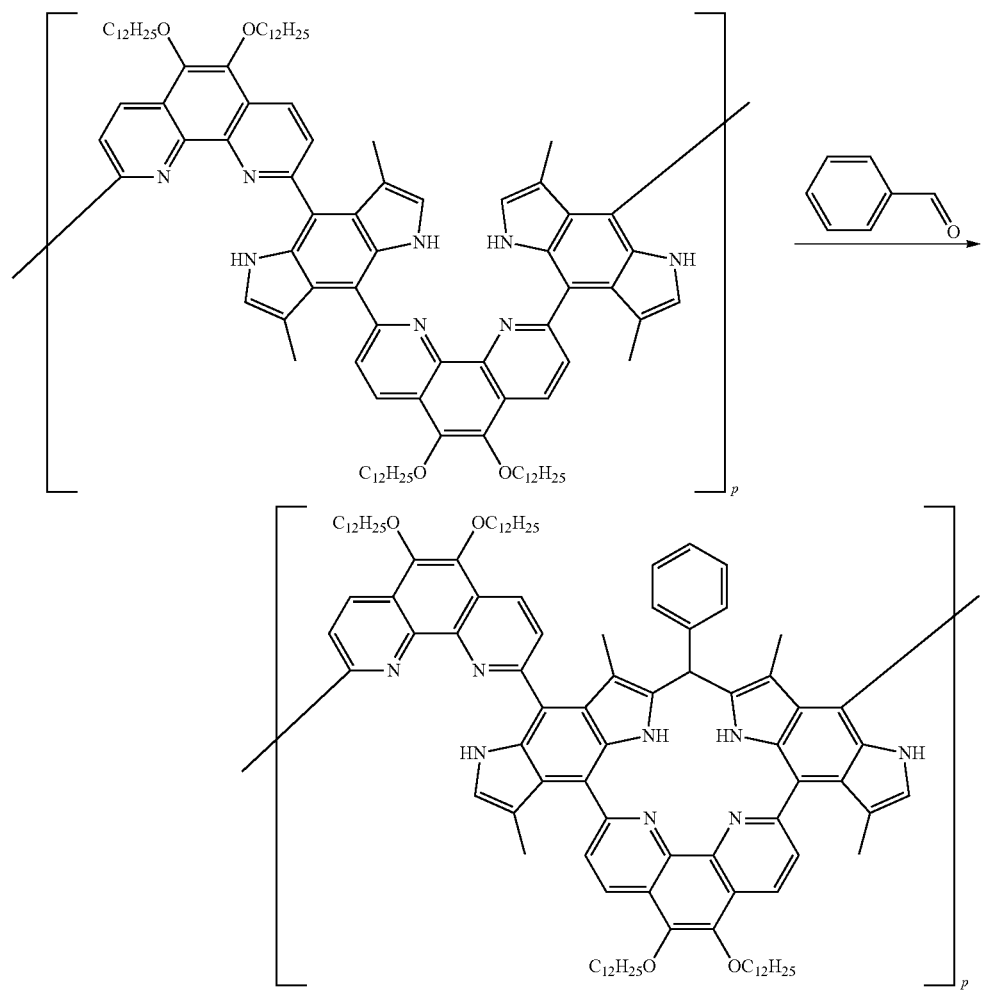

The aromatic compound of the invention may also be synthesized by using a high molecular compound produced according to the following reaction formula.

[Chemical Formula 107]

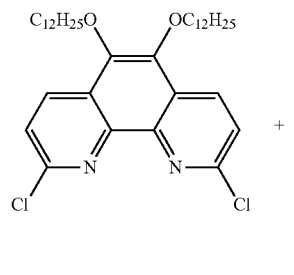

+

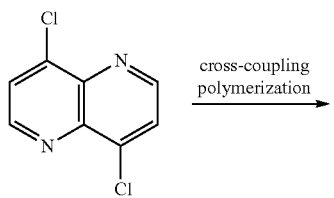

cross-coupling polymerization →

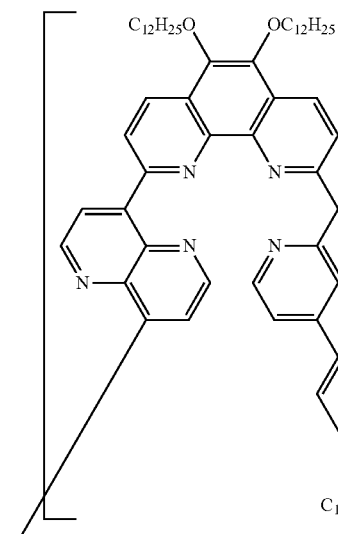

[Chemical Formula 108]

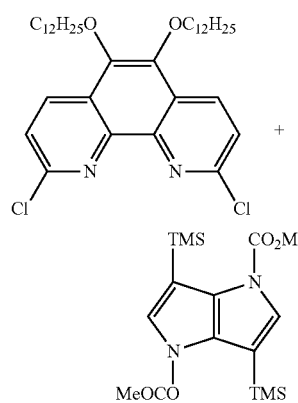

+

TMS, CO₂Me, MeOCO, TMS pyrrolopyrrole cross-coupling polymerization →

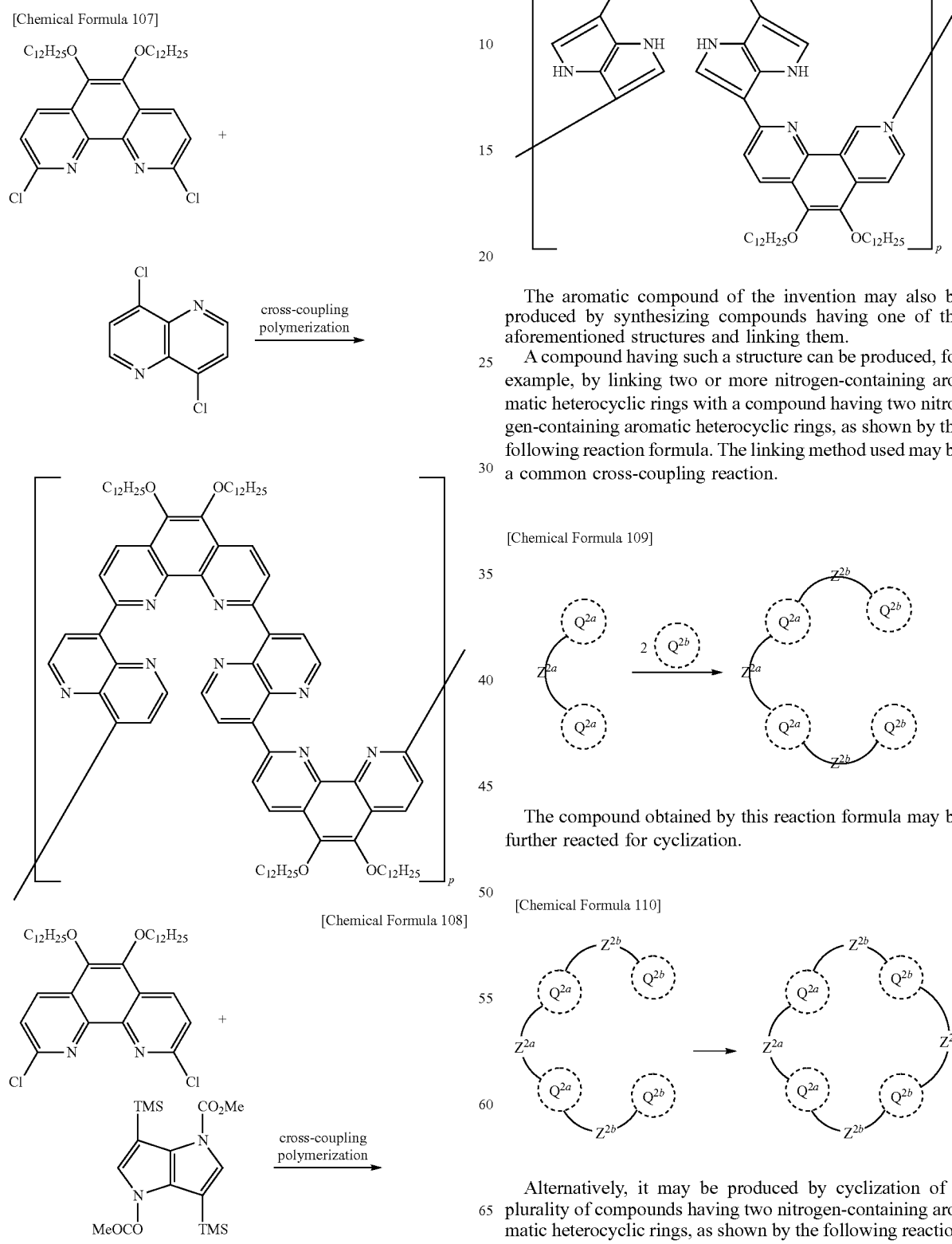

The aromatic compound of the invention may also be produced by synthesizing compounds having one of the aforementioned structures and linking them.

A compound having such a structure can be produced, for example, by linking two or more nitrogen-containing aromatic heterocyclic rings with a compound having two nitrogen-containing aromatic heterocyclic rings, as shown by the following reaction formula. The linking method used may be a common cross-coupling reaction.

[Chemical Formula 109]

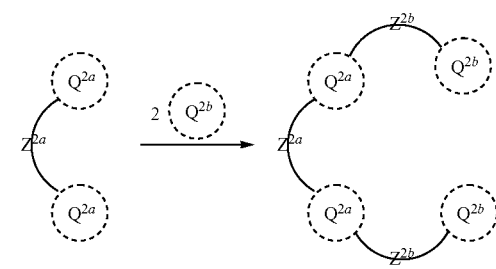

The compound obtained by this reaction formula may be further reacted for cyclization.

[Chemical Formula 110]

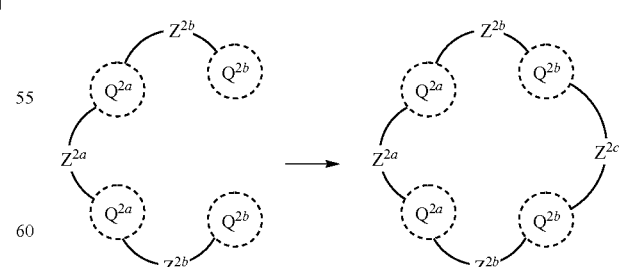

Alternatively, it may be produced by cyclization of a plurality of compounds having two nitrogen-containing aromatic heterocyclic rings, as shown by the following reaction formula.

[Chemical Formula 111]

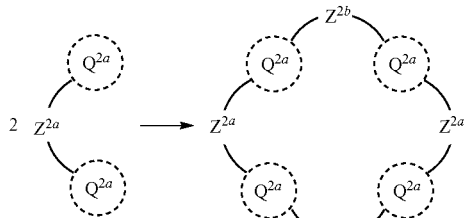

[Chemical Formula 112]

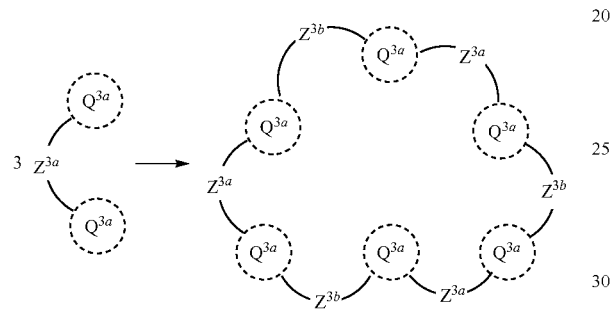

It is also possible to produce a aromatic compound of the invention by linking compounds each having a structure surrounded by at least 4 coordinatable nitrogen atoms, as shown in the following reaction formula. The method of linking them may employ a method of linking compounds with halogen groups by Yamamoto coupling, as represented by the following reaction formula.

[Chemical Formula 113]

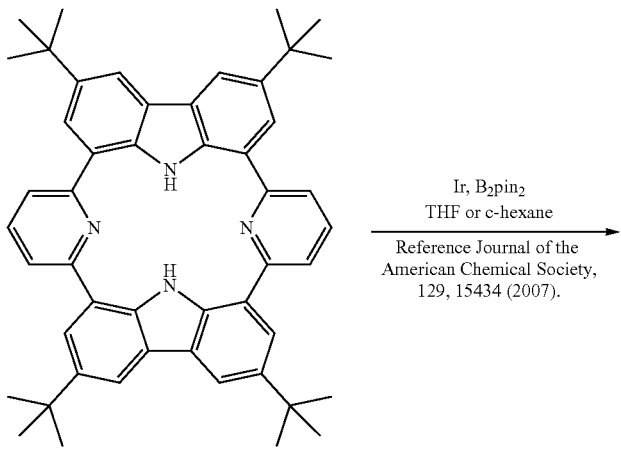

Alternatively, it may employ a method of linking boric acid esters with compounds having halogeno groups by Suzuki coupling, as represented by the following reaction formula.

[Chemical Formula 114]

193 194

-continued

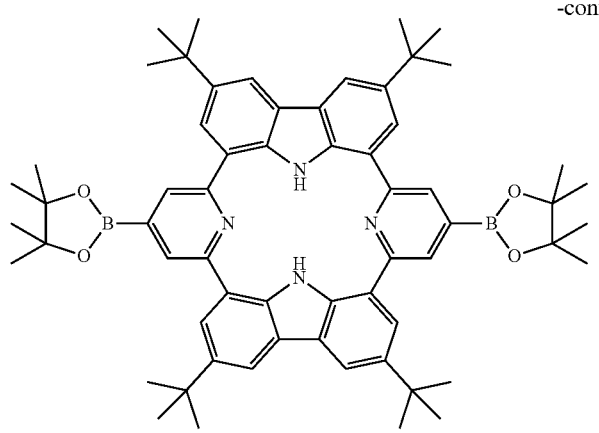
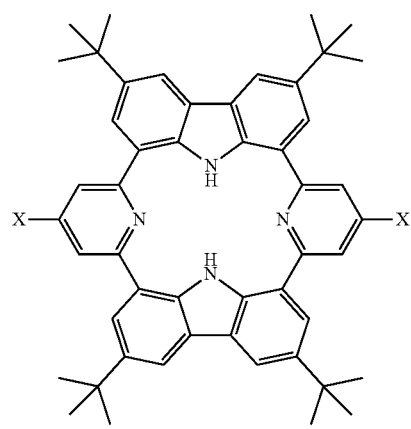

halogenation
CuX₂, or
NBS/NIS

X = Br or I

Suzuki Coupling

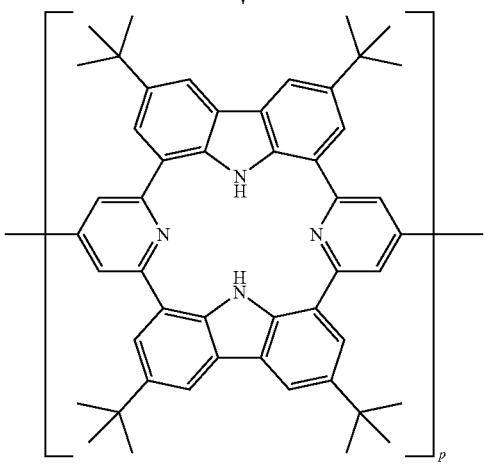

The aromatic compound of the invention may comprise a structure obtained by removing one or more hydrogens from a compound having the structure shown below in addition to the structure satisfying the above mentioned conditions (a) and (b). The hydrogens in the formulas may be substituted with the aforementioned substituents.

[Chemical Formula 115]

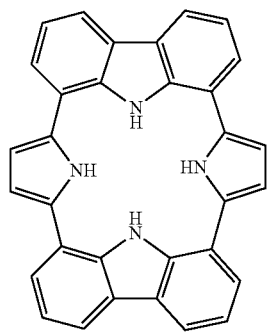

(24)

-continued

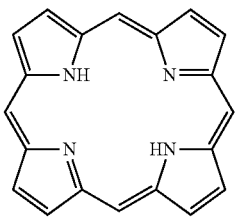

(25)

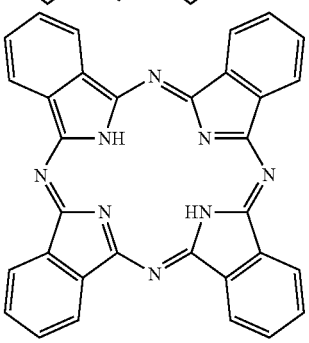

(26)

-continued

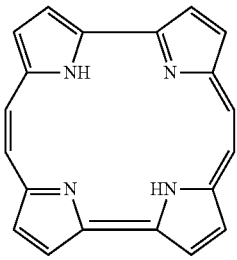
(27)

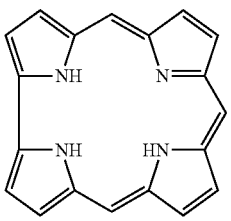
(28)

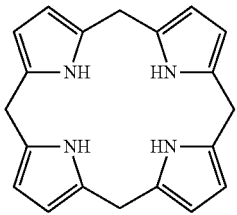
(29)

Compound (24) can be produced by linking two molecules each of dihalogeno-carbazole and pyrrole-boric acid in a cyclic manner, as represented by the following reaction formula. The linking method used may be cross-coupling reaction, with Suzuki coupling being particularly preferred.

[Chemical Formula 116]

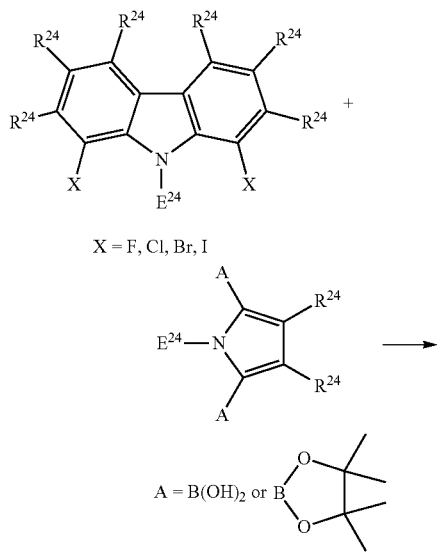

-continued (24)

[In the formulas, $R^{24}$ is hydrogen or a substituent and each may be the same or different, and adjacent substituents may bond together to form a ring. The multiple $E^{24}$ groups each independently represent hydrogen or a protecting group.]

A process for production of a metal complex of the invention will now be described.

A metal complex of the invention may be produced by any method, such as the following, for example.

An aromatic compound to serve as the ligand for the metal complex may be reacted with a reactant that donates a metal atom (hereinafter referred to as "metal donor") in the presence of a solvent to obtain a metal complex according to the invention. A metal donor is a compound with a metal atom, and in most cases a salt having the metal atom as the cation is used. As metal donors there are preferred chloride salts, bromide salts, iodide salts, acetic acid salts, nitric acid salts, sulfuric acid salts and carbonic acid salts.

As solvents to be used for the reaction there may be mentioned water; organic acids such as acetic acid and propionic acid; amines such as ammonia water and triethylamine; alcohols such as methanol, ethanol, n-propanol, isopropyl alcohol, 2-methoxyethanol, 1-butanol and 1,1-dimethylethanol; ethylene glycol, diethyl ether, 1,2-dimethoxyethane, methyl ethyl ether, 1,4-dioxane, tetrahydrofuran; aromatic hydrocarbons such as benzene, toluene, xylene, mesitylene, durene and decalin; halogen-based solvents such as dichloromethane, chloroform, carbon tetrachloride, chlorobenzene and 1,2-dichlorobenzene; N,N'-dimethylformamide, N,N'-dimethylacetamide, N-methyl-2-pyrrolidone, dimethyl sulfoxide, acetone, acetonitrile, benzonitrile, triethylamine, pyridine, pyrazine, diazabicyclo[2,2,2]octane, and the like. These reaction solvents may be used alone or in combinations of two or more. Preferred solvents are those that can dissolve the aromatic compound as the ligand and the metal donor.

The reaction temperature will normally be −10 to 250° C., and is preferably 0-200° C. and most preferably O-150° C.

The reaction time will normally be from 1 minute to 1 week, and is preferably 5 minutes to 24 hours and most preferably 1 hour to 12 hours.

The method of isolation and purification of the target metal complex from the reaction mixture obtained from the reaction may be a publicly known recrystallization, reprecipitation or chromatography method, or a combination of these. Depending on the type of solvent, the target metal complex may be a precipitate in the reaction mixture. In such cases, the precipitated metal complex may be filtered out and washed and dried for isolation and purification of the metal complex.

Also, when a metal complex synthesized from the aromatic compound of the invention is used as a catalyst, it is not necessary to isolate the metal complex, and the aromatic compound and metal donor may be reacted in the solvent together with carbon or the like and the solvent subsequently distilled off to prepare the catalyst.

The aromatic compound, metal complex, composition and modified compound of the invention are useful as fuel cell catalyst materials, automobile catalyst materials, photocatalytic materials, catalyst materials for redox reaction, oxidation catalyst for water, electrode materials in batteries or capacitors, hydrogen storage materials, chemical sensor materials, LEDs, transistors, and organic semiconductor materials such as photoelectric conversion elements.

When the aromatic compounds, metal complexes, compositions and modified forms thereof according to the invention are used as catalyst materials for fuel cells (i.e. electrode catalysts for fuel cells), they may be used as electrode catalysts for cathodes and/or electrode catalysts for anodes, but they are more preferably used as electrode catalysts for cathodes.

The fuel cells in which they are used are preferably solid polymer fuel cells.

A polymer electrolyte membrane used in the solid polymer fuel cell may be a polymer electrolyte membrane comprising a polymer electrolyte having proton conductivity, such as NAFION®, or a polymer electrolyte having anionic conductivity. Hydroxide ion (OH⁻) is an example of an anion.

The fuel cell of the invention can operate as a solid polymer fuel cell or an alkaline fuel cell when the fuel is hydrogen, or as a direct alcohol fuel cell when the fuel is an alcohol such as methanol or ethanol.

A fuel cell employing an electrode catalyst for a fuel cell according to the invention is useful, for example, as an automobile power source, electrical appliance power source, or a miniature power source for a mobile device such as a cellular phone or portable personal computer.

EXAMPLES

The present invention will now be explained by examples.

Example 1

Synthesis of Aromatic Compound P1

Aromatic compound P1 was synthesized according to the following reaction formula.

[Chemical Formula 117]

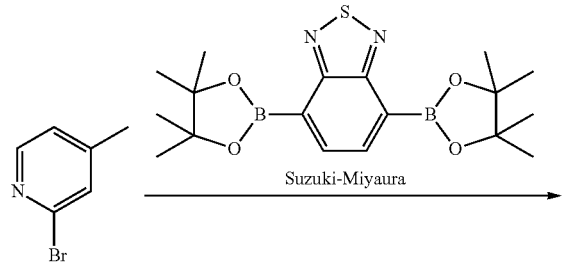

Suzuki-Miyaura

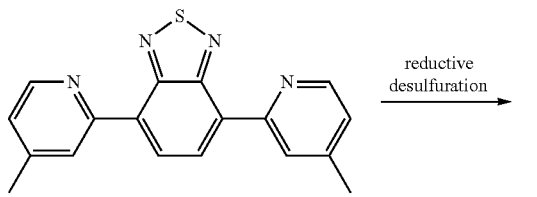

reductive desulfuration

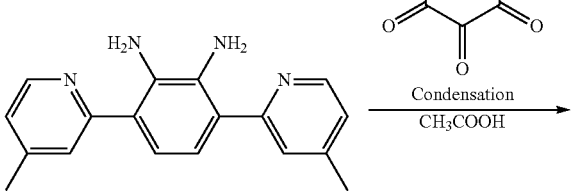

Compound 1

Condensation
CH$_3$COOH

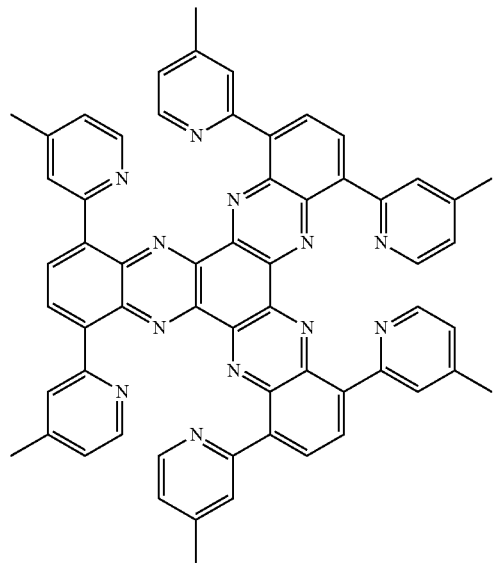

Aromatic compound P1

First, compound 1 (1,4-bis-(4-methylpyridin-2-yl)-3,4-diaminobenzene) to be used as the starting material for aromatic compound P1 was synthesized by the following method.

[Chemical Formula 118]

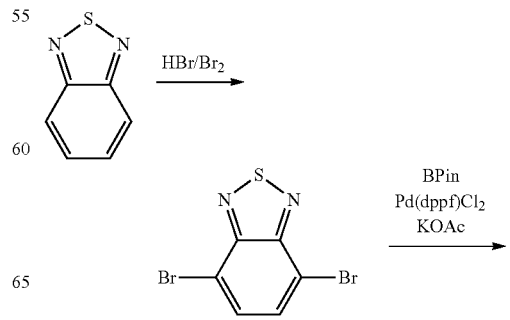

HBr/Br$_2$

BPin
Pd(dppf)Cl$_2$
KOAc

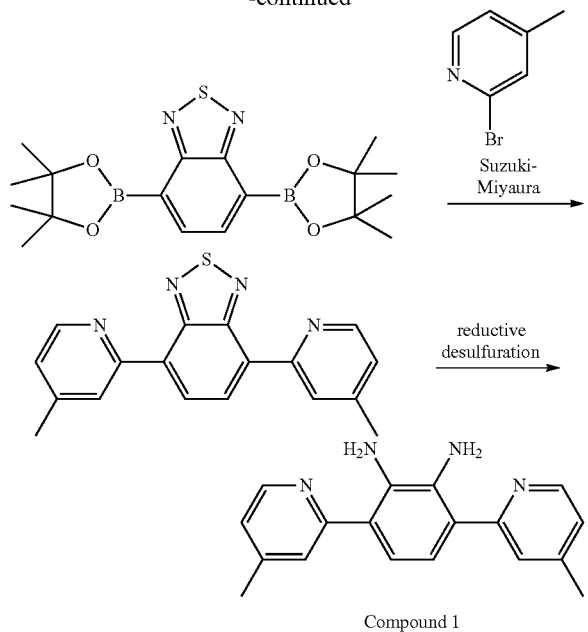

Compound 1

Specifically, 4,7-bis-pinacolato-diborane-2,1,3-benzothiadiazole was synthesized by a procedure described in the literature (JACS, 129, 2007, 3472) and then reacted with 2-bromo-methylpyridine to obtain 4,7-bis(4-methylpyridin-2-yl)-2,1,3-benzothiadiazole.

Next, the 4,7-bis(4-methylpyridin-2-yl)-2,1,3-benzothiadiazole was subjected to reductive desulfuration reaction by the following procedure to synthesize compound 1. Specifically, 0.213 g (0.669 mmol) of 4,7-bis(4-methylpyridin-2-yl)-2,1,3-benzothiadiazole was added to 80 ml of a mixed solution of hydrochloric acid/ethanol/water (3:3:2) containing 5 equivalents of Sn and 10 mol equivalents of $SnCl_2$, and the mixture was circulated for 3 hours. An ammonia solution was added to adjust the pH to 10, and dichloromethane was used for extraction. The obtained crude product was subjected to column purification (methanol/ethyl acetate/dichloromethane) to obtain 0.143 g of compound 1 at a yield of 74%. The same procedure was repeated to obtain the amount necessary for the following reaction.

Results of NMR Analysis and MS Analysis of Compound 1
$^1$H-NMR (250 MHz, $CD_2Cl_2$): δ=8.505 ppm (d, 2H); 7.578 ppm (s, 2H); 7.143 ppm (s, 2H); 7.057 ppm (d, 2H); 5.648 ppm (s, 4H); 2.422 ppm (s, 6H)
$^{13}$C-NMR (250 MHz, $CD_2Cl_2$): δ=159.69 ppm; 148.63 ppm; 148.13 ppm; 137.12 ppm; 123.79 ppm; 123.22 ppm; 122.67 ppm; 118.96 ppm; 21.62 ppm
MS (FD, 8 kV) Found: m/z 290.4. Calculated: m/z: 290.36

Next, the obtained compound 1 and hexaketocyclohexane were subjected to condensation reaction to synthesize aromatic compound P1. Specifically, 0.388 g (1.336 mmol) of compound 1 (1,4-bis-(4-methylpyridin-2-yl)-3,4-diaminobenzene) was added to 20 ml of acetic acid, and the solution was heated to 50° C. and aerated with argon gas for 45 minutes. After adding 0.126 g (0.405 mmol) of hexaketocyclohexane to the solution, the mixture was heated at 105° C. for 36 hours. The crude product was purified with a column (solvent: triethylamine/methanol/ethyl acetate/dichloromethane) to obtain aromatic compound P1 at a yield of 62%.

Results of NMR Analysis and MS Analysis of Aromatic Compound P1
$^1$H-NMR (250 MHz, $CF_3COOD$): δ=9.035 ppm (s, 6H); 8.678 ppm (s, 6H); 8.360 ppm (d, 6H); 8.039 ppm (d, 6H); 2.841 ppm (s, 18H)
$^{13}$C-NMR (250 MHz, $CF_3COOD$): δ=166.21 ppm; 150.08 ppm; 145.82 ppm; 143.64 ppm; 142.83 ppm; 138.45 ppm; 134.14 ppm; 132.08 ppm; 130.38 ppm; 23.92 ppm
MS (FD, 8 kV) Found: m/z 931.4 (100.0%, M$^+$); 465.7 (81.5%, M$^{2+}$), Calculated: m/z: 931.06 (100.0%, M$^+$)

Example 2

Synthesis of Aromatic Compound P2

Aromatic compound P2 was synthesized according to the following reaction formula.

[Chemical Formula 119]

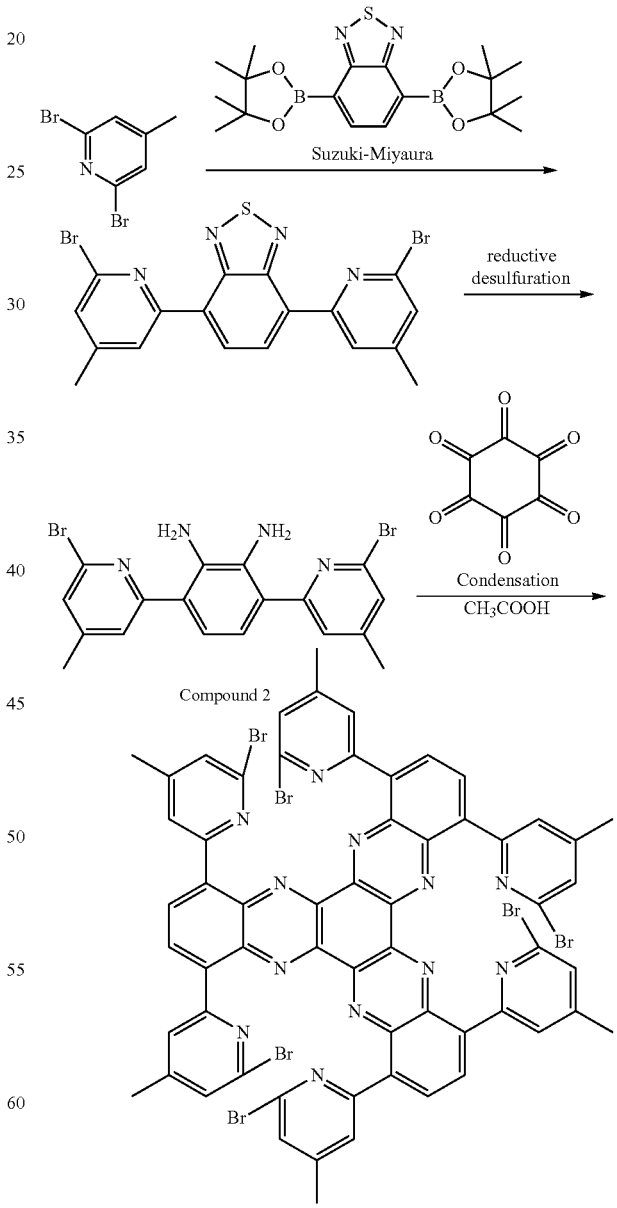

Aromatic compound P2

First, compound 2 (1,4-bis-(2-bromo-4-methylpyridin-6-yl)-3,4-diaminobenzene) to be used as the starting material was synthesized via 4,7-bis-(2-bromo-4-methylpyridin-6-yl)-2,1,3-benzothiadiazole.

Specifically, 4.930 g of 2,6-dibromo-4-methylpyridine (0.0196 mol) and 0.762 g of 4,7-bis-pinacolato-diborane-2,1,3-benzothiadiazole (0.00196 mol) were dissolved in 120 ml of toluene to obtain a toluene solution. To the toluene solution there were added 10 ml of an aqueous solution dissolving 10 g of $K_2CO_3$, and 0.032 g of trioctylmethylammonium chloride (trade name: Aliquat336 by Aldrich Co., hereunder referred to as "Aliquat336"). After deaerating the solution with argon, 0.1132 g of tetrakis-(triphenylphosphin)-Pd(0)(0.098 mmol) was added and the mixture was heated at 80° C. for 1 week. This was followed by column purification (dichloromethane/hexane/ethyl acetate) to obtain 0.507 g of 4,7-bis-(2-bromo-4-methylpyridin-6-yl)-2,1,3-benzothiadiazole at a yield of 54%.

Results of NMR Analysis and MS Analysis of 4,7-bis-(2-bromo-4-methylpyridin-6-yl)-2,1,3-benzothiadiazole $^1$H-NMR (250 MHz, $CD_2Cl_2$): δ=8.684 ppm (s, 2H); 8.625 ppm (s, 2H); 7.385 ppm (s, 2H); 2.484 ppm (s, 6H)

MS (FD, 8 kV) Found: m/z 476.2 ($M^+$). Calculated: m/z: 476.19 ($M^+$)

Next, a $HCl/EtOH/H_2O$ (40:10:5) solution containing 0.201 g (0.422 mmol) of 4,7-bis-(2-bromo-4-methylpyridin-6-yl)-2,1,3-benzothiadiazole was prepared and heated to 50° C., and after adding 2.362 g (0.0199 mol) of Sn and 3.773 g (0.0199 mol) of $SnCl_2$ to the solution, it was circulated for 14 hours. The solution was rendered alkaline with NaOH, and then extracted with dichloromethane and subjected to column purification (ethyl acetate/hexane) to obtain 0.149 g of compound 2 at a yield of 79%.

NMR Analysis and MS Analysis of Compound 2

$^1$H-NMR (250 MHz, $CD_2Cl_2$): δ=7.509 ppm (s, 2H); 7.255 ppm (s, 2H); 7.086 ppm (s, 2H); 5.458 ppm (s, 4H); 2.389 ppm (s, 6H)

$^{13}$C-NMR (250 MHz, $CD_2Cl_2$): δ=160.26 ppm; 151.91 ppm; 140.71 ppm; 137.41 ppm; 126.66 ppm; 123.13 ppm; 122.13 ppm; 119.16 ppm; 21.56 ppm MS (FD, 8 kV) Found: m/z 448.4 ($M^+$). Calculated: m/z: 448.15 ($M^+$)

Next, the obtained compound 2 and hexaketocyclohexane were subjected to condensation reaction to obtain aromatic compound P2. Specifically, 0.102 g (0.227 mmol) of compound 2 was added to 5 ml of acetic acid, and the solution was heated to 50° C. and aerated with argon gas for 45 minutes. After adding 0.024 g (0.076 mmol) of hexaketocyclohexane to the obtained solution, the mixture was heated at 105° C. for 18 hours. The mixture was rendered alkaline with sodium hydroxide and then extracted with dichloromethane (100 ml×5 times) to obtain 0.120 g of a crude product. The crude product was purified with a column (solvent: dichloromethane/hexane/ethyl acetate) to obtain aromatic compound P2 at a yield of 67%.

NMR Analysis and MS Analysis of Aromatic Compound P2

$^1$H-NMR (250 MHz, $CD_2Cl_2$): δ=8.857 ppm (s, 12H); 8.273 ppm (s, 6H); 7.397 ppm (s, 6H); 1.790 ppm (s, 18H)

$^1$H-NMR (300 MHz, $CD_2Cl_2$): δ=8.863 ppm (s, 6H); 8.275 ppm (d, 6H); 7.406 ppm (d, 6H); 1.798 ppm (s, 18H)

MS (FD, 8 kV): m/z 1405.7 ($M^+$); 703.1 ($M^{2+}$). Calculated: m/z: 1404.43 ($M^+$)

Example 3

Synthesis of Aromatic Compound P3

Aromatic compound P3 was synthesized according to the following reaction formula.

[Chemical Formula 120]

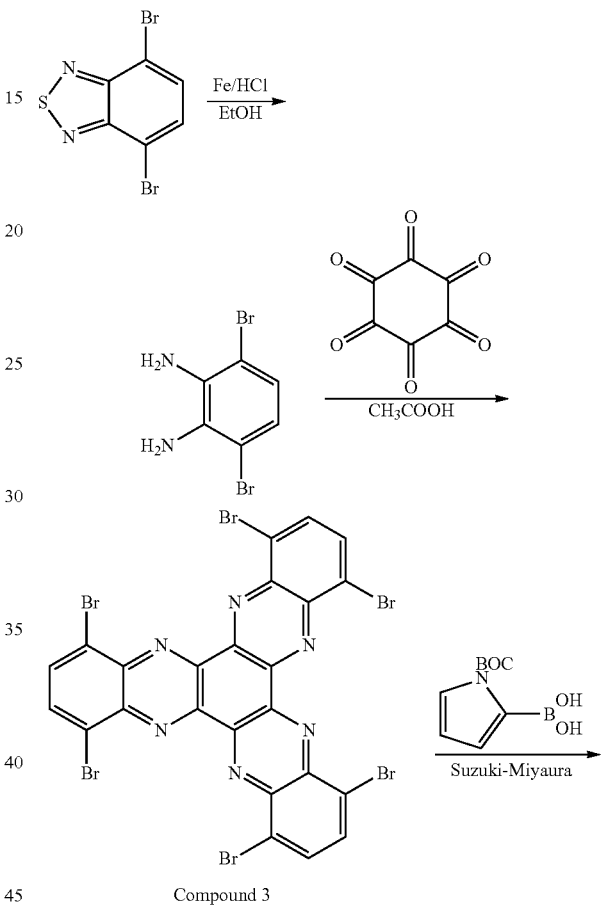

Compound 3

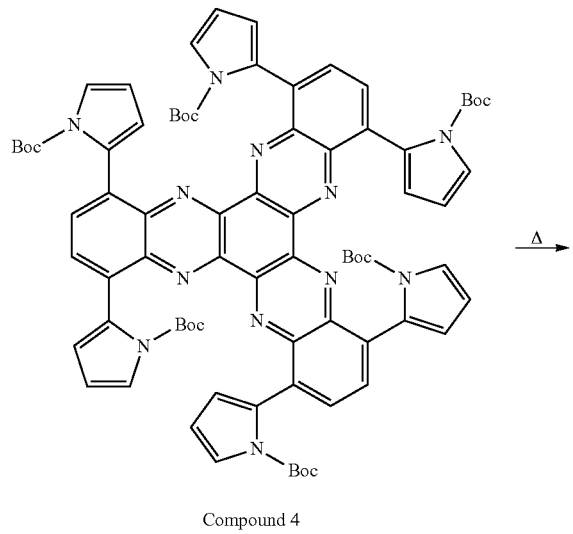

Compound 4

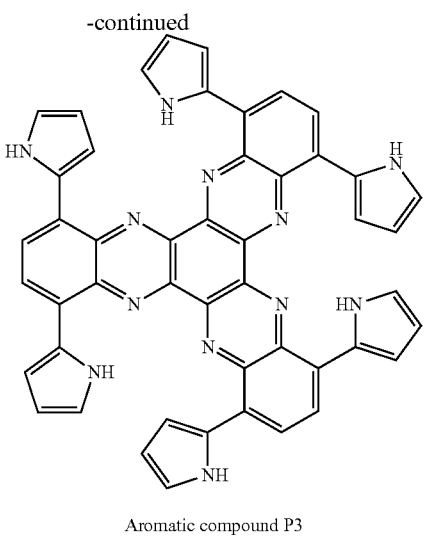

Aromatic compound P3

First, compound 3 (1,4,7,10,13,16-hexa-bromo-5,6,11,12,17,18-hexaaza-trinaphtylene) as the starting material was synthesized by the following method. Specifically, 1,4-dibromo-2,3-diaminobenzene was synthesized according to the procedure described in the literature (*Journal of Organic Chemistry* 71 (2006) 3350). After heating 10 ml of acetic acid containing 0.600 g (2.256 mmol) of 1,4-dibromo-2,3-diaminobenzene to 50° C., it was deaerated with argon for 1 hour. After then adding 0.234 g (0.752 mmol) of hexaketocyclohexane to the obtained solution, the mixture was heated at 110° C. for 10 hours. The obtained reaction mixture was poured into ice water and the solution was rendered alkaline with NaOH. A faint green product was obtained as a precipitate, and after filtering the precipitate, it was washed with water and dichloromethane to obtain 0.499 g of compound 3.

Results of Mass Spectrometry for Compound 3
MS (FD, 8 kV) Found: m/z 857.5 ($M^+$); 429.7 ($M^{2+}$).
Calculated: m/z 857.57 ($M^+$)
MALDI-TOF in TCNO: m/z 858 ($M^+$)

The obtained compound 3 was then used to synthesize compound 4 (1,4,7,10,13,16-hexa-(1'-N-BOC-pyrrole-2'-yl)-5,6,11,12,17,18-hexaaza-trinaphtylene) as a precursor for aromatic compound P3. Specifically, 3.416 g (16.2 mmol) of 1-N—BOC-pyrrole-2-boronic acid, 0.024 g of Aliquat 336 and 13.35 g (0.0966 mol) of $K_2CO_3$ were added to a mixture of 100 ml of THF containing 1.381 g (1.61 mmol) of compound 3, and 40 ml of toluene, and the mixture was deaerated with argon for 1 hour. After adding 0.669 (0.580 mmol) of tetrakis-(triphenylphosphin)-Pd(0) to the reaction mixture, it was heated at 85° C. for one day, 12 ml of deaerated water was added, and heating was continued for 2 days to obtain a crude product. The crude product was purified by column (ethyl acetate/dichloromethane/hexane) to obtain compound 4.

Results of Mass Spectrometry for Compound 4
MS (FD, 8 kV) Found: m/z 1374.5. Calculated: m/z 1374.59

Next, the obtained compound 4 was heated for deprotection of the pyrrole group, to obtain aromatic compound P3 (1,4,7,10,13,16-hexa-(pyrrole-2'-yl)-5,6,11,12,17,18-hexaaza-trinaphtylene).

Specifically, 0.340 g of compound 4 was heated at 180° C. for 30 minutes under reduced pressure of 0.2 mbar to obtain aromatic compound P3.

Results of Mass Spectrometry for Aromatic Compound P3
MS (FD, 8 kV) Found: m/z 386.6 ($M^{2+}$); 774.0 ($M^+$)
Calculated: m/z 387.14 ($M^2$); 774.27 ($M^+$)
MALDI-TOF (TCNQ): m/z 775 ($M^+$); 1549 (2 $M^+$)

Example 4

Synthesis of Aromatic Compound P4

Aromatic compound P4 was synthesized according to the following reaction formula.

[Chemical Formula 121]

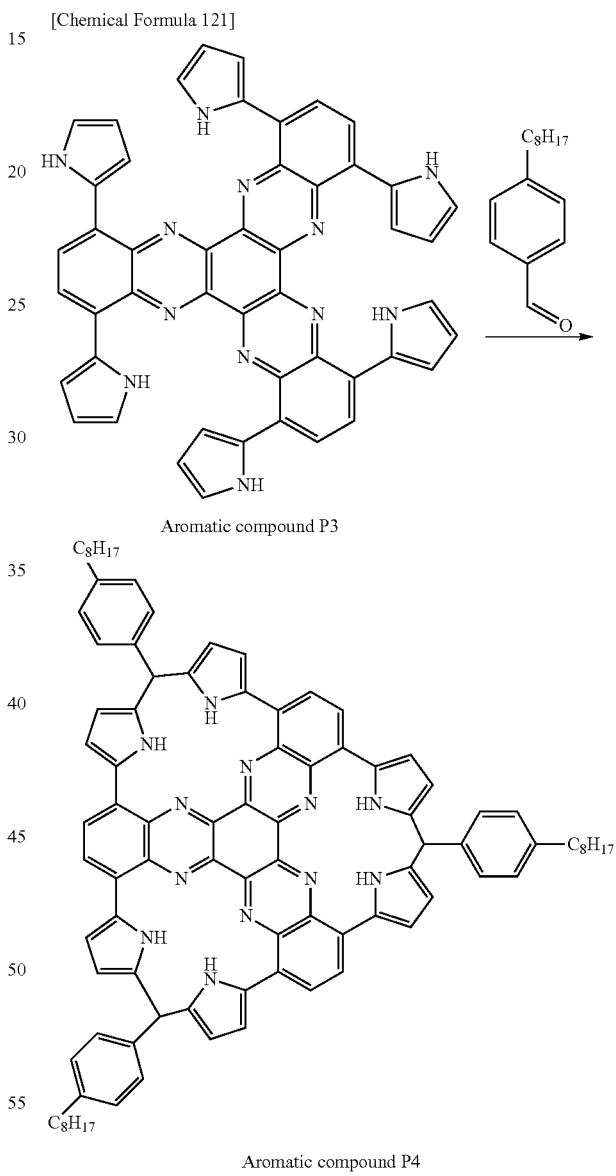

Aromatic compound P4

Specifically, 0.207 g (0.267 mmol) of aromatic compound P3 was added to a mixed solution of 1 ml of trifluoromethanesulfonic acid, 1.5 ml of p-n-octyl-benzaldehyde and 3 ml of dichloromethane, and the mixture was then deaerated with argon. The obtained solution was placed in a microwave reactor and reacted for 2 hours at 50 watts. Next, $NH_4OH$ was added to the reaction mixture, the organic phase was washed with water, and the obtained organic phase was dried to solid with an evaporator and washed with water and hexane. A 0.349 g (0.254 mmol) portion of aromatic compound P4 was obtained at a yield of 95%.

Results of Mass Spectrometry for Aromatic Compound P4
MS (FD, 8 kV) Found: m/z 1375.5 ($M^+$). Calculated: m/z 1375.74 ($M^+$)
MALDI-TOF (TCNQ): m/z 1373 ($M^+$); 2746 (2 $M^+$)

Example 5

Synthesis of Aromatic Compound P5

Aromatic compound P5 was synthesized according to the following reaction formula.

[Chemical Formula 122]

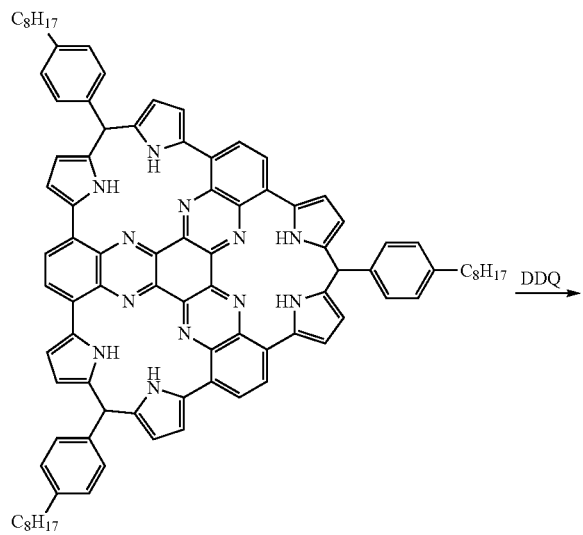

Aromatic compound P4

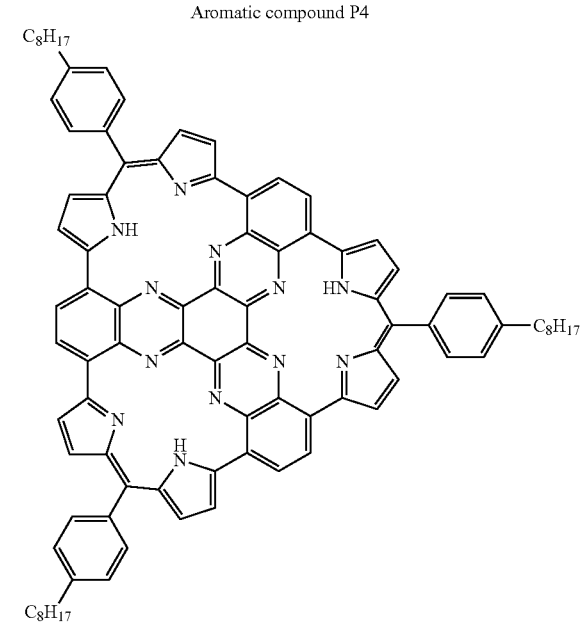

Aromatic compound P5

Specifically, 0.100 g (0.0374 mmol) of aromatic compound P4 and 0.058 g (0.254 mmol) of DDQ were placed in a 35 ml microwave tube, 15 ml of dehydrated toluene was added, and argon was bubbled through for 30 minutes. After heating in a microwave reactor at 140° C. for 2 hours, 3 ml of triethylamine was added, and the black precipitate was filtered out and washed with water and hexane to obtain aromatic compound P5 at a yield of 99%.

Results of Mass Spectrometry for Aromatic Compound P5
MALDI-TOF (TCNQ) Found: m/z 1370 ($M^+$); 2740 (2 $M^+$) Calculated: m/z 1369 ($M^+$)

Example 6

Synthesis of Metal Complex MC1

Metal complex MC1 was synthesized according to the following reaction formula.

[Chemical Formula 123]

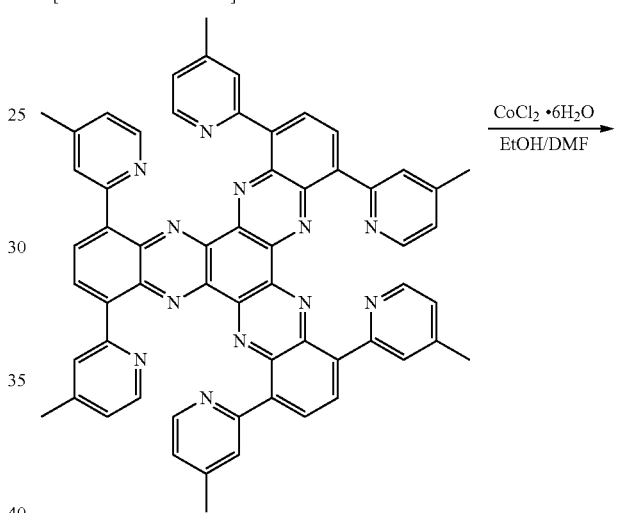

Aromatic compound P1

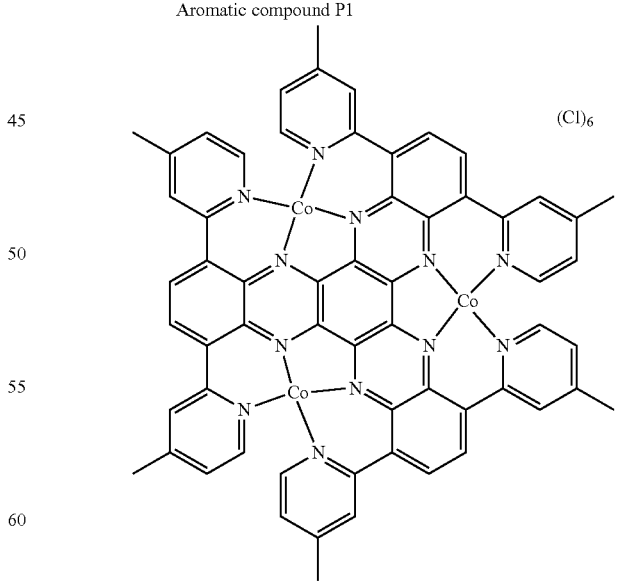

Metal complex MC1

Specifically, 0.125 g (0.091 mmol) of aromatic compound P1 and 1.218 g (5.119 mmol) of cobalt chloride hexahydrate were dissolved in a mixture of 6 ml of ethanol and 2 ml of DMF, and the mixture was circulated for 3 days under an argon atmosphere. After allowing the reaction mixture to cool, the reaction mixture was subjected to FD-Mass Spectrometry to confirm that the product contained metal complex MC1.

MS (FD, 8 kV) Found: 1319.3 ($[M_3LCl_6]^+$); 405 ($[M_3LCl_3]^{3+}$); 359.4 ($[M_2LCl]^{3+}$ Calculated: 1318.98 ($[M_3LCl_6]^+$); 404.74 ($[M_3LCl_3]^{3+}$)

Example 7

Synthesis of metal complex MC2

Metal complex MC2 was synthesized according to the following reaction formula.

[Chemical Formula 124]

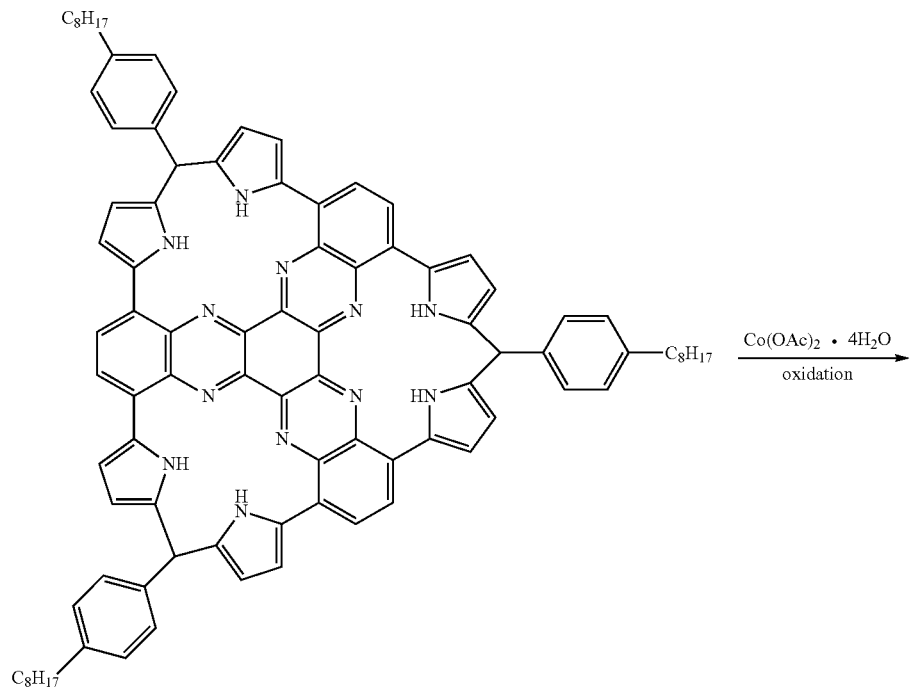

Aromatic compound P4

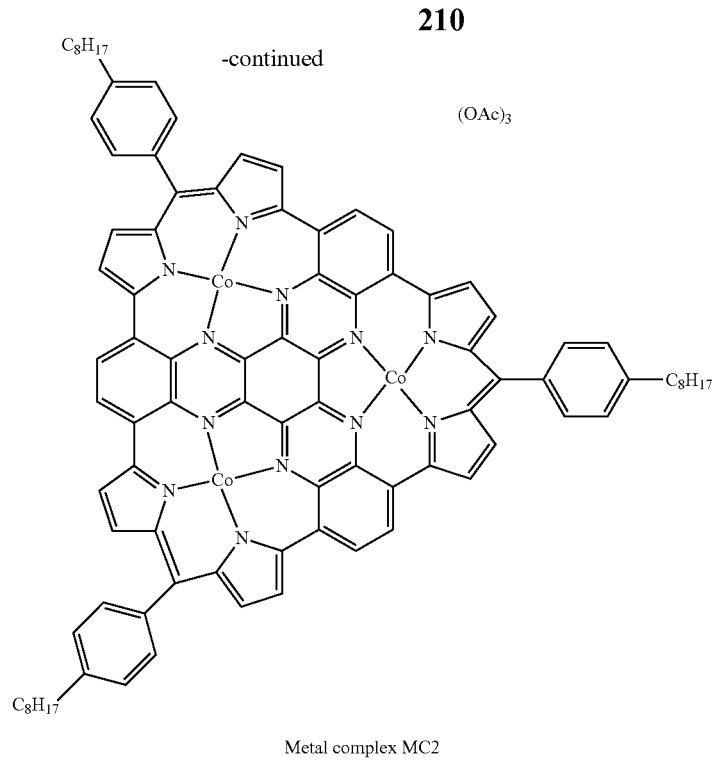

Metal complex MC2

Specifically, 0.125 g (0.091 mmol) of aromatic compound P4 and 0.079 g (0.318 mmol) of cobalt acetate tetrahydrate were placed in a microwave test tube, 5 ml of DMF was added, and a microwave apparatus was used for 2 hours of reaction at 200° C. with an output of 200 W. The reaction solution was poured into 25 ml of ice water and the produced precipitate was filtered out and washed with water and hexane to obtain metal complex MC2.

MALDI-TOF (TCNQ) Found: m/z 1543 (M$^+$); 1569 (M$^+$+CN$^-$); 1595 (M$^+$+2CN$^-$); 1621 (M$^+$+3CN$^-$). Calculated: m/z 1543.5 (M$^+$)

Example 8

Synthesis of metal complex MC3

Metal complex MC3 was synthesized according to the following reaction formula.

[Chemical Formula 125]

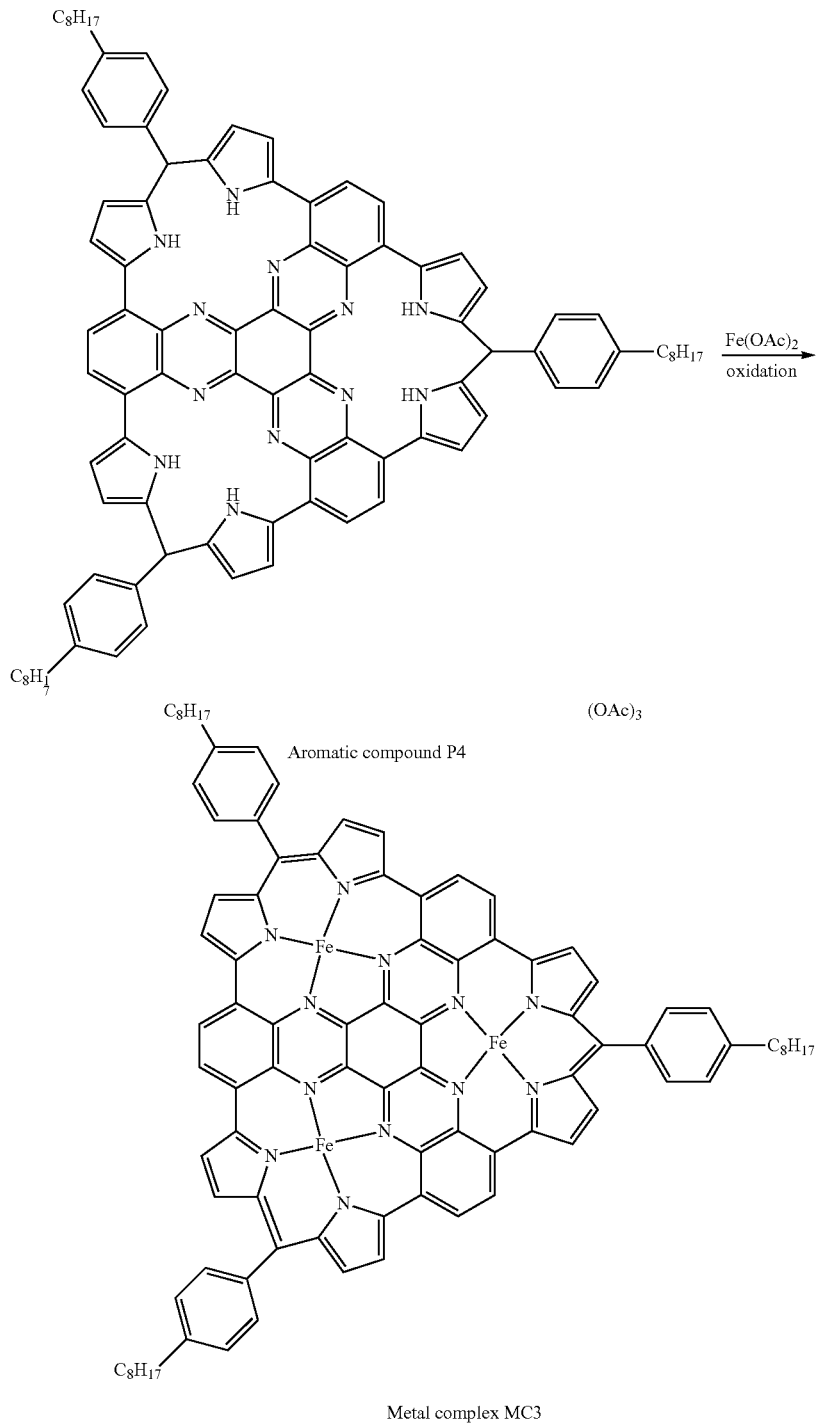

Aromatic compound P4

Metal complex MC3

Specifically, 0.096 g (0.091 mmol) of aromatic compound P4 and 0.053 g (0.304 mmol) of iron acetate were placed in a microwave test tube, 5 ml of DMF was added, and a microwave apparatus was used for 4 hours of reaction at 200° C. with an output of 200 W The reaction solution was poured into 25 ml of ice water and the produced precipitate was filtered out and washed with water and hexane to obtain metal complex MC3.

MALDI-TOF (TCNQ) Found: m/z 1534 ($M^+$); 1560 ($M^++CN^-$); 1586 ($M^++2CN^-$); 1603 ($M^++3CN^-$). Calculated: m/z 1534 ($M^+$)

Example 9
Synthesis of metal complex MC4
Metal complex MC4 was synthesized according to the following reaction formula.
[Chemical Formula 126]
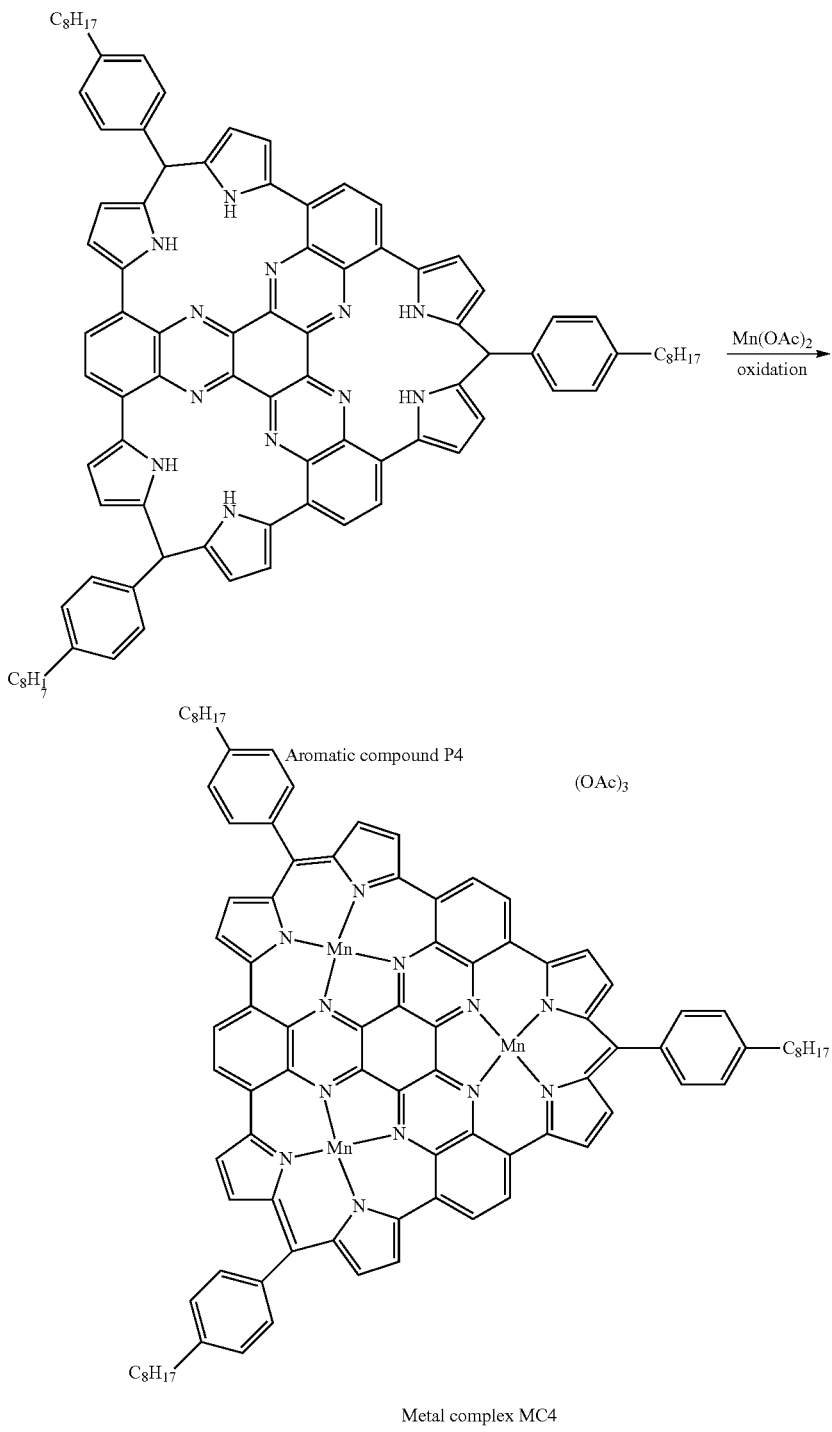
For Example 8, metal complex MC4 was synthesized in the same manner as Example 8, except that iron acetate was changed to manganese acetate.

Synthesis Example 1

Synthesis of Metal Complex MC5)

Chloroform containing Schiff base ligand and ethanol containing cobalt acetate tetrahydrate were mixed and reacted according to the following reaction formula, to synthesize metal complex MC5. The Schiff base ligand and metal complex MC5 as starting materials for the complex were synthesized according to a method described in the literature (A Chemistry, European Journal, 1999, 5, 1460).

[Chemical Formula 127]

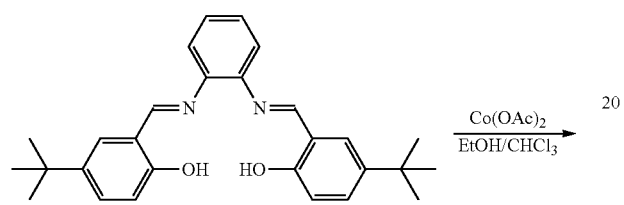

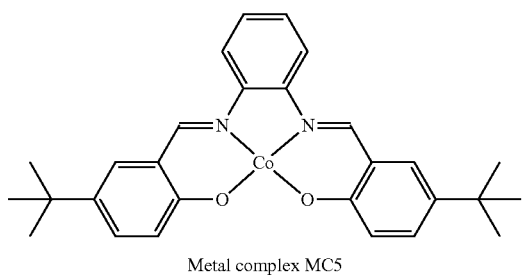

Metal complex MC5

Example 10

Synthesis of Metal Complex MC6

Metal complex MC6 was synthesized according to the following reaction formula.

[Chemical Formula 128]

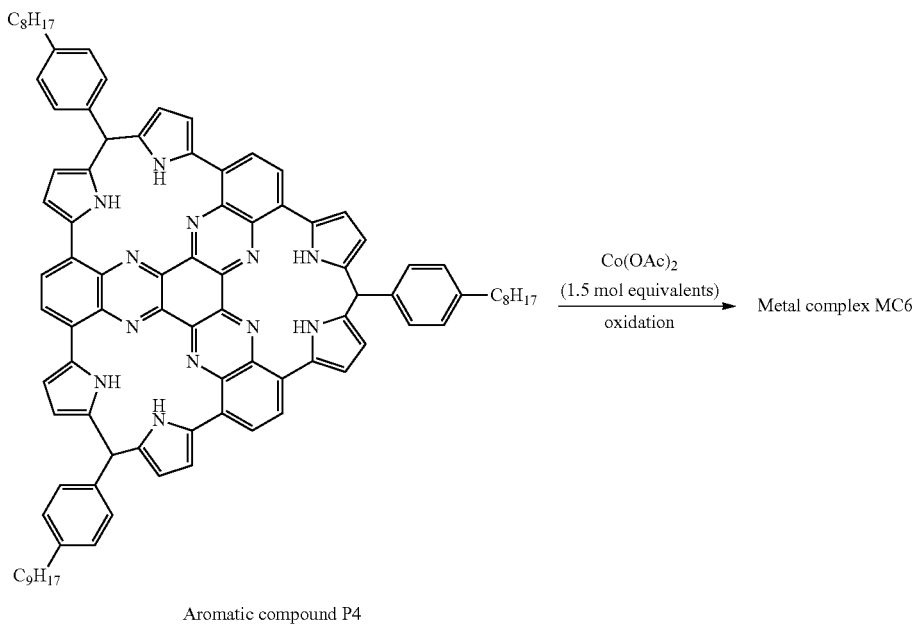

Aromatic compound P4

The basic procedure for the synthesis was the same as in Example 7, but in this case the metal complex MC6 was obtained by reacting 1.5 mol equivalents of cobalt acetate with aromatic compound P4.

<Evaluation 1>

The metal complex MC2 was loaded onto a carbon support to produce electrode catalyst 1. Specifically, 40 mg of metal complex MC2 and 160 mg of the carbon support (trade name: KETCHEN BLACK EC600 JD, by Lion Corp.) were mixed in methanol, and after distilling off the solvent with an evaporator, it was dried overnight under reduced pressure of 200 Pa to obtain electrode catalyst 1.

For evaluation of the electrode catalyst, the oxygen reduction was evaluated with a rotating ring-disk electrode. The electrode used was a ring-disk electrode with a disk section of glassy carbon (diameter: 6.0 mm) and a ring section of platinum (ring inner diameter: 7.0 mm, ring outer diameter: 9.0 mm)

After adding 1 mL of 2-propanol to a sample bottle containing 8 mg of the electrode catalyst 1, it was dispersed with ultrasonic waves. After then dropping 21.6 μL of the obtained suspension onto the disk section of the electrode and drying it, a 5 μL NAFION® solution (by Aldrich, solution obtained by diluting 5 wt % solution 20-fold with 2-propanol) was dropped onto the disk section and dried at room temperature to obtain a measuring electrode.

The current value for oxygen reduction reaction was measured by using this measuring electrode with the Measuring apparatus and Measuring conditions described below. The current value was measured in a nitrogen-saturated state and an oxygen-saturated state, and the value obtained by subtracting the current value obtained by measurement in the nitrogen atmosphere from the current value obtained by measurement in the oxygen atmosphere was recorded as the oxygen reduction current value. The current value was divided by the surface area of the measuring electrode to determine the current density. The results are shown in Table 1. The measuring apparatus and measuring conditions were as follows, and the current density is the value with 0.6 V on the reversible hydrogen electrode.

[Measuring Apparatus]

RRDE-1 rotating ring-disk electrode apparatus by Nikko Keisoku.

ALS model 701C Dual Electrochemical Analyzer

[Measuring Conditions]

Cell solution: 0.5 mol/L sulfuric acid aqueous solution (oxygen saturation or nitrogen saturation)

Solution temperature: 25° C.

Reference electrode: silver/silver chloride electrode (saturated potassium chloride)

Counter electrode: platinum wire

Sweep rate: 5 mV/sec

Electrode rotational speed: 900 rpm

<Evaluation 2>

An electrode catalyst 2 was fabricated and the oxygen reduction evaluated in the same manner as <Evaluation 1> above, except that the metal complex MC2 was changed to metal complex MC3. The results are shown in Table 1. A portion of the obtained electrode catalyst 2 was heated in a tubular furnace at 600° C. in a nitrogen atmosphere. The tubular furnace and heating conditions used were as follows (same for <Evaluation 3> to <Evaluation 5> below).

Tubular furnace: Program-controlled shutter tubular furnace EPKRO-14R, Isuzu Seisakusho Co., Ltd.

Heating conditions (heating atmosphere): nitrogen gas flow (200 ml/min)

Heating conditions (temperature-elevating rate and temperature-lowering rate): 200° C./hr <Evaluation 3>

An electrode catalyst 3 was fabricated and the oxygen reduction evaluated in the same manner as <Evaluation 1> above, except that the metal complex MC2 was changed to metal complex MC4. The results are shown in Table 1. A portion of the obtained electrode catalyst 3 was heated in a tubular furnace at 600° C. or 800° C. in a nitrogen atmosphere.

<Evaluation 4>

After stirring 10 mg of aromatic compound P3 and 10 mg of cobalt acetate tetrahydrate together with 40 mg of a carbon support (trade name: KETCHEN BLACK EC600 JD, by Lion Corp.) in methanol, the solvent was distilled off with an evaporator and the residue was dried overnight under reduced pressure of 200 Pa to obtain electrode catalyst 4. A portion of the obtained electrode catalyst 4 was heated in a tubular furnace at 600° C. or 800° C. in a nitrogen atmosphere. The oxygen reduction was evaluated by the heating method and evaluation method described above. The results are shown in Table 1.

<Evaluation 5>

After stirring 3 mg of aromatic compound P1 and 34 mg of cobalt acetate tetrahydrate together with 150 mg of a carbon support (trade name: KETCHEN BLACK EC600 JD, by Lion Corp.) in methanol, the solvent was distilled off with an evaporator and the residue was dried overnight under reduced pressure of 200 Pa to obtain electrode catalyst 5. A portion of the obtained electrode catalyst 5 was heated in a tubular furnace at 800° C. in a nitrogen atmosphere. The oxygen reduction was evaluated by the heating method and evaluation method described above. The results are shown in Table 1.

<Evaluation C1>

An electrode catalyst 6 was fabricated and the oxygen reduction evaluated in the same manner as <Evaluation 1> above, except that the metal complex MC2 was changed to metal complex MC5. The results are shown in Table 1.

TABLE 1

| Evaluation | Electrode catalyst | Aromatic compound or metal complex | Heating temperature (° C.) | Heating time (hrs) | Current density (mA/cm$^2$) |
|---|---|---|---|---|---|
| 1 | 1 | Metal complex MC2 | No heating | — | 2.86 |
| 2 | 2 | Metal complex MC3 | No heating | — | 0.51 |
|   |   |   | 600 | 2 | 2.73 |
| 3 | 3 | Metal complex MC4 | 600 | 2 | 0.38 |
|   |   |   | 800 | 2 | 0.14 |
| 4 | 4 | Aromatic compound P3 | No heating | — | 0.95 |
|   |   |   | 600 | 2 | 2.31 |
|   |   |   | 800 | 2 | 1.33 |

TABLE 1-continued

| Evaluation | Electrode catalyst | Aromatic compound or metal complex | Heating temperature (° C.) | Heating time (hrs) | Current density (mA/cm$^2$) |
|---|---|---|---|---|---|
| 5 | 5 | Aromatic compound P1 | 800 | 2 | 1.83 |
| C1 | 6 | Metal complex MC5 | No heating | — | 0.06 |

[Evaluation]
According to Table 1, the current densities of electrode catalysts 1-5 are higher than the current density of electrode catalyst 6, and therefore electrode catalysts 1-5 were shown to exhibit more excellent oxygen reduction activity than electrode catalyst 6.

[Comparison of 4-electron Reduction]
The 4-electron reduction in oxygen reduction reaction was determined by the following formula.

$$\% \ H_2O = \frac{i_D - i_R/N_{r/d}}{i_D + i_R/N_{r/d}} \times 100 \quad \text{[Formula 1]}$$

Here, $i_D$ represents the disk current, $i_R$ represents the ring current and $N_{r/d}$ represents the collection efficiency of the disk reaction product on the ring electrode. The collection efficiency was measured using an $[Fe(CN)_6]^{3-/4-}$ oxidation reduction system, and it was 0.38 for the electrodes used in <Evaluation 1> to <Evaluation 5> and <Evaluation C1>. The 4-electron reductions in <Evaluation 1> (metal complex MC2) and <Evaluation C1> (metal complex MC5) were 89.1% and 55.3%, respectively. This was attributed to increased accumulation of active sites in the electrode catalyst of <Evaluation 1> (metal complex MC2).

<Evaluation 7>
The metal complex MC2 was loaded onto a carbon support to produce electrode catalyst 7. Specifically, 2 mg of metal complex MC2 and 8 mg of a carbon support (trade name: Vulcan XC-72, product of Cabot Japan, KK.) were mixed in dichloromethane, and after 15 minutes of ultrasonic treatment, the mixture was dried overnight to obtain electrode catalyst 7.

For evaluation of the electrode catalyst 7, the oxygen reduction activity was evaluated with a rotating disk electrode. The electrode used was a disk electrode having a glassy carbon disk section (diameter: 3.0 mm)

After adding 1 mL of a 0.5% NAFION® solution (a 5% NAFION® solution diluted 10-fold with ethanol) to a sample bottle containing 1 mg of the electrode catalyst 7, it was dispersed with ultrasonic waves for 15 minutes. After then dropping 1.8 μL of the obtained suspension onto the disk section of the electrode and drying it, it was dried for 3 hours with a drier heated to 80° C., to obtain a measuring electrode.

The current value for oxygen reduction reaction was measured by using this measuring electrode with the Measuring apparatus and Measuring conditions described below. The current value was measured in a nitrogen-saturated state and an oxygen-saturated state, and the value obtained by subtracting the current value obtained by measurement in the nitrogen atmosphere from the current value obtained by measurement in the oxygen atmosphere was recorded as the current value for the oxygen reduction reaction. The current value was divided by the surface area of the measuring electrode to determine the current density. The results are shown in Table 2. The measuring apparatus and measuring conditions were as follows, and the current density is the value with −0.8 V on a silver/silver chloride electrode.

[Measuring Apparatus]
RDE evaluator: Autolab
Electrochemical analyzer: PARSTAT 2273 Advanced Electrochemical System.

[Measuring Conditions]
Cell solution: 0.1 mol/L Potassium hydroxide aqueous solution (oxygen saturation or nitrogen saturation).
Solution temperature: 25° C.
Reference electrode: silver/silver chloride electrode (3M potassium chloride)
Counter electrode: platinum wire
Sweep rate: 10 mV/sec
Electrode rotational speed: 1600 rpm <Evaluations 8-11>
Electrode catalyst 8, electrode catalyst 9, electrode catalyst 10 and electrode catalyst 11 were fabricated in the same manner as in <Evaluation 7>, except that metal complex MC2 was changed to metal complex MC3, metal complex MC4, metal complex MC6 and aromatic compound P4, respectively, and the oxygen reduction activity of each was evaluated. The results are shown in Table 2.

TABLE 2

| Evaluation | Electrode catalyst | Aromatic compound or metal complex | Heating temperature (° C.) | Heating time (hr) | Current density (mA/cm$^2$) |
|---|---|---|---|---|---|
| 7 | 7 | Metal complex MC2 | No heating | — | 5.8 |
| 8 | 8 | Metal complex MC3 | No heating | — | 3.6 |
| 9 | 9 | Metal complex MC4 | No heating | — | 4.4 |
| 10 | 10 | Metal complex MC6 | No heating | — | 4.0 |
| 11 | 11 | Aromatic compound P4 | No heating | — | 3.1 |

Example 11

Synthesis of Compound 5

Compound 5 was synthesized according to the following reaction formula.

[Chemical Formula 129]

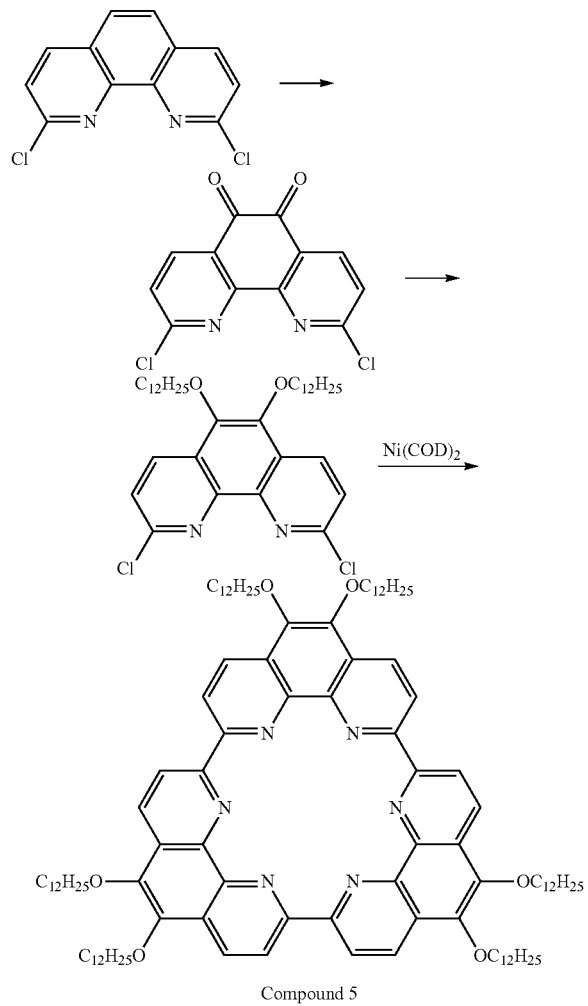

Compound 5

First, 2,9-dichloro-1,10-phenanthroline and then 2,9-dichloro-1,10-phenanthroline-5,6-dione were synthesized as starting materials, according to a procedure described in the literature (Bull. Chem. Soc. Jpn., 1990, 63, 2710). The obtained 2,9-dichloro-1,10-phenanthroline-5,6-dione was used to synthesize 2,9-dichloro-5,6-bis(dodecyloxy)-1,10-phenanthroline.

Specifically, 0.75 g (2.33 mmol) of tetrabutylammonium bromide and 3.77 g (21.66 mmol) of $Na_2S_2O_4$ were added to a mixed solution of 20 ml of water and 20 ml of THF containing 1.0 g of 2,9-dichloro-1,10-phenanthroline-5,6-dione, and then 3.0 g of dodecyl bromide was further added. Next, 20 ml of an aqueous solution dissolving 3.0 g of KOH was slowly added to the obtained solution, and the mixture was stirred at 40° C. for 2 days. After diluting the reaction mixture with water, ethyl acetate was used for extraction of the product. The organic phase was washed with water, and then $Na_2SO_4$ was added, the mixture was dried and the solvent was distilled off with an evaporator to obtain a crude product. Column purification (dichloromethane/ethyl acetate) was performed to obtain 1.5 g of 2,9-dichloro-5,6-bis(dodecyloxy)-1,10-phenanthroline at a yield of 67%.

NMR Results for 2,9-dichloro-5,6-bis(dodecyloxy)-1,10-phenanthroline $^1$H-NMR ($CD_2Cl_2$): δ=8.53 (2H, d, J=8.69 Hz), 7.64 (2H, d, J=8.69 Hz), 4.23 (4H, t, J=6.64 Hz) 1.86 (4H, m), 1.61-1.10 (36H, m), 0.87 (6H, t, J=6.89 Hz)ppm $^{13}$C-NMR ($CD_2Cl_2$): δ=150.6, 143.0, 142.9, 134.1, 126.3, 124.7, 74.6, 32.3, 30.7, 30.0, 29.7, 29.6, 26.5, 23.1, 14.3 ppm Next, 427 mg of Ni(COD)$_2$ (1.55 mmol), 243 mg of bipyridine (1.55 mmol) and 0.19 ml of cyclooctadiene (1.55 mmol) were added to a mixed solvent comprising 20 ml of DMF and 40 ml of toluene, and the mixture was stirred at 60° C. for 20 minutes. After slowly adding 385 mg of 2,9-dichloro-5,6-bis(dodecyloxy)-1,10-phenanthroline (0.62 mmol) to the obtained mixture, it was stirred at 60° C. for 3 days. The solution was allowed to cool to room temperature, diethyl ether was added, and the organic phase was washed with 2 M hydrochloric acid. MgSO$_4$ was added to the organic phase, the mixture was dried, and then the solvent was distilled off with an evaporator to obtain a crude product. Column purification (dichloromethane/methanol) was performed to obtain 89 mg of compound 5.

Results of NMR Analysis of Compound 5

$^1$H-NMR ($CD_2Cl_2$): δ 8.98 (6H, d, J=8.66 Hz), 8.75 (6H, d, J=8.78 Hz)ppm, 4.37 (12H, t, J=6.64 Hz), 1.86 (12H, m), 1.61-1.10 (108H, m), 0.87 (18H, t, J=6.89 Hz)ppm $^{13}$C-NMR ($CD_2Cl_2$): δ=153.4, 144.3, 143.2, 133.4, 128.0, 122.9, 74.6, 32.3, 30.7, 30.0, 29.7, 29.6, 26.5, 23.1, 14.3 ppm

Example 12

Synthesis of Compound 6

The synthesized 2,9-dichloro-1,10-phenanthroline was used to synthesize compound 6 according to the following reaction formula.

[Chemical Formula 130]

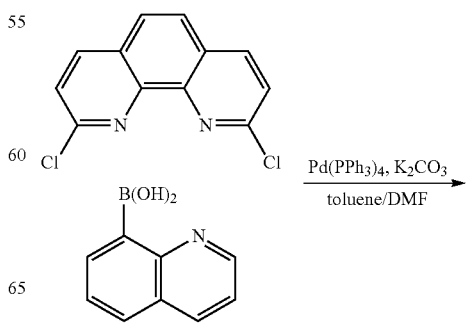

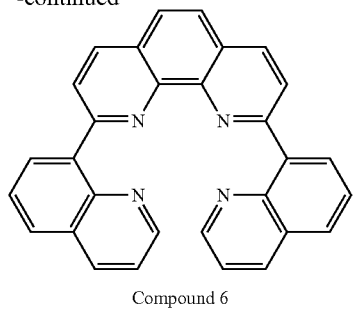

Compound 6

Specifically, 100 mg (0.40 mmol) of 2,9-dichloro-1,10-phenanthroline and 278 mg of 8-quinoline-boric acid (1.61 mmol, product of Aldrich Co.) were added to a mixed solvent comprising 3 ml of toluene and 5 ml of DMF, and the mixture was purged with argon gas. Next, 37 mg of Pd (PPh$_3$)$_4$ (0.0321 mmol) and 333 mg of K$_2$CO$_3$ (2.41 mmol) were added and the mixture was stirred at 100° C. for 18 hours. Column purification was performed to obtain 65 mg of compound 6 at a yield of 37%.

Results of Mass Spectrometry for Compound 6

MS (FD, 8 kV) Found: m/z 435.4 (M$^+$), Calculated: 434.15

Example 13

Synthesis of Compound 7

Compound 7 was synthesized according to the following reaction formula.

Specifically, first 7-bromo-3-methyl-1H-indole was synthesized as the starting material according to a procedure described in the literature (J. Org. Chem. 2001, 66, 638). Next, 500 mg of 7-bromo-3-methyl-1H-indole (2.38 mmol), 22 mg of Pd$_2$(dba)$_3$, 78 mg of 2-dicyclohexylphosphino-2', 6'-dimethoxybiphenyl, 604 mg of bis(pinacolato)diboron and 467 mg of potassium acetate were introduced into a 50 ml Schlenk flask, 20 ml of anhydrous DMF was added under an argon atmosphere and the mixture was stirred overnight at 80° C. After allowing the solution to cool to room temperature, dichloromethane was added, the organic phase was washed with water and the solvent was distilled off. The residue was purified with a column (hexane/ethyl acetate) to obtain 3-methyl-7-(4,4,5,5-tetramethyl-1,3,2-dioxaborolan-2-yl)-1H-indole.

NMR Analysis Results for 3-methyl-7-(4,4,5,5-tetramethyl-1,3,2-dioxaborolan-2-yl)-1H-indole $^1$H-NMR (250 MHz, CDCl$_3$): δ=9.20 (brs, 1H), 7.63 (d, 1H), 7.46 (d, 1H), 7.02 (t, 1H), 6.44 (s, 1H), 2.40 (s, 3H), 1.42 (s, 12H)

Next, 186 mg of 2,9-dichloro-1,10-phenanthroline (0.748 mmol) and 500 mg of 3-methyl-7-(4,4,5,5-tetramethyl-1,3, 2-dioxaborolan-2-yl)-1H-indole (1.944 mmol) were dissolved in 20 ml of DMF, and 6 ml of 2 M aqueous sodium carbonate was added. After then adding Pd (PPh$_3$)$_4$ under an argon stream, the solution was stirred overnight at 80° C. The solution was allowed to cool to room temperature, dichloromethane was added, the organic phase was washed with water, the solvent was distilled off and column purification was performed to obtain compound 7.

Results of NMR Analysis and Mass Spectrometry for Compound 7

$^1$H-NMR (250 MHz, CDCl$_3$): δ=12.10 (s, 2H), 8.73 (d, 2H), 8.56 (d, 2H), 8.15 (s, 2H), 8.09 (d, 2H), 7.80 (d, 2H), 7.36 (t, 2H), 6.85 (s, 2H), 2.42 (s, 3H)]

[Chemical Formula 131]

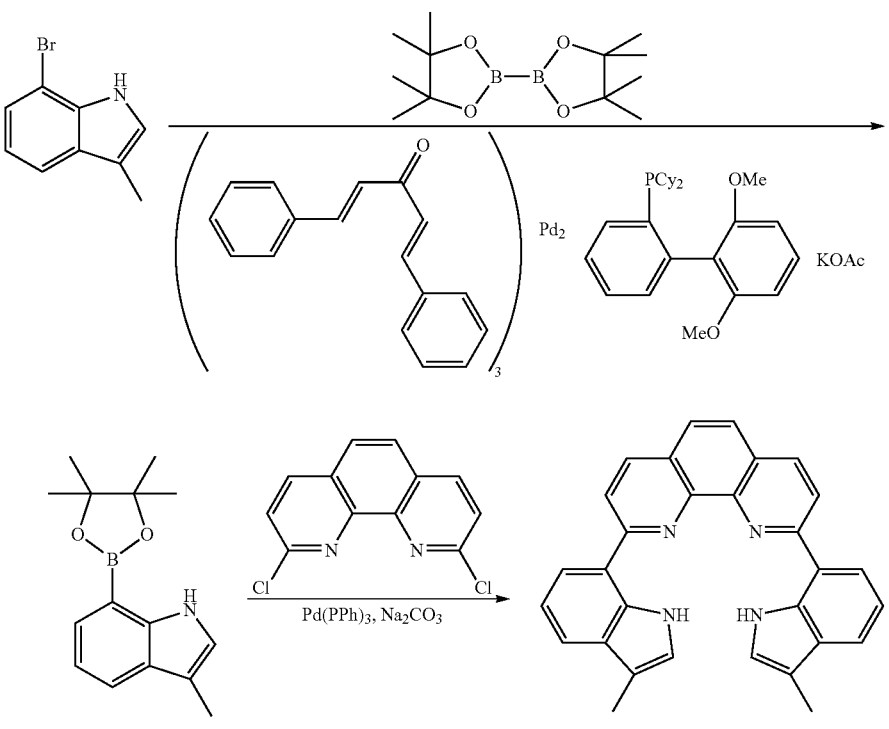

Compound 7

FD-MS Found: m/z 439.0. Calculated: 438.18.

Example 14

Synthesis of Compound 8

Compound 8 was synthesized according to the following reaction formula.

[Chemical Formula 132]

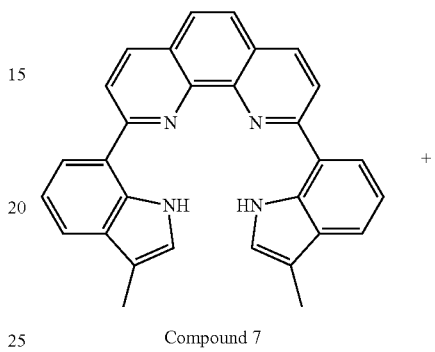

Compound 7

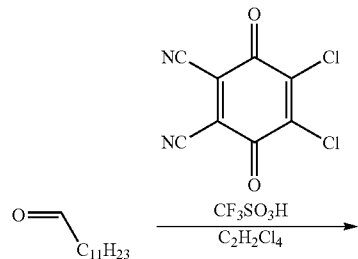

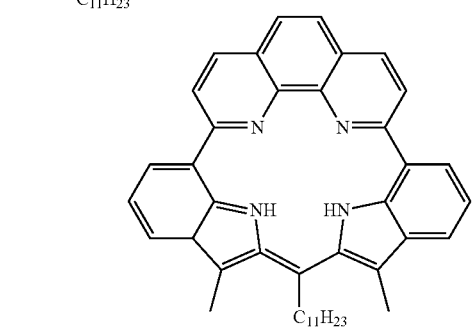

Compound 8

Specifically, 21 mg of n-dodecylaldehyde (0.114 mmol) and 50 mg of 2,9-bis(3-methyl-1H-indol-7-yl)-1,10-phenanthroline (0.114 mmol) were added to 10 ml of tetrachloroethane, and the mixture was deaerated with argon gas for 10 minutes. A catalytic amount of trifluoromethanesulfonic acid was added, and after 48 hours of circulation, a toluene solution (3 ml) containing 52 mg of 4,5-dichloro-3,6-dioxo-cyclohexa-1,4-diene-1,2-dicarbonitrile (0.228 mmol) was added and the mixture was further circulated for 8 hours. After allowing the mixture to cool to room temperature, the dichloromethane-added organic phase was dried over anhydrous sodium sulfate and dried under reduced pressure to obtain compound 8.

Results of Mass Spectrometry for Compound 8
FD-MS Found: 601. Calculated: 602.34

Example 15

Synthesis of Compound 9

Compound 9 was synthesized according to the following reaction formula.

[Chemical Formula 133]

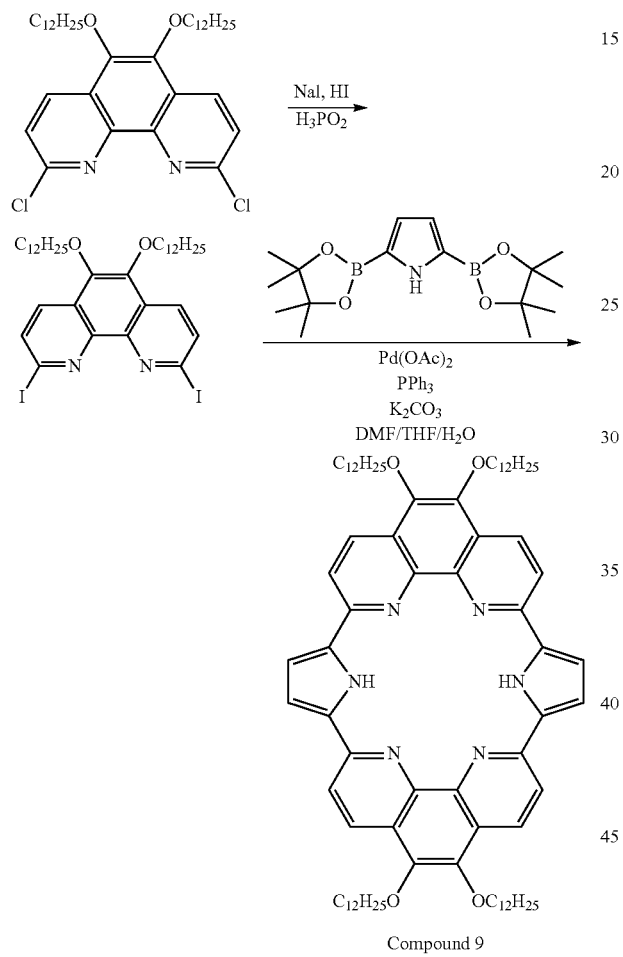

Compound 9

As the starting material there was synthesized 2,5-bis(4,4,5,5-tetramethyl-1,3,2-dioxaborolan-2-yl)-1H-pyrrole according to the literature (*Tetrahedron Letters*, 2002, 43, 5649), and then 5,6-bis(dodecyloxy)-2,9-diiodo-1,10-phenanthroline was synthesized by the following procedure.

Specifically, 4.4 ml of 57% hydroiodic acid and 0.12 ml of hypophosphorous acid (50%) were added to a flask containing 1.36 g of 2,9-dichloro-5,6-bis(dodecyloxy)-1,10-phenanthroline (2.21 mmol) and 1.33 g of sodium iodide (8.84 mmol) while stirring, and then the mixture was heated overnight at 80° C. After cooling to 0° C., ammonia water was added until the solution became alkaline. The precipitate was filtered out, rinsed several times with water and then dried under reduced pressure. It was then purified with a column (dichloromethane:heptane) to obtain 5,6-bis(dodecyloxy)-2,9-diiodo-1,10-phenanthroline at a yield of 58%.

Results of NMR analysis and mass spectrometry for 5,6-bis(dodecyloxy)-2,9-diiodo-1,10-phenanthroline $^1$H-NMR (250 MHz, CD$_2$Cl$_2$): δ=8.15 (d, J=8.51 Hz, 2H), 7.97 (d, J=8.51 Hz, 2H), 4.21 (t, J=6.61, 4H), 1.92-1.80 (m, 4H), 1.58-1.47 (m, 4H), 1.4-1.27 (m, 32H), 0.88 (t, J=6.32, 6H)

$^{13}$C-NMR (CD$_2$Cl$_2$): δ=144.4, 143.2, 134.8, 132.3, 126.6, 118.0, 74.6, 32.3, 30.7, 30.1, 30.0, 29.9, 29.8, 29.7, 26.5, 23.1, 14.3 ppm MALDI-TOF analysis, Found: 801.264, Calculated: 801.235

Next, there was prepared a mixed solution with 150 ml of DMF and 40 ml of THF, containing 124.4 mg of 2,9-diiodo-5,6-bis(dodecyloxy)-1,10-phenanthroline (0.155 mmol), 24.8 mg of 2,5-bis(4,4,5,5-tetramethyl-1,3,2-dioxaborolan-2-yl)-1H-pyrrole (0.078 mmol), 5.7 mg of palladium acetate (0.025 mmol) and 13.6 mg of triphenylphosphine (0.052 mmol). A 10 ml aqueous solution dissolving 45.3 mg of potassium carbonate was added to the mixed solution and subjected to a deaeration procedure, after which it was stirred at 80° C. for 4 hours under an argon atmosphere. The solution was allowed to cool to room temperature, the solvent was distilled off, and the residue was dissolved in dichloromethane, passed through a filter and then purified to obtain compound 9 at a yield of 16%.

Results of NMR analysis and mass spectrometry for compound 9

$^1$H-NMR (500 MHz, THF-d$_8$, 60° C.): δ=12.54 (s, 2H), 8.39 (d, J=8.52 Hz, 4H), 7.83 (d, J=8.51 Hz, 4H), 6.86 (s, 4H), 4.25 (t, J=6.27, 8H), 1.95-1.89 (m, 8H), 1.63-1.45 (m, 8H), 1.46-1.31 (m, 64H), 0.89 (t, J=6.27, 12H)ppm $^{13}$C-NMR (THF-d$_8$, 60° C.): δ=149.2, 144.9, 143.3, 135.6, 131.4, 125.7, 118.8, 110.4, 74.7, 32.9, 31.4, 30.7, 30.6, 30.5, 30.3, 27.3, 25.9, 23.5, 14.4 ppm MALDI-TOF analysis, Found: 1222.884, Calculated: 1222.890

Reference Example 1

Synthesis of Compound 10

Compound 10 was synthesized according to the following reaction formula.

[Chemical Formula 134]

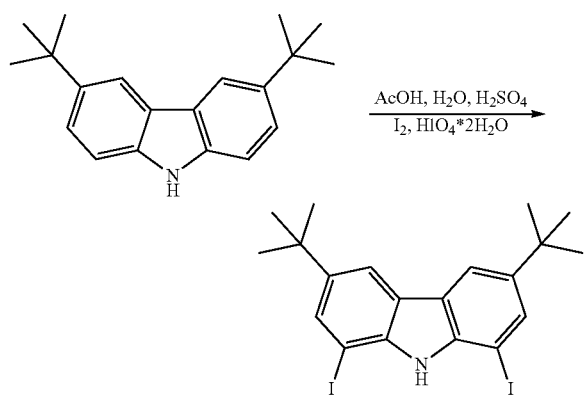

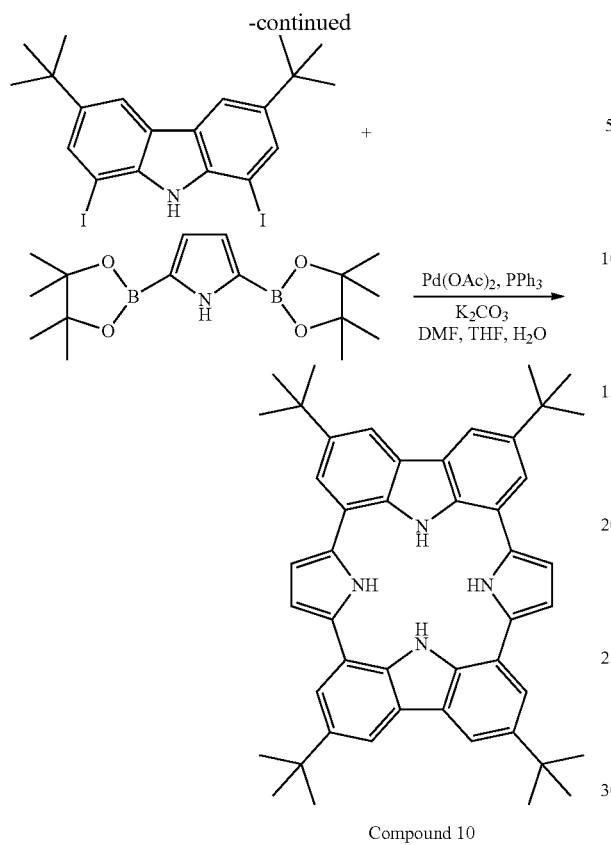

Compound 10

First, 3,6-di-tert-butyl-9H-carbazole was synthesized according to a method described in the literature (*JACS* 2006, 128, 5592). Next, 3,6-di-tert-butyl-1,8-diiodo-9H-carbazole was synthesized with reference to a method described in the literature (*JACS* 2003, 125, 1140).

Specifically, 100 mg (0.23 mmol) of 3,6-di-tert-butyl-9H-carbazole was dissolved in a mixed solvent comprising 3.5 ml of acetic acid, 1.0 ml of water and 0.1 ml of sulfuric acid. To the obtained solution there were added 26.1 mg (0.115 mmol) of $HIO_4 \cdot 2H_2O$ and 58.4 mg (0.23 mmol) of $I_2$, and the mixture was heated at 80° C. for 18.5 hours. The reaction mixture was allowed to cool to room temperature and then poured into water. After solvent extraction 3 times with ethyl acetate, the organic phase was washed with a saturated $NaHCO_3$ aqueous solution, a saturated $Na_2S_3O_3$ aqueous solution and then with brine, and then dried over $MgSO_4$, and the solvent was distilled off with an evaporator to obtain a crude product. The crude product was recrystallized from ethanol to obtain 62 mg of 3,6-di-tert-butyl-1,8-diiodo-9H-carbazole at a yield of 50%.

Results of NMR analysis for 3,6-di-tert-butyl-1,8-diiodo-9H-carbazole $^1$H-NMR ($CD_2Cl_2$): δ=1.47 (s, 18H, —$CH_3$), 7.70 (d, 2H), 8.07 (d, 2H), 8.26 (s, 1H, —NH)ppm.

$^{13}$C-NMR ($CD_2Cl_2$): δ=32.0 (—$CH_3$), 35.1 (—$C(CH_3)_3$), 76.0 (—$C_{arom}$ Br), 117.6 ($C_{arom}$), 124.5 ($C_{arom}$), 33.21 ($C_{arom}$), 139.7 ($C_{arom}$), 145.6 ($C_{arom}$) ppm.

Next, 80 mg of 2,5-bis(4,4,5,5-tetramethyl-1,3,2-dioxaborolan-2-yl)-1H-pyrrole (0.25 mmol) and 132 mg of 3,6-di-tert-butyl-1,8-diiodo-9H-carbazole (0.25 mmol) were added to a mixed solvent comprising 480 ml of DMF and 130 ml of THF, under an argon atmosphere. After then adding 141 mg of $K_2CO_3$ (1.025 mmol) and 100 ml of water to the obtained solution mixture, 7.3 mg of $Pd(OAc)_2$ and 17.2 mg of $PPh_3$ were added and reaction was conducted at 80° C. for 14 hours while stirring. Upon completion of the reaction, the mixture was allowed to cool to room temperature and the solvent was distilled off with an evaporator. The obtained dark brown crude product was dissolved in dichloromethane, and then the impurities were removed with a filter and the solvent was dried off to obtain compound 10.

Results of MALDI-TOF analysis for compound 10
Found: 684.38, Calculated: 684.42

Example 16

Synthesis of Compound 11

Compound 11 was synthesized according to the following reaction formula.

[Chemical Formula 135]

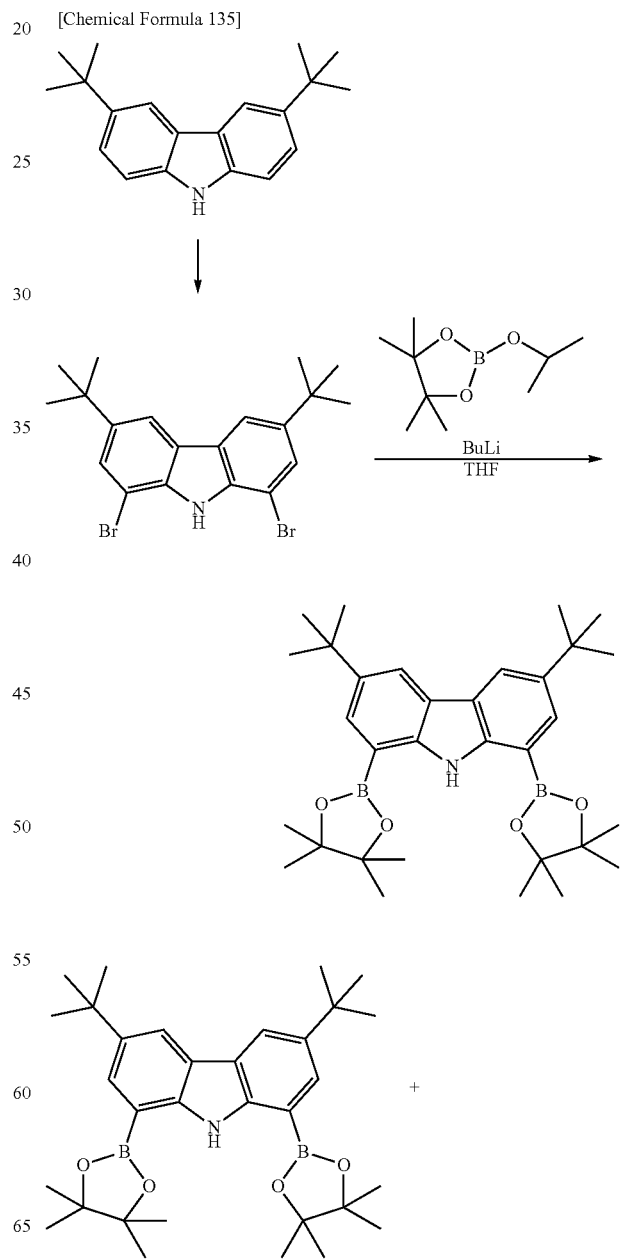

-continued

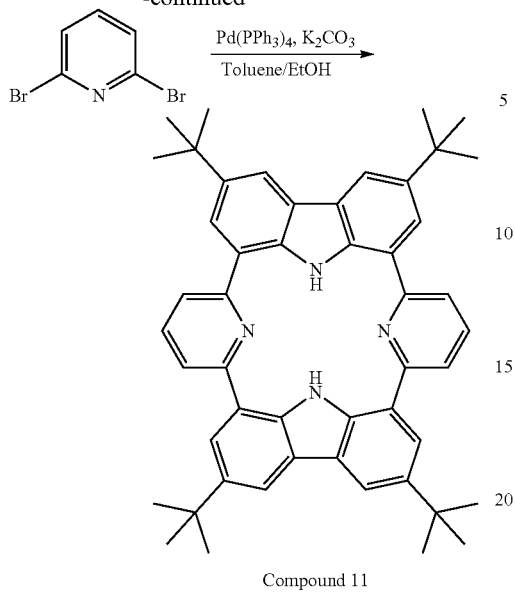

Compound 11

Results of NMR analysis and mass spectrometry for compound 11

$^1$H-NMR (CD$_2$Cl$_2$): δ=1.52 (s, 36H, —CH$_3$), 7.61 (d, 4H, $^4$J=1.85 Hz), 7.68 (d, 4H, $^3$J=7.83 Hz), 8.22 (t, 4H, $^3$J=7.57 Hz), 8.24 (d, 4H, $^4$J=1.69 Hz), 9.66 (s, 2H, —NH) ppm.

$^{13}$C-NMR (CD$_2$Cl$_2$): δ=32.1 (—CH$_3$), 35.0 (—C(CH$_3$)$_3$), 117.2, 122.6, 124.1, 124.7, 125.9, 136.1, 138.8, 143.4, 159.7 ppm.

MALDI-TOF analysis, Found: 708.23, Calculated: 708.42

Example 17

Synthesis of Metal Complex MC7

Metal complex MC7 was synthesized according to the following reaction formula.

[Chemical Formula 136]

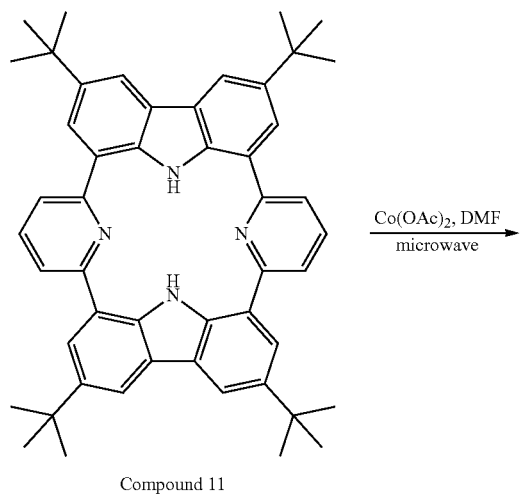

Compound 11

-continued

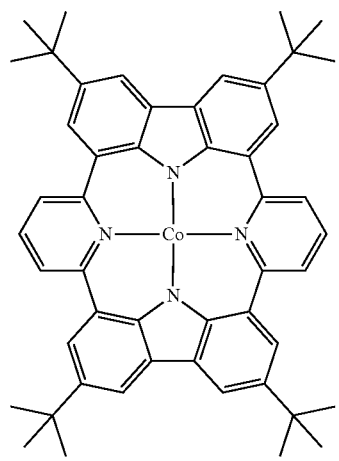

Metal Complex MC7

After dissolving 25 mg (0.035 mmol) of compound 11 and 8 mg (0.046 mmol) of Co(OAc)$_2$ in 2 ml of DMF, the obtained solution was placed in a microwave reactor and reacted for 4 hours at 170° C., 300 watts. After cooling to room temperature, the reacted solution was poured into ice water to form a precipitate. The precipitate was filtered and then dried to obtain 24 mg (0.031 mmol) of metal complex MC7 at a yield of 91%.

MALDI-TOF analysis, Found: 764.8, Calculated: 765.34

Example 18

Synthesis of Compound 12

Compound 12 was synthesized according to the following reaction formula. The 2,6-dibromo-4-chloropyridine used as the starting material was synthesized according to the following reaction formula, with reference to a method described in the literature (*European Journal of Organic Chemistry*, 2009, 1781-1795).

[Chemical Formula 137]

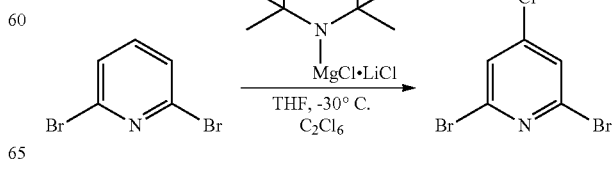

233
-continued

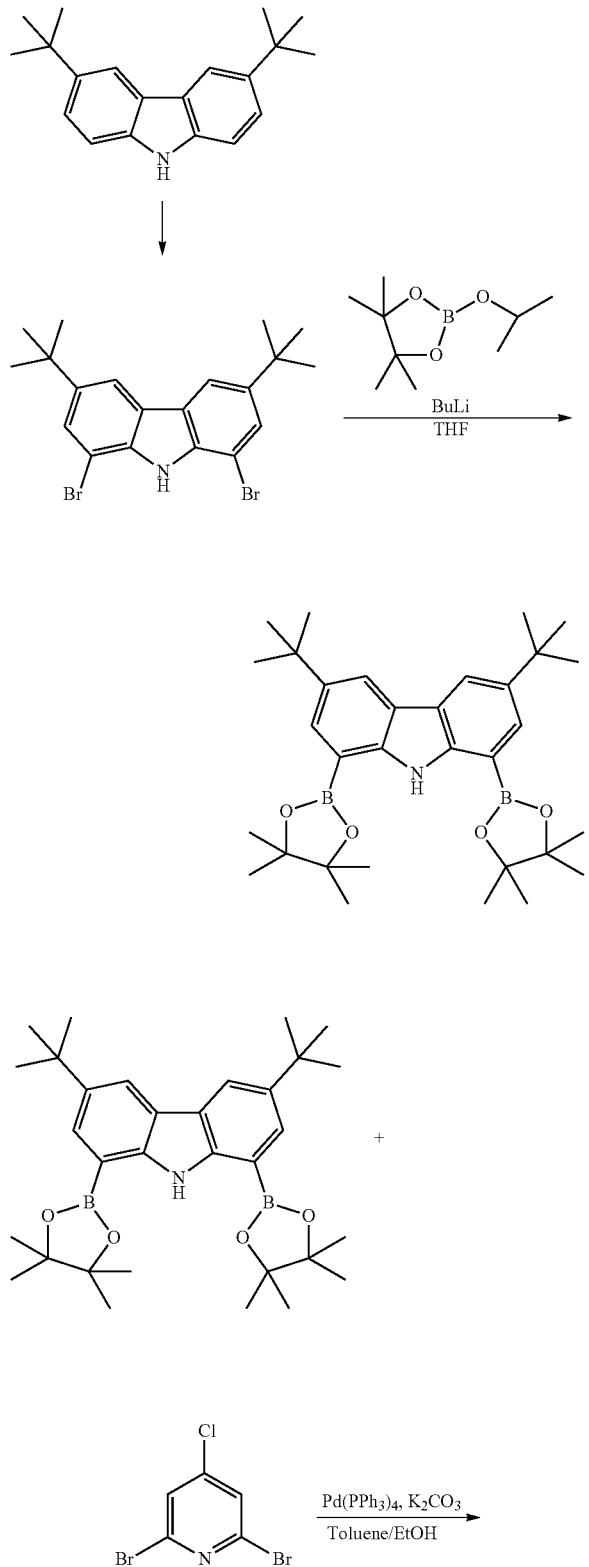

[Chemical Formula 138]

234
-continued

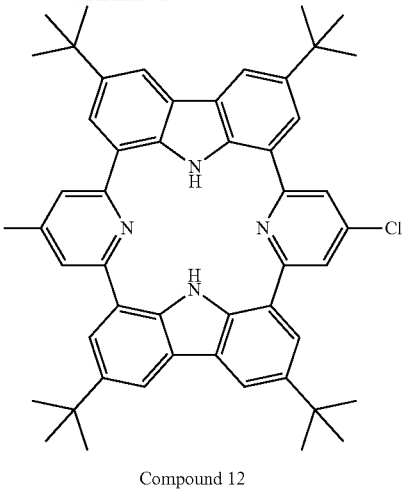

Compound 12

First, 2,6-dibromo-4-chloropyridine to be used as the starting material was synthesized by the following method. 5 g (21 mmol) of 2,6-dibromopyridine was dissolved in 20 ml of dry THF under argon atmosphere and cooled to −30° C. To the solution, 32 ml (32 mmol) of a 1M THF solution of 2,2,6,6-tetramethylpiperidinylmagnesium chloride lithium chloride was added dropwise and the reaction mixture was stirred 30 min at −30° C. 7.5 g (32 mmol) of hexachloroethane dissolved in 10 ml of THF was added and the reaction mixture was allowed to warm to room temperature while stirring. The reaction mixture was quenched with saturated $NH_4Cl$ solution and then ethyl acetate was added. The organic phase was separated and the aqueous layer was extracted two times with ethyl acetate. The combined organic layers were washed with brine and then dried over $MgSO_4$, filtered and the solvent was distilled off from the filtrate. The crude product was purified by column (hexane/dichloromethane) and recrystallized from ethanol to obtain 1.8 g of 2,6-dibromo-4-chloropyridine at a yield of 32%.

Results of NMR analysis and mass spectrometry for 2,6-dibromo-4-chloropyridine $^1$H-NMR ($CD_2Cl_2$, 300 MHz, 25° C.): δ=7.53 (s, 2H) ppm.

$^{13}$C-NMR ($CD_2Cl_2$, 75 MHz, 25° C.): δ=127.6, 141.2, 146.8 ppm.

FD-MS, Found (m/z): 268.9. Calculated: 268.8

Next, 3,6-di-tert-butyl-1,8-bis(4,4,5,5-tetramethyl-1,3,2-dioxaborolan-2-yl)-9 Hcarbazole was synthesized by the following method. n-BuLi (7.8 ml, 1.6 M in hexane, 12.5 mmol) was added to a solution of 1,8-dibromocarbazole (5 g, 11.5 mmol) in degassed THF (250 ml) at 0° C. After stirring for 1 h, the reaction mixture was allowed to warm to rt while $CO_2$ gas was bubbled through the solution. The solvent was then distilled off from the reaction solution and the residue was redissolved in degassed THF (250 ml). t-BuLi (29.4 ml, 1.7 M in pentane, 49.9 mmol) was added slowly at −78° C., and the reaction mixture was stirred at 0° C. for 3 h. After the solution was cooled to −78° C. again, 2-isopropoxytetramethyl-dioxaborolane (11.6 ml, 57.5 mmol) was added and the reaction mixture was allowed to warm to rt slowly. The mixture was hydrolyzed at 0° C. by the addition of 1M aqueous HCl and then ethyl acetate was added. The organic phase was washed with 1M aqueous NaOH and then with 1M $NaHCO_3$ solutions, dried over $MgSO_4$. After the solvent was distilled off on a rotary evaporator, the crude product was purified by recrystallisation from hot hexane to obtain 2.7 g of 3,6-di-tert-butyl-1,8-bis(4,4,5,5-tetramethyl-1,3,2-dioxaborolan-2-yl)-9 Hcarbazole at a yield of 50%.

Results of NMR analysis for 3,6-di-tert-butyl-1,8-bis(4,4,5,5-tetramethyl-1,3,2-dioxaborolan-2-yl)-9 H-carbazole $^1$H-NMR (CD$_2$Cl$_2$, 300 MHz, 25° C.): δ=1.47 (s, 42H), 7.85 (d, 2H), 8.24 (d, 2H), 9.99 (s, 1H) ppm.

$^{13}$C-NMR (CD$_2$Cl$_2$, 75 MHz, 25° C.): δ=24.9, 31.8, 34.5, 83.76, 119.9, 121.7, 129.8, 140.9, 143.6 ppm.

Next, compound 12 was synthesized by the following method. 608.68 mg (1.12 mmol) of 3,6-di-tert-butyl-1,8-bis(4,4,5,5-tetramethyl-1,3,2-dioxaborolan-2-yl)-9 Hcarbazole, 307.93 mg (1.12 mmol) of 2,6-dibromo-4-chloropyridine and 25 mg (0.02 mmol) of Pd(PPh$_3$)$_4$ were dissolved in toluene (1000 ml). Ethanol (400 ml) and 2M aqueous potassium carbonate (60 ml) were added to the solution and the reaction mixture was degassed 3 times. The reaction mixture was stirred at 85° C. for 3d. The solvents were removed on a rotary evaporator, the crude product was redissolved in dichloromethane. The organic layer was washed with water and then with brine, and dried over MgSO$_4$. The organic layer was filtered and the solvent was distilled off from the filtrate with an evaporator to obtain a crude product. The crude product was purified by column (hexane/dichloromethane) and recrystallized from hot hexane to yield 40 mg compound 12 at a yield of 5%.

Results of NMR analysis and mass spectrometry for compound 12

$^1$H-NMR (CD$_2$Cl$_2$, 300 MHz, 25° C.): δ=1.52 (s, 36H), 7.61 (d, 4H, 4J=1.79 Hz), 7.72 (s, 4H), 8.28 (t, 4H, 4J=1.69 Hz), 9.59 (s, 2H, —NH) ppm.

$^{13}$C-NMR (CD$_2$Cl$_2$, 75 MHz, 25° C.): δ=32.1, 35.1, 117.9, 122.5, 122.9, 124.9, 126.0, 136.1, 143.7, 146.3, 161.2 ppm.

MALDI-Tof Found (m/z): 776.90, Calculated: 776.34

Example 19

Synthesis of Aromatic Compound P5

Aromatic compound P5 was synthesized according to the following reaction formula.

[Chemical Formula 139]

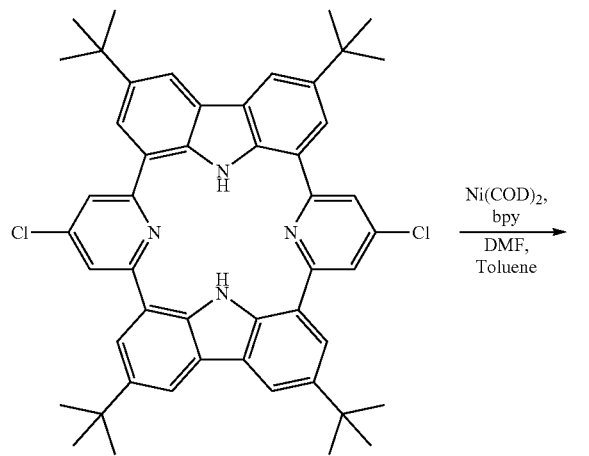

Compound 12

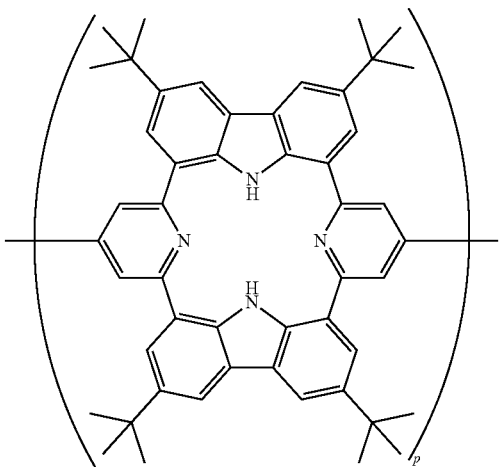

Aromatic compound P5

[In this formula, p represents the number of repeating units.]

22 mg (0.08 mmol) of bis(1,5-cyclooctadiene) nickel(0) (Ni(COD)$_2$), 9 mg (0.08 mmol) of 1,5-cyclooctadiene, 12 mg (0.08 mmol) of 2,2-bipyridine (bpy) were dissolved in a mixed solvent of 0.3 ml of DMF and 0.45 ml of toluene, and the reaction solution was stirred for 30 min at 60° C. 30 mg (0.04 mmol) of compound 12 dissolved in 0.2 ml of toluene was added to the solution, and the reaction solution was stirred at 60° C. for 3d. Methanol was added to the reaction solution, and the produced precipitate was filtered out to obtain aromatic compound P5.

Results of GPC analysis for aromatic compound P5

Mn (number average molecular weight)=3272.83 g/mol

Mw (weight-average molecular weight)=13693.00 g/mol

PDI (polydispersity index)=4.18

Example 20

Synthesis of Aromatic Compound P6

Aromatic compound P6 was synthesized according to the following reaction formula.

[Chemical Formula 140]
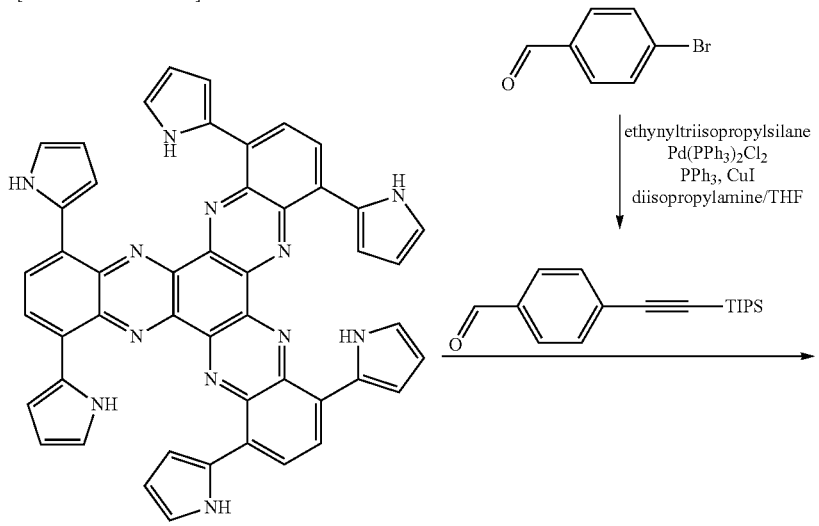
Aromatic compound P3
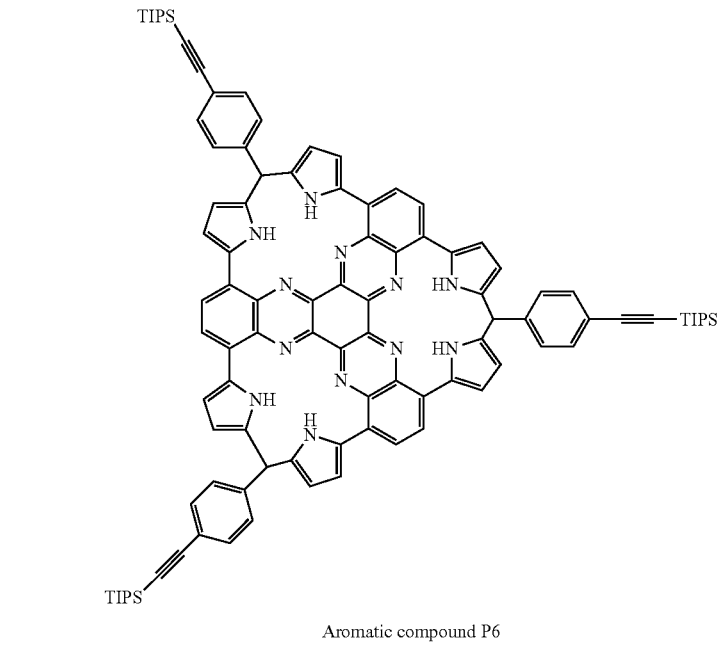
Aromatic compound P6
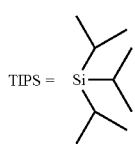

First, 4-((Triisopropylsilyl)ethynyl)benzaldehyde to be used as the starting material was synthesized by the following method.

1 g (5.40 mmol) of 4-bromobenzaldehyde, 38 mg (0.054 mmol) of Pd(PPh$_3$)$_2$Cl$_2$, 10 mg (0.054 mmol) of copper(I) iodide and 33 mg (0.129 mmol) of PPh$_3$ were dissolved in a mixed solvent of 4 ml of THF and 16 ml of diisopropylamine under an argon atmosphere. The reaction mixture was heated to 60° C. and stirred for 30 min. 1.45 ml (6.49 mmol) of ethynyltriisopropylsilane was added to the solution and further stirred for 2 h. After the solvents were removed from the reaction solution on a rotary evaporator, the crude product was purified by column (hexane/dichloromethane) to yield 1.3 g of 4-((Triisopropylsilyl)ethynyl)benzaldehyde at a yield of 84%.

Results of NMR analysis for 4-((triisopropylsilyl)ethynyl)benzaldehyde $^1$H-NMR (CD$_2$Cl$_2$, 300 MHz, 25° C.): δ=1.14 (s, 21H), 7.64 (d, 3J=8.3 Hz, 2H), 7.81 (d, 3J=8.3 Hz, 2H), 10.00 (s, 1H) ppm.

$^{13}$C-NMR (CD$_2$Cl$_2$, 75 MHz, 25° C.): δ=11.7, 18.8, 95.9, 106.3, 129.7, 129.9, 132.8, 136.1, 191.6 ppm.

Next, aromatic compound P6 was synthesized by the following method. 308.0 mg (0.40 mmol) of aromatic compound P3 and 683.3 mg (2.38 mmol) of 4-((triisopropylsilyl)ethynyl)benzaldehyde were suspended in a mixed solvent of 12 ml of dichloromethane and 4 ml of THF. To this solution, 2 ml of trifluoroacetic acid was added and the reaction solution was degassed. The reaction solution was placed in a tube for a microwave reactor, and the reaction was done in a microwave reactor for 6 h at 85° C. and 50 W. The reaction solution is concentrated in vacuum and methanol was added to the reaction solution to obtain the crude product as precipitate. The crude product was extracted by using a soxhlet apparatus which acetone is used as a solvent to obtain 234 mg of aromatic compound P6 at a yield of 45%.

Results of NMR analysis and mass spectrometry for aromatic compound P6

$^1$H-NMR(C$_3$D$_2$F$_6$O plus 0.1% C$_2$DF$_3$O$_2$, 500 MHz, 25° C.): δ=1.09 (s, 9H), 1.10 (s, 54H), 6.06 (d, 6H, 3J=4.8 Hz), 6.15 (d, 6H, 3J=4.8 Hz), 6.55 (s, 6H), 7.00 (d, 6H, 3J=8.2 Hz), 7.43 (d, 6H, 3J=8.2 Hz) ppm.

$^{13}$C-NMR(C$_3$D$_2$F$_6$O plus 0.1% C$_2$DF$_3$O$_2$, 125 MHz, 25° C.): δ=9.2, 15.3, 95.3, 103.5, 127.6, 128.8, 130.0, 131.8, 133.9, 135.2, 143.5, 144.1, 146.9, 149.9 ppm.

MALDI-Tof Found (m/z): 1576.94, Calculated: 1578.77

Example 21

Synthesis of Aromatic Compound P7

Aromatic compound P7 was synthesized according to the following reaction formula.

[Chemical Formula 141]

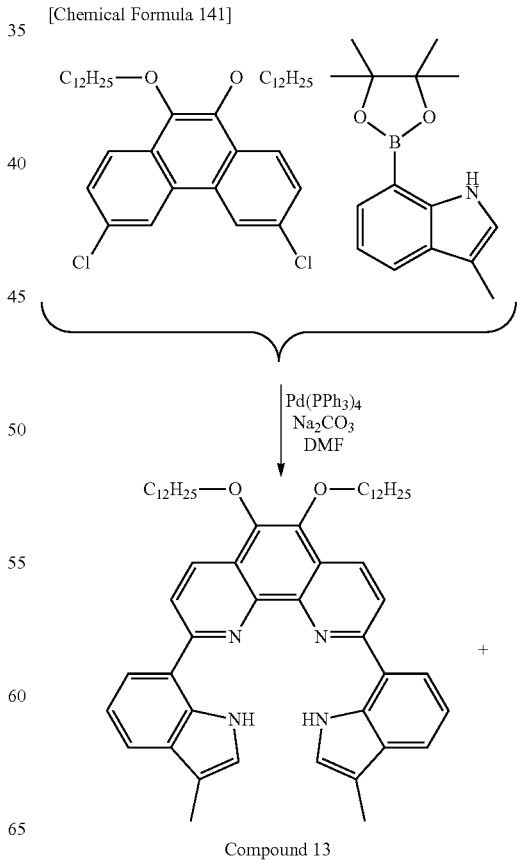

Compound 13

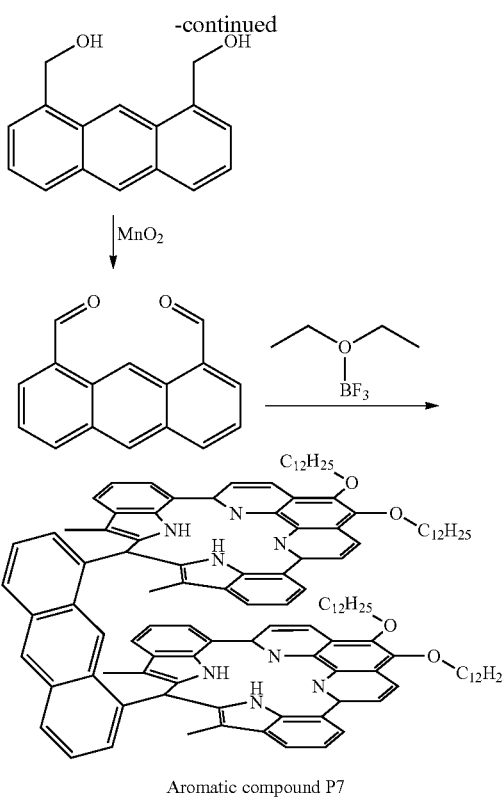

Aromatic compound P7

First, compound 13 was synthesized in the same manner as in the synthetic method of compound 7, except that 2,9-dichloro-5,6-bis(dodecyloxy)-1,10-phenanthlorine and 3-methyl-7-(4,4,5,5-tetramethyl-1,3,2-dioxaborolan-2-yl)-1H-indole were used as starting materials.
Next, anthracene-1,8-dicarbaldehyde was synthesized by the following method. To a suspension of 250 mg of 1,8-Bis(hydroxymethyl)anthracene (1.1 mmol) in dichloromethane (20 mL), 383 mg of $MnO_2$ (4.4 mmol) was added. After stirring for 1 h at room temperature, 3.8 g of $MnO_2$ (44 mmol) was further added. After additional stirring overnight, the reaction mixture was filtered. The solvent was distilled off from the obtained filtrate with an evaporator, and the residue was purified by column purification to obtain 181 mg of anthracene-1,8-dicarbaldehyde at a yield of 70%.
Results of NMR analysis for anthracene-1,8-dicarbaldehyde
$^1$H-NMR ($CD_2Cl_2$, 250 MHz) δ=11.2 (s, 1H), 10.6 (s, 2H), 8.56 (s, 1H), 8.20 (d, 2H), 8.01 (dd, 2H), 7.55 (dd, 1.8 Hz, 2H).
Next, aromatic compound P7 was synthesized by the following method.
100 mg of compound 13 (0.124 mmol) and 0.014 mg of anthracene-1,8-dicarbaldehyde (0.062 mmol) was placed in a Schlenks' tube under a argon atmosphere, and then 20 ml of tetrachloroethane and 0.038 ml of boron trifluoride etherate ($BF_3.O(Et)_2$) (0.310 mmol) was added. The reaction mixture was stirred at 105° C. for 24 h and then saturated $NH_4Cl$ solution was added. After washed with water, the residue was purified by column purification to obtain 40 mg of aromatic compound P7 at a yield of 35%.
Results of NMR analysis and mass spectrometry for aromatic compound P7
$^1$H-NMR ($CD_2Cl_2$, 250 MHz) δ=10.02 (bs, 4 H), 8.25 (dd, 8 H), 7.92 (m, 4 H), 7.72 (t, 4 H), 7.45 (m, 4 H), 7.15 (m, 4 H), 6.24 (s, 2 H), 3.95 (m, 8 H), 2.76 (s, 12 H), 1.75 (m, 8 H), 1.34 (m, 72 H), 0.96 (t, 12 H)
Maldi-Tof Found (m/z): 1812, Calculated: 1811

<Evaluation 12>

The metal complex MC2 was loaded onto a carbon support to produce electrode catalyst 12. Specifically, 2 mg of metal complex MC2 and 8 mg of the carbon support (trade name: KETCHEN BLACK EC600 JD, by Lion Corp.) were mixed in methanol, and after ultrasonic treatment for 15 minutes and distilling off the solvent with an evaporator, it was dried overnight under reduced pressure of 200 Pa to obtain electrode catalyst 12.

For evaluation of the electrode catalyst 12, the water-oxidation activity was evaluated with a rotating disk electrode. The electrode used was a disk electrode having a glassy carbon disk section (diameter: 6.0 mm).

After adding 1 mL of a 0.5% NAFION® solution (a 5% NAFION® solution diluted 10-fold with ethanol) to a sample bottle containing 1 mg of the electrode catalyst 12, it was dispersed with ultrasonic waves for 15 minutes. After then dropping 1.8 μL of the obtained suspension onto the disk section of the electrode and drying it, it was dried for 3 hours with a drier heated to 80° C., to obtain a measuring electrode.

The current value for oxidation reaction of water was measured by using this measuring electrode with the Measuring apparatus and Measuring conditions described below. The current value was measured in a nitrogen-saturated state. The current value was then divided by the surface area of the measuring electrode to determine the current density. The results are shown in Table 3. The measuring apparatus and measuring conditions were as follows, and the current density is the value with 1 V on a silver/silver chloride electrode.

[Measuring Apparatus]
RRDE-1 rotating ring-disk electrode apparatus by Nikko Keisoku.
ALS model 701C Dual Electrochemical Analyzer
[Measuring Conditions]
Cell solution: 1 mol/L sodium hydroxide aqueous solution (nitrogen saturation).
Solution temperature: 25° C.
Reference electrode: silver/silver chloride electrode (3M potassium chloride)
Counter electrode: platinum wire
Sweep rate: 10 mV/sec
Electrode rotational speed: 900 rpm <Evaluation 13>

Electrode catalyst 13 was fabricated in the same manner as in <Evaluation 12>, except that metal complex MC2 was changed to manganese dioxide (Product code: 203750, by Aldrich Co.), and oxidation reaction with water was evaluated. The results are shown in Table 3.

<Evaluation 14>

Electrode catalyst 14 was fabricated in the same manner as in <Evaluation 12>, except that electrode catalyst 12 was replaced with platinum-supported carbon (20 wt %-loaded, Electrochem, Inc.), and oxidation reaction with water was evaluated. The results are shown in Table 3.

TABLE 3

| Evaluation | Electrode catalyst | Current density (mA/cm$^2$) |
|---|---|---|
| 12 | 12 | 84 |
| 13 | 13 | 6.2 |
| 14 | 14 | 18 |

The invention claimed is:

1. An aromatic compound comprising 2 or more covalently-bound sections, the aromatic compound containing no metal atoms, satisfying the following conditions (a) and (b):
   (a) individually, each of the 2 or more sections, which may be the same or different, includes at least 4 coordinatable nitrogen atoms, and the at least 4 coordinatable nitrogen atoms in each individual section are coordinatable with a single metal atom within each individual section,
   (b) at least one of the nitrogen atoms in each individual section is a nitrogen atom in a 6-membered nitrogen-containing heterocyclic ring,
   wherein the sections are selected from the group consisting of sections represented by the following formulae:

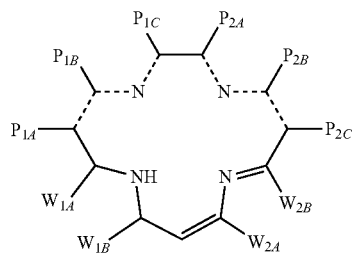

wherein represents a bond in an aromatic ring;
wherein each $P_{1A}$, $P_{1B}$ and $P_{1C}$ is part of a first polycyclic aromatic heterocyclic ring comprising two 6-membered aromatic rings, at least one of which is a heterocyclic ring; each $P_{2A}$, $P_{2B}$ and $P_{2C}$ is part of a second polycyclic aromatic heterocyclic ring comprising two 6-membered aromatic rings, at least one of which is a heterocyclic ring; each $W_{1A}$ and $W_{1B}$ is part of a first 5-membered heterocyclic ring; and each $W_{2A}$ and $W_{2B}$ is part of a second 5-membered heterocyclic ring; and wherein hydrogens therein may be substituted with halogeno, hydroxy, carboxyl, mercapto, sulfonic acid, nitro, amino, cyano, phosphonic acid, silyl substituted with $C_{1-4}$ alkyl, $C_{1-50}$ straight-chain or branched alkyl, $C_{3-50}$ cyclic alkyl, alkenyl, alkynyl, alkoxy, $C_{6-60}$ aryl, $C_{7-50}$ aralkyl, or monovalent heterocyclic groups, and
wherein:
$W_{1A}$ and $W_{1B}$ can form a 5-membered ring with each other;
$W_{2A}$ and $W_{2B}$ can form a 5-membered ring with each other;
$P_{1A}$ and $P_{1B}$ can form a 6-membered ring with each other;
$P_{1B}$ and $P_{1C}$ can form a 6-membered ring with each other;
$P_{2A}$ and $P_{2B}$ can form a 6-membered ring with each other;
$P_{2B}$ and $P_{2C}$ can form a 6-membered ring with each other; and
$P_{1C}$ and $P_{2A}$ can form a 6-membered ring with each other.

2. The aromatic compound according to claim 1, wherein the ratio of the total mass of nitrogen atoms with respect to the total mass of carbon atoms in the aromatic compound is greater than 0 and no greater than 1.1.

3. A metal complex having a metal atom or metal ion, and a ligand comprising the aromatic compound according claim 1.

4. The metal complex according to claim 3, wherein the metal atom or metal ion is a transition metal atom or its ion, from between period 4 and period 6 of the Periodic Table.

5. A composition comprising the aromatic compound according to claim 1, and a carbon particle, a $C_{60}$ fullerene, a $C_{70}$ fullerene, a carbon nanotube, a carbon nanohorn, or a carbon fiber, and/or polymer material.

6. A catalyst comprising the aromatic compound according to claim 1.

7. An electrode comprising the aromatic compound according to claim 1.

8. An electrode catalysts for fuel cell comprising the aromatic compound according to claim 1.

9. A polymer electrolyte fuel cell using the electrode catalysts for fuel cell according to claim 8.

10. The polymer electrolyte fuel cell according to claim 9, wherein a polymer electrolyte membrane of the polymer electrolyte fuel cell is the one having proton conductivity.

11. The polymer electrolyte fuel cell according to claim 9, wherein a polymer electrolyte membrane of the polymer electrolyte fuel cell is the one having anion conductivity.

* * * * *